United States Patent
Song et al.

(10) Patent No.: US 12,398,124 B2
(45) Date of Patent: Aug. 26, 2025

(54) PYRROLOBENZODIAZEPINE DIMER PRODRUG AND LIGAND-LINKER CONJUGATE COMPOUND OF THE SAME

(71) Applicant: LegoChem Biosciences, Inc., Daejeon (KR)

(72) Inventors: Ho Young Song, Daejeon (KR); Sung Min Kim, Daejeon (KR); Hyoungrae Kim, Daejeon (KR); Kyung Eun Park, Daejeon (KR); Chul-Woong Chung, Daejeon (KR); Yun-Hee Park, Daejeon (KR); Hyo Jung Choi, Daejeon (KR); Su In Lee, Daejeon (KR); Juyuel Baek, Daejeon (KR); Hyeun Joung Lee, Daejeon (KR); Ju Young Lee, Daejeon (KR); Ji Hye Oh, Daejeon (KR); Jeiwook Chae, Daejeon (KR); Yeong Soo Oh, Daejeon (KR); Yong Zu Kim, Daejeon (KR)

(73) Assignee: LigaChem Biosciences Inc., Daejeon (KR)

(*) Notice: Subject to any disclaimer, the term of this patent is extended or adjusted under 35 U.S.C. 154(b) by 0 days.

(21) Appl. No.: 18/113,948

(22) Filed: Feb. 24, 2023

(65) Prior Publication Data

US 2023/0270868 A1    Aug. 31, 2023

Related U.S. Application Data

(63) Continuation of application No. 16/328,256, filed as application No. PCT/KR2018/003744 on Mar. 29, 2018, now Pat. No. 11,654,197.

(30) Foreign Application Priority Data

Mar. 29, 2017 (KR) .................. 10-2017-0039841

(51) Int. Cl.
| | | |
|---|---|---|
| *C07D 405/14* | (2006.01) | |
| *A61K 47/55* | (2017.01) | |
| *A61K 47/68* | (2017.01) | |
| *A61P 35/00* | (2006.01) | |

(52) U.S. Cl.
CPC .......... *C07D 405/14* (2013.01); *A61K 47/552* (2017.08); *A61K 47/68035* (2023.08); *A61P 35/00* (2018.01)

(58) Field of Classification Search
CPC ... C07D 405/14; C07D 519/00; C07D 487/04
See application file for complete search history.

(56) References Cited

U.S. PATENT DOCUMENTS

| | | |
|---|---|---|
| 5,112,739 A | 5/1992 | Meneghini et al. |
| 5,266,575 A | 11/1993 | Gerster et al. |
| 5,935,995 A | 8/1999 | Bosslet et al. |
| 6,218,519 B1 | 4/2001 | Kenten et al. |
| 6,759,509 B1 | 7/2004 | King et al. |
| 8,039,273 B2 | 10/2011 | Jeffrey |
| 8,227,578 B2 | 7/2012 | Nakamura et al. |
| 8,568,728 B2 | 10/2013 | Jeffrey |
| 9,919,057 B2 | 3/2018 | Kim et al. |
| 9,993,568 B2 | 6/2018 | Kim et al. |
| 10,118,965 B2 | 11/2018 | Kim et al. |
| 10,183,997 B2 | 1/2019 | Kim et al. |
| 10,383,949 B2 | 8/2019 | Kim et al. |
| 10,980,890 B2 | 4/2021 | Kim et al. |
| 11,167,040 B2 | 11/2021 | Kim et al. |
| 11,173,214 B2 | 11/2021 | Kim et al. |
| 11,184,191 B1 | 11/2021 | Indiradevi et al. |
| 11,413,353 B2 | 8/2022 | Kim et al. |
| 11,654,197 B2 | 5/2023 | Song et al. |
| 11,707,533 B2 | 7/2023 | Park et al. |
| 11,827,703 B2 | 11/2023 | Yin |
| 11,975,076 B2 | 5/2024 | Kim et al. |
| 2005/0238649 A1 | 10/2005 | Doronina et al. |
| 2006/0088522 A1 | 4/2006 | Boghaert et al. |
| 2008/0057063 A1 | 3/2008 | Rinkenberger et al. |
| 2009/0299038 A1 | 12/2009 | Nakamura et al. |
| 2009/0326205 A1 | 12/2009 | Nakamura et al. |
| 2012/0030858 A1 | 2/2012 | Duffin |
| 2012/0058051 A1 | 3/2012 | Rader et al. |

(Continued)

FOREIGN PATENT DOCUMENTS

| | | |
|---|---|---|
| CA | 2921707 A1 | 4/2015 |
| CA | 3039832 A1 | 4/2018 |
| CA | 3058360 A1 | 10/2018 |
| CN | 1185786 A | 6/1998 |

(Continued)

OTHER PUBLICATIONS

Dorywalska et al., "Effect of attachment site on stability of cleavable antibody drug conjugates." Bioconjugate Chemistry 26.4 (2015): 650-659.

(Continued)

*Primary Examiner* — Jonathan S Lau

(74) *Attorney, Agent, or Firm* — Foley Hoag LLP; David P. Halstead; Lucas P. Watkins

(57) ABSTRACT

The present invention relates to a pyrrolobenzodiazepine dimer prodrug and a ligand-linker conjugate compound thereof, a composition containing these, and therapeutic use thereof particularly as an anticancer drug. The stability of the compounds themselves and the stability thereof in plasma are excellent and the compounds are advantageous in terms of manifestation of toxicity, and thus the compounds are industrially useful in that it is possible to target proliferative diseases such as cancer, to perform a specific treatment, to maximize the drug efficacy, and to minimize the occurrence of side effects.

29 Claims, 1 Drawing Sheet

(56) References Cited

U.S. PATENT DOCUMENTS

| | | |
|---|---|---|
| 2012/0107332 A1 | 5/2012 | Jeffrey |
| 2012/0308584 A1 | 12/2012 | Kim et al. |
| 2013/0251723 A1 | 9/2013 | Rohlff et al. |
| 2013/0281922 A1 | 10/2013 | Teige |
| 2014/0031535 A1 | 1/2014 | Jeffrey |
| 2014/0032535 A1 | 1/2014 | Singla |
| 2014/0072558 A1 | 3/2014 | Park et al. |
| 2014/0088292 A1 | 3/2014 | Kim et al. |
| 2014/0161829 A1 | 6/2014 | Kim et al. |
| 2014/0187756 A1 | 7/2014 | Kim et al. |
| 2014/0286969 A1 | 9/2014 | Tschoepe et al. |
| 2015/0105541 A1 | 4/2015 | Kim et al. |
| 2016/0031887 A1* | 2/2016 | Howard ............. A61K 47/6809 540/496 |
| 2016/0184451 A1 | 6/2016 | Kim et al. |
| 2016/0208018 A1 | 7/2016 | Chen et al. |
| 2016/0256561 A1 | 9/2016 | Howard et al. |
| 2016/0257709 A1 | 9/2016 | Kline et al. |
| 2016/0310612 A1 | 10/2016 | Lyon et al. |
| 2017/0088614 A1 | 3/2017 | Kim et al. |
| 2017/0088621 A1 | 3/2017 | Kim et al. |
| 2017/0095576 A1 | 4/2017 | Kim et al. |
| 2018/0142018 A1 | 5/2018 | Fischer |
| 2018/0193481 A1 | 7/2018 | Chang et al. |
| 2018/0265593 A1 | 9/2018 | Chen et al. |
| 2018/0369406 A1 | 12/2018 | Lannutti et al. |
| 2019/0151465 A1 | 5/2019 | Kim et al. |
| 2019/0381185 A1 | 12/2019 | Kim et al. |
| 2020/0069816 A1 | 3/2020 | Kim et al. |
| 2020/0095317 A1 | 3/2020 | Song et al. |
| 2020/0297865 A1 | 9/2020 | Kim et al. |
| 2021/0069342 A1 | 3/2021 | Park et al. |
| 2021/0139473 A1 | 5/2021 | Charnley et al. |
| 2021/0214432 A1 | 7/2021 | Lim et al. |
| 2022/0073509 A1 | 3/2022 | Wu et al. |
| 2022/0218830 A1 | 7/2022 | Song et al. |
| 2022/0218840 A1 | 7/2022 | Kim et al. |
| 2022/0339291 A1 | 10/2022 | Park et al. |
| 2023/0270868 A1 | 8/2023 | Song et al. |
| 2023/0272070 A1 | 8/2023 | Song et al. |
| 2023/0405139 A1 | 12/2023 | Park et al. |

FOREIGN PATENT DOCUMENTS

| | | |
|---|---|---|
| CN | 101287500 A | 10/2008 |
| CN | 101573384 A | 11/2009 |
| CN | 101636502 A | 1/2010 |
| CN | 101835803 A | 9/2010 |
| CN | 103648530 A | 3/2014 |
| CN | 105358579 A | 2/2016 |
| CN | 107530423 A | 1/2018 |
| CN | 107847596 A | 3/2018 |
| CN | 110903395 A | 3/2020 |
| EP | 2913064 A1 | 9/2015 |
| EP | 3156424 A1 | 4/2017 |
| EP | 3604311 A1 | 2/2020 |
| JP | 2009501800 A | 1/2009 |
| JP | 2019/503979 A | 2/2019 |
| KR | 10-2009-0088893 A | 8/2009 |
| KR | 10-2012-0113175 A | 10/2012 |
| KR | 2014/0035393 A | 3/2014 |
| KR | 10-2015-0137015 | 6/2016 |
| KR | 10-2014-0192328 | 7/2016 |
| KR | 10-2018-0110645 A | 10/2018 |
| KR | 10-2019-0018400 A | 2/2019 |
| KR | 10-2019-0028350 A | 3/2019 |
| KR | 10-2020-0084802 A | 7/2020 |
| RU | 2191021 C2 | 10/2002 |
| RU | 2218922 C2 | 12/2003 |
| RU | 2651776 C2 | 4/2018 |
| TW | 201524520 A | 7/2015 |
| WO | WO-98/19705 A1 | 5/1998 |
| WO | WO-2004050089 A1 | 6/2004 |
| WO | WO-2005/066170 A1 | 7/2005 |
| WO | WO-2006/009832 A1 | 1/2006 |
| WO | WO-2006/091647 A2 | 8/2006 |
| WO | WO-2007/011968 A2 | 1/2007 |
| WO | WO-2008/034120 A2 | 3/2008 |
| WO | WO-2009/016647 A1 | 2/2009 |
| WO | WO-2009/054863 A2 | 4/2009 |
| WO | WO-2009/118296 A2 | 10/2009 |
| WO | WO-2010/124188 A1 | 10/2010 |
| WO | WO-2011/130598 A1 | 10/2011 |
| WO | WO-2011/145068 A1 | 11/2011 |
| WO | WO-2012/045085 A1 | 4/2012 |
| WO | WO-2012/076066 A1 | 6/2012 |
| WO | WO-2012/138102 A2 | 10/2012 |
| WO | WO-2012/153193 A2 | 11/2012 |
| WO | WO-2011066418 A1 | 11/2012 |
| WO | WO-2013055990 A1 | 4/2013 |
| WO | WO-2013103707 A1 | 7/2013 |
| WO | WO-2014/096368 A1 | 6/2014 |
| WO | WO-2014/194030 A2 | 12/2014 |
| WO | WO-2015/052322 A1 | 4/2015 |
| WO | WO-2015/057699 A2 | 4/2015 |
| WO | WO-2015/095755 A1 | 6/2015 |
| WO | WO-2015/182984 A1 | 12/2015 |
| WO | WO-2016/033570 A1 | 3/2016 |
| WO | WO-2016/040684 A1 | 3/2016 |
| WO | WO-2016/094517 A1 | 6/2016 |
| WO | WO-2016/115559 A1 | 7/2016 |
| WO | WO-2016108587 A1 | 7/2016 |
| WO | WO-2016/142768 A1 | 9/2016 |
| WO | WO-2017/051249 A1 | 3/2017 |
| WO | WO-2017/051254 A1 | 3/2017 |
| WO | WO-2017/066136 A2 | 4/2017 |
| WO | WO-2017/089894 A1 | 6/2017 |
| WO | WO-2017/089895 A1 | 6/2017 |
| WO | WO-2017089890 A1 | 6/2017 |
| WO | WO-2017/127664 A1 | 7/2017 |
| WO | WO-2017/181128 A1 | 10/2017 |
| WO | WO-2018/069490 A1 | 4/2018 |
| WO | WO-2018/083535 A1 | 5/2018 |
| WO | WO-2018/119314 A1 | 6/2018 |
| WO | WO-2018/146199 A1 | 8/2018 |
| WO | WO-2018/182341 A1 | 10/2018 |
| WO | WO-2018/200812 A1 | 11/2018 |
| WO | WO-2018/237335 A1 | 12/2018 |
| WO | WO-2019/050362 A2 | 3/2019 |
| WO | WO-2019/051489 A1 | 3/2019 |
| WO | WO-2019/104289 A1 | 5/2019 |
| WO | WO-2019/114666 A1 | 6/2019 |
| WO | WO-2019/215510 A2 | 11/2019 |
| WO | WO-2019/225777 A1 | 11/2019 |
| WO | WO-2019/225992 A1 | 11/2019 |
| WO | WO-2019/243825 A1 | 12/2019 |
| WO | WO-2020/092617 A1 | 5/2020 |
| WO | WO-2020/180121 A1 | 9/2020 |
| WO | WO-2019/215510 A8 | 11/2020 |
| WO | WO-2020/249773 A1 | 12/2020 |
| WO | WO-2021/014365 A1 | 1/2021 |
| WO | WO-2021/026009 A1 | 2/2021 |
| WO | WO-2021/044208 A1 | 3/2021 |
| WO | WO-2021/046426 A1 | 3/2021 |
| WO | WO-2022/086853 A1 | 4/2022 |
| WO | WO-2022/147532 A1 | 7/2022 |
| WO | WO-2022/155518 A1 | 7/2022 |
| WO | WO-2022/177307 A1 | 8/2022 |
| WO | WO-2022/211508 A1 | 10/2022 |
| WO | WO-2022/254376 A1 | 12/2022 |
| WO | WO-2023/209441 A1 | 11/2023 |
| WO | WO-2024/100449 A1 | 5/2024 |
| WO | WO-2024/100452 A2 | 5/2024 |
| WO | WO-2024/189428 A1 | 9/2024 |

OTHER PUBLICATIONS

Dubowchik et al., "Cathepsin B-labile dipeptide linkers for lysosomal release of doxorubicin from internalizing immunoconjugates: model studies of enzymatic drug release and antigen-specific in vitro anticancer activity." Bioconjugate Chemistry 13.4 (2002): 855-869.

(56) References Cited

OTHER PUBLICATIONS

Al Qaraghuli et al., "Antibody-protein binding and conformational changes: identifying allosteric signaling pathways to engineer a better effector response", Sci Rep 10: 13696 (2020).
Behrens et al., "Methods for Site-specific Drug Conjugation to Antibodies," MAbs, 6(1): 46-53 (2014).
Bender et al., "A Mechanistic Pharmacokinetic Model Elucidating the Disposition of Trastuzumab Emtansine (T-DM1), an Antibody-Drug Conjugate (ADC) for Treatment of Metastatic Breast Cancer," The AAPS Journal, 16: 994-1008 (2014).
Bendig, "Humanization of Rodent Monoclonal Antibodies by CDR Grafting," Methods: A Companion to Methods in Enzymology, 8:83-93 (1995).
Bergmann, CP et al. Dental Ceramics. Microstructure, Properties, and Degradation. 2013, Chapter 2, Biomaterials, p. 9.
Bujak et al., "A Monoclonal Antibody to Human DLK1 Reveals Differential Expression in Cancer and Absence in Healthy Tissues." Antibodies, 4(2):71-87 (2015).
Carey, FA. Organic Chemistry 6th Ed. McGraw Hill. 2006, chapter 1, p. 9.
Christie et al., "Stabilization of cysteine-linked antibody drug conjugates with N-aryl maleimides," Journal of Controlled Release, 220:660-670 (2015).
Chu et al., "Antibody-drug Conjugates for the Treatment of B-cell Non-Hodgkin's Lymphoma and Leukemia," Future Oncol, 9(3): 355-368 (2013).
Collins et al., "The emergence of oxime click chemistry and its utility in polymer science," Polymer Chemistry, 23: 3812-3826 (2016).
Colman, "Effects of Amino Acid Sequence Changes on Antibody-Antigen Interactions," Research in Immunology, 145: 33-36 (1994).
Connolly et al., "Discovery of Orally Active 4-amino-6-arylaminopyrimidine-5-carbaldehyde Oximes with Dual EGFR and HER2 Inhibitory Activity," AACR 104th Annual Meeting, Abstract 2456 (2013).
Desbene, S. et al. Doxorubicin prodrugs with reduced cytotoxicity suited for tumour-specific activation. Anti-Cancer Drug Design. 1998, vol. 13,p. 955.
Dunn, PJ. et al. Green Chemistry Principle #8. ACS What is Green Chemistry. Accessed from ACS Website on Jan. 8, 2016.
Edwards et al., "The remarkable flexibility of the human antibody repertoire; isolation of over one thousand different antibodies to a single protein, BLyS," J Mol Biol, 334(1): 103-118 (2003).
Extended European Search Report for Application No. EP 18774896 dated Dec. 15, 2020.
Extended European Search Report for EP Application No. 15799360.1 dated Dec. 21, 2017.
Extended European Search Report for EP Application No. 16868091.6 dated May 17, 2019.
Extended European Search Report for EP Application No. 16868095.7 dated Jul. 29, 2019.
Extended European Search Report for EP Application No. 16868096.5 dated Jun. 21, 2019.
Extended European Search Report for EP Application No. 19799713.3 dated Apr. 13, 2022.
Gaertner et al., "Chemo-enzymic Backbone Engineering of Proteins ," J. Biol. Chem., 269(10):7224-7230 (1994).
Grinda, M. et al., A Self-Immolative Dendritic Glucuronide Prodrug of Doxorubicin, Medicinal Chemistry Communications, (2012) vol. 3, No. 1, pp. 68-70.
Guan., "Metabolic Activation and Drug Targeting," Drug Delivery: Principles and Applications: 201-244 (2005).
International Search Report and Written Opinion for International Application No. PCT/IB2016/001772 mailed Apr. 6, 2017.
International Search Report and Written Opinion for International Application No. PCT/IB2016/001810 dated Apr. 19, 2017.
International Search Report and Written Opinion for International Application No. PCT/IB2016/001811 dated Apr. 19, 2017.
International Search Report and Written Opinion for International Application No. PCT/IB2019/000577 dated Nov. 28, 2019.
International Search Report and Written Opinion for International Application No. PCT/IB2020/000649 dated Nov. 27, 2020.
International Search Report and Written Opinion for International Application No. PCT/KR2015/005299 dated Jul. 17, 2015.
Jeffrey et al., "Development and properties of β-glucuronide linkers for monoclonal antibody-drug conjugates," Bioconjugate Chem, 17:835 (2006).
Jeffrey et al., "Minor groove binder antibody conjugates employing a water soluable β-glucuronide linker," Bioorganic & Medicinal Chemistry Letters, 17:2278-2280 (2007).
Kim et al., "A dimeric form of a small-sized protein binder exhibits enhanced anti-tumor activity through prolonged blood circulation," Journal of Controlled Release, 279: 282-191 (2018).
Kim et al., "Protein conjugation with genetically encoded unnatural amino acids," Current Opinion in Chemical Biology, 17: 412-419 (2013).
Kim et al., "Strategies and Advancement in Antibody-Drug Conjugate Optimization for Targeted Cancer Therapeutics," Biomolecular Therapeutics, 23: 493-509 (2015).
Kim et al., "Synthesis of Bispecific Antibodies Using Genetically Encoded Unnatural Amino Acids," J Am Chem Soc, 134: 9918-9921 (2012).
Lartigue, "Antibody-Drug Conjugates: Guided Missiles Deployed Against Cancerous Cells," Oncology Live, p. 1 (2012).
Lee et al., "Enzymatic prenylation and oxime ligation for the synthesis of stable and homogeneous protein-drug conjugates for targeted therapy." Angewandte Chemie, 54(41):12020-12024 (2015).
Leong, KW. Biomaterials. El Sevier. Accessed on Sep. 26, 2016.
Lockard et al., "Efficacy and toxicity of the solvent polyethylene glycol 400 in monkey model." Epilepsia 20.1: 77-84 (1979).
Lu et al., "Linkers Having a Crucial Role in Antibody - Drug Conjugates," Int J Molec Sci 17(561):1-22 (2016).
Mariuzza et al., "The structural basis of antigen-antibody recognition." Annual review of biophysics and biophysical chemistry 16.1: 139-159 (1987).
Mashkovsky., "Medicines", Medicine, p. 8, (1993).
McCombs et al., "Antibody Drug Conjugates: Design and Selection of Linker, Payload and Conjugation Chemistry," AAPS J, 17(2): 339-351 (2015).
Merriam-Webster. Biomaterial Definition. Accessed on Sep. 26, 2016.
Murphy et al., "Enhancing recombinant antibody performance by optimally engineering its format," Journal of Immunological Methods, 463: 127-133 (2018).
Murphy et al., "Targeting Sema3D in pancreatic cancer: A novel therapeutic strategy," Journal of Clinical Oncology: Abstract 4129 pp. 1-2 (2015).
Paul., "Fundamental Immunology Third Edition," Raven Press New York: 292-295 (1993).
Qi et al., "Blocking neuropilin-1 function has an additive effect with anti-VEGF to inhibit tumor growth." Cancer cell 11.1: 53-67 (2007).
Rose et al., "Preparation of well-defined protein conjugates using enzyme-assisted reverse proteolysis," Bioconjugate Chem, 2(3):154-159 (1991).
Rudikoff et al., "Single amino acid substitution altering antigen-binding specificity," PNAS, 79(6): 1979-1983 (1982).
Sagnou et al., "Design and synthesis of novel pyrrolobenzodiazepine (PBD) prodrugs for ADEPT and GDEPT," Bioorganic and Medicinal Chemistry Letters, 10(18): 2083-2086 (2000).
Schwarz et al., "[15] Enzymatic C-terminal biotinylation of proteins," Methods Enzymol 184:160-162 (1990).
Skriec et al., "Non-immunoglobulin scaffolds: a focus on their targets," Trends in Biotechnology, 33(7): 408-418 (2015).
Tranoy-Opalinski et al., "β-Glucuronidase-responsive prodrugs for selective cancer chemotherapy: an update," Eur J Med Chem, 74:302-313 (2014).
Translation of International Search Report for International Application No. PCT/KR2020/003100 dated Jun. 24, 2020 (4 pages).
Varvounis, "An Update on the Synthesis of Pyrrolo[1,4]benzodiazepines," Molecules, 21(154):1-55 (2016).

(56) References Cited

OTHER PUBLICATIONS

Wermuth, "Similarity in drugs: reflections on analogue design," Drug Discov Today, 11(Issues 7-8): 248-254 (2006).

Yewale et al., "Epidermal growth factor receptor targeting in cancer: A review of trends and strategies," Biomaterials, 34: 8690-8707 (2013).

Zimmerman et al., "Production of Site-Specific Antibody-Drug Conjugates Using Optimized Non-Natural Amino Acids in a Cell-Free Expression System," Bioconjugate Chem., 25(2):351-361 (2014).

U.S. Appl. No. 17/475,109, Pending.

Extended European Search Report for EP Application No. 20765639.8 dated Feb. 23, 2023.

Marei et al., "Potential of antibody-drug conjugates (ADCs) for cancer therapy," Cancer Cell International 22(255): pp. 1-12 (2022).

Jin et al., "New Technologies Bloom Together for Bettering Cancer Drug Conjugates," Pharmacological Reviews 74: pp. 680-713 (2022).

U.S. Appl. No. 15/779,446, Granted.

Chuprakov et al., "Tandem-cleavage linkers improve the in vivo stability and tolerability of antibody-drug conjugates," Bioconjugate Chemistry 32 (2021): 746-775.

International Search Report and Written Opinion for International Application No. PCT/IB24/00114 dated Aug. 14, 2024.

Alouane et al., "Self-immolative spacers: kinetic aspects, structure-property relationships, and applications." Angewandte Chemie International Edition, 54(26), 7492-7509. (2015).

Burnouf et al., "Glucuronides: From biological waste to bio-nanomedical applications." Journal of Controlled Release, 349, 765-782 (2022).

Katoh et al., "Canonical and Non-Canonical WNT Signaling in Cancer Stem Cells and Their Niches: Cellular Heterogeneity, Omics Reprogramming, Targeted Therapy and Tumor Plasticity (Review)," Int J Oncol, 51(5): pp. 1357-1369 (2017).

Diebold et al., "Innate Antiviral Responses by Means of TLR7-Mediated Recognition of Single-Stranded RNA," Science 303: pp. 1529-1531 (2004).

Extended European Search Report for EP application No. 20861806.6 dated Oct. 20, 2023.

Grimmig et al., "TLR7 and TLR8 expression increases tumor cell proliferation and promotes chemoresistance in human pancreatic cancer," International Journal of Oncology, 47: pp. 857-866 (2015).

International Search Report for Application No. PCT/IB2023/000251 dated Sep. 18, 2023.

Kanzler et al., "Therapeutic targeting of innate immunity with Toll-like receptor agonists and antagonists," Nature Medicine, 13: pp. 552-559 (2007).

Schon et al., "TLR7 and TLR8 as targets in cancer therapy," Oncogene, 27: pp. 190-199 (2008).

U.S. Appl. No. 14/865,778, Issued.
U.S. Appl. No. 14/898,932, Issued.
U.S. Appl. No. 16/005,245, Issued.
U.S. Appl. No. 16/545,869, Subject to Reissue.
U.S. Appl. No. 18/234,732, Pending.
U.S. Appl. No. 15/276,231, Issued.
U.S. Appl. No. 15/276,209, Issued.
U.S. Appl. No. 15/779,444, Issued.
U.S. Appl. No. 17/525,582, Pending.
U.S. Appl. No. 15/779,450, Issued.
U.S. Appl. No. 16/408,002, Allowed.
U.S. Appl. No. 17/946,782, Pending.
U.S. Appl. No. 16/328,256, Issued.
U.S. Appl. No. 16/940,326, Granted.
U.S. Appl. No. 18/209,299, Pending.
U.S. Appl. No. 16/964,965, Pending.

Burdette et al., "STING and the innate immune response to nucleic acids in the cytosol." *Nature immunology* 14.1 (2013): 19-26.

Chen et al., "Regulation and function of the cGAS-STING pathway of cytosolic DNA sensing." Nature immunology 17.10 : 1142-1149 (2016).

International Search Report and Written Opinion for International Application No. PCT/IB23/00670 dated Apr. 9, 2024.

Woo et al., "STING-dependent cytosolic DNA sensing mediates innate immune recognition of immunogenic tumors." Immunity 41.5: 830-842 (2014).

* cited by examiner

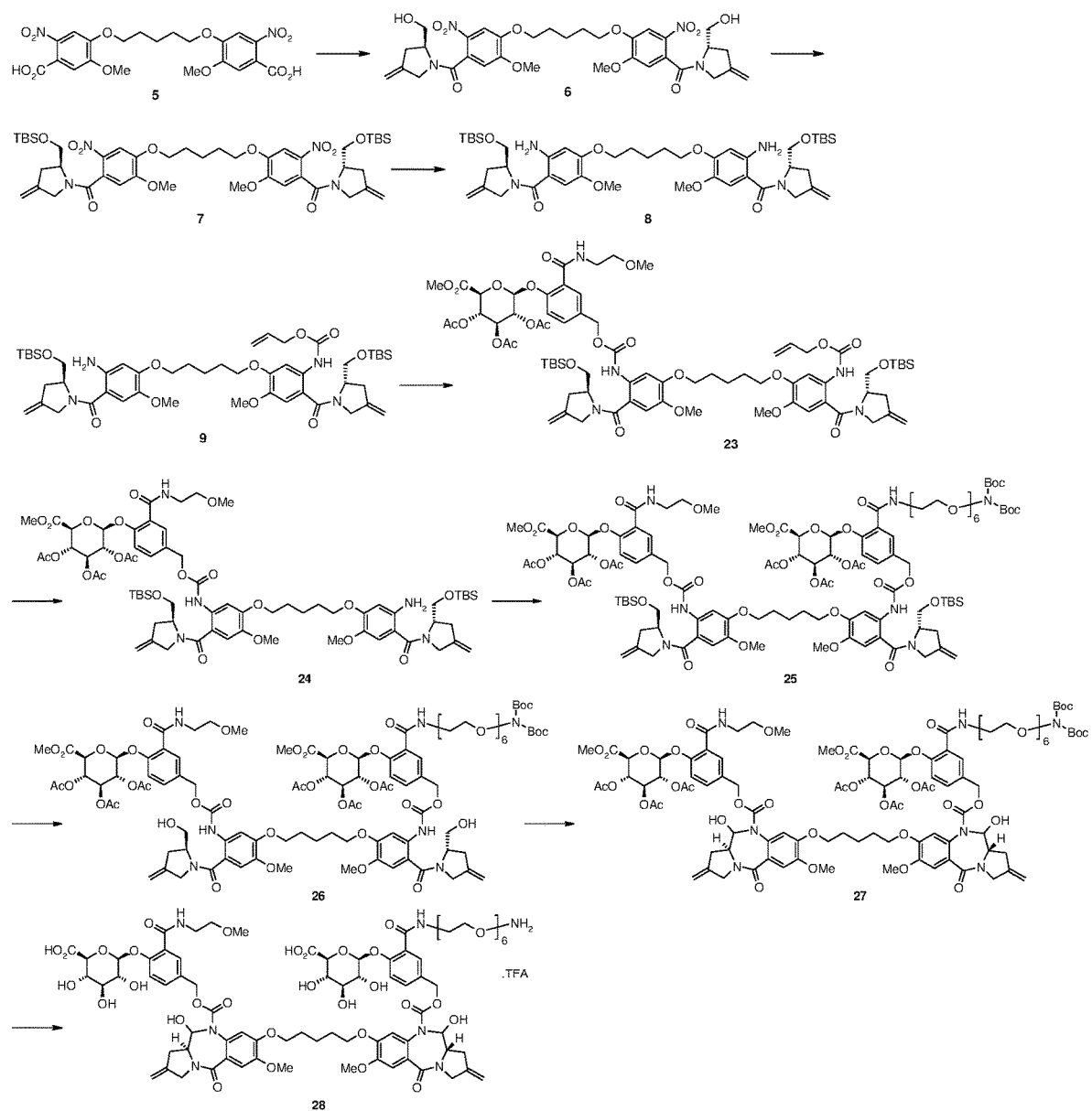

PYRROLOBENZODIAZEPINE DIMER PRODRUG AND LIGAND-LINKER CONJUGATE COMPOUND OF THE SAME

RELATED APPLICATIONS

This application is a continuation of U.S. Ser. No. 16/328,256, now U.S. Pat. No. 11,654,197, filed Feb. 25, 2019, which is a national-stage filing under 35 U.S.C. 371 of International Application PCT/KR2018/003744, filed Mar. 29, 2018, which claims the benefit of priority to Korean Patent Application serial number 10-2018-0036895, filed Mar. 29, 2018, and Korean Patent Application serial number 10-2017-0039841, filed Mar. 29, 2017; the contents of U.S. Ser. No. 16/328,256 and the International Application are fully incorporated by reference in their entirety.

TECHNICAL FIELD

The present invention relates to a pyrrolobenzodiazepine dimer prodrug, a ligand-linker conjugate compound thereof, a composition containing these, and therapeutic use thereof particularly as an anticancer drug.

BACKGROUND ART

Pyrrolobenzodiazepines (PBD) are known as natural substances which are produced by various actinomycetes and exhibit antibiotic or antitumor activity. Pyrrolobenzodiazepines are sequence selective DNA alkylating anticancer drugs which covalently bind to cellular DNA. Pyrrolobenzodiazepines are a DNA-crosslinking agent known to exhibit significantly more potent anticancer activity than systemic chemotherapeutic drugs and can prevent the division of cancer cells without destroying the DNA helix.

Pyrrolobenzodiazepines have the following general structure.

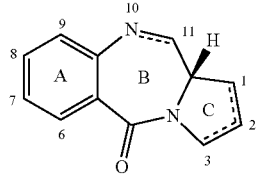

The pyrrolobenzodiazepines differ in the number, type, and position of substituents in the aromatic ring A and pyrrolo ring C, and in the degree of saturation of the ring C. In the ring B, an imine (N—C), carbinolamine (NH—CH(OH)), or carbinolamine methyl ether (NH—CH(OMe)) is present at the N10-C11 position which is the electrophilic center responsible for the alkylation of DNA.

Some pyrrolobenzodiazepine dimers is under Phase 1 clinical trial as a dPBD conjugate for acute myelogenous leukemia (AML) disease as SGN-CD123A developed by Seattle Genetics to treat patients with acute myelocytic leukemia (AML).

It is known that Kolltan Pharmaceuticals and Genentech/Roche are developing antibody-drug conjugates with pyrrolobenzodiazepines as cytotoxic drugs. In addition, Spirogen has been developing a therapeutic agent technology for acute myeloid leukemia based on pyrrolobenzodiazepines.

In this connection, there are a published patent relating to pyrrolobenzodiazepines and conjugates thereof (MedImmune, LLC, Patent Literature 1), a published patent relating to an asymmetric pyrrolobenzodiazepine dimer for the treatment of proliferative disease (MedImmune, LLC, Patent Literature 2), a registered patent relating to a pyrrolobenzodiazepine (MedImmune, LLC, Patent Literature 3), a registered patent relating to a pyrrolobenzodiazepine for the treatment of proliferative disease (MedImmune, LLC, Patent Literature 4), a published patent relating to a pyrrolobenzodiazepine (MedImmune, LLC, Patent Literature 5), a registered patent relating to a pyrrolobenzodiazepine (Spirogen, Patent Literature 6), and the like. These merely disclose that the structure of pyrrolobenzodiazepine compound is modified to enhance the antitumor activity or that the pyrrolobenzodiazepine compound having such a modified structure can be administered in the form of an antibody-drug conjugate to enhance the anticancer activity.

Meanwhile, there are a technology relating to an antibody-drug conjugate having a form to be carbamate-linked to the form of a pyrrolobenzodiazepine dimer, a paper which discloses that a pyrrolobenzodiazepine compound in the form of a monomer exhibits low cytotoxicity and is stable when being changed into the form of a prodrug, and research papers on the preparation and activity of N10-(4-nitrobenzyl)carbamate-protected pyrrolobenzodiazepine prodrug (see Non Patent Literature 7, Non Patent Literature 8, and Non Patent Literature 9).

However, in the case of these technologies, there is a limit in that scale-up is not easy since the yield in the synthesis of pyrrolobenzodiazepine is low and that the problem of poor stability of pyrrolobenzodiazepine in blood after administration is insufficiently solved. Hence, it is required to develop a manufacturing method capable of increasing the yield of pyrrolobenzodiazepines and a technology for preparing a prodrug so as to increase the stability of pyrrolobenzodiazepine in blood after administration and decrease the toxicity thereof after administration.

Meanwhile, antibody-drug conjugates (ADCs) are target-oriented new technologies in which a toxin or drug is bound to an antibody which binds with an antigen and then toxic substances are released inside the cell to lead the cancer cells and the like to death. It is a technology in which the drug is accurately transferred to the target cancer cells while minimally affecting healthy cells and released only under specific conditions, thus the drug exhibits superior efficacy than an antibody therapeutic agent itself, and the risk of side effects can be greatly diminished as compared to conventional anticancer drugs.

The basic structure of such an antibody-drug conjugate is composed of "antibody-linker-low molecular drug (toxin)". Here, the linker is required not only to have a functional role of linking the antibody with the drug but also to stably reach the target cell when circulating in the body and cause the drug to enter the cells, fall off by the antibody-drug dissociation phenomenon (for example, as a result of hydrolysis by enzyme), thus be effective against the target cancer cell. In other words, linkers play a significantly important role in terms of efficacy and safety such as systemic toxicity of antibody-drug conjugates depending on the stability of linker (Discovery Medicine 2010, 10 (53): 329-39).

The inventors of the present invention have developed a linker containing an effective self-immolative group which is more stable in plasma and stable even when circulating in the body and by which the drug can be easily released in cancer cells and exhibit the drug efficacy and obtained a patent for this (Korean Registered Patent No. 1,628,872 and the like).

CITATION LIST

Patent Literature

[Patent Literature 1]
Korean Patent Application Laid-Open No. 2013-0040835 (published on Apr. 24, 2013)
[Patent Literature 2]
Korean Patent Application Laid-Open No. 2011-0075542 (published on Jun. 30, 2011)
[Patent Literature 3]
Korean Registered Patent No. 1,700,460 (registered on Jan. 20, 2017)
[Patent Literature 4]
Korean Registered Patent No. 1,687,054 (registered on Dec. 9, 2016)
[Patent Literature 5]
Korean Patent Application Laid-Open No. 2015-0016245 (published on Feb. 11, 2015)
[Patent Literature 6]
Korean Registered Patent No. 1,059,183 (registered on Aug. 18, 2011)
[Patent Literature 7]
PCT/US2016/063564
[Patent Literature 8]
PCT/US2016/063595
[Patent Literature 9]
Korean Patent Application Laid-Open No. 2014-0035393 (published on Mar. 21, 2014)
[Patent Literature 10]
WO 2017/160569 (published on Sep. 21, 2017)
[Patent Literature 11]
U.S. Pat. No. 8,697,688 (registered on Apr. 15, 2014)
[Patent Literature 12]
U.S. Pat. No. 9,713,647 (registered on Jul. 25, 2017)
[Patent Literature 13]
U.S. Patent Application Laid-Open No. 2015-0283258 (published on Oct. 8, 2015)

Non Patent Literature

[Non Patent Literature 1]
Kemp Gary C et al., Synthesis and in vitro evaluation of SG3227, a pyrrolobenzodiazepine dimer antibody-drug conjugate payload based on sibiromycin, Bioorganic & Medicinal Chemistry Letters Vol. 27 No. 5, 1154-1158 (2017)
[Non Patent Literature 2]
Julia Mantaj et al., From Anthramycin to Pyrrolobenzodiazepine (PBD)-Containing Antibody-Drug Conjugates (ADCs), Angewandte Chemie International Edition Vol. 56 No. 2, 462-488 (2017)
[Non Patent Literature 3]
Giddens Anna C. et al., Analogues of DNA minor groove cross-linking agents incorporating aminoCBI, an amino derivative of the duocarmycins: Synthesis, cytotoxicity, and potential as payloads for antibody-drug conjugates, Bioorganic & Medicinal Chemistry Vol. 24 No. 22, 6075-6081 (2016)
[Non Patent Literature 4]
Hartley, J A, The development of pyrrolobenzodiazepines as antitumour agents, EXPERT OPIN INV DRUG, 20(6) 733-744 (2011)
[Non Patent Literature 5]
Kamal Ahmed et al., Synthesis, anticancer activity and mitochondrial mediated apoptosis inducing ability of 2,5-diaryloxadiazole-pyrrolobenzodiazepine conjugates, Bioorganic & Medicinal Chemistry Vol. 18 No. 18, 6666-6677 (2010)
[Non Patent Literature 6]
Guichard S. M et al., Influence of P-glycoprotein expression on in vitro cytotoxicity and in vivo antitumour activity of the novel pyrrolobenzodiazepine dimer SJG-136, European Journal of Cancer Vol. 41 No. 12, 1811-1818 (2005)
[Non Patent Literature 7]
Zhang, Donglu et al, Linker Immolation Determines Cell Killing Activity of Disulfide-Linked Pyrrolobenzodiazepine Antibody-Drug Conjugates, ACS Medicinal Chemistry Letters, 7(11), 988-993 (2016)
[Non Patent Literature 8]
Masterson, Luke A. et al., Synthesis and biological evaluation of novel pyrrolo[2,1-c][1,4]benzodiazepine prodrugs for use in antibody directed enzyme prodrug therapy, Bioorganic & Medicinal Chemistry Letters, 16(2), 252-256 (2006)
[Non Patent Literature 9]
Sangnou, M. J. et al., Design and synthesis of novel pyrrolobenzodiazepine (PBD) prodrugs for ADEPT and GDEPT, Bioorganic & Medicinal Chemistry Letters, 10(18), 2083-2086 (2000)
[Non Patent Literature 10]
Nature Rev. Cancer 2005, 5(5), pp. 405-12; Nature Chemical Biology, 2010, 17, pp. 498-506; Lane K T, Bees L S, Structural Biology of Protein of Farnesyltransferase and Geranylgeranyltransferase Type I, Journal of Lipid Research, 47, pp. 681-699 (2006); Patrick J. Kasey, Miguel C. Seabra; Protein Prenyltransferases, The Journal of Biological Chemistry, Vol. 271, No. 10, Issue of March 8, pp. 5289-5292 (1996)
[Non Patent Literature 11]
Benjamin P. Duckworth et al, ChemBioChem 2007, 8, 98; Uyen T. T. Nguyen et al, ChemBioChem 2007, 8, 408; Guillermo R. Labadie et al, J. Org. Chem. 2007, 72(24), 9291; James W. Wollack et al, ChemBioChem 2009, 10, 2934
[Non Patent Literature 12]
Iran M. Bell, J. Med. Chem. 2004, 47(8), 1869
[Non Patent Literature 13]
Berge, et al., J. Pharm. Sci., 66, 1-19 (1977)

SUMMARY OF INVENTION

Technical Problem

In the present invention, it is intended to provide a pyrrolobenzodiazepine dimer prodrug having a novel structure capable of enhancing the stability in blood of pyrrolobenzodiazepine, which exhibits poor stability in blood after administration.

In the present invention, it is also intended to provide a drug prodrug-linker-ligand system in which the pyrrolobenzodiazepine dimer prodrug stably reaches the target cells and effectively exhibits the drug efficacy and the toxicity is significantly diminished by combining a linker technology containing a self-immolative group which is more stable in plasma and stable even when circulating in the body and by which the drug can be easily released in cancer cells and exhibit maximized drug efficacy.

Solution to Problem

The present invention relates to a pyrrolobenzodiazepine dimer prodrug or a pharmaceutically acceptable salt or solvate thereof.

More specifically, the present invention provides a pyrrolobenzodiazepine dimer prodrug or a pharmaceutically acceptable salt or solvate thereof, in which any one selected from the group consisting of —C(O)O*, —S(O)O*, —C(O)*, —C(O)NR*, —S(O)$_2$NR*, —P(O)R'NR*, —S(O)NR*, and —PO$_2$NR* is independently attached at each of N10 and N'10 positions of a pyrrolobenzodiazepine dimer, in which

* denotes a portion to which a linker is attached,

R and R' each independently denote H, OH, N$_3$, CN, NO$_2$, SH, NH$_2$, ONH$_2$, NHNH$_2$, halo, substituted or unsubstituted C$_{1-8}$ alkyl, substituted or unsubstituted C$_{3-8}$ cycloalkyl, substituted or unsubstituted C$_{1-8}$ alkoxy, substituted or unsubstituted C$_{1-8}$ alkylthio, substituted or unsubstituted C$_{3-20}$ heteroaryl, substituted or unsubstituted C$_{5-20}$ aryl, or mono- or di-C$_{1-8}$ alkylamino, in which the C$_{1-8}$ alkyl, C$_{3-8}$ cycloalkyl, C$_{1-8}$ alkoxy, C$_{1-8}$ alkylthio, C$_{3-20}$ heteroaryl, and C$_{5-20}$ aryl are substituted with a substituent selected from the group consisting of H, OH, N$_3$, CN, NO$_2$, SH, NH$_2$, ONH$_2$, NNH$_2$, halo, C$_{1-6}$ alkyl, C$_{1-6}$ alkoxy, and C$_{6-12}$ aryl when being substituted.

In an aspect of the present invention, a pyrrolobenzodiazepine dimer prodrug is provided. The pyrrolobenzodiazepine dimer prodrug is required to be converted into an effective drug by an additional reaction at the time of exposure to blood in the case of being administered in a form of the prodrug according to the present invention, and it is thus advantageous as compared to conventional PBD drugs in that the occurrence of side effects which may occur at the time of unexpected decomposition of linker can be prevented in advance, toxicity to normal cells diminishes, and the drug is more stable.

In addition, in the preparation of antibody-drug conjugate, an antibody-drug conjugate prepared by the conventional method has high content of impurities and there is a possibility that the exposed imine group is attacked by nucleophiles and a drug having an unwanted structure is thus formed. However, the antibody-drug conjugate prepared by the method according to the present invention has an advantage of being easily separated since the purity thereof is high and exhibits improved physical properties as compared to the conventional PBD or PBD dimer.

In an aspect of the present invention, in the pyrrolobenzodiazepine dimer prodrug or a pharmaceutically acceptable salt or solvate thereof, the pyrrolobenzodiazepine dimer prodrug has a structure represented by the following Chemical Formula Ia or Ia':

[Chem. Ia]

in which a dotted line represents arbitrary presence of a double bond between C1 and C2 or between C2 and C3, R$_1$ is selected from the group consisting of H, OH, =O, =CH$_2$, CN, R$^m$, OR$^m$, =CH—R$^{m'}$, =C(R$^{m'}$)$_2$, O—SO$_2$—R$^m$, CO$_2$R$^m$, COR$^m$, halo, and dihalo, in which R$^{m'}$ is selected from the group consisting of R$^m$, CO$_2$R$^m$, COR$^m$, CHO, CO$_2$H, and halo, R$^m$ is selected from the group consisting of substituted or unsubstituted C$_{1-12}$ alkyl, substituted or unsubstituted C$_{2-12}$ alkenyl, substituted or unsubstituted C$_{2-12}$ alkynyl, substituted or unsubstituted C$_{5-20}$ aryl, substituted or unsubstituted C$_{5-20}$ heteroaryl, substituted or unsubstituted C$_{3-6}$ cycloalkyl, substituted or unsubstituted 3- to 7-membered heterocyclyl, substituted or unsubstituted 3- to 7-membered heterocycloalkyl, and substituted or unsubstituted 5- to 7-membered heteroaryl, in which when the C$_{1-12}$ alkyl, C$_{1-12}$ alkoxy, C$_{2-12}$ alkenyl, C$_{2-12}$ alkynyl, C$_{5-20}$ aryl, C$_{5-20}$ heteroaryl, C$_{3-6}$ cycloalkyl, 3- to 7-membered heterocyclyl, 3- to 7-membered heterocycloalkyl, or 5- to 7-membered heteroaryl is substituted, respective hydrogen atoms in the C$_{1-12}$ alkyl, C$_{1-12}$ alkoxy, C$_{2-12}$ alkenyl, C$_{2-12}$ alkynyl, C$_{5-20}$ aryl, C$_{5-20}$ heteroaryl, C$_{3-6}$ cycloalkyl, 3- to 7-membered heterocyclyl, 3- to 7-membered heterocycloalkyl, or 5- to 7-membered heteroaryl are each independently substituted with any one or more selected from the group consisting of C$_{1-12}$ alkyl, C$_{2-12}$ alkenyl, C$_{2-12}$ alkynyl, C$_{5-20}$ aryl, C$_{5-20}$ heteroaryl, C$_{3-6}$ cycloalkyl, 3- to 7-membered heterocyclyl, 3- to 7-membered heterocycloalkyl, and 5- to 7-membered heteroaryl;

R$_2$, R$_3$, and R$_5$ are each independently selected from the group consisting of H, R$^m$, OH, OR$^m$, SH, SR$^m$, NH$_2$, NHR$^m$, NR$^m$R$^{m'}$, NO$_2$, Me$_3$Sn, and halo, in which R$^m$ and R$^{m'}$ are as defined above;

R$_4$ is selected from the group consisting of H, R$^m$, OH, OR$^m$, SH, SR$^m$, NH$_2$, NHR$^m$, NR$^m$R$^{m'}$, NO$_2$, Me$_3$Sn, halo, substituted or unsubstituted C$_{1-6}$ alkyl, substituted or unsubstituted C$_{1-6}$ alkoxy, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted 3- to 7-membered heterocycloalkyl, substituted or unsubstituted C$_{5-12}$ aryl, substituted or unsubstituted 5- to 7-membered heteroaryl, —CN, —NCO, —OR'', —OC(O)R'', —OC(O)NR''R''', —OS(O)R'', —OS(O)$_2$R'', —SR'', —S(O)R'', —S(O)$_2$R'', —S(O)NR''R''', —S(O)$_2$NR''R''', —OS(O)NR''R''', —OS(O)$_2$NR''R''', —NR''R''', —NR''C(O)R°, —NR''C(O)OR°, —NR''C(O)NR°R°', —NR''S(O)R°, —NR''S(O)$_2$R°, —NR''S(O)NR°R°', —NR''S(O)$_2$NR°R°', —C(O)R'', —C(O)OR'', and —C(O)NR''R''', in which respective hydrogen atoms in the C$_{1-6}$ alkyl, C$_{1-6}$ alkoxy, C$_{2-6}$ alkenyl, C$_{2-6}$ alkynyl, C$_{3-6}$ cycloalkyl, 3- to 7-membered heterocycloalkyl, C$_{5-12}$ aryl, and 5- to 7-membered heteroaryl may be each independently substituted with the C$_{1-6}$ alkyl, C$_{1-6}$ alkoxy, C$_{2-6}$ alkenyl, C$_{2-6}$ alkynyl, C$_{3-6}$ cycloalkyl, 3- to 7-membered heterocycloalkyl, C$_{5-12}$ aryl, 5- to 7-membered heteroaryl, —OR$^p$, —OC(O)R$^p$, —OC(O)NR$^p$R$^{p'}$, —OS(O)R$^p$, —OS(O)$_2$R$^p$, —SR$^p$, —S(O)R$^p$, —S(O)$_2$R$^p$, —S(O)NR$^p$R$^{p'}$, —S(O)$_2$NR$^p$R$^{p'}$, —OS(O)NR$^p$R$^{p'}$, —OS(O)$_2$NR$^p$R$^{p'}$, —NR$^p$R$^{p'}$, —NR$^p$C(O)R$^q$, —NR$^p$C(O)OR$^q$, —NR$^p$C(O)NR$^q$R$^{q'}$, —NR$^p$S(O)R$^q$, —NR$^p$S(O)$_2$R$^q$, —NR$^p$S(O)NR$^q$R$^{q'}$, —NR$^p$S(O)$_2$NR$^q$R$^{q'}$, —C(O)R$^p$, —C(O)OR$^p$, or —C(O)NR$^p$R$^p$ when the C$_{1-6}$ alkyl, C$_{1-6}$ alkoxy, C$_{2-6}$ alkenyl, C$_{2-6}$ alkynyl, C$_{3-6}$ cycloalkyl, 3- to 7-membered heterocycloalkyl, C$_{5-12}$ aryl, and 5- to 7-membered heteroaryl are substituted, in which R'', R°, R$^p$, and R$^q$ are each independently selected from the group consisting of H, C$_{1-7}$ alkyl, C$_{2-7}$ alkenyl, C$_{2-7}$ alkynyl, $C_{3-13}$ cycloalkyl, 3- to 7-membered heterocycloalkyl, $C_{6-10}$ aryl, and 5- to 7-membered heteroaryl;

any one selected from the group consisting of —C(O)O*, —S(O)O*, —C(O)*, —C(O)NR*, —S(O)$_2$NR*, —P(O)R'NR*, —S(O)NR*, and —PO$_2$NR* is independently attached to each of X and X', in which

* denotes a portion to which a linker is attached,

R and R' each independently denote H, OH, N$_3$, CN, NO$_2$, SH, NH$_2$, ONH$_2$, NHNH$_2$, halo, substituted or unsubstituted $C_{1-8}$ alkyl, substituted or unsubstituted $C_{3-8}$ cycloalkyl, substituted or unsubstituted $C_{1-8}$ alkoxy, substituted or unsubstituted $C_{1-8}$ alkylthio, substituted or unsubstituted $C_{3-20}$ heteroaryl, substituted or unsubstituted $C_{5-20}$ aryl, or mono- or di-$C_{1-8}$ alkylamino, in which the $C_{1-8}$ alkyl, $C_{3-8}$ cycloalkyl, $C_{1-8}$ alkoxy, $C_{1-8}$ alkylthio, $C_{3-20}$ heteroaryl, and $C_{5-20}$ aryl are substituted with a substituent selected from the group consisting of H, OH, N$_3$, CN, NO$_2$, SH, NH$_2$, ONH$_2$, NNH$_2$, halo, $C_{1-6}$ alkyl, $C_{1-6}$ alkoxy, and $C_{6-12}$ aryl when being substituted;

Y and Y' are each independently selected from the group consisting of O, S, and N(H);

$R_6$ denotes a substituted or unsubstituted saturated or unsaturated $C_{3-12}$ hydrocarbon chain, in which the chain may be interrupted by one or more heteroatoms, NMe, or a substituted or unsubstituted aromatic ring, the chain or aromatic ring may be substituted with —NH, —NR'''', —NHC(O)R''', —NHC(O)CH$_2$—[OCH$_2$CH$_2$]$_n$—R, or —[CH$_2$CH$_2$O]$_n$—R at any one or more positions of hydrogen atoms on the chain or aromatic ring or unsubstituted, in which R''' and R are each as defined for R''' and R above, and n is an integer from 1 to 12; and $R_7$ denotes H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted 3- to 7-membered heterocycloalkyl, substituted or unsubstituted $C_{6-10}$ aryl, substituted or unsubstituted 5- to 7-membered heteroaryl, —OR$^r$, —OC(O)R$^r$, —OC(O)NR'R$^{r'}$, —OS(O)R$^r$, —OS(O)$_2$R$^r$, —SR$^r$, —S(O)R$^r$, —S(O)$_2$R$^r$, —S(O)NR'R$^{r'}$, —S(O)$_2$NR'R$^{r'}$, —OS(O)NR'R$^{r'}$, —OS(O)$_2$NR'R$^{r'}$, —NR'R$^{r'}$, —NR'C(O)R$^s$, —NR'C(O)OR$^s$, —NR'C(O)NR$^s$R$^{s'}$, —NR'S(O)R$^s$, —NR'S(O)$_2$R$^s$, —NR'S(O)NR$^s$R$^{s'}$, —NR'S(O)$_2$NR'R$^s$, —C(O)R$^r$, —C(O)OR$^s$, or —C(O)NR'R$^{r'}$, in which respective hydrogen atoms in the $C_{1-6}$ alkyl, $C_{2-6}$ alkenyl, $C_{2-6}$ alkynyl, $C_{3-6}$ cycloalkyl, 3- to 7-membered heterocycloalkyl, $C_6$-10 aryl, and 5- to 7-membered heteroaryl are each independently substituted with $C_{1-6}$ alkyl, $C_{2-6}$ alkenyl, $C_{2-6}$ alkynyl, $C_{3-6}$ cycloalkyl, 3- to 7-membered heterocycloalkyl, $C_{6-10}$ aryl, 5- to 7-membered heteroaryl, —OR$^t$, —OC(O)R$^t$, —OC(O)NR'R$^{t'}$, —OS(O)R$^t$, —OS(O)$_2$R$^t$, —SR$^t$, —S(O)R$^t$, —S(O)$_2$R$^t$, —S(O)NR'R$^{t'}$, —S(O)$_2$NR'R$^{t'}$, —OS(O)NR'R$^{t'}$, —OS(O)$_2$NR'R$^{t'}$, —NR'R$^{t'}$, —NR'C(O)R$^u$, —NR'C(O)OR$^u$, —NR'C(O)NR$^u$R$^{u'}$, —NR'S(O)R$^u$, —NR'S(O)$_2$R$^u$, —NR'S(O)NR$^u$R$^{u'}$, —NR'S(O)$_2$NR$^u$R$^{u'}$, —C(O)R$^t$, —C(O)OR$^t$, or —C(O)NR'R$^{t'}$ when the $C_{1-6}$ alkyl, $C_{2-6}$ alkenyl, $C_{2-6}$ alkynyl, $C_{3-6}$ cycloalkyl, 3- to 7-membered heterocycloalkyl, $C_{6-10}$ aryl, and 5- to 7-membered heteroaryl are substituted, in which $R^r$, $R^{r'}$, $R^s$, $R^{s'}$, $R^t$, $R^{t'}$, $R^u$, and $R^{u'}$ are each independently selected from the group consisting of H, $C_{1-7}$ alkyl, $C_{2-7}$ alkenyl, $C_{2-7}$ alkynyl, $C_{3-13}$ cycloalkyl, 3- to 7-membered heterocycloalkyl, $C_{5-10}$ aryl, and 5- to 7-membered heteroaryl;

[Chem. Ia']

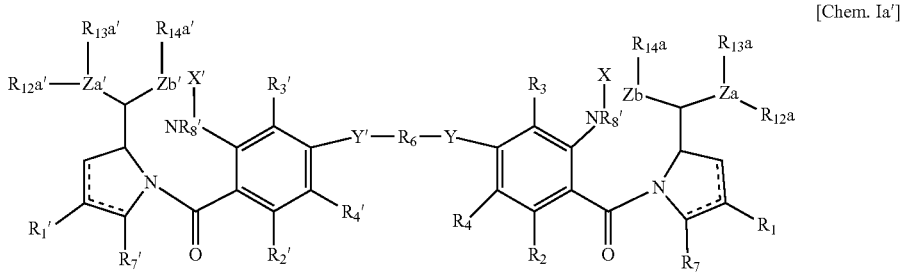

in which $R_1$, $R_2$, $R_3$, $R_4$, $R_6$, $R_7$, and X are as defined in Chemical Formula Ia above, $R_8$ is selected from the group consisting of H, halo, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ heteroalkyl, substituted or unsubstituted 3- to 7-membered heterocycloalkyl, substituted or unsubstituted $C_{5-10}$ aryl, substituted or unsubstituted 5- to 7-membered heteroaryl, —CN, —NO$_2$, —NCO, —OH, OR''', —OC(O)R''', —OC(O)NR'''R''', —OS(O)R''', —OS(O)$_2$R''', —SR''', —S(O)R''', —S(O)$_2$R''', —S(O)NR'''R'''', —S(O)$_2$NR'''R'''', —OS(O)NR'''R'''', —OS(O)$_2$NR'''R'''', —NR'''R'''', —NR'''C(O)R'', —NR'''C(O)OR'', —NR'''C(O)NR''R'''', —NR'''S(O)R'', —NR'''S(O)$_2$R'', —NR'''S(O)NR''R'''', —NR'''S(O)$_2$NR''R'''', —C(O)R''', —C(O)OR''', and —C(O)NR'''R''', in which respective hydrogen atoms in the $C_{1-6}$ alkyl, $C_{2-6}$ alkenyl, $C_{2-6}$ alkynyl, $C_{3-6}$ heteroalkyl, 3- to 7-membered heterocycloalkyl, $C_{5-10}$ aryl, or 5- to 7-membered heteroaryl are each independently substituted with $C_{1-6}$ alkyl, $C_{2-6}$ alkenyl, $C_2$-6 alkynyl, $C_{3-6}$ heteroalkyl, 3- to 7-membered heterocycloalkyl, $C_{5-10}$ aryl, 5- to 7-membered heteroaryl, —OR''', —OC(O)R''', —OC(O)NR'''R''', —OS(O)R''', —OS(O)$_2$R''', —SR''', —S(O)R''', —S(O)$_2$R''', —S(O)NR'''R'''', —S(O)$_2$NR'''R'''', —OS(O)NR'''R'''', —OS(O)$_2$NR'''R'''', —NR'''R''', —NR'''C(O)R'', —NR'''C(O)OR'', —NR'''C(O)NR''R'''', —NR'''S(O)R'', —NR'''S(O)$_2$R'', —NR'''S(O)NR''R'''', —NR'''S(O)$_2$NR''R'''', —C(O)R''', —C(O)OR''', or —C(O)NR'''R''' when the $C_{1-6}$ alkyl, $C_{2-6}$ alkenyl, $C_{2-6}$ alkynyl, $C_{3-6}$ heteroalkyl, 3- to 7-membered heterocycloalkyl, $C_{5-10}$ aryl, or 5- to 7-membered heteroaryl is substituted, in which $R^m$, $R^{m'}$, $R^n$, and $R^{n'}$ are as defined in Chemical Formula Ia above, $Z_a$ and $Z_b$ each independently denote O, N, or S, $R^{12a}$, $R^{13a}$, and $R^{14a}$ each independently denote H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted 3- to 7-membered heterocycloalkyl, substituted or unsubstituted $C_{5-10}$ aryl, substituted or unsubstituted 5- to 7-membered heteroaryl, —C(O)$R^{15a}$, —C(O)O$R^{15a}$, or —C(O)NR$^{15a}$R$^{15a'}$, in which $R^{15a}$ and $R^{15a'}$ are as defined for $R^m$, respective hydrogen atoms in the $C_{1-6}$ alkyl, $C_{2-6}$ alkenyl, $C_{2-6}$ alkynyl, $C_{3-6}$ cycloalkyl, 3- to 7-membered heterocycloalkyl, $C_{5-10}$ aryl, and 5- to 7-membered heteroaryl are each independently substituted with $C_{1-6}$ alkyl, $C_{2-6}$ alkenyl, $C_{2-6}$ alkynyl, $C_{3-6}$ cycloalkyl, 3- to 7-membered heterocyclyl, 3- to 7-membered heterocycloalkyl, $C_{5-10}$ aryl, 5- to 7-membered heteroaryl, —OR$^o$, —OC(O)R$^o$, —OC(O)NR$^o$R$^{o'}$, —OS(O)R$^o$, —OS(O)$_2$R$^o$, —SR$^o$, —S(O)R$^o$, —S(O)$_2$R$^o$, —S(O)NR$^o$R$^{o'}$, —S(O)$_2$NR$^o$R$^{o'}$, —OS(O)NR$^o$R$^{o'}$, —OS(O)$_2$NR$^o$R$^{o'}$, —NR$^o$R$^{o'}$, —NR$^o$C(O)R$^p$, —NR$^o$C(O)OR$^p$, —NR$^o$C(O)NR$^p$R$^{p'}$, —NR$^o$S(O)R$^p$, —NR$^o$S(O)$_2$R$^p$, —NR$^o$S(O)NR$^p$R$^{p'}$, —NR$^o$S(O)$_2$NR$^p$R$^{p'}$, —C(O)R$^o$, —C(O)OR$^o$, or —C(O)NR$^o$R$^{o'}$ when the $C_{1-6}$ alkyl, $C_{2-6}$ alkenyl, $C_{2-6}$ alkynyl, $C_{3-6}$ cycloalkyl, 3- to 7-membered heterocycloalkyl, $C_{5-10}$ aryl, and 5- to 7-membered heteroaryl are substituted, in which $R^{13a}$ and $R^{14a}$ may bind with an atom to which these are attached to form a 3- to 7-membered heterocyclyl or a 3- to 7-membered heterocycloalkyl, or $R^{13a}$ and $R^{14a}$ may bind with an atom to which these are attached to form a 3- to 7-membered heteroaryl, in which respective hydrogen atoms present in 3- to 7-membered heterocyclyl, 3- to 7-membered heterocycloalkyl, or 3- to 7-membered heteroaryl are each independently substituted with $C_{1-6}$ alkyl, $C_{2-6}$ alkenyl, $C_{2-6}$ alkynyl, $C_{3-6}$ cycloalkyl, 3- to 7-membered heterocycloalkyl, $C_{5-10}$ aryl, 5- to 7-membered heteroaryl, —OR$^o$, —OC(O)R$^o$, —OC(O)NR$^o$R$^{o'}$, —OS(O)R$^o$, —OS(O)$_2$R$^o$, —SR$^o$, —S(O)R$^o$, —S(O)$_2$R$^o$, —S(O)NR$^o$R$^{o'}$, —S(O)$_2$NR$^o$R$^{o'}$, —OS(O)NR—R$^{o'}$, —OS(O)$_2$NR$^o$R$^{o'}$, —NR$^o$R$^{o'}$, —NR$^o$C(O)R$^p$, —NR$^o$C(O)OR$^p$, —NR$^o$C(O)NR$^p$R$^{p'}$, —NR$^o$S(O)R$^p$, —NR$^o$S(O)$_2$R$^p$, —NR$^o$S(O)NR$^p$R$^{p'}$, —NR$^o$S(O)$_2$NR$^p$R$^{p'}$, —C(O)R$^o$, —C(O)OR$^o$, or —C(O)NR$^o$R$^{o'}$; in which $R^n$, $R^{n'}$, $R^o$, $R^{o'}$, $R^p$, and $R^{p'}$ are each independently selected from the group consisting of H, $C_{1-7}$ alkyl, $C_{2-7}$ alkenyl, $C_{2-7}$ alkynyl, $C_{3-13}$ cycloalkyl, 3- to 7-membered heterocycloalkyl, $C_{5-10}$ aryl, and 5- to 7-membered heteroaryl; and $R_1'$, $R_2'$, $R_3'$, $R_4'$, $R_5'$, $R_7'$, and $R_8'$ are as defined for $R_1$, $R_2$, $R_3$, $R_4$, $R_5$, $R_7$, and $R_8$, respectively.

In an aspect of the present invention, a dotted line represents the presence of a double bond between C2 and C3.

In an aspect of the present invention, $R_1$ is selected from the group consisting of substituted or unsubstituted $C_{1-6}$ alkyl, substituted or unsubstituted $C_{2-6}$ alkenyl, substituted or unsubstituted $C_{5-7}$ aryl, and substituted or unsubstituted $C_3$-6 heteroaryl.

In an aspect of the present invention, $R_2$, $R_3$, and $R_5$ each independently denote H or OH.

In an aspect of the present invention, $R_4$ denotes $C_{1-6}$ alkoxy and more specifically $R_4$ denotes methoxy, ethoxy, or butoxy.

In an aspect of the present invention, X and X' are each independently selected from the group consisting of —C(O)O*, —C(O)*, and —C(O)NR*, in which Rs each independently denote H, OH, $N_3$, CN, $NO_2$, SH, $NH_2$, $ONH_2$, $NNH_2$, halo, substituted or unsubstituted $C_{1-8}$ alkyl, or substituted or unsubstituted $C_{1-8}$ alkoxy, in which $C_{1-8}$ alkyl or $C_{1-8}$ alkoxy is substituted with H, OH, $N_3$, CN, $NO_2$, SH, $NH_2$, $ONH_2$, $NNH_2$, or halo when being substituted.

In an aspect of the present invention, Y and Y' denote O.

In an aspect of the present invention, $R_6$ denotes a substituted or unsubstituted saturated or unsaturated $C_{3-8}$ hydrocarbon chain, in which the chain may be interrupted by one or more heteroatoms or a substituted or unsubstituted aromatic ring, in which the heteroatom is O, S, or N(H) and the aromatic ring is benzene, pyridine, imidazole, or pyrazole, and the chain or aromatic ring may be substituted with —NHC(O)CH$_2$—[OCH$_2$CH$_2$]$_n$—R or —[CH$_2$CH$_2$O]$_n$—R at any one or more positions of hydrogen atoms on the chain or aromatic ring, in which R is as defined for R above, and n is an integer from 1 to 6.

In an aspect of the present invention, there is provided a pyrrolobenzodiazepine dimer prodrug selected from the following or a pharmaceutically acceptable salt or solvate thereof:

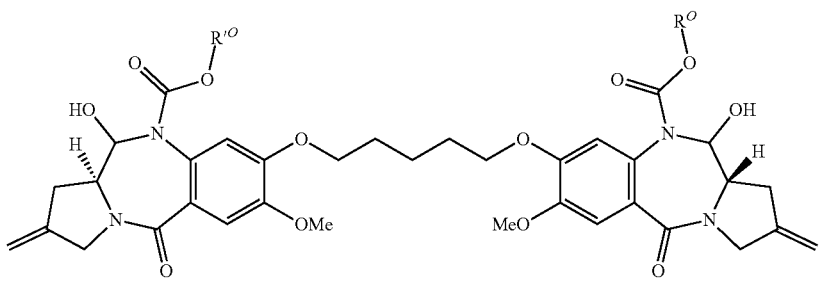

—S(O)$_2$NR$^o$R$^{o'}$, —OS(O)NR—R$^{o'}$, —OS(O)$_2$NR$^o$R$^{o'}$, —NR$^o$R$^{o'}$, —NR$^o$C(O)R$^p$, —NR$^o$C(O)OR$^p$, —NR$^o$C(O)NR$^p$R$^{p'}$, —NR$^o$S(O)R$^p$, —NR$^o$S(O)$_2$R$^p$, in which $R^O$ and $R'^O$ each denote an oxygen protecting group and may be the same as or different from each other.

In the present invention, compounds having the following structures are excluded:

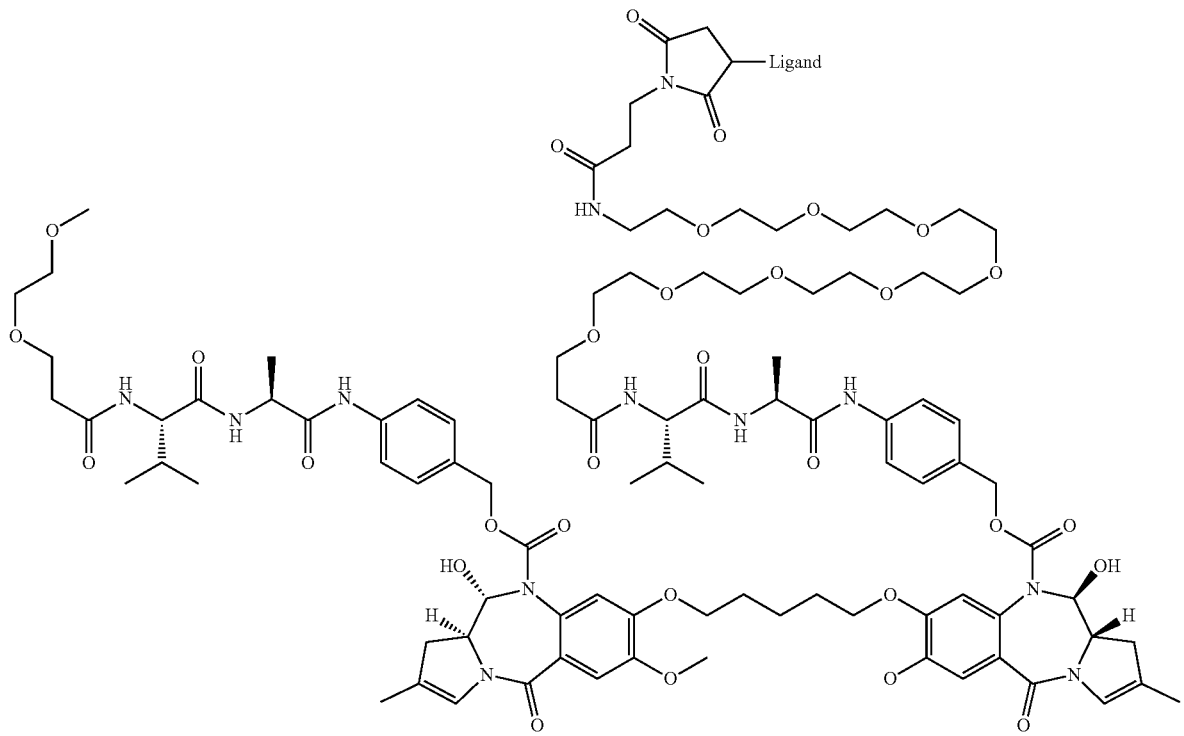

The present invention also provides a conjugate having a structure represented by the following Chemical Formula IIa or a pharmaceutically acceptable salt or solvate thereof:

Ligand-(L-D)$_n$   [Chem. IIa]

in which,
Ligand denotes a ligand,
L denotes a linker,
D denotes a pyrrolobenzodiazepine dimer prodrug described above, in which the linker is bound with D at a N10 position, N10' position, or N10 and N10' positions of D described above; or via X, X', or X and X' of D described above, and
n is an integer from 1 to 20.

In an aspect of the present invention, the linker is bound with D at N10 and N10' positions of D described above or via X and X' of D described above 0.

In an aspect of the present invention, n is an integer from 1 to 10.

The present invention also provides a pyrrolobenzodiazepine dimer prodrug-linker compound having a structure represented by the following Chemical Formula IIb or IIb' or a pharmaceutically acceptable salt or solvate thereof:

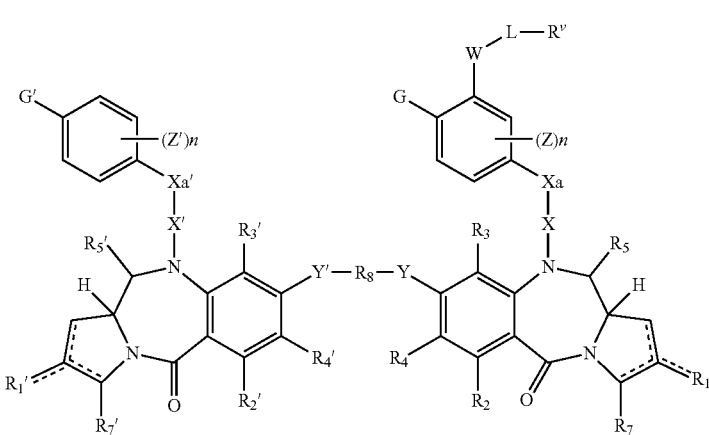

[Chem. IIb]

-continued

[Chem. IIb']

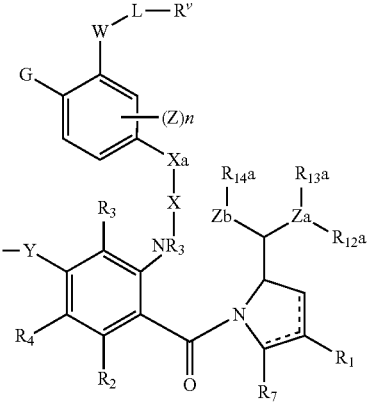

in which
a dotted line, $R_1$, $R_2$, $R_3$, $R_4$, $R_5$, $R_6$, $R_7$, X, Y, $R_1'$, $R_2'$, $R_3'$, $R_4'$, $R_5'$, $R_7'$, X', Y', $R_8$, $Z_a$, $Z_b$, $R_{12a}$, $R_{13a}$, $R_{14a}$, $R_8'$, $Z_a'$, $Z_b'$, $R_{12a}'$, $R_{13a}'$, and $R_{14a}'$ are as defined for the compounds represented by Chemical Formula Ia and Chemical Formula Ia', respectively, Xa and Xa' each independently denote a bond or substituted or unsubstituted $C_{1-6}$ alkylene, in which $C_{1-6}$ alkylene is substituted with hydrogen, $C_{1-8}$ alkyl, or $C_{3-8}$ cycloalkyl when being substituted, G and G' denote a glucuronide group, a galactoside group, or any derivative of the glucuronide group or galactoside group, Z and Z' are each independently selected from the group consisting of H, $C_{1-8}$ alkyl, halo, $NO_2$, CN,

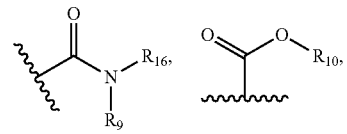

and $-(CH_2)_m-OCH_3$, in which
$R_9$, $R_{10}$, and $R_{16}$ are each independently selected from the group consisting of H, $C_{1-8}$ alkyl, $C_{2-6}$ alkenyl, $C_{1-6}$ alkoxy, and methyloxyalkyl, and m is from 0 to 12, n is an integer from 1 to 3, and respective Zs may be the same as or different from one another when n is an integer of 2 or more, W denotes $-C(O)-$, $-C(O)NR''-$, $-C(O)O-$, $-S(O)_2NR''-$, $-P(O)R'''NR''-$, $-S(O)NR''-$, or $-PO_2NR''$, in which R'' and R''' each independently denote H, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl, or $C_{6-20}$ aryl, L denotes one or more units selected from the group consisting of a branching unit, a connection unit, and a binding unit or a combination of these units, in which
the connection unit connects W with a binding unit, W with a branching unit, a branching unit with another branching unit, or a branching unit with a binding unit and the branching unit connects a connection unit with W or the connection unit with another connection unit,
the branching unit is a $C_{2-100}$ alkenyl (in which a carbon atom of the alkenyl may be substituted with one or more heteroatoms selected from the group consisting of N, O, and S and the alkenyl may be further substituted with one or more $C_{1-20}$ alkyls), a hydrophilic amino acid, $-C(O)-$, $-C(O)NR''''-$, $C(O)O-$, $-(CH_2)_s-NHC(O)-(CH_2)_t-$, $-(CH_2)_u-C(O)NH-(CH_2)_v-$, $-(CH_2)_s-NHC(O)-(CH_2)_t-C(O)-$, $-(CH_2)_u-C(O)NH-(CH_2)_v-C(O)-$, $-S(O)_2NR''''-$, $-P(O)R'''''NR''''-$, $-S(O)NR''''-$, or $-PO_2NR''''-$ (in which R'''' and R''''' each independently denote H, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl, or $C_{5-20}$ aryl and s, t, u, and v each independently denote an integer from 0 to 10), the connection unit is $-(CH_2)_r(V(CH_2)_p)_q-$, in which r is an integer from 0 to 10, p is an integer from 0 to 12, q is an integer from 1 to 20, and V denotes a single bond, $-O-$, or $S-$,
the binding unit is

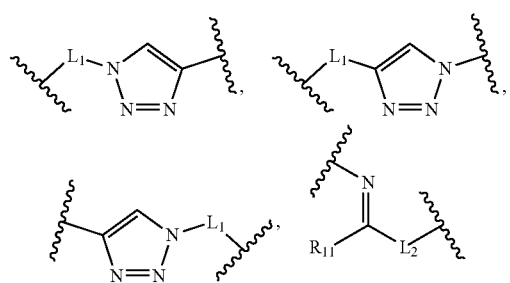

in which $L_1$ denotes a single bond or $C_{2-30}$ alkenyl, $R_{11}$ denotes H or $C_{1-10}$ alkyl, and $L_2$ denotes $C_{2-30}$ alkenyl;
$R^v$ denotes $-NH_2$, $N_3$, substituted or unsubstituted $C_{1-12}$ alkyl, $C_{1-12}$ alkynyl, $C_{1-3}$ alkoxy, substituted or unsubstituted $C_{3-20}$ heteroaryl, $C_{3-20}$ heterocyclyl, or substituted or unsubstituted $C_{5-20}$ aryl, in which
one or more hydrogen atoms present in the $C_{3-20}$ heteroaryl, $C_{3-20}$ heterocyclyl, or $C_{5-20}$ aryl are each independently substituted with OH, =O, halo, $C_{1-6}$ alkyl, $C_{1-6}$ alkoxy, $C_{2-6}$ alkenyloxy, carboxy, $C_{1-6}$ alkoxycarbonyl, $C_{1-6}$ alkylcarbonyl, formyl, $C_{3-8}$ aryl, $C_{5-12}$ aryloxy, $C_{5-12}$ arylcarbonyl, or $C_{3-6}$ heteroaryl when the $C_{1-12}$ alkyl, $C_{3-20}$ heteroaryl, $C_{3-20}$ heterocyclyl, or $C_{5-20}$ aryl is substituted.

In an aspect of the present invention, Xa and Xa' each independently denote a bond or $C_{1-3}$ alkyl.

In an aspect of the present invention, Z and Z' are each independently selected from the group consisting of H,

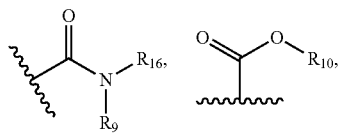

and —(CH$_2$)$_m$—OCH$_3$, in which

R$_9$, R$_{10}$, and R$_{16}$ are each independently selected from the group consisting of H, C$_{1-3}$ alkyl, C$_{1-3}$ alkoxy and methyloxyalkyl and m is from 1 to 6.

In an aspect of the present invention, W denotes —C(O)—, —C(O)NR'''—, or —C(O)O—, in which R''' denotes H or C$_{1-8}$ alkyl, L denotes one or more units selected from the group consisting of a branching unit, a connection unit, and a binding unit or a combination of these units, in which the connection unit connects W with a binding unit, W with a branching unit, a branching unit with another branching unit, or a branching unit with a binding unit and the branching unit connects a connection unit with W or the connection unit with another connection unit, the binding unit is

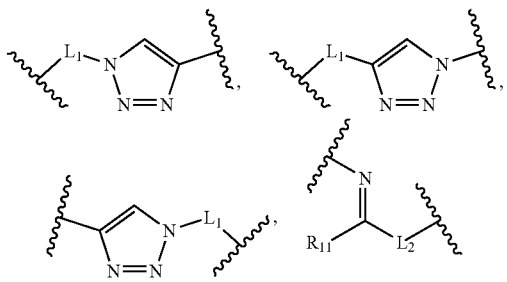

in which L$_1$ denotes a single bond or C$_{2-8}$ alkenyl, R$_{11}$ denotes H or C$_{1-6}$ alkyl, and L$_2$ denotes C$_{2-8}$ alkenyl; and the connection unit is —(CH$_2$)$_r$(V(CH$_2$)$_p$)$_q$—, in which r is an integer from 0 to 8, p is an integer from 1 to 12, q is an integer from 1 to 10, and V denotes a single bond or —O—.

In an aspect of the present invention, G and G' each may independently denote a β-glucuronide group, a galactoside group, or any derivative thereof.

In an aspect of the present invention, there is provided a pyrrolobenzodiazepine dimer prodrug-linker compound having a structure represented by the following Chemical Formula IIc or a pharmaceutically acceptable salt or solvate thereof.

[Chem. IIc]

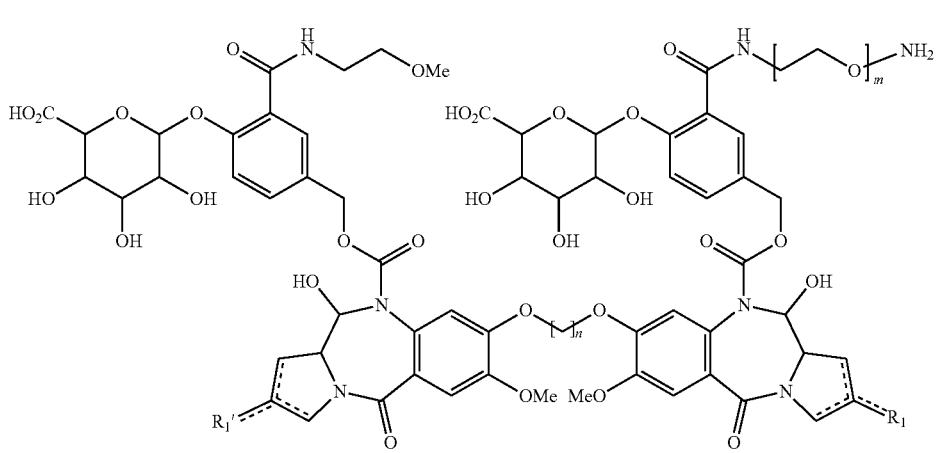

the branching unit is a C$_{2-8}$ alkenyl (in which a carbon atom of the alkenyl may be substituted with one or more heteroatoms selected from the group consisting of N, O, and S and the alkenyl may be further substituted with one or more C$_{1-6}$ alkyls), a hydrophilic amino acid, —C(O)—, —C(O)NR''''—, —C(O)—, —(CH$_2$)$_s$—NHC(O)—(CH$_2$)$_t$—, —(CH$_2$)$_u$—C(O)NH—(CH$_2$)$_2$—, —(CH$_2$)$_s$—NHC(O)—(CH$_2$)$_t$—C(O)—, or —(CH$_2$)$_u$—C(O)NH—(CH$_2$)$_v$—C(O)— (in which R'''' denotes H, C$_{1-8}$ alkyl, C$_{3-8}$ cycloalkyl, C$_{1-8}$ alkoxy, C$_{1-8}$ alkylthio, mono- or di-C$_{1-s}$ alkylamino, C$_3$-20 heteroaryl, or C$_{5-20}$ aryl and s, t, u, and v each independently denote an integer from 0 to 5), the connection unit is —(CH$_2$)$_r$(V(CH$_2$)$_p$)$_q$—, in which r is an integer from 0 to 10, p is an integer from 0 to 12, q is an integer from 1 to 20, and V denotes a single bond or —O—, in which a dotted line represents arbitrary presence of a double bond between C1 and C2 or between C2 and C3, R$_1$ is selected from the group consisting of methyl, ethyl, methylene, methoxy, and substituted or unsubstituted phenyl, in which phenyl is substituted with a substituent selected from the group consisting of H, OH, halo, C$_{1-6}$ alkyl, C$_{1-6}$ alkoxy, and C$_{6-12}$ aryl when being substituted, m is an integer from 1 to 10, and n is an integer from 1 to 10.

In an aspect of the present invention, R$_1$ in Chemical Formula IIc above may denote methyl, methylene; or phenyl substituted with a substituent selected from the group consisting of H, OH, halo, C$_{1-6}$ alkyl, and C$_{1-6}$ alkoxy or unsubstituted.

In an aspect of the present invention, m in Chemical Formula IIc above may be an integer from 2 to 8, specifically an integer from 3 to 7, and more specifically an integer from 4 to 6.

In an aspect of the present invention, n in Chemical Formula IIc above may be an integer from 2 to 8, specifically an integer from 3 to 7, and more specifically an integer from 4 to 6.

The present invention also provides a pyrrolobenzodiazepine dimer prodrug-linker compound having the following chemical structures or a pharmaceutically acceptable salt or solvate thereof. However, the following pyrrolobenzodiazepine dimer prodrug-linker compounds are illustrative and those skilled in the art can prepare and use a variety of pyrrolobenzodiazepine dimer-linker compounds within the scope described above:

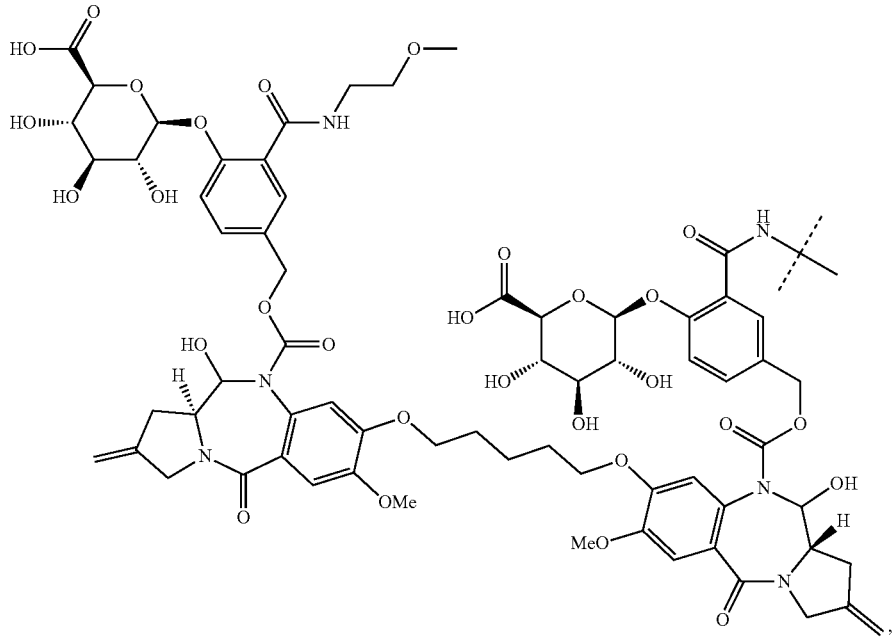

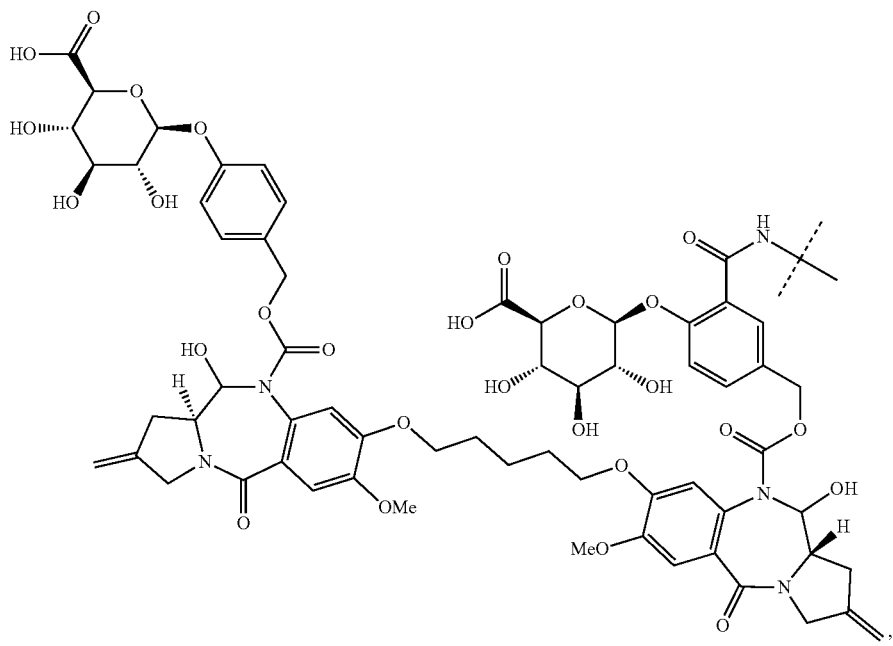

-continued
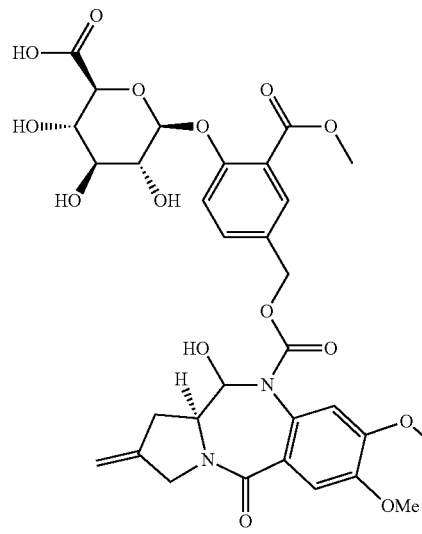
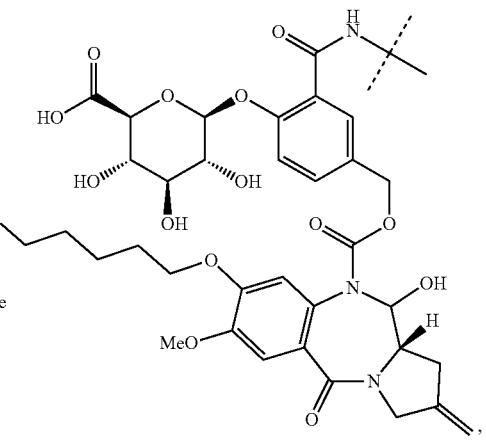
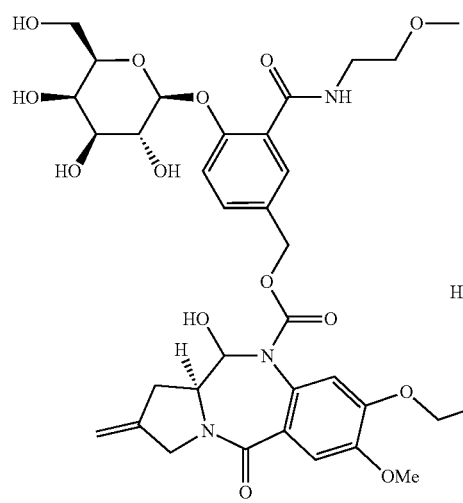
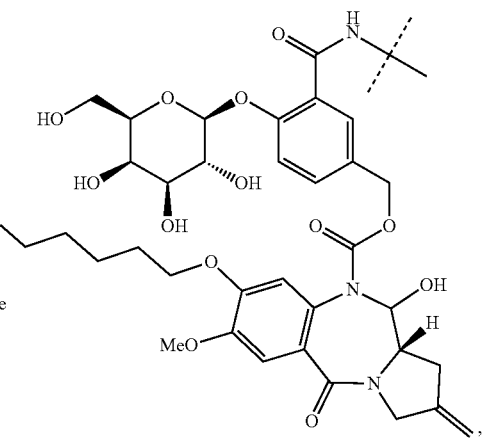

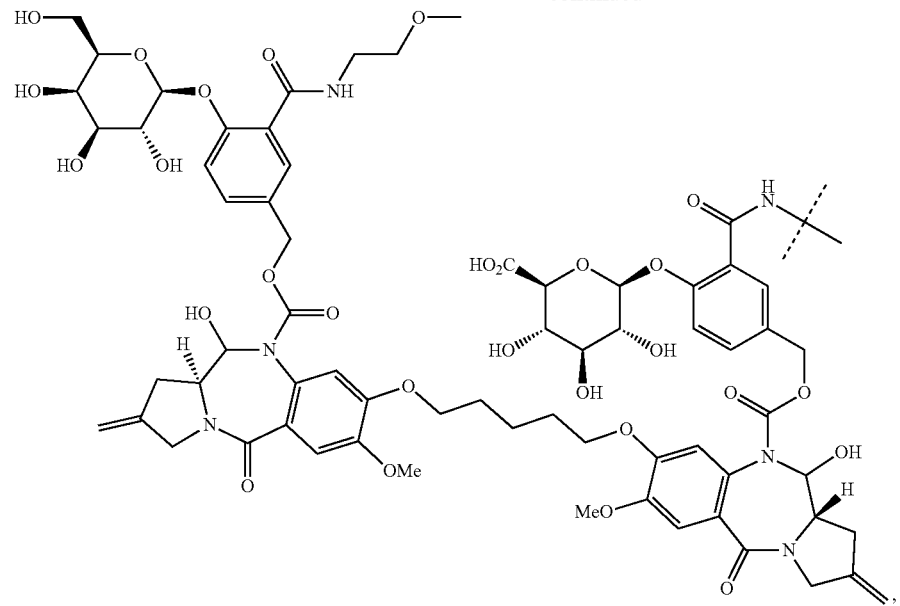
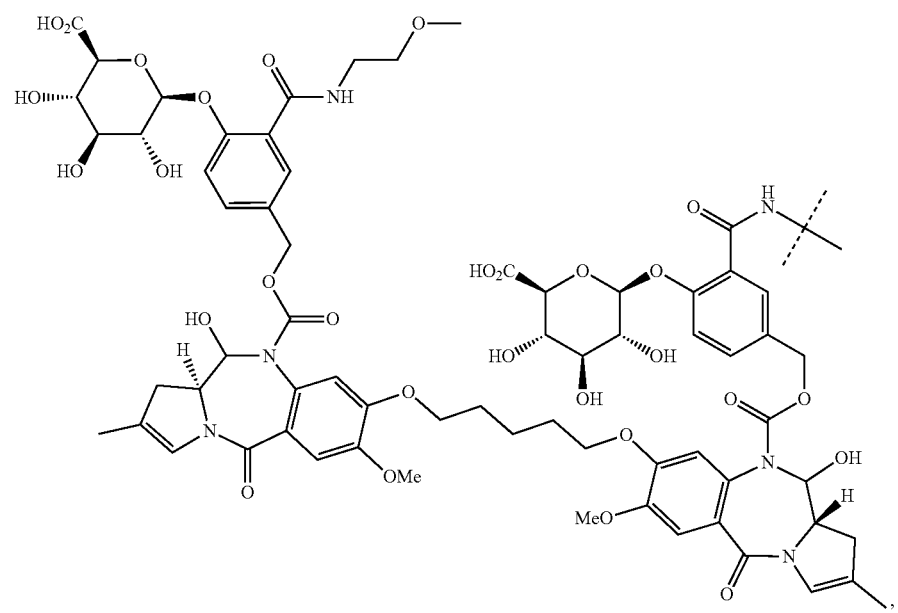

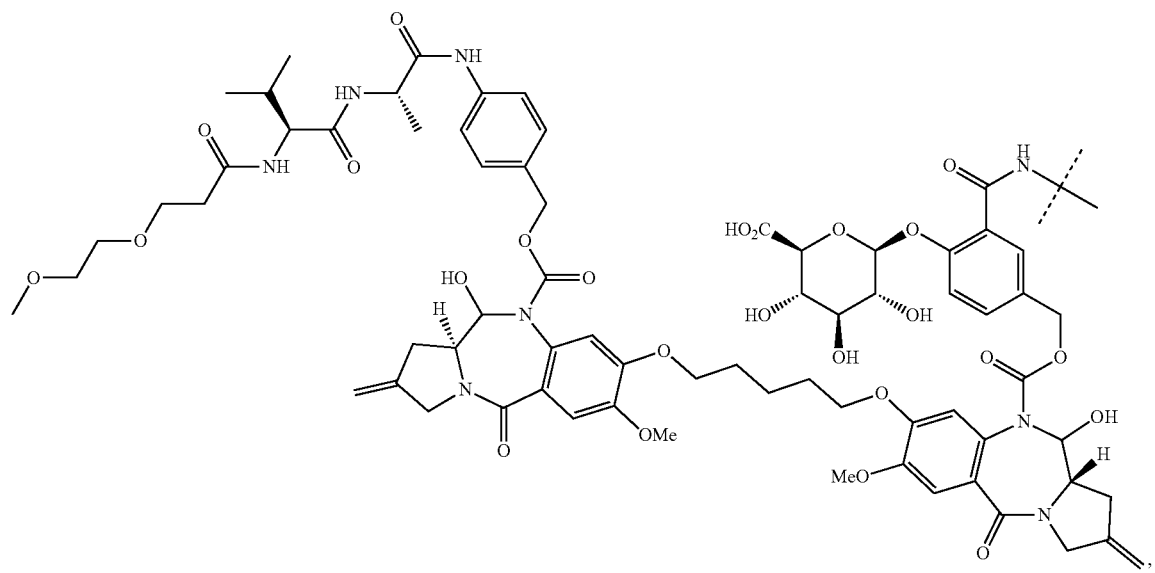
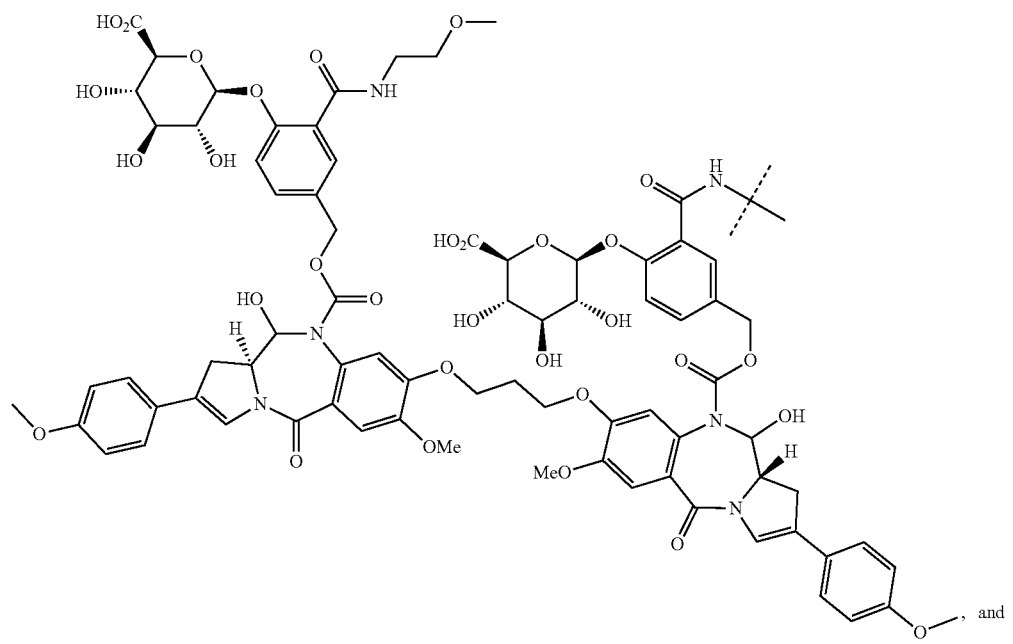
, and

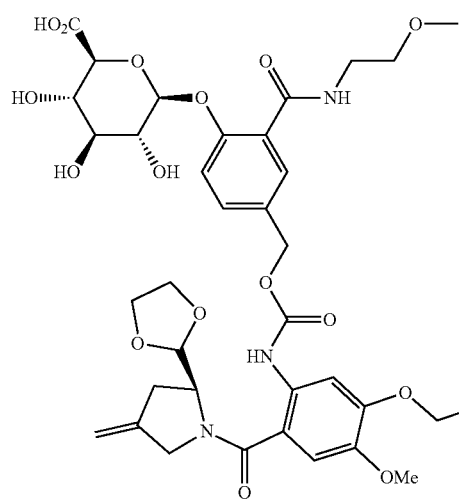
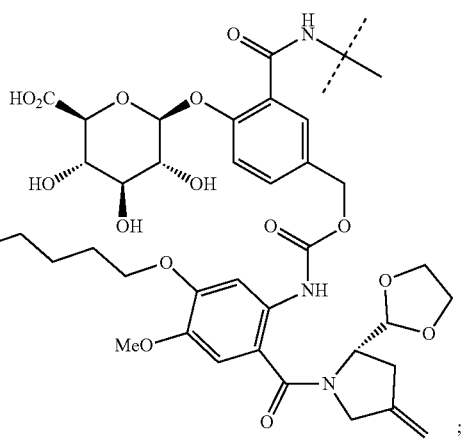

wherein the bond overlaid with a dashed line represents a connection point to L.

The present invention also provides a pyrrolobenzodiazepine dimer prodrug-linker-ligand conjugate having a structure represented by the following Chemical Formula IIIa or IIIb or a pharmaceutically acceptable salt or solvate thereof:

in which a dotted line, $R_1$, $R_2$, $R_3$, $R_4$, $R_5$, $R_6$, $R_7$, X, Y, $R_1'$, $R_2'$, $R_3'$, $R_4'$, $R_5'$, $R_7'$, X', Y', $R_8$, $Z_a$, $Z_b$, $R_{12a}$, $R_{13a}$, $R_{14a}$, $R_8'$, $Z_a'$, $Z_b'$, $R^{12a'}$, $R^{13a'}$, and $R^{14a'}$ are as defined for the compounds represented by Chemical Formula Ia and Chemical Formula Ia', respectively,

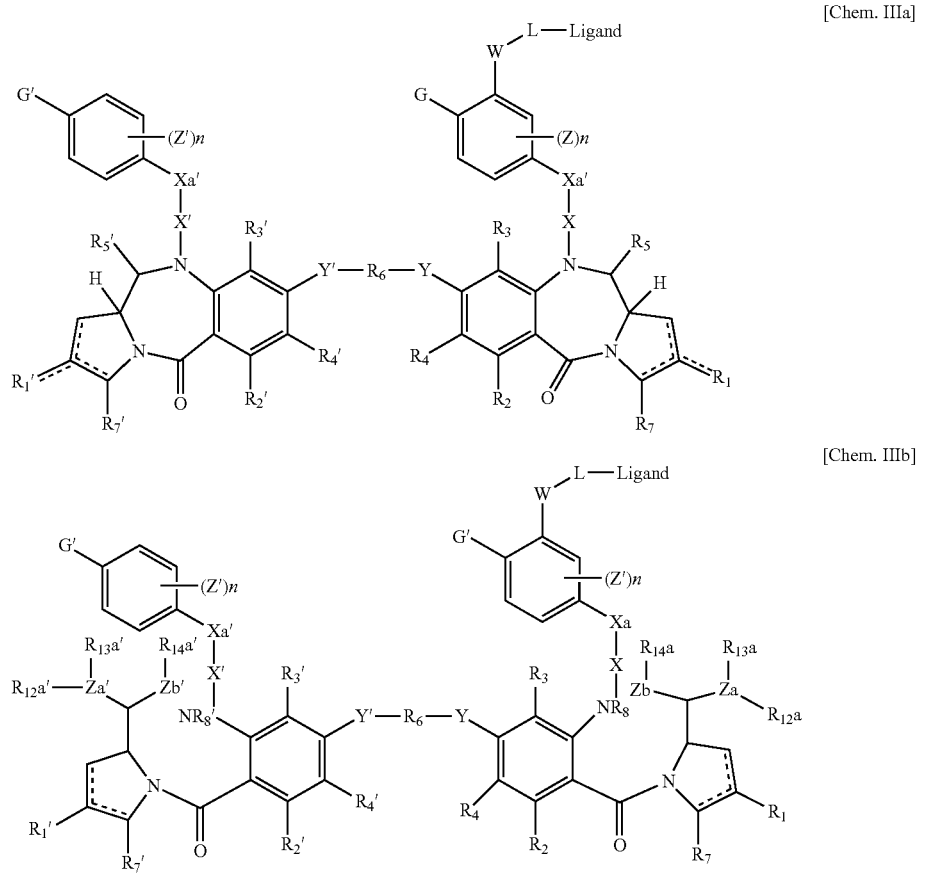

Xa, G, Z, W, L, Xa', G', and Z' are as defined for the compound represented by Chemical Formula IIb, respectively; and Ligand denotes an antigen-binding moiety.

In an aspect of the invention, Ligand is a protein.

In an aspect of the invention, the protein is an oligopeptide, a polypeptide, an antibody, or a fragment or a repebody of an antigenic polypeptide.

In an aspect of the invention, the protein has one or more amino acid motifs which can be recognized by an isoprenoid transferase. In other words, the C-terminus (fragment, analog or derivative thereof) of the protein may be bound to an amino acid motif which can be recognized by an isoprenoid transferase.

In an aspect of the present invention, a spacer unit composed of an amino acid, an oligopeptide, or a polypeptide may be further included between the protein and the amino acid motif.

In an aspect of the invention, the protein is covalently bound to the linker via the amino acid motif.

In an aspect of the present invention, the amino acid motif may be covalently bound to the C-terminus of the protein or to at least one spacer unit to be covalently bound to the C-terminus of the protein. The protein may be covalently bound directly to the amino acid motif or linked to the amino acid motif by being covalently bound to a spacer unit. The amino acid spacer unit is composed of from 1 to 20 amino acids, and a glycine unit is preferable among these.

In an aspect of the invention, the C-terminus of the protein is of a light or heavy chain of antibody.

In an aspect of the present invention, the protein is a monoclonal antibody.

In an aspect of the present invention, the isoprenoid transferase includes FTase (farnesyl protein transferase) or GGTase (geranylgeranyl transferase), and each of these involves the transfer of the panesyl or geranyl-geranyl residue to the C-terminal cysteine(s) of the target protein. GGTase may be classified into GGTase I and GGTase II. FTase and GGTase I can recognize a CAAX motif.

In an aspect of the present invention, the amino acid motif is CYYX, XXCC, XCXC or CXX, in which C denotes cysteine, Y denotes an aliphatic amino acid, and X denotes an amino acid which determines the substrate specificity of isoprenoid transferase.

In an aspect of the present invention, the protein having an amino acid motif is selected from the group consisting of A-HC-(G)$_z$CVIM, A-HC-(G)zCVLL, A-LC-(G)$_z$CVIM, and A-LC-(G)$_z$CVLL, in which A denotes an antibody, HC denotes a heavy chain, LC denotes a light chain, G denotes a glycine unit, and z denotes an integer from 0 to 20.

Isoprenoid transferases can recognize substrates as well as isosubstrates. An isosubstrate refers to a substrate analogue having modification to the substrate. An isoprenoid transferase alkylates a certain amino acid motif (for example, CAAX motif) at the C-terminus of protein (see Benjamin P. Duckworth et al, ChemBioChem 2007, 8, 98; Uyen T. T. Nguyen et al, ChemBioChem 2007, 8, 408; Guillermo R. Labadie et al, J. Org. Chem. 2007, 72(24), 9291; James W. Wollack et al, ChemBioChem 2009, 10, 2934). Functionalizing proteins can be produced using isoprenoid transferases and isosubstrates through alkylation at the C-terminal cysteine(s).

For example, the cysteine residue of a C-terminal CAAX motif can be reacted with an isosubstrate using an isoprenoid transferase. In a certain case, AAX can then be removed by protease. The cysteine obtained can be then methylated at the carboxy terminus by an enzyme (see Iran M. Bell, J. Med. Chem. 2004, 47 (8), 1869).

The protein of the present invention can be prepared by any molecular biological or cell biological method well known in the art. For example, a transient transfection method may be used. The genetic sequence encoding a specific amino acid motif which can be recognized by an isoprenoid transferase can be inserted into a known plasmid vector by a standard PCR technology so as to express a protein (fragment or analog thereof) having a specific amino acid motif at its C-terminus. In this manner, a protein having one or more amino acid motifs which can be recognized by an isoprenoid transferase can be expressed.

In an aspect of the present invention, when the protein is a monoclonal antibody, one or more light chains of the monoclonal antibody, one or more heavy chains of the monoclonal antibody, or both the light chains and the heavy chains may include an amino acid moiety having an amino acid motif which may be recognized by an isoprenoid transferase, and those skilled in the art can readily select a protein (for example, a target cell of a subject) which selectively binds a target of interest.

In an aspect of the present invention, the protein may include an antibody or a fragment of an antigen which specifically binds to a target of interest.

In an aspect of the present invention, the amino acid motif is CYYX, XXCC, XCXC or CXX (where C denotes cysteine, Y denotes an aliphatic amino acid, and X denotes an amino acid which determines the substrate specificity of isoprenoid transferase), and it is more preferable that the amino acid motif is CYYX.

The present invention also provides a pharmaceutical composition for preventing or treating a proliferative disease, containing the pyrrolobenzodiazepine dimer prodrug-linker-ligand conjugate described above or a pharmaceutically acceptable salt or solvate thereof.

The present invention also provides a pharmaceutical composition for preventing or treating a proliferative disease, containing the pyrrolobenzodiazepine dimer prodrug-linker-ligand conjugate described above or a pharmaceutically acceptable salt or solvate thereof; and a pharmaceutically acceptable excipient.

The present invention also provides a pharmaceutical composition for preventing or treating a proliferative disease, containing the pyrrolobenzodiazepine dimer prodrug-linker-ligand conjugate described above or a pharmaceutically acceptable salt or solvate thereof, one or more therapeutic co-agents; and a pharmaceutically acceptable excipient.

In an aspect of the present invention, the therapeutic co-agent may be an agent which exhibits a preventive, ameliorative, or therapeutic effect on a proliferative disease, or an agent which can diminish the adverse effects manifested at the time of administration of a therapeutic agent for a proliferative disease, or an agent which exhibits an immunity-enhancing effect, and the like, but it is not limited thereto. It means that any agent may be applied in combination as long as it exhibits, when being applied in the form of a compounding agent together with a pyrrolobenzodiazepine, a therapeutically useful effect, and/or further improves the stability of pyrrolobenzodiazepine, and/or diminishes the side effects which may be exhibited when a pyrrolobenzodiazepine is administered, and/or exhibits the effect of maximizing the therapeutic effect through the enhancement of immunity.

In an aspect of the present invention, the proliferative disease refers to a cell proliferation-related disease in which undesirably excessive or abnormal cells are undesirably not controlled such as neoplasia or hyperplastic growth in vitro or in vivo. The proliferative disease may be selected from the group consisting of neoplasia, tumor, cancer, leukemia, psoriasis, bone disease, fibrosing disease, and atherosclerosis. Examples of neoplasia and tumor may include histiocytoma, glioma, astrocytoma, and osteoma.

In an aspect of the present invention, the cancer may be selected from the group consisting of lung cancer, small cell lung cancer, gastrointestinal cancer, colorectal cancer, bowel cancer, breast cancer, ovarian cancer, prostate cancer, testicular cancer, liver cancer, kidney cancer, bladder cancer, pancreatic cancer, brain cancer, sarcoma, osteosarcoma, Kaposi sarcoma, and melanoma. However, the present invention can be applied to all carcinomas for which pyrrolobenzodiazepines can exhibit a therapeutic effect.

The present invention also provides a method of treating a proliferative disease in a subject having a proliferative disease, including administering a pyrrolobenzodiazepine dimer prodrug-linker-ligand conjugate or a pharmaceutically acceptable salt or solvate thereof to the subject in an amount effective for the treatment of the proliferative disease.

In an aspect of the present invention, there is provided a method of treating cancer, including administering the pharmaceutical composition described above to a patient.

The present invention is suitable to be used to provide a PBD compound at a target position in a subject. The conjugate according to the present invention releases an active PBD compound which does not have any linker moiety and does not contain anything that can affect the reactivity of PBD compound.

Definition

The following definitions apply in the present specification:

The term "conjugates" in the present specification refers to cell binding agents which are covalently bound to one or more molecules of a cytotoxic compound. Here, "cell binding agent" is a molecule having affinity for a biological target, for example, it may be a ligand, a protein, an antibody, specifically a monoclonal antibody, a protein or antibody fragment, a peptide, an oligonucleotide, or an oligosaccharide, and the binding agent functions to induce a biologically active compound to a biological target. In an aspect of the present invention, the conjugate may be designed so as to target tumor cells through cell surface antigens. The antigen may be a cell surface antigen which is overexpressed or expressed in an abnormal cell type. Specifically, the target antigen may be expressed only on proliferative cells (for example, tumor cells). The target antigen may be selected on the basis of different expression, usually between proliferative tissues and normal tissues. In the present invention, a ligand is bound to a linker.

The term "antibody" in the present specification refers to an immunoglobulin molecule which can specifically bind to a target, for example, carbohydrates, polynucleotides, lipids, or polypeptides through at least one antigen recognition site located in the variable region of the immunoglobulin molecule. The term "antibody" used in the present specification encompasses not only an intact polyclonal or monoclonal antibody but also an arbitrary antigen-binding portion (for example, an "antigen-binding fragment") of an intact antibody which retains the ability to specifically bind to a predetermined antigen, or a single chain thereof, a fusion protein including an antibody, and an arbitrary other modified sequence of an immunoglobulin molecule including an antigen recognition site, for example, but not limited to, Fab; Fab'; F(ab')$_2$Fd fragment; Fv fragment; single domain antibody (dAb) fragment; isolated complementarity determining region (CDR); single chain (scFv) and single domain antibodies (for example, shark and camelid antibodies), maxibody, minibody, intrabody, diabody, triabody, tetrabody, v-NAR, and bis-scFv (see, for example, literature: Hollinger and Hudson, 2005, Nature Biotechnology 23 (9): 1126-1136).

Antibodies include an arbitrary class of antibodies, for example, IgG, IgA, or IgM (or subclasses thereof), the antibody is not required to be of an arbitrary specific class. Depending on the amino acid sequence in the constant region of the heavy chain of antibody, the immunoglobulin may be assigned to a different class. There are five major classes of immunoglobulins: IgA, IgD, IgE, IgG, and IgM, and some of these may be further classified as subclasses (isoforms), such as IgG1, IgG2, IgG3, IgG4, IgA1, and IgA2. The heavy chain (HC) constant domains corresponding to different classes of immunoglobulins are called alpha, delta, epsilon, gamma and mu, respectively. Subunit structures and three-dimensional coordinates of different classes of immunoglobulins are well known. The antibody of the present invention can be prepared by technologies well known in the related art, for example, recombinant technology, phage display technology, synthetic technology, or combinations of these technologies or other technologies readily known in the related art.

The term "isolated antibody" in the present specification refers to an antibody which is substantially free of other antibodies having different antigen specificity, and it may be substantially free of other cellular substances and/or chemical substances.

The term "biological target" in the present specification refers to an antigen located on the surface of tumor, cancer cell, extracellular matrix.

The term "linker" in the present specification refers to a compound which covalently binds a cytotoxic compound to a ligand. In an aspect of the present invention, the linkers disclosed in PCT/US2016/063564 and PCT/US2016/063595 may be used.

The term "therapeutic agent" in the present specification refers to an agent which exerts cytotoxicity, cell proliferation inhibition, and/or an immunomodulatory effect on a proliferative disease, for example, cancer cells or activated immune cells. Examples of therapeutic agent may include cytotoxic agents, chemotherapeutic agents, cell proliferation inhibitors, and immunomodulators.

The term "chemotherapeutic agent" in the present specification refers to a chemical compound useful for treatment of cancer.

The term "subject" in the present specification is intended to include human and non-human animals, particularly mammals. Examples of subject may include human subjects, and the subject is a concept including a human patient having, for example, the disorders described in the present specification, more specifically, a cancer or a normal subject. The term "non-human animal" includes all vertebrate animals, for example, non-mammals (for example, chickens, amphibians, and reptiles) and mammals, for example, non-human primates, animals useful for livestock and/or agriculture (for example, sheep, dogs, cats, cows, pigs, and the like) and rodents (for example, mice, rats, hamsters, guinea pigs, and the like). In a certain embodiment, the subject is a human patient.

The term "treatment" or "to treat" in the present specification refers to both a therapeutic treatment and prophylactic or preventative measures. A subject in need of treatment includes a subject already having a disease, and a subject susceptible to a disease or a subject to be prevented from a disease. Hence, when being used with regard to a disease or a subject in need of treatment, the term includes, but is not limited to, inhibiting or slowing the progression of the disease, preventing symptoms, decreasing the severity of the disease and/or symptom, or decreasing the duration of the disease as compared to an untreated subject.

The term "administration" or "to administrate" in the present specification refers to provision and/or contact and/or delivery of a compound or compounds by an arbitrary suitable route in order to achieve the desired effect. Administration may include, but is not limited to, oral, sublingual, parenteral (for example, intravenous, subcutaneous, intradermal, intramuscular, intraarticular, intraarterial, intrathecal, intrasternal, intraspinal, intralesional or intracranial injection), transdermal, topical, buccal, rectal, vaginal, nasal, ophthalmic, and inhalation administration and administration through an implant.

In the present specification, the term "unsubstituted or substituted" means a parent group which may be unsubstituted or substituted, the term "substituted" means a parent group having one or more substituents, and the term "substituent" means a chemical moiety which is covalently bound to a parent group or is fused to a parent group.

The term "halo" in the present specification refers to fluorine, chlorine, bromine, iodine, and the like.

The term "alkyl" in the present specification refers to a monovalent moiety obtained by removing a hydrogen atom from a carbon atom of an aliphatic or alicyclic, saturated or unsaturated (unsaturated, fully unsaturated) hydrocarbon compound, examples of saturated alkyl may include methyl, ethyl, propyl, butyl, pentyl, hexyl, and heptyl, examples of saturated straight chain alkyl may include methyl, ethyl, n-propyl, n-butyl, n-pentyl(amyl), n-hexyl, and n-heptyl, and examples of saturated branched chain alkyl may include isopropyl, isobutyl, sec-butyl, tert-butyl, isopentyl, and neopentyl.

The term "alkoxy" in the present specification means —OR where R is an alkyl group, examples thereof may include methoxy, ethoxy, n-propoxy, isopropoxy, n-butoxy, sec-butoxy, isobutoxy, and tert-butoxy.

The term "aryl" in the present specification means a monovalent moiety obtained by removing a hydrogen atom from an aromatic ring atom of an aromatic compound having a ring atom.

The term "alkenyl" in the present specification is an alkyl having one or more carbon-carbon double bonds, and examples of an unsaturated alkenyl group may include ethynyl (vinyl, —CH=CH$_2$), 1-propenyl (—CH=CH—CH$_3$), 2-propenyl, isopropenyl, butenyl, pentenyl, and hexenyl.

The term "alkynyl" in the present specification is an alkyl group having one or more carbon-carbon triple bonds, and examples of an unsaturated alkynyl group may include ethynyl and 2-propynyl.

The term "carboxy" in the present specification refers to —C(=O)OH.

The term "formyl" in the present specification refers to —C(=O)H.

The term "aryl" in the present specification refers to a monovalent moiety obtained by removing a hydrogen atom from an aromatic ring atom of an aromatic compound. For example, "$C_{5-7}$ aryl" means a monovalent moiety which is obtained by removing a hydrogen atom from an aromatic ring atom of an aromatic compound and in which the moiety has from 5 to 7 ring atoms, and "$C_{5-10}$ aryl" means a monovalent moiety which is obtained by removing a hydrogen atom from an aromatic ring atom of an aromatic compound and in which the moiety has from 5 to 10 ring atoms. Here, the prefixes ($C_{5-7}$, $C_{5-10}$, and the like) refer to the number of ring atoms or the range of the number of ring atoms regardless of whether these are carbon atoms or hetero atoms. For example, "$C_{5-6}$ aryl" refers to an aryl group having 5 or 6 ring atoms. Here, the ring atoms may be all carbon atoms as in a "carboaryl group". Examples of carboaryl group may include, but are not limited to, those derived from benzene, naphthalene, azulene, anthracene, phenanthrene, naphthacene, and pyrene. Examples of an aryl group including a fused ring of which at least one is an aromatic ring may include, but are not limited to, groups derived from indane, indene, isoindene, tetralin, acenaphthene, fluorene, phenalene, acephenanthrene, and aceanthrene. Alternatively, the ring atom may include one or more heteroatoms as in a "heteroaryl group".

The term "heteroaryl" in the present specification refers to aryl containing one or more heteroatoms, examples thereof may include pyridine, pyrimidine, benzothiophene, furyl, dioxalanyl, pyrrolyl, oxazolyl, pyridyl, pyridazinyl, and pyrimidinyl, and more specific examples thereof may include $C_9$ which has two fused rings and is derived from benzofuran, isobenzofuran, indole, isoindole, indolizine, indoline, isoindoline, purine (adenine or guanine), benzimidazole, indazole, benzoxazole, benzisoxazole, benzodioxole, benzofuran, benzotriazole, benzothiofuran, benzothiazole, or benzothiadiazole, $C_{10}$ which has two fused rings and is derived from chromene, isochromene, chromane, isochromane, benzodioxane, quinoline, isoquinoline, quinolizine, benzoxazine, benzodiazine, pyridopyridine, quinoxaline, quinazoline, cinnoline, phthalazine, naphthyridine, or pteridine, $C_{11}$ which has two fused rings and is derived from benzodiazepine, $C_{13}$ which has three fused rings and is derived from carbazole, dibenzofuran, dibenzothiophene, carboline, perimidine, or pyridoindole, and $C_{14}$ which has three fused rings and is derived from acridine, xanthene, thioxanthene, oxantrene, phenoxathin, phenazine, phenoxazine, phenothiazine, thianthrene, phenanthridine, phenanthroline, or phenazine.

The term "cycloalkyl" in the present specification means an alkyl group which is a cyclic group and refers to a monovalent moiety obtained by removing a hydrogen atom from an alicyclic ring atom of a cyclic hydrocarbon compound. Examples of the cycloalkyl group may include, but are not limited to, those derived from the following:

saturated single ring hydrocarbon compounds: cyclopropane, cyclobutane, cyclopentane, cyclohexane, cycloheptane, methylcyclopropane, dimethylcyclopropane, methylcyclobutane, dimethylcyclobutane, methylcyclopentane, dimethylcyclopentane, and methylcyclohexane;

unsaturated single ring hydrocarbon compounds: cyclopropene, cyclobutene, cyclopentene, cyclohexene, methylcyclopropene, dimethylcyclopropene, methylcyclobutene, dimethylcyclobutene, methylcyclopentene, dimethylcyclopentene, and methylcyclohexene; and saturated heterocyclic hydrocarbon compounds: norcarane, norphinane, norbornane.

The term "heterocyclyl" in the present specification refers to a monovalent moiety obtained by removing a hydrogen atom from a ring atom of a heterocyclic compound.

In the present specification, the prefixes (for example, $C_{1-12}$ and $C_{3-8}$) refer to the number of ring atoms or the range of the number of ring atoms regardless of whether these are carbon atoms or hetero atoms. For example, the term "$C_{3-6}$ heterocyclyl" used in the present specification refers to a heterocyclyl group having from 3 to 6 ring atoms.

Examples of a single ring heterocyclyl group may include, but are not limited to, those derived from the following:

$N_1$: aziridine, azetidine, pyrrolidine, pyrroline, 2H- or 3H-pyrrole, piperidine, dihydropyridine, tetrahydropyridine, and azepine;

$N_2$: imidazolidine, pyrazolidine, imidazoline, pyrazoline, and piperazine;

$O_1$: oxirane, oxetane, oxolane, oxole, oxane, dihydropyran, pyran, and oxepine;

$O_2$: dioxolane, dioxane, and dioxepane;

$O_3$: trioxane;

$N_1O_1$: tetrahydrooxazole, dihydrooxazole, tetrahydroisoxazole, dihydroisoxazole, morpholine, tetrahydrooxazine, dihydrooxazine, and oxazine, $S_1$: thiirane, thiethane, thiolane, thiane, and thiepane;

$N_1S_1$: thiazoline, thiazolidine, and thiomorpholine;

$N_2O_1$: oxadiazine;

$O_1S_1$: oxathiole, oxathiane; and $N_1O_1S_1$: oxathiazine.

The term "prodrug" in the present specification refers to a compound which can be directly or indirectly converted into a pyrrolobenzodiazepine drug by the action of an enzyme and gastric acid under physiological conditions in vivo (for example, enzymatic oxidation, reduction and/or hydrolysis).

As the "pharmaceutically acceptable salt" in the present specification, an acid addition salt formed by a pharmaceutically acceptable free acid can be used, and an organic acid or an inorganic acid can be used as the free acid.

The organic acid may include, but is not limited to, citric acid, acetic acid, lactic acid, tartaric acid, maleic acid, fumaric acid, formic acid, propionic acid, oxalic acid, trifluoroacetic acid, benzoic acid, gluconic acid, methansulfonic acid, glycolic acid, succinic acid, 4-toluenesulfonic acid, glutamic acid, and aspartic acid. In addition, the inorganic acid may include, but is not limited to, hydrochloric acid, bromic acid, sulfuric acid, and phosphoric acid.

For example, when the compound is an anion or has a functional group which may be an anion (for example, —COOH may be —COO—), a salt can be formed with a suitable cation.

Examples of a suitable inorganic cation may include, but are not limited to, alkali metal ions such as $Na^+$ and $K^+$, alkaline earth metal cations such as $Ca^{2+}$ and $Mg^{2+}$, and other cations such as $Al^{3+}$. Examples of a suitable organic cation may include, but are not limited to, ammonium ion (namely, $NH^{4+}$) and substituted ammonium ions (for example, $NH_3R^+$, $NH_2R_2^+$, $NHR_3^+$, and $NR_4^+$).

Examples of some suitable substituted ammonium ions may include those derived from the following: amino acids, for example, lysine and arginine as well as ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine. An example of a typical quaternary ammonium ion is $N(CH_3)_4^+$.

When the compound is a cation or has a functional group which can be a cation (for example, —$NH_2$ may be —$NH_3^+$), a salt can be formed with a suitable anion. Examples of a suitable inorganic anion may include, but are not limited to, those derived from the following inorganic acids: hydrochloric acid, hydrobromic acid, hydroiodic acid, sulfuric acid, sulfurous acid, nitric acid, nitrous acid, phosphoric acid, and phosphorous acid.

Examples of a suitable organic anion may include, but are not limited to, those derived from the following organic acids: 2-acetoxybenzoic acid, acetic acid, ascorbic acid, aspartic acid, benzoic acid, camphorsulfonic acid, cinnamic acid, citric acid, edetic acid, ethanedisulfonic acid, ethanesulfonic acid, fumaric acid, glucoheptonic acid, gluconic acid, glutamic acid, glycolic acid, hydroxymaleic acid, hydroxynaphthalenecarboxylic acid, isethionic acid, lactic acid, lactobionic acid, lauric acid, maleic acid, malic acid, methanesulfonic acid, mucic acid, oleic acid, oxalic acid, palmitic acid, pamoic acid, pantothenic acid, phenylacetic acid, phenylsulfonic acid, propionic acid, pyruvic acid, salicylic acid, stearic acid, succinic acid, sulfanilic acid, tartaric acid, toluenesulfonic acid, and valeric acid. Examples of a suitable polymeric organic anion may include, but are not limited to, those derived from the following polymeric acids: tannic acid and carboxymethylcellulose.

The term "solvate" in the present specification refers to a molecular complex between the compound according to the present invention and solvent molecules, and examples of the solvate may include, but are not limited to, the compound according to the present invention bound with water, isopropanol, ethanol, methanol, dimethylsulfoxide, ethyl acetate, acetic acid, ethanolamine, or any mixed solvent thereof.

It may be convenient or desirable to prepare, purify and/or handle the corresponding solvates of the active compounds. The term "solvate" is used in the present specification in the conventional sense in order to refer to solutes (for example, active compounds, salts of active compounds) and complexes of solvents. When the solvent is water, the solvate may be conveniently referred to as a hydrate, for example, monohydrate, dihydrate, and trihydrate.

The pharmaceutical composition of the present invention may contain a pharmaceutically acceptable carrier. The pharmaceutically acceptable carrier may include macromolecules which are typically gradually metabolized, for example, proteins, polysaccharides, polylactic acid, polyglycolic acid, polymeric amino acids, amino acid copolymers, and lipid aggregates, and such a pharmaceutically acceptable carrier may be suitably selected and used by those skilled in the art.

The composition containing a pharmaceutically acceptable carrier may be various oral or parenteral forms. In the case of preparing a formulation, the formulation may be prepared using a diluent or excipient such as a filler, an extender, a binder, a wetting agent, a disintegrant, or a surfactant to be commonly used.

Solid formulations for oral administration may include tablets, pills, powders, granules, and capsules. Such solid formulations are prepared by mixing one or more compounds with at least one or more excipients, for example, starch, calcium carbonate, sucrose or lactose, and gelatin. In addition to simple excipients, lubricants such as magnesium stearate and talc may also be used.

Liquid formulations for oral administration may include suspensions, solutions, emulsions, and syrups. In addition to water and liquid paraffin which are simple diluents to be commonly used, the liquid formulation may contain various excipients, for example, wetting agents, sweeteners, fragrances, and preservatives.

Formulations for parenteral administration may include sterile aqueous solutions, non-aqueous solutions, suspensions, emulsions, freeze-dried formulations, and suppositories. As the non-aqueous solvent and suspending agent, propylene glycol, polyethylene glycol, vegetable oil such as olive oil, and an injectable ester such as ethyl oleate may be used. As a base for suppositories, witepsol, macrogol, tween 61, cacao butter, laurin butter, and glycerogelatin may be used.

The pharmaceutical composition may have any one formulation selected from the group consisting of injections, tablets, pills, powders, granules, capsules, suspensions, solutions, emulsions, syrups, sterile aqueous solutions, non-aqueous solvents, suspensions, emulsions, freeze-dried formulations, and suppositories.

For intravenous, skin, or subcutaneous injection and the like, the active ingredient may be in the form of an acceptable aqueous solution for parenteral administration, which is pyrogen-free and has suitable pH, isotonicity, and stability. Those skilled in the art can prepare suitable solutions using isotonic vehicles, for example, aqueous sodium chloride solution, Ringer's solution, and lactate Ringer's solution, and preservatives, stabilizers, buffers, antioxidants, or other additives may be contained in the solutions if necessary. Solid forms suitable for injection may also be prepared as emulsions or in the form of polypeptides encapsulated in liposomes.

The phrase "effective amount" or "therapeutically effective amount" used in the present specification refers to the amount required to achieve the intended therapeutic result (for dosage and duration and means of administration). The effective amount is at least the minimum amount of active agent required to confer a therapeutic benefit to a subject, and is less than the toxic amount. For example, the active agent may be administered at a dosage in a range of from about 100 ng/kg to about 100 mg/kg per patient and more typically in a range of from about 1 μg/kg to about 10 mg/kg per patient. When the active compound is a salt, an ester, an amide, a prodrug, and the like, the dosage is calculated on the basis of the parent compound and the actual weight used thus proportionally increases. The pyrrolobenzodiazepine compounds according to the present invention may be formulated so as to contain, but is not limited to, from 0.1 mg to 3000 mg, from 1 mg to 2000 mg, or from 10 mg to 1000 mg of active ingredient per unit dosage form. The active ingredient may be administered so as to obtain a peak plasma concentration of the active compound of from about 0.05 μM to 100 μM, from 1 μM to 50 μM, from or 5 μM to 30 μM. For example, the active compound may be arbitrarily administered by intravenous injection of a solution containing the active ingredient at from 0.1 w/v % to 5 w/v % in saline.

The concentration of the active compound in the pharmaceutical composition may be determined by absorption, inactivation, and release rate of the drug and other factors known to those skilled in the art. The dosage may vary depending on the severity of the symptom/disease. In addition, the dosage and the dose regimen for a certain patient may be adjusted according to the occupational judgment of the administration supervisor comprehensively considering the degree of the symptom/disease, necessity, age, responsiveness to the drug, and the like of the patient. The concentration ranges set forth in the present invention are only exemplary and are not intended to limit the embodiments of the claimed compositions to these. In addition, the active ingredient may be administered one time or a smaller dosage may be administered several times in a divided manner.

The prodrug compounds, or prodrug-linker compounds and prodrug-linker-ligand conjugate compounds according to the present invention can be used to treat a proliferative disease, particularly cancer. The term "proliferative disease" refers to undesirable or uncontrolled cell proliferation of undesirable excessive or abnormal cells such as neoplastic or hyperplastic growth in vitro or in vivo. Examples of the proliferative disease may include neoplasia, tumor, cancer, leukemia, psoriasis, bone disease, fibrosing disease, and atherosclerosis, and the proliferative disease may include, but is not limited to, benign, pre-malignant, or malignant cell proliferation. The cancer may be, but is not limited to, lung cancer, small cell lung cancer, gastrointestinal cancer, colorectal cancer, bowel cancer, breast cancer, ovarian cancer, prostate cancer, testicular cancer, liver cancer, kidney cancer, bladder cancer, pancreatic cancer, brain cancer, sarcoma, osteosarcoma, Kaposi sarcoma, and melanoma.

Unless otherwise defined in the present specification, scientific and technical terms used in connection with the present invention have the meanings commonly understood by those skilled in the art.

In an aspect of the present invention, the pyrrolobenzodiazepine prodrug, pyrrolobenzodiazepine prodrug-linker compound, and pyrrolobenzodiazepine-linker-ligand conjugate according to the present invention can be synthesized according to the following procedures.

Synthesis Pathway of Pyrrolobenzodiazepine Prodrug

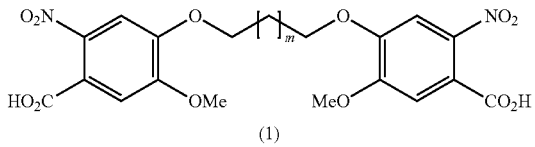

(1)

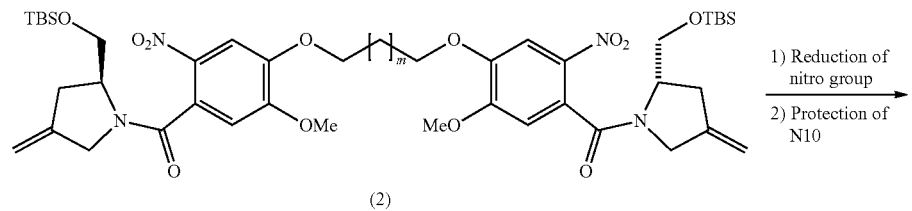

(2)

1) Reduction of nitro group
2) Protection of N10

37 38
-continued
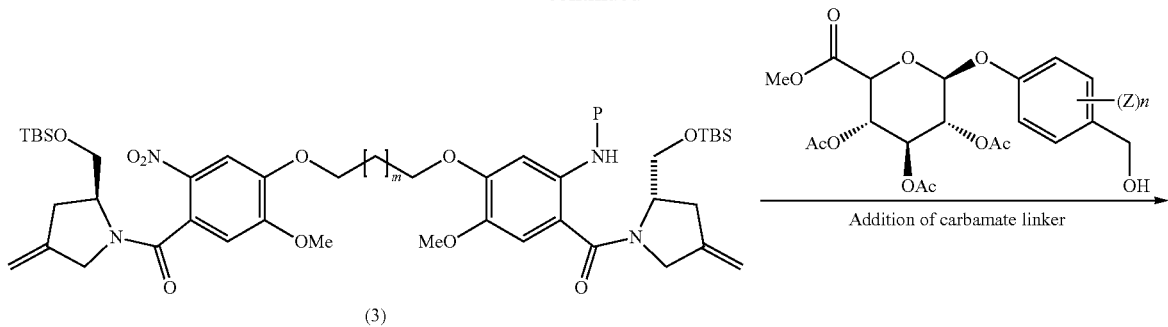
(3)
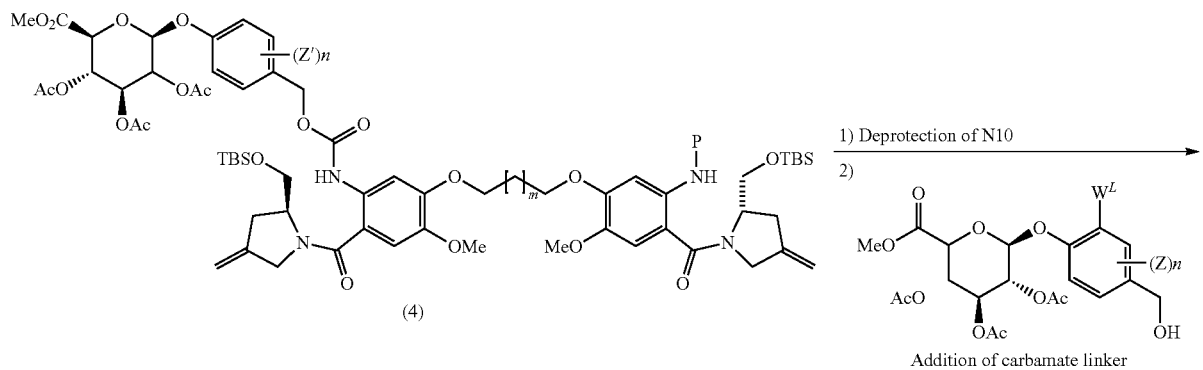
(4)
1) Deprotection of N10
2)
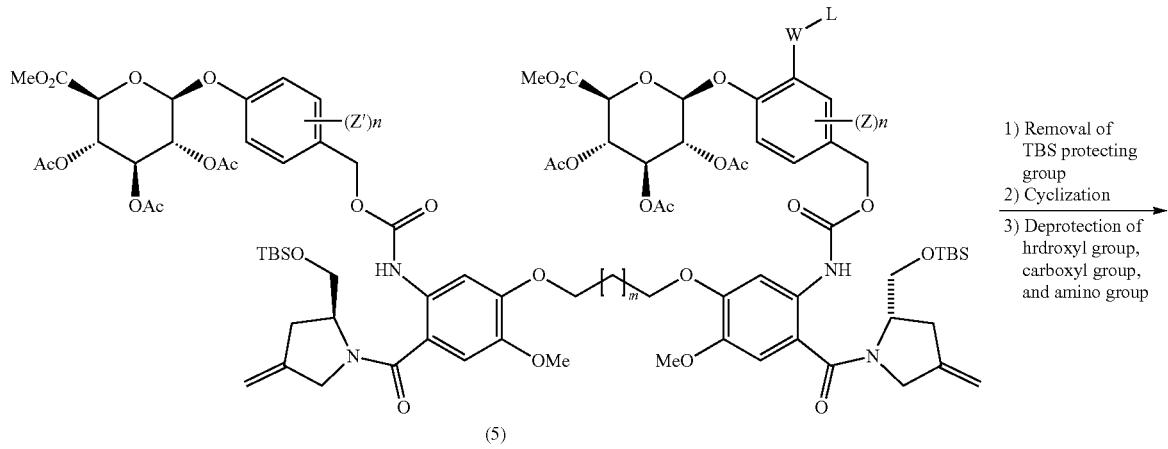
(5)
1) Removal of TBS protecting group
2) Cyclization
3) Deprotection of hrdroxyl group, carboxyl group, and amino group
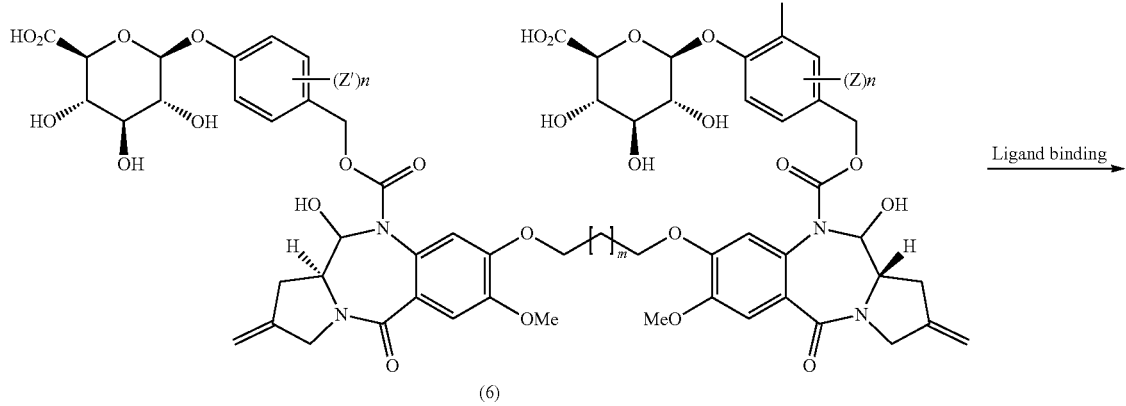
(6)
Ligand binding

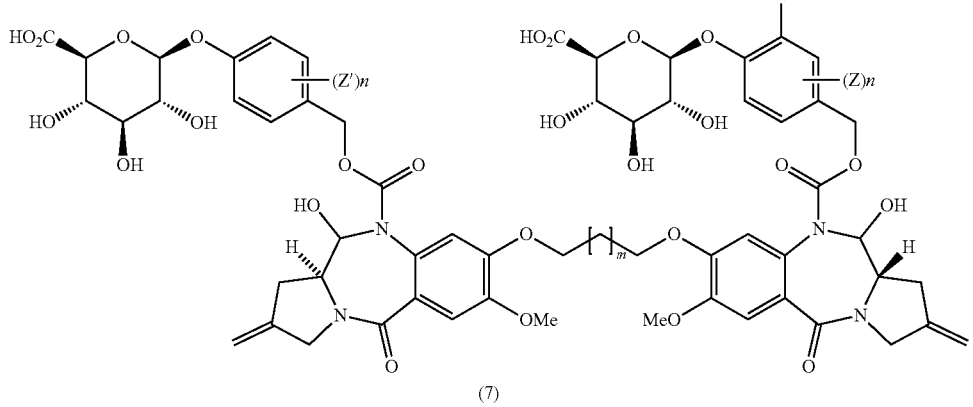

(7)

Synthesis Pathway of Pyrrolobenzodiazepine Prodrug-Linker and Pyrrolobenzodiazepine Prodrug-Linker-Ligand Conjugate The pyrrolobenzodiazepine prodrug-linker compound and pyrrolobenzodiazepine prodrug-linker-ligand conjugate according to the present invention can be prepared using the knowledge of those skilled in the art by the technologies provided in the present specification.

For example, the linkers may be described in PCT/US2016/063564 and PCT/US2016/063595, which are incorporated herein by reference in their entirety, but also may be prepared according to known references by those skied in the art even though not described herein.

Advantageous Effects of Invention

The pyrrolobenzodiazepine dimer prodrug, pyrrolobenzodiazepine dimer prodrug-linker, or pyrrolobenzodiazepine dimer prodrug-linker-ligand conjugate according to the present invention is industrially useful in that it is possible to target proliferative diseases such as cancer, to perform a specific treatment, to maximize the drug efficacy, and to minimize the occurrence of side effects since the stability of the compound itself and the stability thereof in plasma are excellent and the compound is advantageous in terms of manifestation of toxicity.

BRIEF DESCRIPTION OF DRAWINGS

FIG. 1 illustrates an example of the synthesis process of Compound No. 28 according to the present invention.

DESCRIPTION OF EMBODIMENTS

Hereinafter, the present invention will be described in more detail with reference to Examples. However, the following Examples are intended to assist in understanding the present invention and are not intended to limit the scope of the present invention thereto.

<Example 1> Preparation of Compound 4

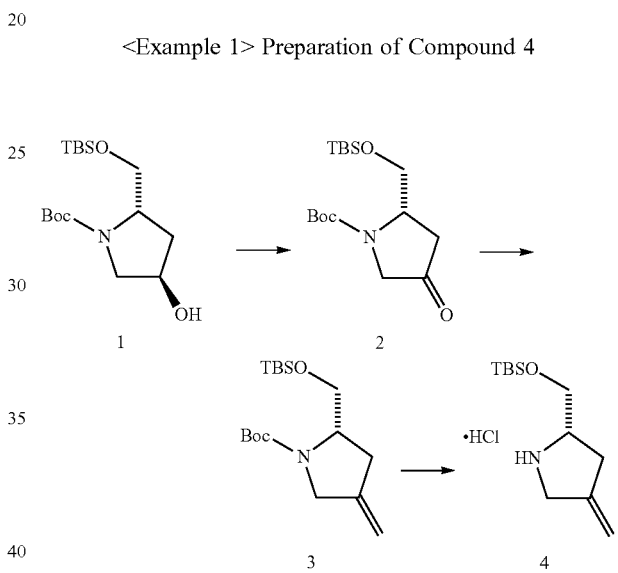

Preparation of Compound 2

Oxalyl chloride (3.1 mL, 36.2 mmol) was dissolved in dichloromethane (40 mL) and dimethylsulfoxide (4.7 mL, 66.4 mmol) was added thereto at −78° C. under a nitrogen atmosphere. After 10 minutes, a solution of Compound 1 (10 g, 30.2 mmol, Compound 1 was prepared by the method described in J. Org. Chem., 2003, 68, 3923-3931) in dichloromethane (140 mL) was gradually added to the mixture, the reaction solution was stirred for 1 hour, then triethylamine (16.7 mL, 120.6 mmol) was added thereto, and the reaction temperature was gradually raised to 0° C. over 2 hours. The reaction solution was diluted with dichloromethane (200 mL), and the organic layer was washed with a saturated aqueous ammonium chloride solution (200 mL) and brine (200 mL) and then dried over anhydrous sodium sulfate. The resultant was filtered, then concentrated, and purified by column chromatography to obtain Compound 2 (9.5 g, 95%).

$^1$H-NMR (400 MHz, CDCl$_3$) (rotamers) δ 4.39-4.26 (m, 1H), 4.03-3.80 (m, 2H), 3.69-3.64 (m, 1H), 3.63-3.51 (m, 1H), 2.70-2.60 (m, 1H), 2.43 (d, J=17.6 Hz), 1.61-1.41 (m, 10H), 0.98-0.67 (m, 6H), 0.08-0.05 (s, 6H).

Preparation of Compound 3

Methyltriphenylphosphonium bromide (7.6 g, 21.2 mmol) was diluted with tetrahydrofuran (80 mL), and then potassium t-butoxide (1 M in THF, 21.2 mL, 21.2 mmol) was added thereto at 0° C. under a nitrogen atmosphere. The mixture was stirred for 1 hour, and then a solution of Compound 2 (5.0 g, 15.2 mmol) in tetrahydrofuran (10 mL) was gradually added thereto. The mixture was stirred for 4 hours while gradually raising the reaction temperature to room temperature. A saturated aqueous ammonium chloride solution (200 mL) was added to the reaction solution and then the mixture was subjected to extraction using diethyl ether (2×200 mL). The combined organic layers were washed with brine (200 mL) and then dried over anhydrous sodium sulfate. The resultant was filtered, then concentrated, and purified by column chromatography to obtain Compound 3 (4.27 g, 86%).

¹H-NMR (400 MHz, CDCl₃) (rotamers) δ 4.97-4.91 (m, 2H), 4.09-3.93 (m, 2H), 3.84-3.80 (m, 1H), 3.65-3.61 (m, 1H), 3.59-3.34 (m, 1H), 2.64-2.55 (m, 2H), 1.69 (s, 9H), 0.87 (s, 9H), 0.03 (s, 6H).

Preparation of Compound 4

Compound 3 (15.5 g, 47.2 mmol) was dissolved in dichloromethane (120 mL), then hydrochloric acid (4 N 1,4-dioxane solution, 82.6 mL, 330.4 mmol) was added thereto at 0° C., and the mixture was stirred for 2 hours under a nitrogen atmosphere. The reaction solution was concentrated under reduced pressure to obtain Compound 4 (6.53 g, 92%) as a white solid.

¹H-NMR (400 MHz, CDCl₃) (rotamers) δ 9.79 (br s, 1H), 9.17 (br s, 1H), 5.15 (d, J=8 Hz, 1H), 4.91 (br s, 1H), 4.10 (m, 5H), 2.76-2.70 (m, 1H), 2.60-2.54 (m, 1H).

<Example 2> Preparation of Compound 9

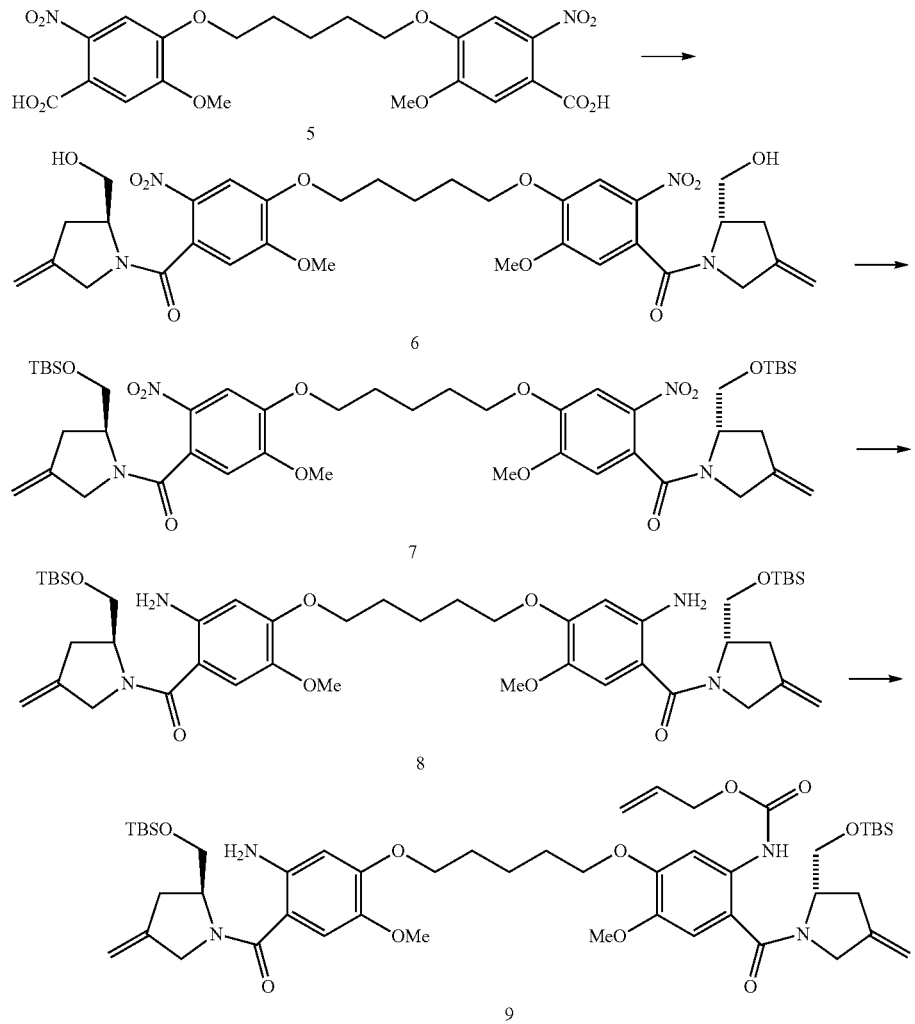

Preparation of Compound 6

Compound 5 (10 g, 20.2 mmol, Compound 5 was prepared by the method described in J. Med. Chem., 2004, 47, 1161-1174) was dissolved in dichloromethane (100 mL) and then oxalyl chloride (6.1 mL, 70.8 mmol) and N,N-dimethylformamide (2 drops) were added thereto at 0° C. under a nitrogen atmosphere. The reaction solution was stirred for 4 hours, then the temperature was raised to room temperature, and the reaction solution was stirred for 10 hours, concentrated under reduced pressure, and vacuum dried. The compound obtained was dissolved in dichloromethane (120 mL), and then Compound 4 (6.2 g, 41.4 mmol) and triethylamine (9.9 mL, 70.8 mmol) were added thereto at 0° C. under a nitrogen atmosphere. The reaction temperature was raised to room temperature, and the mixture was stirred for 3 hours, then a saturated aqueous ammonium chloride solution (200 mL) was added to the reaction solution, and the mixture was subjected to extraction using dichloromethane (2×200 mL). The combined organic layers were washed with brine (200 mL) and then dried over anhydrous sodium sulfate. The resultant was filtered, then concentrated, and purified by column chromatography to obtain Compound 6 (12 g, 87%).

$^1$H-NMR (400 MHz, CDCl$_3$) δ 7.71 (s, 2H), 6.80 (s, 2H), 5.13 (s, 2H), 4.88 (s, 2H), 4.61 (m, 2H), 4.17-4.14 (t, J=6.2 Hz, 4H), 3.98 (s, 6H), 3.94-3.74 (m, 10H), 2.89-2.83 (m, 2H), 2.52-2.48 (m, 2H), 2.04-1.96 (m, 4H), 1.77-1.71 (m, 2H).

Preparation of Compound 7

Compound 6 (6.4 g, 9.36 mmol) was dissolved in dichloromethane (100 mL), and then imidazole (2.5 g, 37.4 mmol) and t-butyldimethylsilyl chloride (3.5 g, 23.4 mmol) were added thereto at 0° C. under a nitrogen atmosphere. The reaction solution was stirred for 2 hours, then a saturated aqueous ammonium chloride solution (100 mL) was added to the reaction solution, and the mixture was subjected to extraction using dichloromethane (2×100 mL). The combined organic layers were washed with brine (200 mL) and then dried over anhydrous sodium sulfate. The resultant was filtered, then concentrated, and purified by column chromatography to obtain Compound 7 (6.88 g, 75%).

$^1$H-NMR (400 MHz, CDCl$_3$) (rotamers) δ 7.70 (s, 1H), 6.76 (s, 2H), 4.99 (s, 2H), 4.83 (s, 2H), 4.59 (br s, 2H), 4.14, (t, 4H), 3.95 (s, 6H), 3.90 (d, 2H), 3.77-3.69 (m, 4H), 3.57 (q, J=6.2 Hz, 1H), 3.31-3.29 (m, 1H), 2.82-2.67 (m, 4H), 1.99 (t, J=7.2 Hz, 4H), 1.75-1.72 (m, 2H), 0.89 (s, 18H), 0.09 (s, 12H).

Preparation of Compound 8

Compound 7 (3.0 g, 3.29 mmol) was dissolved in ethanol (44 mL), and then zinc dust (12.9 g, 197 mmol) and formic acid (5% ethanol solution, 128 mL) were added thereto. The reaction solution was stirred at room temperature for 15 minutes and then filtered through Celite, and ethyl acetate (500 mL) was added thereto. The organic layer was washed with distilled water (200 mL), a saturated aqueous sodium hydrogencarbonate solution (200 mL), and brine (200 mL) and then dried over anhydrous sodium sulfate. The resultant was filtered, then concentrated, and purified by column chromatography to obtain Compound 8 (2.76 g, 98%).

$^1$H-NMR (400 MHz, CDCl$_3$) δ 6.74 (s, 2H), 6.24 (s, 2H), 4.97 (s, 2H), 4.90 (s, 2H), 4.54 (br s, 2H), 4.33 (br s, 4H), 4.18 (br s, 1H), 4.14 (br s, 2H), 4.14-4.09 (m, 2H), 4.00 (t, J=8 Hz, 4H), 3.77 (s, 6H), 3.62 (br s. 2H), 2.68 (s, 4H), 1.95-1.88 (m, 4H), 1.66-1.64 (m, 2H), 0.87 (s, 18H), 0.02 (s, 12H).

Preparation of Compound 9

Compound 8 (5.0 g, 5.86 mmol) was dissolved in dichloromethane (300 mL) and then pyridine (0.94 mL, 11.7 mmol) and allyl chloroformate (0.62 mL, 5.86 mmol) were added thereto at −78° C. under a nitrogen atmosphere. The reaction solution was stirred for 1 hour, then the reaction temperature was raised to room temperature, and reaction solution was concentrated and then purified by column chromatography to obtain Compound 9 (2.23 g, 41%).

$^1$H-NMR (400 MHz, CDCl$_3$) δ 7.84 (s, 1H), 6.81 (s, 1H), 6.74 (s, 1H), 6.24 (s, 1H), 5.98-5.92 (m, 1H), 5.37, (dd, J=17.6 Hz, J=1.2 Hz, 1H), 5.25 (dd, J=10.4 Hz, J=1.2 Hz, 1H), 4.97 (br s, 2H), 4.90 (br s, 2H), 4.63-4.62 (m, 4H), 4.34 (br s, 2H), 4.21-4.18 (m, 2H), 4.10 (t, J=6.4 Hz, 3H), 3.99 (t, J=6.4 Hz, 3H), 3.83 (s, 3H), 3.77 (s, 3H), 3.63 (bs, 1H), 2.68 (br s, 4H), 1.97-1.89 (m, 4H), 1.69-1.61 (m, 2H), 0.87 (s, 18H), 0.02 (br s, 12H).

<Example 3> Preparation of Compound 12

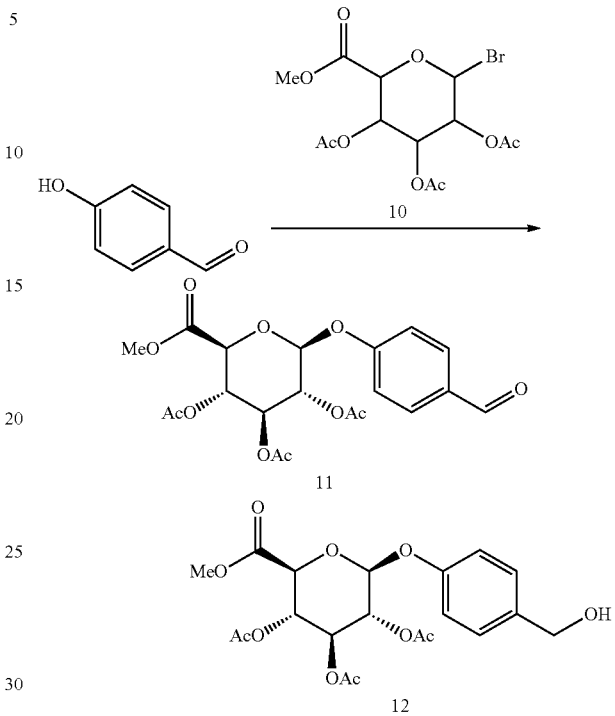

Preparation of Compound 11

In acetonitrile (40 mL), 4-hydroxybenzaldehyde (475 mg, 3.89 mmol) and Compound 10 (1.7 g, 4.28 mmol, Compound 10 was prepared by the method described in Korean Patent No. 1,628,872) were dissolved, then 4 Å molecular sieves (4 g) and silver(I) oxide (3.6 g, 15.6 mmol) were added thereto, and the mixture was stirred at room temperature for 3 hours under a nitrogen atmosphere. The reaction solution was concentrated under reduced pressure, diluted with distilled water (40 mL), and the subjected to extraction using ethyl acetate (2×50 mL). The organic layer extracted was dried over anhydrous sodium sulfate, filtered, concentrated under reduced pressure, and then purified by column chromatography to obtain Compound 11 (1.3 g, 69%).

$^1$H-NMR (400 MHz, CDCl$_3$) δ 9.93 (s, 1H), 7.86 (d, J=8 Hz, 2H), 7.11 (d, J=8.4 Hz, 2H), 5.38-5.29 (m, 4H), 4.25-4.23 (m, 1H), 3.71 (s, 3H), 2.06 (s, 9H).

Preparation of Compound 12

Compound 11 (1.3 g, 2.96 mmol) was dissolved in chloroform/isopropanol (50 mL/10 mL), then silica gel (1.3 g) and sodium borohydride (134 mg, 3.55 mmol) were added thereto at 0° C. under a nitrogen atmosphere, and the mixture was then stirred for 2 hours. Distilled water (40 mL) was added to the reaction solution, and the mixture was subjected to extraction using ethyl acetate (2×50 mL). The organic layer extracted was dried over anhydrous sodium sulfate, filtered, concentrated under reduced pressure, and then purified by column chromatography to obtain Compound 12 (600 mg, 45%).

$^1$H-NMR (400 MHz, CDCl$_3$) δ 7.31 (d, J=8.4 Hz, 2H), 6.99 (d, J=8.4 Hz 2H), 5.35-5.26 (m, 3H), 5.13 (d, J=7.6 Hz, 1H), 4.64 (d, J=5.6 Hz, 2H), 4.18-4.16 (m, 1H), 3.73 (s, 3H), 2.06-2.04 (m, 9H), 1.61 (t, J=5.6 Hz, 1H).

<Example 4> Preparation of Compound 15

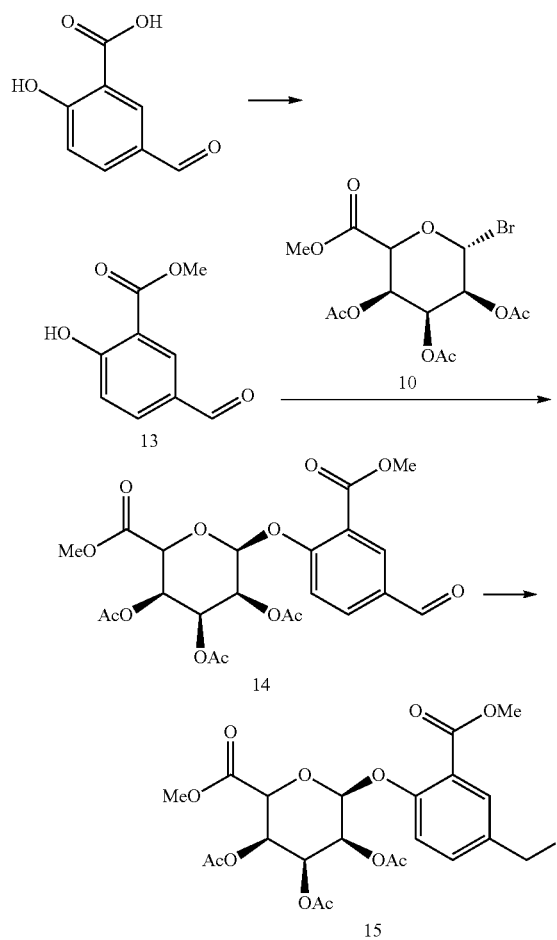

Preparation of Compound 13

In methanol (50 mL), 5-formylsalicylic acid (5.0 g, 30.1 mmol) was dissolved, and concentrated sulfuric acid (2 mL) was added thereto. The reaction solution was heated under reflux for 24 hours, then concentrated under reduced pressure, and diluted with ethyl acetate (100 mL). The organic layer was washed with distilled water (100 mL), saturated aqueous sodium hydrogencarbonate solution (200 mL), and brine (200 mL), and then dried over anhydrous sodium sulfate. The resultant was filtered, then concentrated, and vacuum dried to obtain Compound 13 (4.62 g, 85%) as a white solid.

$^1$H-NMR (400 MHz, CDCl$_3$) δ 11.36 (s, 1H), 9.88 (s, 1H), 8.38 (d, J=2.4 Hz, 1H), 8.00 (dd, J=8.4 Hz, J=2 Hz, 1H), 7.11 (d, J=8.8 Hz, 1H), 4.01 (s, 3H).

Preparation of Compound 14

Compound 13 (1.7 g, 9.38 mmol) and Compound 10 (4.1 g, 10.3 mmol) were dissolved in acetonitrile (50 mL), then 4 Å molecular sieves (4 g) and silver(I) oxide (8.7 g, 37.5 mmol) were added thereto, and the mixture was stirred at room temperature for 3 hours under a nitrogen atmosphere. The reaction solution was concentrated under reduced pressure, diluted with distilled water (50 mL), and then subjected to extraction using ethyl acetate (2×50 mL). The organic layer extracted was dried over anhydrous sodium sulfate, filtered, concentrated under reduced pressure, and then purified by column chromatography to obtain Compound 14 (2.85 g, 61%).

$^1$H-NMR (400 MHz, CDCl$_3$) δ 9.95 (s, 1H), 8.29 (d, J=2 Hz, 1H), 8.01 (dd, J=8.4 Hz, J=2 Hz, 1H), 7.26 (d, J=8.8 Hz, 1H), 5.42-5.30 (m, 4H), 4.27 (d, J=9.2 Hz, 1H), 3.89 (s, 3H), 3.72 (s, 3H), 2.08 (s, 3H), 2.07 (s, 3H), 2.06 (s, 3H).

Preparation of Compound 15

Compound 14 (2.85 g, 5.74 mmol) was dissolved in chloroform: isopropanol (50 mL/10 mL), then silica gel (2.8 g) and sodium borohydride (434 mg, 11.5 mmol) were added thereto at 0° C. under a nitrogen atmosphere, and the mixture was stirred for 2 hours. Distilled water (40 mL) was added to the reaction solution, and the mixture was subjected to extraction using dichloromethane (2×50 mL). The organic layer extracted was dried over anhydrous sodium sulfate, filtered, concentrated under reduced pressure, and then purified by column chromatography to obtain Compound 15 (1.42 g, 49%).

<Example 5> Preparation of Compound 20

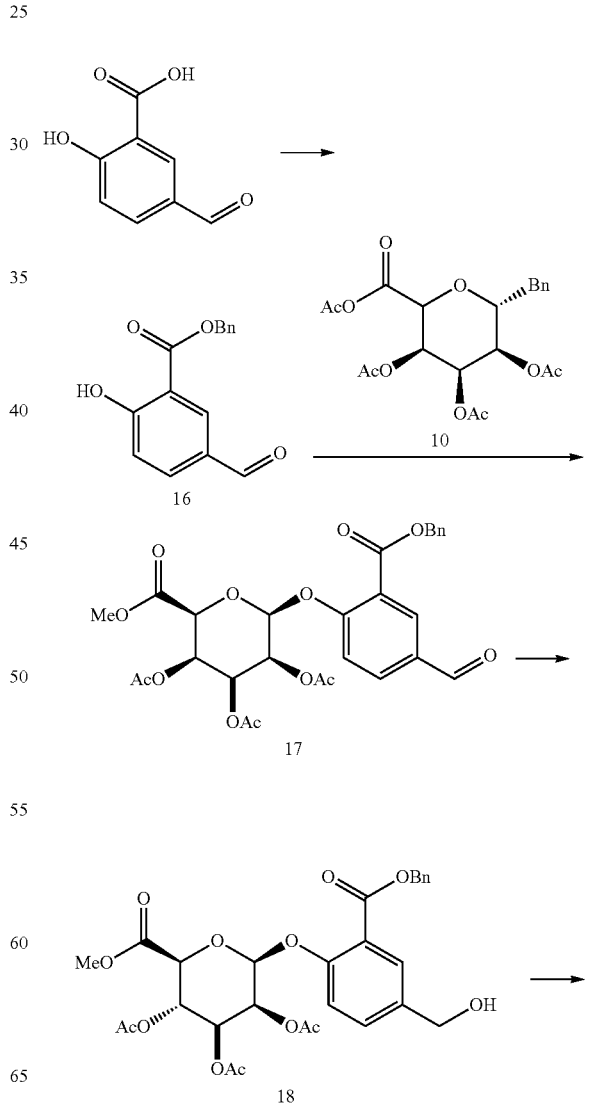

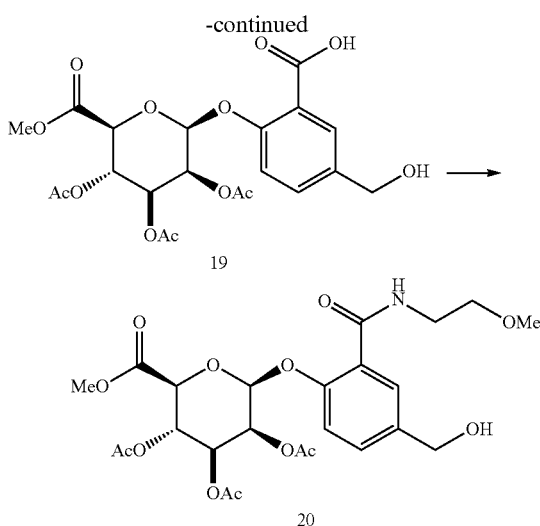

19

20

Preparation of Compound 16

With tetrahydrofuran (30 mL), 5-formylsalicylic acid (10.0 g, 60.1 mmol) was diluted, and then N,N-diisopropylethylamine (29.8 mL, 180 mmol) and benzyl bromide (7.15 mL, 60.1 mmol) were added thereto at room temperature. The reaction solution was heated under reflux for 18 hours, then the temperature was lowered to room temperature, and a 2 N aqueous hydrochloric acid solution (100 mL) was added thereto. The mixture was subjected to extraction using ethyl acetate (2×100 mL), and the combined organic layers were dried over anhydrous sodium sulfate. The resultant was filtered, then concentrated under reduced pressure, and purified by column chromatography to obtain Compound 16 (12.9 g, 83%).

$^1$H-NMR (400 MHz, CDCl$_3$) δ 11.38 (s, 1H), 9.86 (s, 1H), 8.40 (s, 1H), 8.01 (d, J=8.8 Hz, 1H), 7.44 (m, 5H), 7.12 (d, J=8.0 Hz, 1H), 5.42 (s, 2H).

Preparation of Compound 17

Compound 16 (5.0 g, 19.5 mmol) and Compound 10 (8.5 g, 21.4 mmol) were dissolved in acetonitrile (100 mL), 4 Å molecular sieves (10 g) and silver(I) oxide (18.0 g, 78.0 mmol) were added thereto, and the mixture was stirred at room temperature for 12 hours under a nitrogen atmosphere. The reaction solution was concentrated under reduced pressure, diluted with distilled water (100 mL), and subjected to extraction using ethyl acetate (2×200 mL). The organic layer extracted was dried over anhydrous magnesium sulfate, filtered, concentrated under reduced pressure, and then purified by column chromatography to obtain Compound 17 (8.63 g, 77%).

$^1$H-NMR (400 MHz, CDCl$_3$) δ 9.94 (s, 1H), 8.28 (s, 1H), 8.02 (d, J=8.8 Hz, 1H), 7.46-7.28 (m, 6H), 5.41-5.32 (m, 6H), 4.27 (d, J=9.2 Hz, 1H), 3.71 (s, 3H), 2.06-2.04 (m, 9H).

Preparation of Compound 18

Compound 17 (3.10 g, 5.41 mmol) was dissolved in chloroform/isopropanol (45 mL/9 mL), then silica gel (3 g) and sodium borohydride (0.41 g, 10.8 mmol) were added thereto at 0° C. under a nitrogen atmosphere, and the mixture was stirred for 2 hours. Distilled water (100 mL) was added to the reaction solution, and then the mixture was subjected to extraction using ethyl acetate (200 mL). The organic layer extracted was dried over anhydrous magnesium sulfate, filtered, concentrated under reduced pressure, and then purified by column chromatography to obtain Compound 18 (2.73 g, 87%) as a white solid.

$^1$H-NMR (400 MHz, CDCl$_3$) δ 7.74 (s, 1H), 7.48-7.34 (m, 6H), 7.16 (d, J=8.8 Hz, 1H), 5.35-5.26 (m, 5H), 5.16-5.14 (m, 1H), 4.17-4.15 (m, 1H), 3.73 (s, 3H), 2.04 (s, 9H), 1.73 (t, J=7.2 Hz, 1H).

Preparation of Compound 19

Compound 18 (2.40 g, 4.17 mmol) was dissolved in ethanol (150 mL) and then Raney nickel (240 mg) was added thereto. The reaction solution was stirred at room temperature for 10 minutes under a hydrogen atmosphere. The reaction solution was filtered through Celite and concentrated to obtain Compound 19 (2.10 g) as a white solid.

$^1$H-NMR (400 MHz, CDCl$_3$) δ 8.06 (s, 1H) 7.61 (d, J=8.8 Hz, 1H), 7.23 (d, J=8.0 Hz 1H), 5.43-5.29 (m, 5H), 4.17 (s, 2H), 4.32 (d, J=8.4 Hz, 1H) 3.69 (s, 3H), 2.11-2.08 (m, 9H), 1.24 (t, 1H).

Preparation of Compound 20

Compound 19 (7.0 g, 14.5 mmol) and 2-methoxyethylamine (1.38 mL, 1.59 mmol) were dissolved in N,N-dimethylformamide (14 mL) and then N,N,N',N'-tetramethyl-O-(1H-benzotriazol-1-yl)uronium hexafluorophosphate (6.57 g, 17.3 mmol) and N,N-diisopropylethylamine (5 mL, 28.9 mmol) were added thereto at 0° C. under a nitrogen atmosphere. The reaction solution was stirred at room temperature for 2 hours, then a saturated aqueous ammonium chloride solution (100 mL) was added to the reaction solution, and the mixture was subjected to extraction using ethyl acetate (2×100 mL). The combined organic layers were washed with brine (200 mL) and then dried over anhydrous sodium sulfate. The resultant was filtered, then concentrated, and purified by column chromatography to obtain Compound 20 (7.53 g, 96%).

$^1$H-NMR (400 MHz, CDCl$_3$) b 7.98 (d, J=2 Hz, 1H), 7.49 (br s, 1H), 7.46 (dd, J=8.4 Hz, J=2.4 Hz, 1H), 7.04 (d, J=8.4 Hz, 1H), 5.42-5.28 (m, 4H), 4.66 (s, 1H), 4.19 (d, J=9.2 Hz, 1H), 3.72 (s, 3H), 3.57 (s, 3H), 3.42 (s, 3H), 2.05 (s, 9H).

<Example 6> Preparation of Compound 22

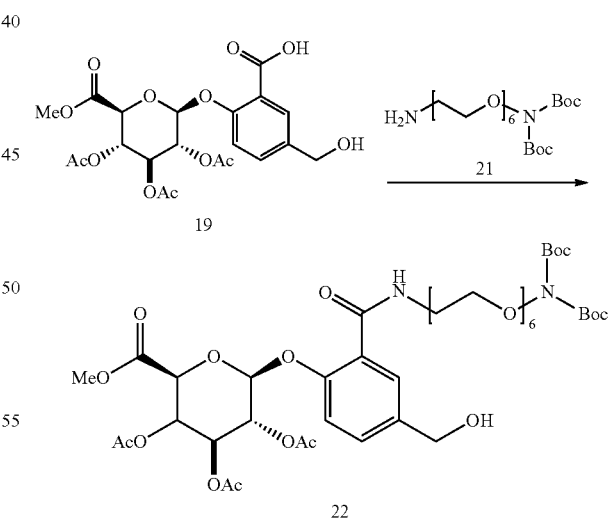

Compound 19 (1.0 g, 2.06 mmol) and Compound 21 (1.49 g, 2.80 mmol, Compound 21 was prepared by the method described in PCT/US2016/063564) were dissolved in N,N-dimethylformamide (10 mL), and then N,N,N',N'-tetramethyl-O-(1H-benzotriazol-1-yl)uronium hexafluorophosphate (1.56 g, 4.12 mmol) and N,N-diisopropylethylamine (1.07 mL, 6.18 mmol) were added thereto at 0° C. under a nitrogen atmosphere. The reaction solution was stirred at room temperature for 12 hours, then a saturated aqueous ammonium chloride solution (100 mL) was added to the reaction solution, and the mixture was subjected to extraction using ethyl acetate (2×100 mL). The combined organic layers were washed with brine (200 mL) and dried over anhydrous sodium sulfate. The resultant was filtered, then concentrated, and purified by column chromatography to obtain Compound 22 (1.6 g, 80%).

$^1$H-NMR (400 MHz, CDCl$_3$) δ 7.98 (s, 1H), 7.46 (dd, J=8.4 Hz, J=2.4 Hz, 1H), 7.41 (br s, 1H), 7.04 (d, J=8.4 Hz, 1H), 5.93-5.25 (m, 4H), 4.67 (d, J=5.2 Hz, 2H), 4.20 (d, J=9.6 Hz, 1H), 4.08 (t, J=4.8 Hz, 2H), 3.74 (s, 6H), 3.72-3.49 (m, 22H), 2.06 (s, 9H), 1.53 (s, 18H).

<Example 7> Preparation of Compound 25

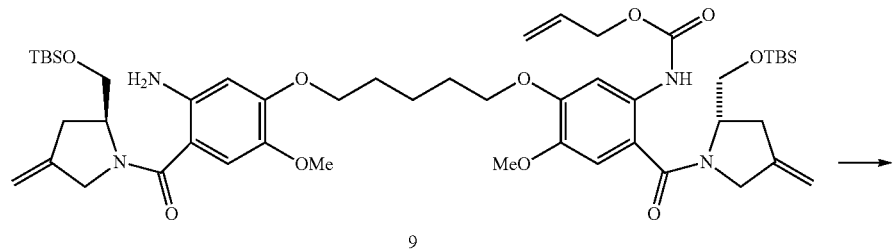

9

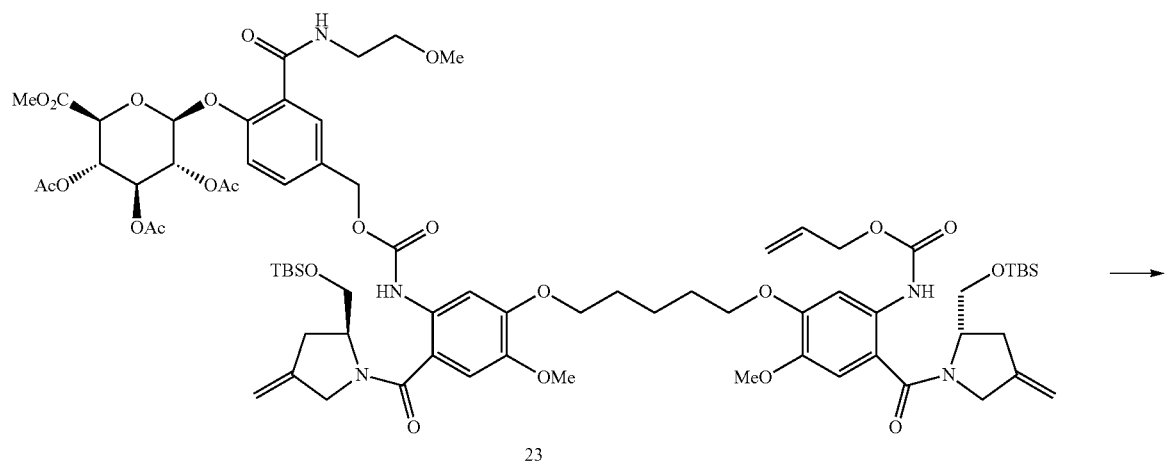

23

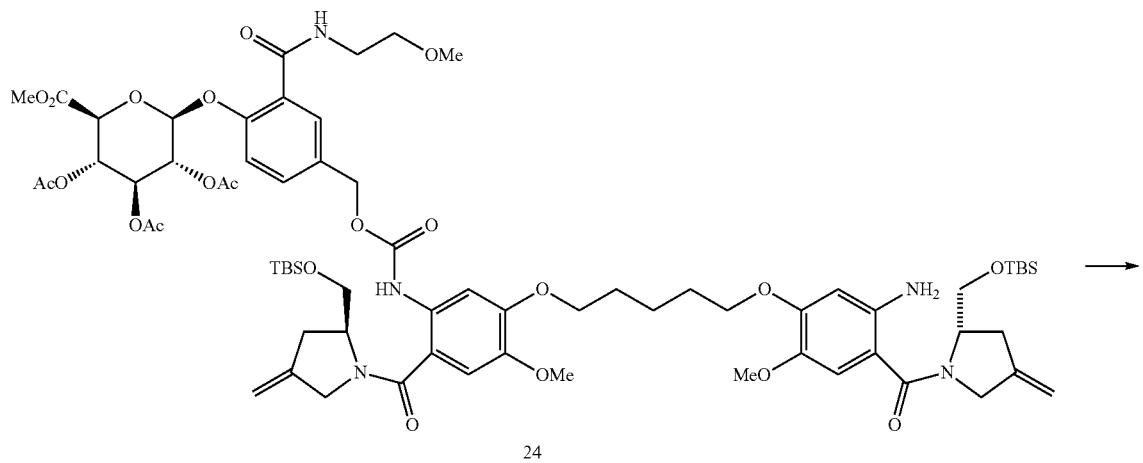

24

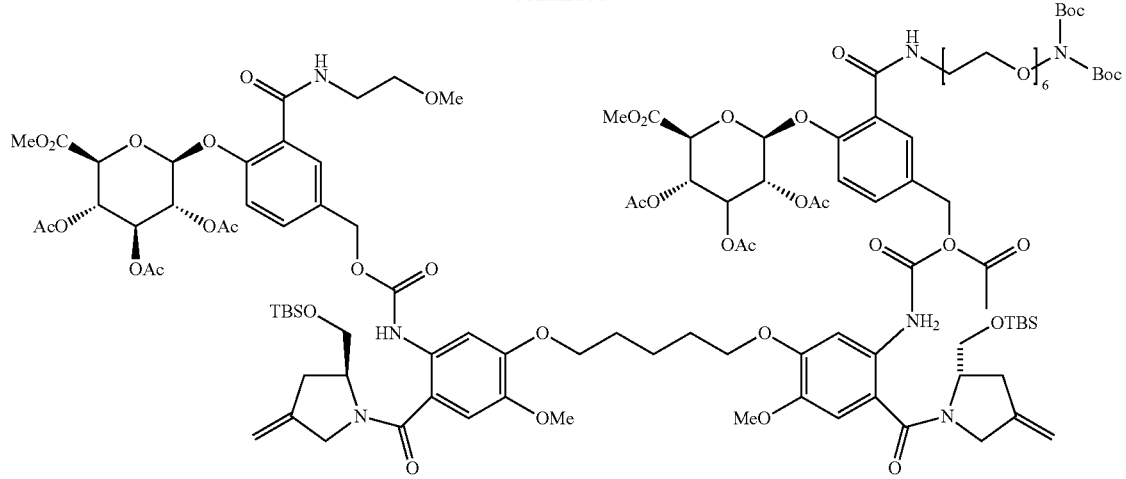

25

Preparation of Compound 23

Compound 9 (2.2 g, 2.34 mmol) was dissolved in toluene (65 mL), then triphosgene (250 mg, 0.84 mmol) and triethylamine (0.44 mL, 3.16 mmol) were added thereto at −10° C., and the mixture was stirred for 1 hour under a nitrogen atmosphere. Compound 20 (1.39 g, 2.58 mmol) was dissolved in dry tetrahydrofuran (65 mL), triethylamine (0.44 mL, 3.16 mmol) was added thereto, and then this solution was gradually added to the reaction solution. After 30 minutes, the reaction solution was heated under reflux and stirred for 4 hours. The reaction solution was concentrated, diluted with dichloromethane (100 mL), washed with brine (50 mL), and dried over anhydrous sodium sulfate. The resultant was filtered, concentrated under reduced pressure, and then purified by column chromatography to obtain Compound 23 (2.5 g, 72%).

EI-MS m/z: [M+H]$^+$ 1504.7, ½[M+H]$^+$ 753.5.

Preparation of Compound 24

Compound 23 (2.0 g, 1.33 mmol) was dissolved in dichloromethane (15 mL), then pyrrolidine (0.13 mL, 1.59 mmol) and tetrakis(triphenylphosphine)palladium(0) (76 mg, 0.066 mmol) were added thereto, and the mixture was stirred at room temperature for 6 hours under a nitrogen atmosphere. The reaction solution was concentrated under reduced pressure and then purified by column chromatography to obtain Compound 24 (1.7 g, 90%).

EI-MS m/z: [M+H]$^+$ 1420.6, ½[M+H]$^+$ 711.2.

Preparation of Compound 25

Compound 24 (1.2 g, 0.84 mmol) was dissolved in toluene (24 mL), triphosgene (90 mg, 0.30 mmol) and pyridine (0.33 mL, 4.22 mmol) were added thereto at −10° C., and the mixture was stirred for 1 hour under a nitrogen atmosphere. Compound 22 (974 mg, 1.01 mmol) was dissolved in dry tetrahydrofuran (24 mL), N,N-diisopropylethylamine (0.21 mL, 1.26 mmol) was added thereto, and then this solution was gradually added to the reaction solution. After 30 minutes, the reaction solution was heated under reflux and stirred for 4 hours. The reaction solution was concentrated, diluted with dichloromethane (50 mL), washed with brine (30 mL), and dried over anhydrous sodium sulfate. The resultant was filtered, concentrated under reduced pressure, and then purified by column chromatography to obtain Compound 25 (800 mg, 40%).

EI-MS m/z: [M+H]$^+$ 2409.9, ½[M+Na]$^+$ 1214.3.

<Example 8> Preparation of Compound 28

25 ⟶

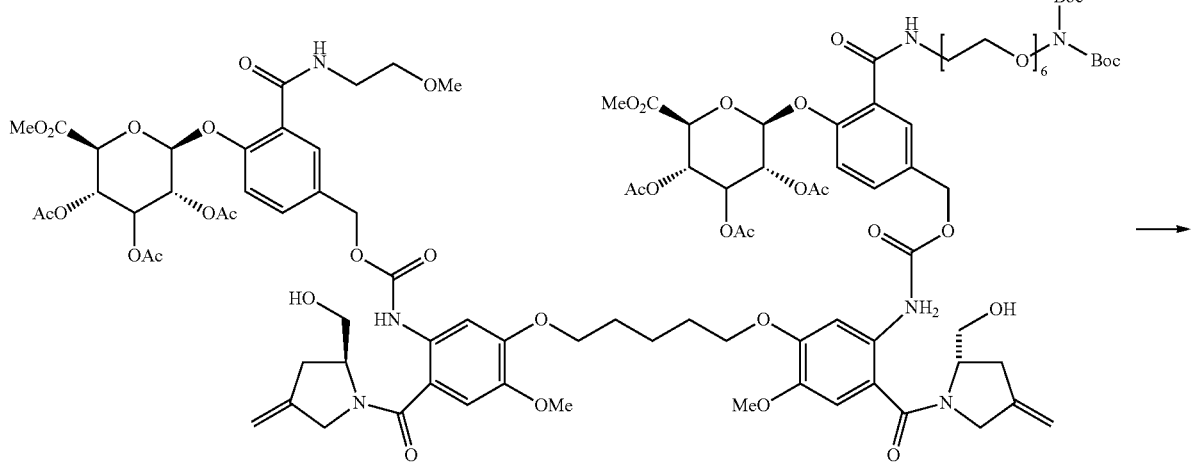

26

-continued

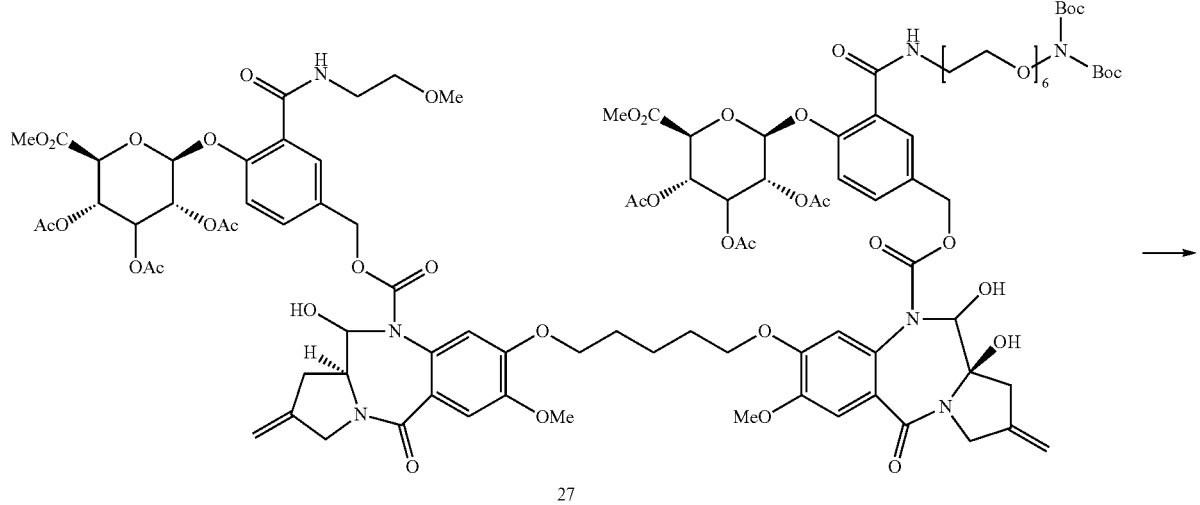

27

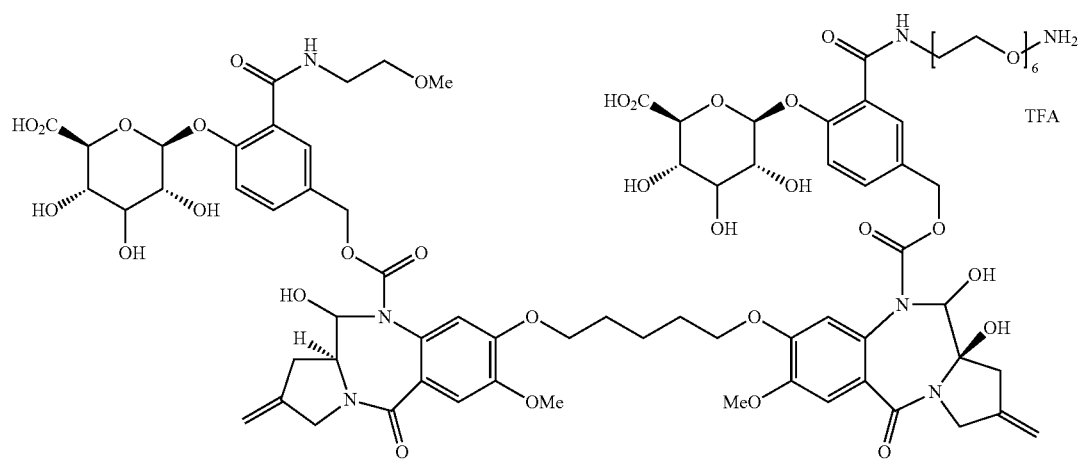

28

Preparation of Compound 26

Compound 25 (800 mg, 0.33 mmol) was dissolved in tetrahydrofuran/distilled water (4 mL/4 mL), acetic acid (8 mL) was added thereto, and then the mixture was stirred at room temperature for 16 hours under a nitrogen atmosphere. The reaction solution was concentrated under reduced pressure and then purified by column chromatography to obtain Compound 26 (660 mg, 90%).

EI-MS m/z: [M+H]$^+$ 2181.6, ½[M-Boc+H]$^+$1041.5.

Preparation of Compound 27

Compound 26 (660 mg, 0.15 mmol) was dissolved in dichloromethane (15 mL), then Dess-Martin periodinane (141 mg, 0.33 mmol) was added thereto, and the mixture was stirred at room temperature for 3.5 hours under a nitrogen atmosphere. The reaction solution was concentrated under reduced pressure and then purified by column chromatography to obtain Compound 27 (477 mg, 70%).

EI-MS m/z: [M+H]$^+$ 2177.6, ½[M+H]$^+$ 1089.5.

Preparation of Compound 28

Compound 27 (150 mg, 0.068 mmol) was dissolved in methanol/tetrahydrofuran (3 mL/3 mL), and then a solution of lithium hydroxide (26 mg, 0.62 mmol) in distilled water (3 mL) was gradually added thereto at −40° C. The mixture was stirred for 2 hours while gradually raising the reaction temperature to 0° C. The reaction solution was neutralized with acetic acid, then concentrated under reduced pressure, and vacuum dried. The solid obtained was diluted with dichloromethane (5 mL), then trifluoroacetic acid (1.2 mL) was added thereto at 0° C., and the mixture was stirred for 2 hours. The reaction solution was concentrated under reduced pressure, then purified by HPLC, and freeze-dried to obtain Compound 28 (20 mg, 16%) as a white solid.

EI-MS m/z: [M+H]$^+$ 1697.5, ½[M+H]$^+$ 849.3.

<Example 9> Preparation of Compound 29
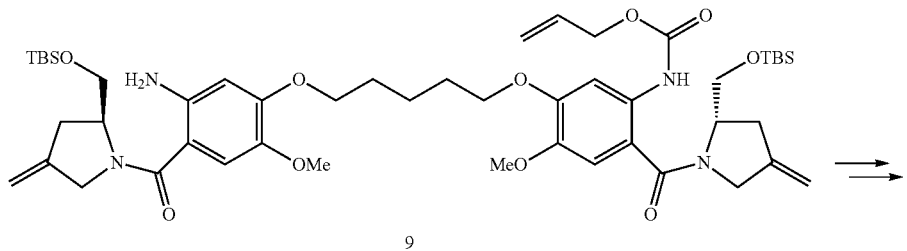
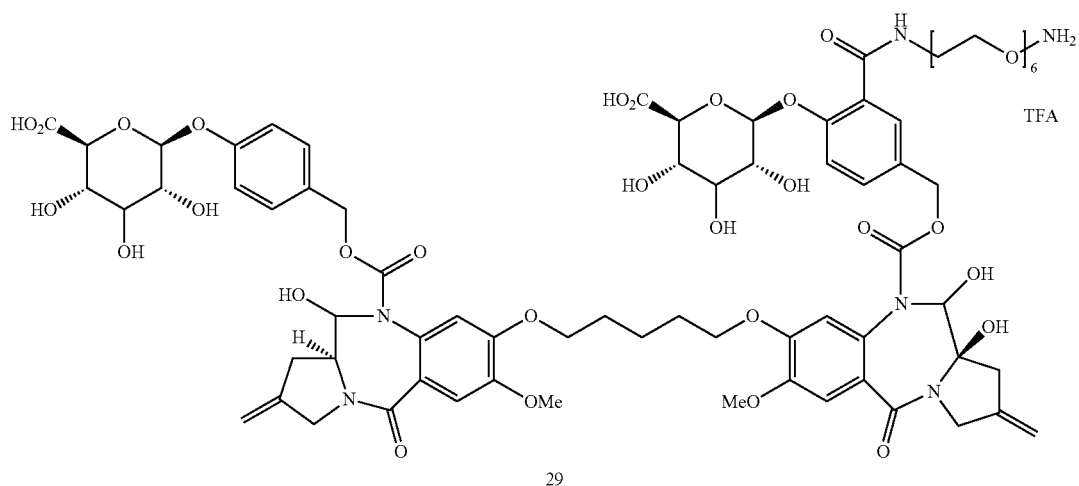
Compound 29 was prepared from Compound 9 and Compound 12 by a method similar to that for the synthesis of Compound 28.
EI-MS m/z: [M+H]$^+$ 1596.9, ½[M+H]$^+$ 799.3.
<Example 10> Preparation of Compound 30
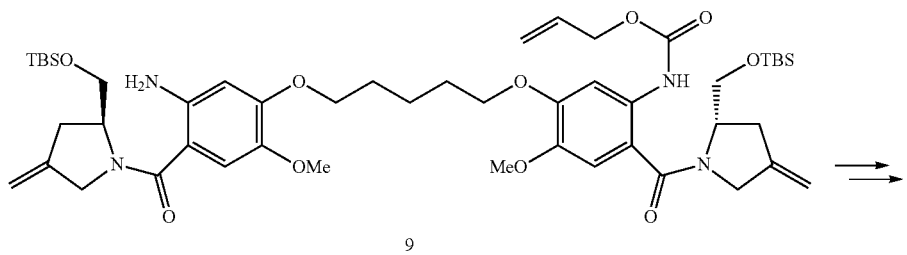

-continued

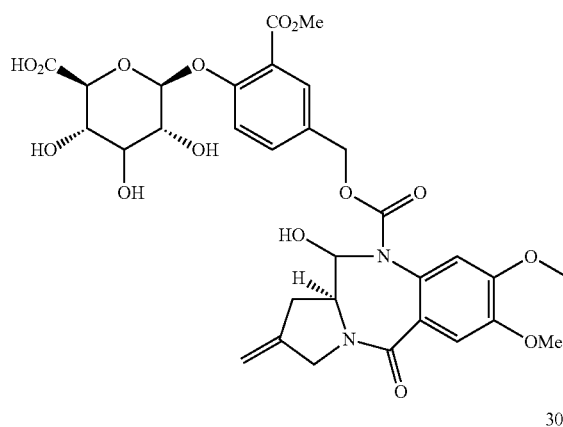
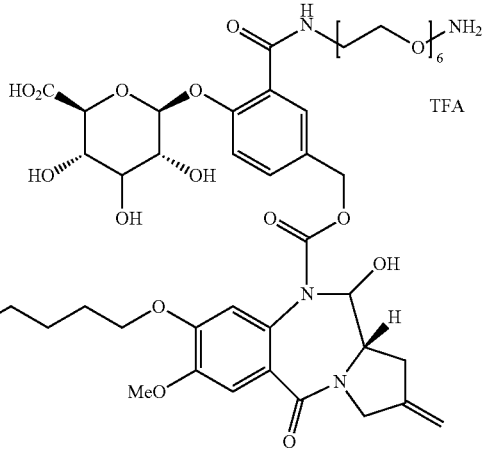

30

Compound 30 was prepared from Compound 9 and Compound 15 by a method similar to that for the synthesis of Compound 28.

<Example 11> Preparation of Compound 32

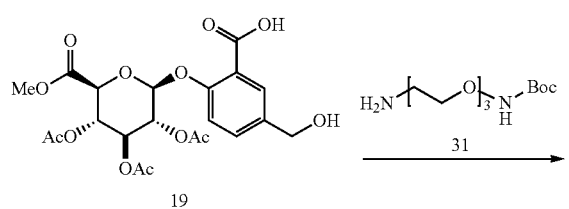

19

-continued

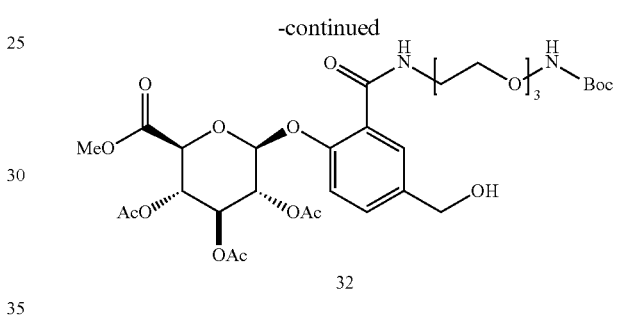

32

Compound 32 was prepared from Compound 19 and Compound 31 (Compound 31 was prepared by the method described in PCT/US2016/063564) by a method similar to that for the synthesis of Compound 22.

$^1$H-NMR (400 MHz, CDCl$_3$) δ 7.97 (s, 1H), 7.46 (dd, J=8.4 Hz, J=2.4 Hz, 1H), 7.41 (bs, 1H), 7.04 (d, J=8.4 Hz, 1H), 5.72 (s, 1H), 5.42-5.27 (m, 4H), 4.66 (d, J=5.2 Hz, 2H), 4.25 (d, J=9.6 Hz, 1H), 3.97 (t, J=4.8 Hz, 2H), 3.78 (s, 3H), 3.74-3.64 (m, 10H), 2.04 (s, 9H), 1.53 (s, 9H). EI-MS m/z: [M+H]$^+$ 731.5.

<Example 12> Preparation of Compound 34

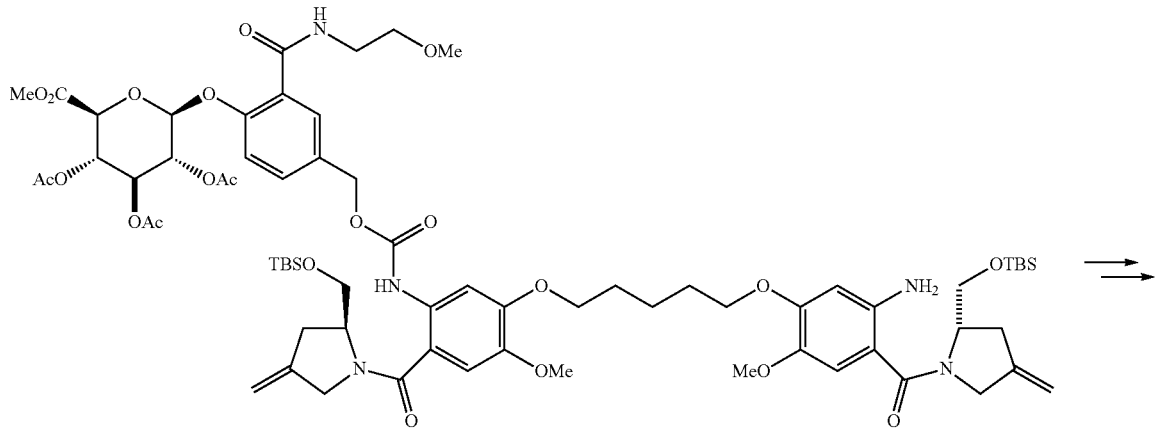

24

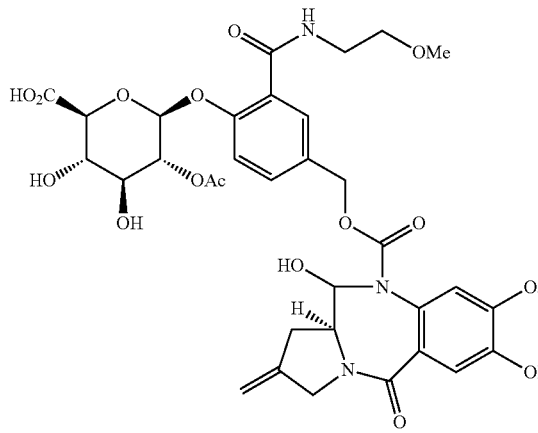
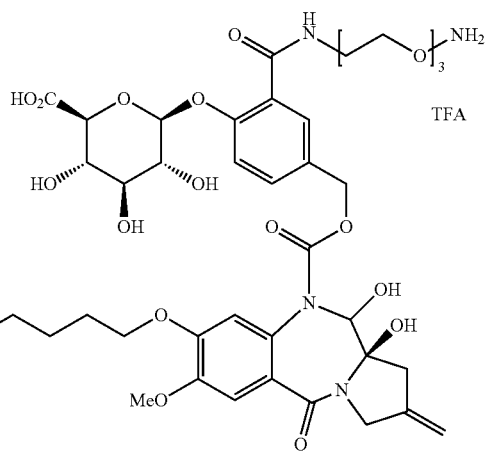
34
Compound 34 was prepared from Compound 24 and Compound 32 by a method similar to that for the synthesis of Compound 28.
EI-MS m/z: [M+H]$^+$ 1565.5, ½[M+H]$^1$ 783.4.
<Example 13> Preparation of Compound 39
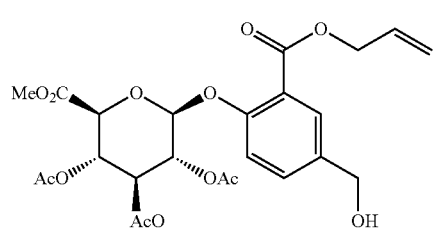
35
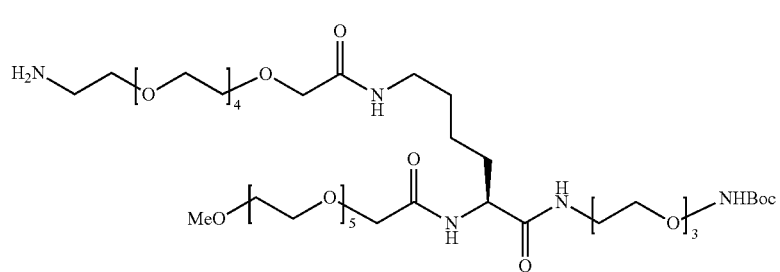
36
Compound 35 and Compound 36 were prepared by the method described in PCT/US2016/063564.

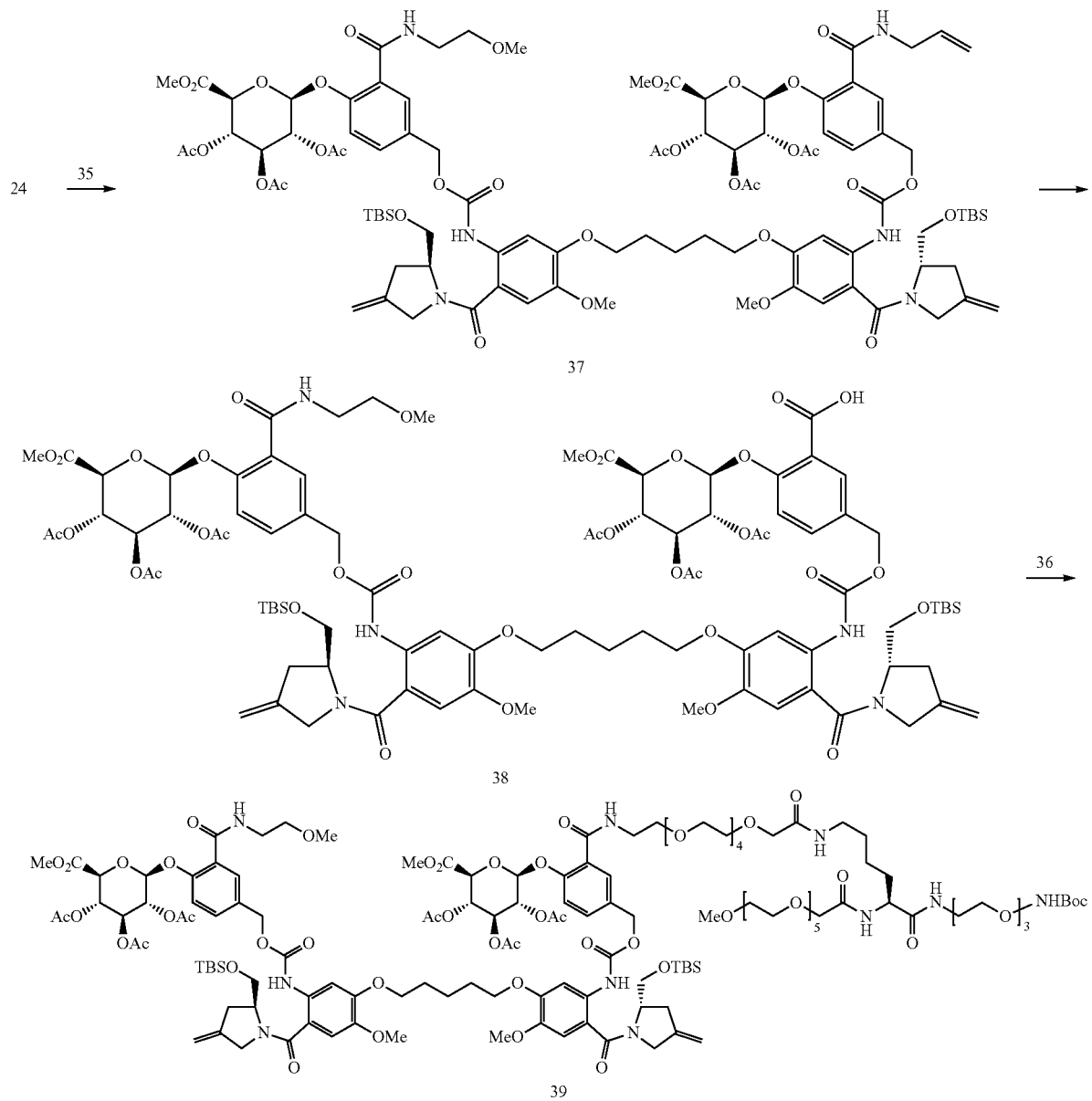

Preparation of Compound 37

Compound 24 (400 mg, 0.28 mmol) was dissolved in toluene (10 mL), then triphosgene (30 mg, 0.10 mmol) and triethylamine (0.053 mL, 0.38 mmol) were added thereto at −10° C., and the mixture was stirred for 1 hour under a nitrogen atmosphere. Compound 35 (177 mg, 0.33 mmol) was dissolved in dry tetrahydrofuran (10 mL), triethylamine (0.053 mL, 0.38 mmol) was added thereto, and then this solution was gradually added to the reaction solution. After 30 minutes, the reaction solution was heated under reflux and stirred for 4 hours. The reaction solution was concentrated, diluted with dichloromethane (50 mL), washed with brine (30 mL), and dried over anhydrous sodium sulfate. The resultant was filtered, concentrated under reduced pressure, and then purified by column chromatography to obtain Compound 37 (192 mg, 34%).

EI-MS m/z: [M+H]$^+$ 1971.8, ½[M+H]$^+$ 986.6.

Preparation of Compound 38

Compound 37 (192 mg, 0.097 mmol) was dissolved in dichloromethane (5 mL), then pyrrolidine (0.012 mL, 0.14 mmol) and tetrakis(triphenylphosphine)palladium(0) (11.2 mg, 0.096 mmol) were added thereto, and the mixture was stirred at room temperature for 6 hours under a nitrogen atmosphere. The reaction solution was concentrated under reduced pressure and then purified by column chromatography to obtain Compound 38 (180 mg, 96%).

EI-MS m/z: [M+H]$^+$ 1932.8, ½[M+H]$^+$ 966.5

Preparation of Compound 39

Compound 38 (180 mg, 0.093 mmol) and Compound 36 (112 mg, 0.116 mmol) were dissolved in N,N-dimethylformamide (2 mL), and then 1-[bis(dimethylamino)methylene]-1H-1,2,3-triazolo[4,5-b]pyridinium 3-oxid hexafluorophosphate (HATU, 46 mg, 0.121 mmol) and N,N-diisopropylethylamine (0.032 mL, 0.186 mmol) were added thereto at 0° C. under a nitrogen atmosphere. The reaction solution was stirred at room temperature for 36 hours, then distilled water (20 mL) was added to the reaction solution, and the mixture was subjected to extraction using ethyl acetate (2×20 mL). The combined organic layers were washed with brine (20 mL) and then dried over anhydrous sodium sulfate. The resultant was filtered, then concentrated, and purified by column chromatography to obtain Compound 39 (133 mg, 50%).

EI-MS m/z: [M+H]$^+$ 2876.4, ½[M+H]$^+$ 1438.6.

<Example 14> Preparation of Compound 42 was stirred at room temperature for 3.5 hours under a nitrogen atmosphere. The reaction solution was concentrated under reduced pressure and then purified by column chromatography to obtain Compound 41 (43 mg, 65%).

EI-MS m/z: [M+H]$^+$ 2643.1, ½[M+H]$^+$ 1322.5.

Preparation of Compound 42

Compound 41 (43 mg, 0.016 mmol) was dissolved in methanol/tetrahydrofuran (0.5 mL/0.5 mL) and then a solution of lithium hydroxide (6.8 mg, 0.16 mmol) in distilled water (0.5 mL) was gradually added thereto at −40° C. The mixture was stirred for 2 hours while gradually raising the

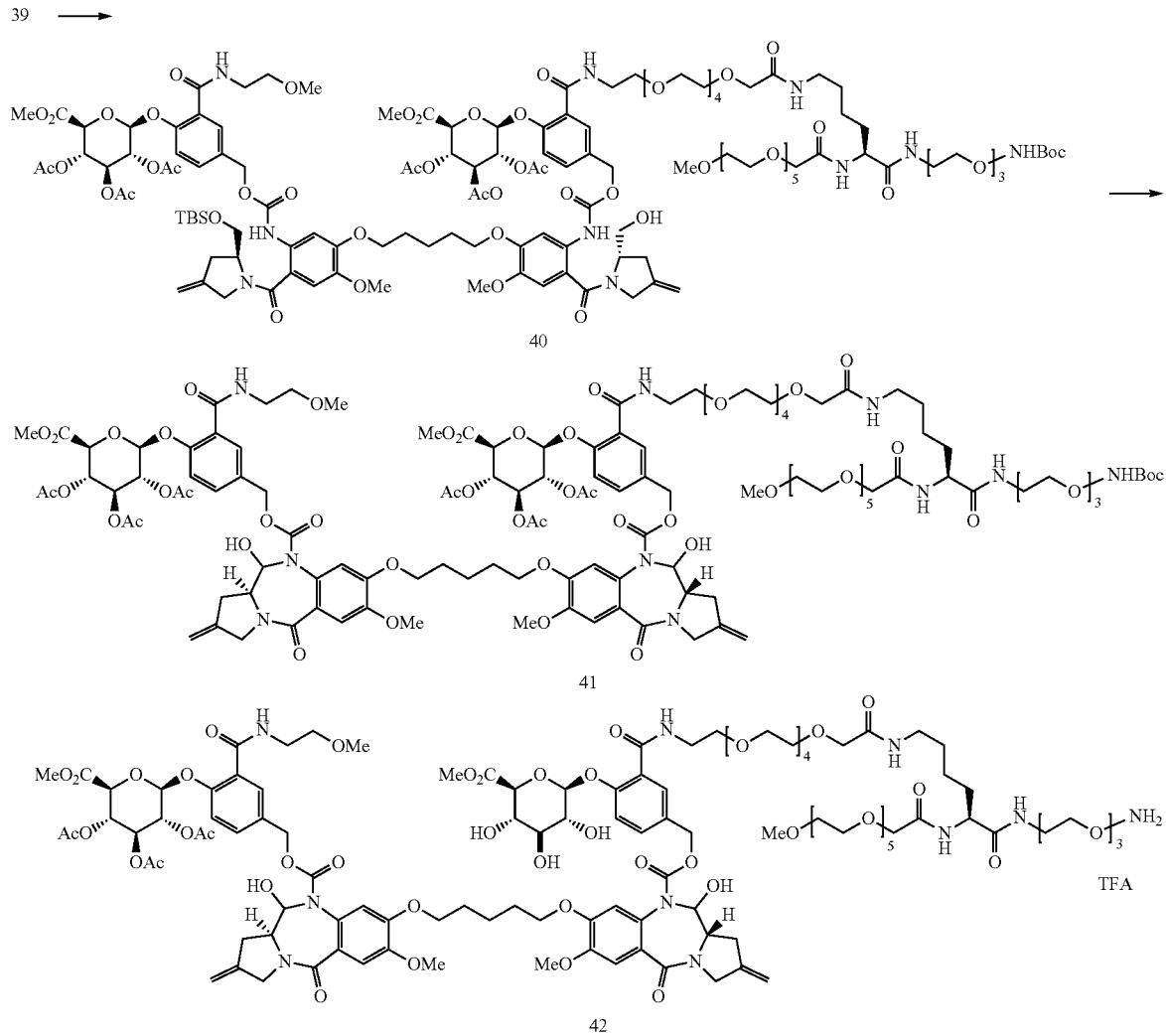

Preparation of Compound 40

Compound 39 (133 mg, 0.046 mmol) was dissolved in tetrahydrofuran/distilled water (1 mL/1 mL), acetic acid (2 mL) was added thereto, and then the mixture was stirred at room temperature for 16 hours under a nitrogen atmosphere. The reaction solution was concentrated under reduced pressure and then purified by column chromatography to obtain Compound (67.4 mg, 55%).

EI-MS m/z: [M+H]$^+$ 2647.4, ½[M+H]$^+$ 1324.5.

Preparation of Compound 41

Compound 40 (67.4 mg, 0.025 mmol) was dissolved in dichloromethane (2 mL), then Dess-Martin periodinane (23.7 mg, 0.056 mmol) was added thereto, and the mixture reaction temperature to −10° C. The reaction solution was neutralized with acetic acid, then concentrated under reduced pressure, and vacuum dried. The solid obtained was diluted with dichloromethane (1 mL), then trifluoroacetic acid (0.2 mL) was added thereto at 0° C., and the mixture was stirred for 2 hours. The reaction solution was concentrated under reduced pressure, then purified by HPLC, and freeze-dried to obtain Compound 42 as a white solid (7.0 mg).

EI-MS m/z: [M+H]$^+$ 2263.4, ½[M+H]$^+$ 1132.3.

<Example 15> Preparation of Compound 48

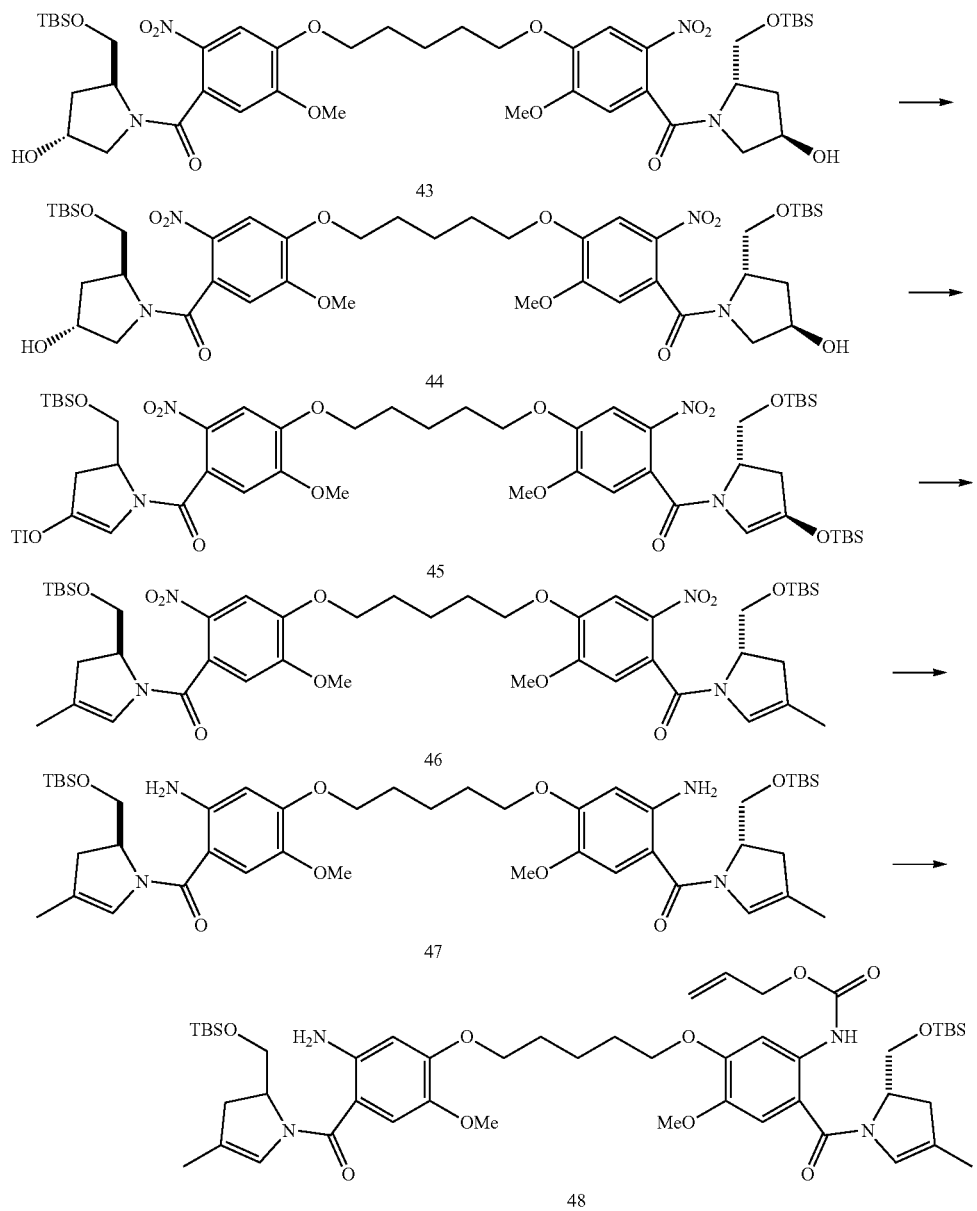

Preparation of Compound 44

Compound 43 (37 g, 40.2 mmol, Compound 43 was prepared by the method described in J. Med. Chem., 2004, 47, 1161-1174) was dissolved in dichloromethane (400 mL), then trichloroisocyanuric acid (14.9 g, 64.3 mmol) and 2,2,6,6-tetramethyl-1-piperidinyloxy (1.3 g, 8.0 mmol) were added thereto at 0° C., and the mixture was stirred for 1 hour under a nitrogen atmosphere. The reaction solution was diluted by addition of dichloromethane (400 mL), washed with a saturated aqueous sodium hydrogencarbonate solution (400 mL), sodium thiosulfate (0.2 M, 400 mL), and brine (200 mL) in this order, and then dried over anhydrous sodium sulfate. The resultant was filtered, then concentrated under reduced pressure, and purified by column chromatography to obtain Compound 44 (35 g, 83%).

$^1$H-NMR (400 MHz, CDCl$_3$) (rotamers) δ 7.72 (s, 2H), 6.73 (s, 2H), 4.97 (d, 2H), 4.31 (d, 2H), 4.12 (t, 4H), 3.95-3.96 (m, 6H), 3.71 (d, 2H), 3.64 (d, 2H), 3.45 (d, 2H), 2.82-2.75 (m, 2H), 2.55 (d, 2H), 1.99 (m, 4H), 1.72 (m, 2H), 0.85 (s, 18H), 0.08 (d, 12H).

Preparation of Compound 45

Compound 44 (5 g, 5.45 mmol) was dissolved in dichloromethane (90 mL), then 2,6-lutidine (5.1 ml, 43.8 mmol) and triflic anhydride (5.5 ml, 39.0 mmol) were added thereto at −40° C., and the mixture was stirred for 1 hour under a nitrogen atmosphere. The reaction solution was diluted by addition of dichloromethane (90 mL), washed with a saturated aqueous sodium hydrogencarbonate solution (90 mL), distilled water (90 mL), and brine (90 mL), and then dried over anhydrous sodium sulfate. The resultant was filtered, then concentrated under reduced pressure, and purified by column chromatography to obtain Compound 45 (4.0 g, 62%).

¹H-NMR (400 MHz, CDCl₃) (rotamers) δ 7.71 (s, 2H), 6.77 (s, 2H), 6.08 (s, 2H), 4.79-4.78 (m, 2H), 4.18-4.09 (m, 6H), 4.02-3.92 (m, 8H), 3.22-3.14 (m, 2H), 3.01-2.97 (m, 2H), 2.02-1.97 (m, 4H), 0.91 (s, 18H), 0.11 (s, 12H).

Preparation of Compound 46

Compound 45 (3.1 g, 2.6 mmol) was dissolved in toluene (45 mL), then methylboronic acid (1.1 g, 18.2 mmol), silver(I) oxide (4.8 g, 20.9 mmol), potassium phosphate (6.6 g, 31.5 mmol), triphenylarsine (642 mg, 2.1 mmol), and bis(triphenylphosphine)palladium(II) dichloride (184 mg, 0.3 mmol) were added thereto under an argon atmosphere, and the mixture was heated and stirred at 80° C. for 3 hours. The reaction solution was filtered through Celite, then concentrated, and purified by column chromatography to obtain Compound 46 (955 mg, 40%).

¹H-NMR (400 MHz, CDCl₃) (rotamers) δ 7.68 (s, 2H), 6.77 (s, 2H), 5.52 (s, 2H), 4.66-4.64 (m, 2H), 4.14-4.07 (m, 6H), 3.94-3.92 (m, 8H), 2.75-2.73 (m, 2H), 2.55-2.51 (m, 2H), 1.99-1.93 (m, 4H), 1.72-1.68 (m, 2H), 1.60 (s, 6H), 0.88 (s, 18H), 0.09 (s, 12H).

Preparation of Compound 47

Compound 46 (2.9 g, 3.17 mmol) was dissolved in ethanol (44 mL), and then zinc dust (12.9 g, 197 mmol) and formic acid (5% ethanol solution, 128 mL) were added thereto. The reaction solution was stirred at room temperature for 15 minutes and then filtered through Celite, and ethyl acetate (500 mL) was added thereto. The organic layer was washed with distilled water (200 mL), a saturated aqueous sodium hydrogencarbonate solution (200 mL), and brine (200 mL) in this order and then dried over anhydrous sodium sulfate. The resultant was filtered, then concentrated, and purified by column chromatography to obtain Compound 47 (3.0 g, 82%).

¹H-NMR (400 MHz, CDCl₃) (rotamers) δ 6.74 (s, 2H), 6.23 (s, 2H), 6.18 (bs, 2H), 4.64 (bs, 2H), 4.34 (s, 3H), 4.07-3.93 (m, 6H), 3.80-3.76 (m, 7H), 2.74-2.68 (m, 2H), 2.53 (d, 2H), 1.91 (m, 4H), 1.67-1.62 (m, 8H), 0.88 (s, 18H), 0.05 (d, 12H).

Preparation of Compound 48

Compound 47 (3.0 g, 3.51 mmol) was dissolved in dichloromethane (175 mL), and then pyridine (0.57 mL, 7.03 mmol) and allyl chloroformate (0.34 mL, 3.16 mmol) were added thereto at −78° C. under a nitrogen atmosphere. The reaction solution was stirred for 1 hour, then the reaction temperature was raised to room temperature, and the reaction solution was concentrated and then purified by column chromatography to obtain Compound 48 (1.33 g, 44%).

¹H-NMR (400 MHz, CDCl₃) (rotamers) δ 8.80 (br s, 1H), 7.82 (s, 1H), 6.78 (s, 1H), 6.74 (s, 1H), 6.23 (s, 1H), 6.19 (br s, 2H), 5.99-5.90 (m, 1H), 5.34 (d, 1H), 5.23 (d, 1H), 4.63 (m, 4H), 4.35 (br s, 2H), 4.10 (t, 2H), 3.99 (t, 3H), 3.99 (m, 2H), 3.80 (s, 5H), 3.76 (s, 4H), 2.73 (m, 2H), 2.55 (m, 2H), 1.95-1.90 (m, 4H), 1.68-1.63 (m, 8H), 0.88 (s, 18H), 0.05 (d, 12H).

<Example 16> Preparation of Compound 49

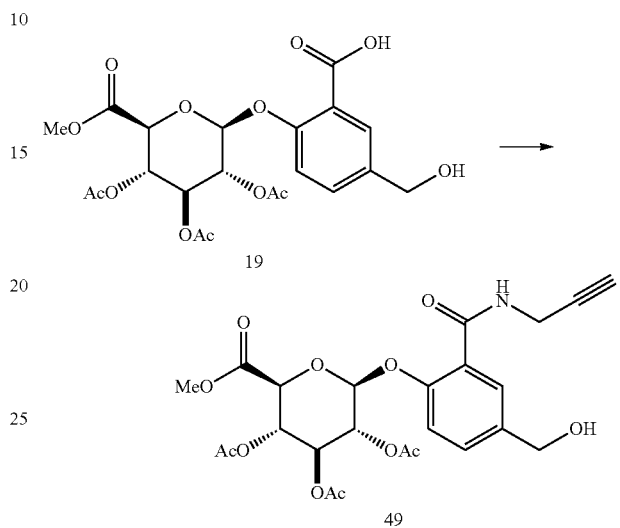

Compound 19 (3.7 g, 7.56 mmol) and propargylamine (0.43 mL, 7.07 mmol) were dissolved in N,N-dimethylformamide (50 mL), and then N-(3-dimethylaminopropyl)-N'-ethylcarbodiimide hydrochloride (2.32 g, 12.1 mmol) and 1-hydroxybenzotriazole (2.04 g, 15.1 mmol) were added thereto. The reaction solution was stirred at room temperature for 12 hours, then distilled water (100 mL) was added to the reaction solution, and the mixture was subjected to extraction using ethyl acetate (2×100 mL). The combined organic layers were washed with brine (200 mL) and then dried over anhydrous sodium sulfate. The resultant was filtered, then concentrated, and purified by column chromatography to obtain Compound 49 (3.4 g, 86%).

¹H-NMR (400 MHz, CDCl₃) δ 8.01 (d, 1H), 7.57 (t, 1H), 7.49 (dd, 1H), 7.02 (d, 1H), 5.42-5.38 (m, 1H), 5.36-5.28 (m, 2H), 4.67 (d, 2H), 4.31-4.13 (m, 3H), 2.23 (t, 1H), 2.07-2.06 (m, 9H), 1.88 (t, 1H).

<Example 17> Preparation of Compound 53

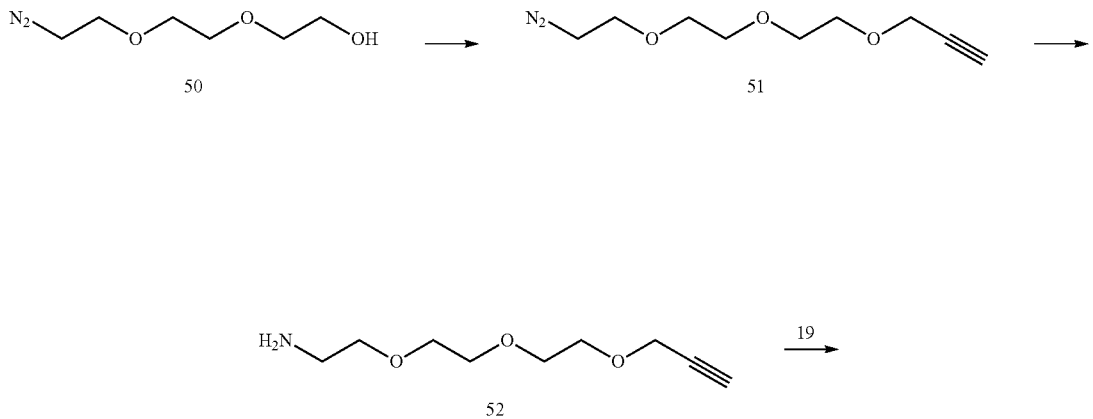

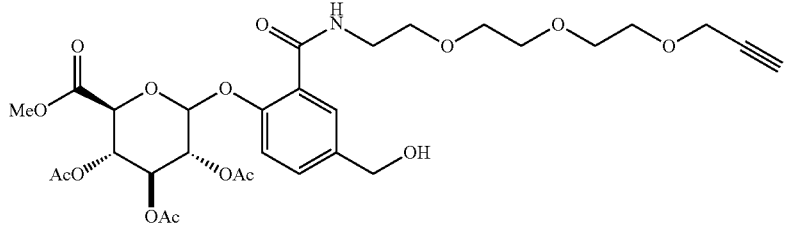

53

Preparation of Compound 51

Compound 50 (4.5 g, 25.68 mmol) was dissolved in N,N-dimethylformamide (50 mL), then sodium hydride (1.23 g, 30.82 mmol) was added thereto at 0° C. under a nitrogen atmosphere, the mixture was stirred for 30 minutes, then propargyl bromide (up to 80% toluene solution, 4.96 mL, 33.4 mmol) was added thereto, and then this mixture was stirred at room temperature for 3 hours. Distilled water (40 mL) was added to the reaction solution, and then the mixture was subjected to extraction using ethyl acetate (2×50 mL). The combined organic layers were washed with brine (100 mL) and then dried over anhydrous sodium sulfate. The resultant was filtered, then concentrated, and purified by column chromatography to obtain Compound 51 (4.35 g, 79%).

$^1$H-NMR (400 MHz, CDCl$_3$) δ 4.21 (d, J=2.4 Hz, 2H), 3.70-3.38 (m, 10H), 3.39 (t, J=5.2 Hz, 2H), 2.43 (t, J=2.4 Hz, 1H).

Preparation of Compound 52

Compound 51 (1.55 g, 7.03 mmol) was dissolved in dry tetrahydrofuran (30 mL)/distilled water (2.53 mL), then triphenylphosphine (2.21 g, 8.44 mmol) was added thereto, and the mixture was stirred at room temperature for 24 hours. The resultant mixture was concentrated and purified by column chromatography to obtain Compound 52 (1.3 g, 99%).

$^1$H-NMR (400 MHz, CDCl$_3$) δ 4.21 (s, 2H), 3.69-3.64 (m, 8H), 3.52-3.49 (m, 2H), 2.88-2.85 (m, 2H), 4.23 (s, 1H). EI-MS m/z: [M+H]$^+$ 188.2.

Preparation of Compound 53

Compound 52 (2.0 g, 10.68 mmol) and Compound 19 (4.7 g, 9.71 mmol) were dissolved in N,N-dimethylformamide (50 mL), and then N,N,N',N'-tetramethyl-O-(1H-benzotriazol-1-yl)uronium hexafluorophosphate (3.71 g, 11.6 mmol) and N,N-diisopropylethylamine (3.38 mL, 19.4 mmol) were added thereto at 0° C. under a nitrogen atmosphere. The reaction solution was stirred at room temperature for 24 hours, then distilled water (100 mL) was added to the reaction solution, and the mixture was subjected to extraction using ethyl acetate (2×100 mL). The combined organic layers were washed with brine (200 mL) and then dried over anhydrous sodium sulfate. The resultant was filtered, then concentrated, and purified by column chromatography to obtain Compound 53 (4.78 g, 75%).

$^1$H-NMR (400 MHz, CDCl$_3$) δ 7.95 (s, 1H), 7.46 (d, J=8.4 Hz, 1H), 7.41-7.37 (m, 1H), 7.04 (d, J=8.8 Hz, 1H), 5.41-5.25 (m, 4H), 4.65 (d, J=4.4 Hz, 2H), 4.21 (d, J=9.2 Hz, 1H), 4.17 (s, 2H), 3.74 (s, 3H), 3.68 (s, 11H), 3.56-3.50 (m, 1H), 2.05 (s, 9H).

<Example 18> Preparation of Compound 55

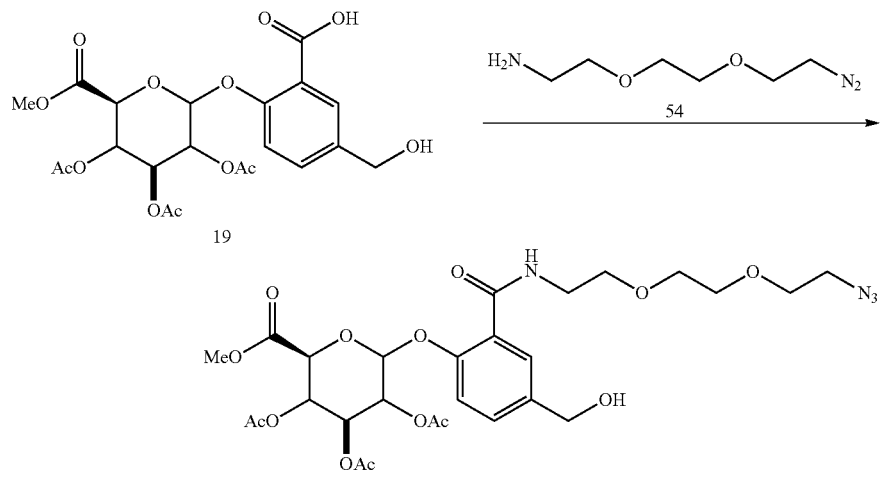

Preparation of Compound 55

Compound 19 (3.68 g, 7.60 mmol) and Compound 54 (1.46 g, 8.40 mmol, Compound 54 was prepared by the method described in PCT/US2016/063564) were dissolved in N,N-dimethylformamide (10 mL), then N,N,N',N'-tetramethyl-O-(1H-benzotriazol-1-yl)uronium hexafluorophosphate (4.53 g, 11.40 mmol) and N,N-diisopropylethylamine (3.97 mL, 22.80 mmol) were added thereto at 0° C. under a nitrogen atmosphere, and then the mixture was stirred at room temperature for 12 hours. A saturated aqueous ammonium chloride solution (100 mL) was added to the reaction solution, the mixture was subjected to extraction using ethyl acetate (2×100 mL), and then the extract was dried over anhydrous sodium sulfate. The resultant was filtered, then concentrated, and purified by column chromatography to obtain Compound 55 (3.31 g, 68%).

$^1$H-NMR (400 MHz, CDCl$_3$) δ 7.99 (s, 1H), 7.47 (d, J=8.4 Hz, 1H), 7.41 (s, 1H), 5.42-5.25 (m, 4H), 4.68 (d, J=5.6 Hz, 2H), 4.20 (d, J=9.2 Hz, 1H), 3.78-3.68 (m, 11H), 3.58-3.52 (m, 1H), 3.39-3.36 (m, 2H), 2.06 (s, 9H), 1.89-1.86 (m, 1H).

<Example 19> Preparation of Compound 58

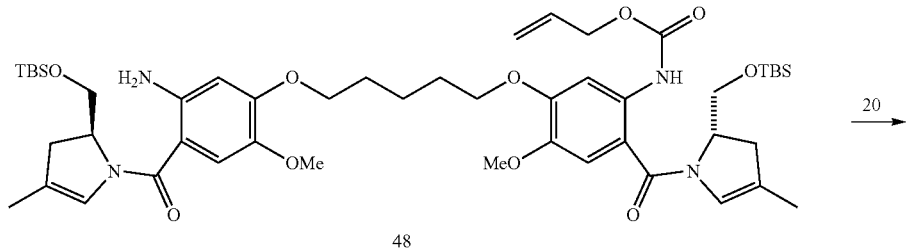

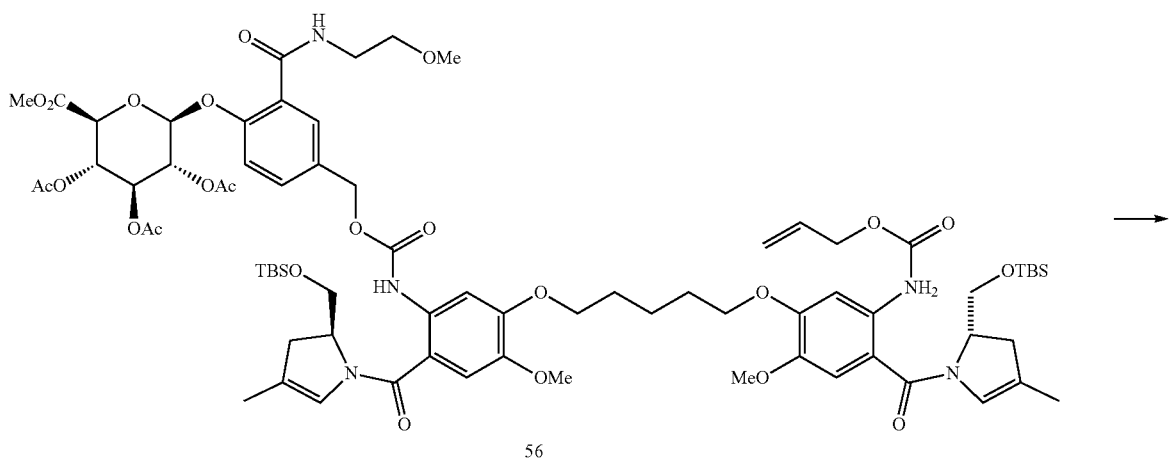

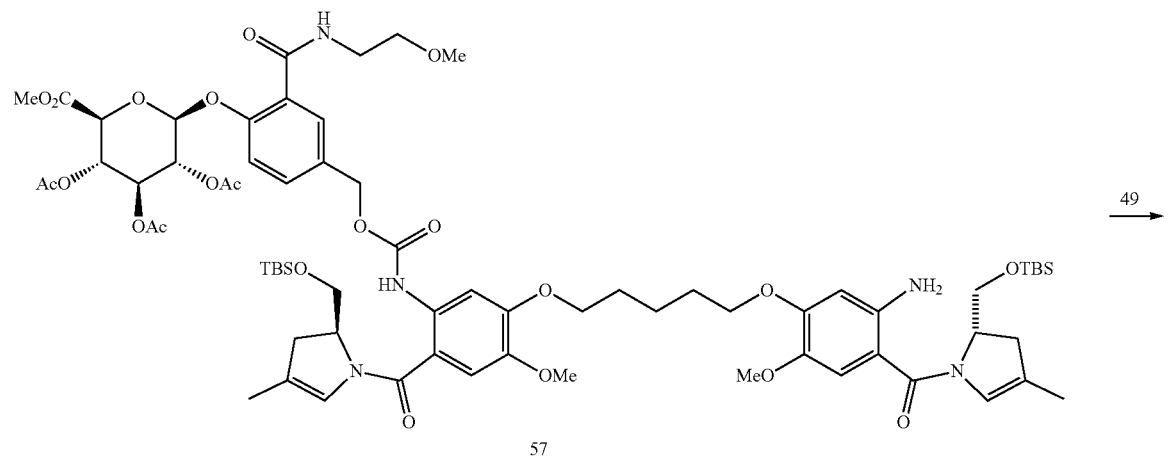

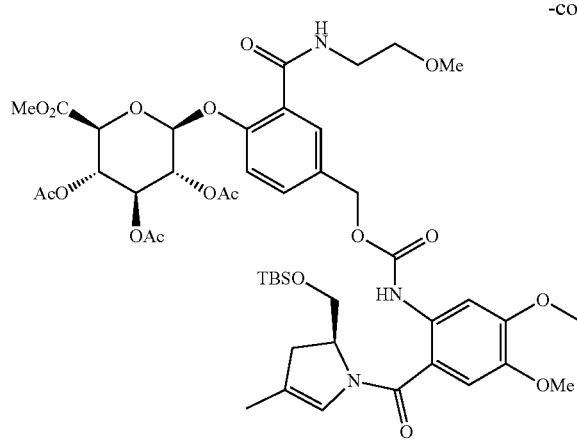
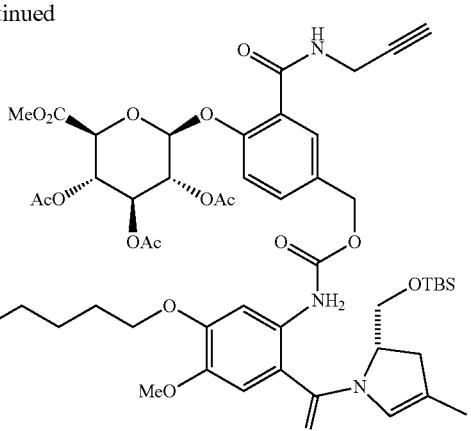

58

Preparation of Compound 56

Compound 48 (1.33 g, 1.41 mmol) was dissolved in toluene (40 mL), then triphosgene (151 mg, 0.51 mmol) and triethylamine (0.26 mL, 1.91 mmol) were added thereto at −10° C., and the mixture was stirred for 1 hour under a nitrogen atmosphere. Compound 20 (845 mg, 1.56 mmol) was dissolved in dry tetrahydrofuran (40 mL), triethylamine (0.26 mL, 1.91 mmol) was added thereto, and then this solution was gradually added to the reaction solution. After 30 minutes, the reaction solution was heated under reflux and stirred for 4 hours. The reaction solution was concentrated, diluted with dichloromethane (30 mL), then washed with brine (20 mL), and dried over anhydrous sodium sulfate. The resultant was filtered, concentrated under reduced pressure, and then purified by column chromatography to obtain Compound 56 (1.15 mg, 54%).

EI-MS m/z: [M+H]$^+$ 1504.7, ½[M+H]$^+$ 753.5.

Preparation of Compound 57

Compound 56 (1.15 g, 0.79 mmol) was dissolved in dichloromethane (10 mL), then pyrrolidine (0.08 mL, 1.35 mmol) and tetrakis(triphenylphosphine)palladium(0) (45 mg, 0.057 mmol) were added thereto, and the mixture was stirred at room temperature for 2 hours under a nitrogen atmosphere. The reaction solution was concentrated under reduced pressure and then purified by column chromatography to obtain Compound 57 (820 mg, 72%).

EI-MS m/z: [M+H]$^+$ 1420.6, ½[M+H]$^+$ 711.2.

Preparation of Compound 58

Compound 57 (730 mg, 0.51 mmol) was dissolved in toluene (20 mL), then triphosgene (54 mg, 0.36 mmol) and pyridine (0.2 mL, 2.56 mmol) were added thereto at −10° C., and the mixture was stirred for 1 hour under a nitrogen atmosphere. Compound 49 (321 mg, 0.61 mmol) was dissolved in dry tetrahydrofuran (20 mL), N,N-diisopropylethylamine (0.14 mL, 0.77 mmol) was added thereto, and then this solution was gradually added to the reaction solution. After 30 minutes, the reaction solution was heated under reflux and stirred for 4 hours. The reaction solution was concentrated, diluted with dichloromethane (50 mL), then washed with brine (30 mL), and dried over anhydrous sodium sulfate. The resultant was filtered, concentrated under reduced pressure, and then purified by column chromatography to obtain Compound 58 (650 mg, 64%).

EI-MS m/z: [M+H]$^+$ 1969.2, ½[M+H]$^+$ 985.2.

<Example 20> Preparation of Compound 61

58 ⟶

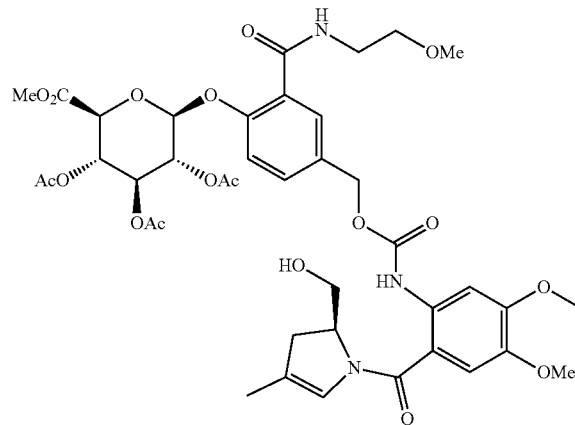
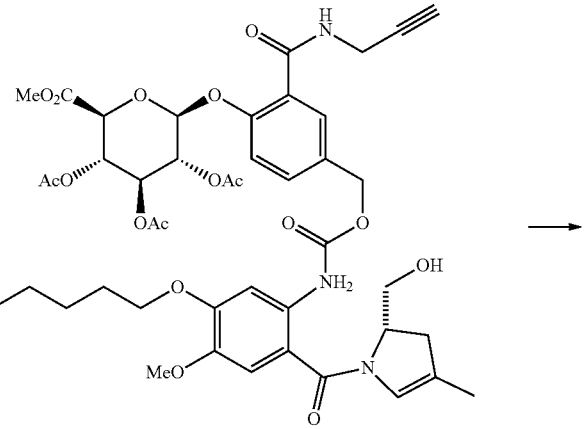

59

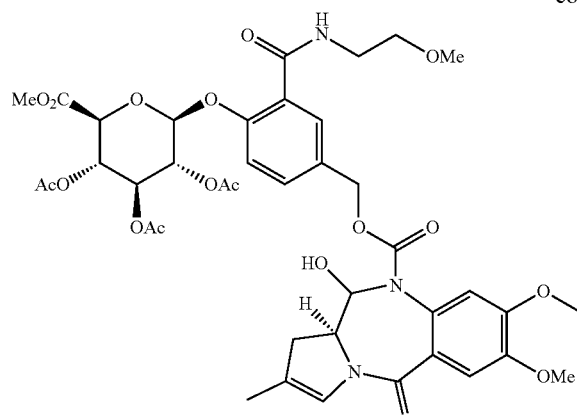

60

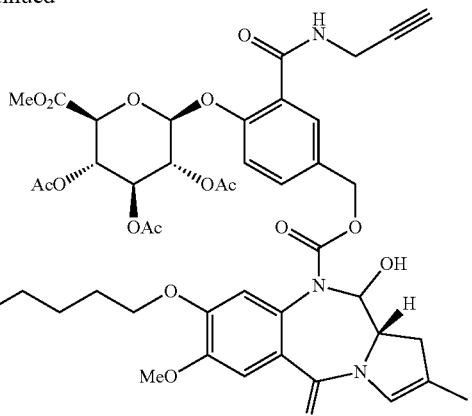 

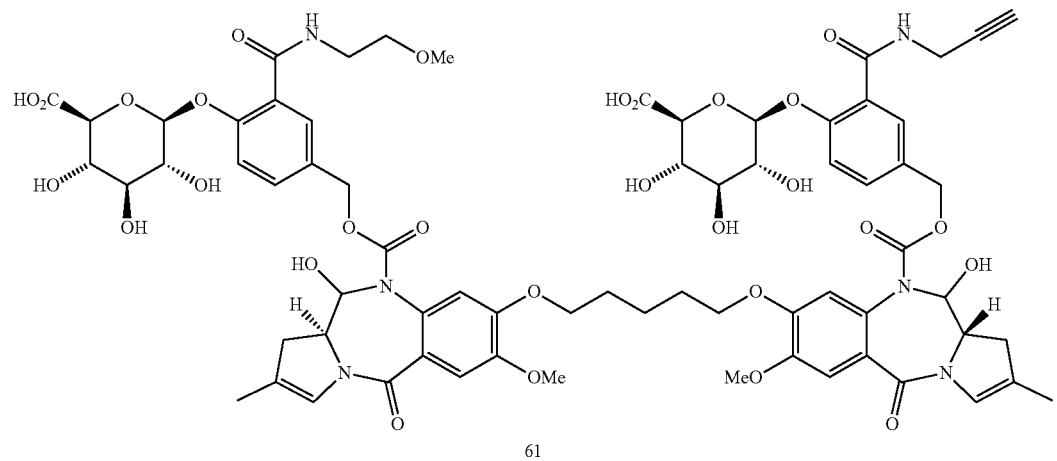

61

Preparation of Compound 59

Compound 58 (650 mg, 0.33 mmol) was dissolved in tetrahydrofuran/distilled water (3.5 mL/3.5 mL), acetic acid (7 mL) was added thereto, and the mixture was stirred at room temperature for 16 hours under a nitrogen atmosphere. The reaction solution was concentrated under reduced pressure and then purified by column chromatography to obtain Compound 59 (440 mg, 78%).

EI-MS m/z: [M+H]$^+$ 1740.0, [M+Na]$^+$ 1762.0, ½[M+H]$^+$ 871.0.

Preparation of Compound 60

Compound 59 (440 mg, 0.25 mmol) was dissolved in dichloromethane (25 mL), then Dess-Martin periodinane (236 mg, 0.55 mmol) was added thereto, and the mixture was stirred at room temperature for 2.5 hours under a nitrogen atmosphere. The reaction solution was concentrated under reduced pressure and then purified by column chromatography to obtain Compound 60 (365 mg, 84%).

EI-MS m/z: [M+H]$^+$ 1736.0, ½[M+H]$^+$ 869.5.

Preparation of Compound 61

Compound 60 (365 mg, 0.21 mmol) was dissolved in methanol/tetrahydrofuran (9 mL/2 mL), and then a solution of lithium hydroxide (58 mg, 1.4 mmol) in distilled water (9 mL) was gradually added thereto at −40° C. The mixture was stirred for 2 hours while gradually raising the reaction temperature to 0° C. The reaction solution was neutralized with acetic acid, then concentrated under reduced pressure, then purified by HPLC, and freeze-dried to obtain Compound 61 (100 mg, 32%) as a white solid.

EI-MS m/z: [M+H]$^+$ 1456.8, ½[M+H]$^+$ 729.5.

<Example 21> Preparation of Compound 62
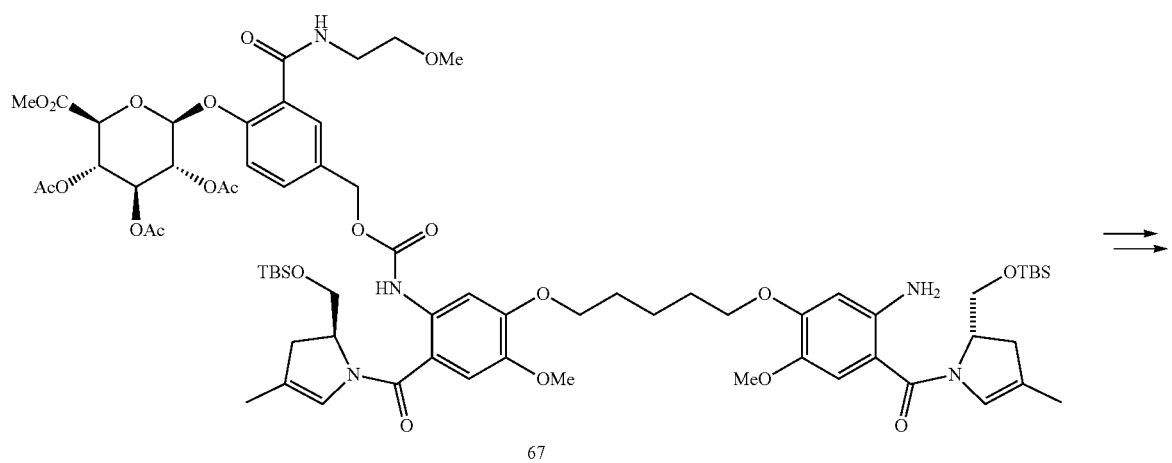
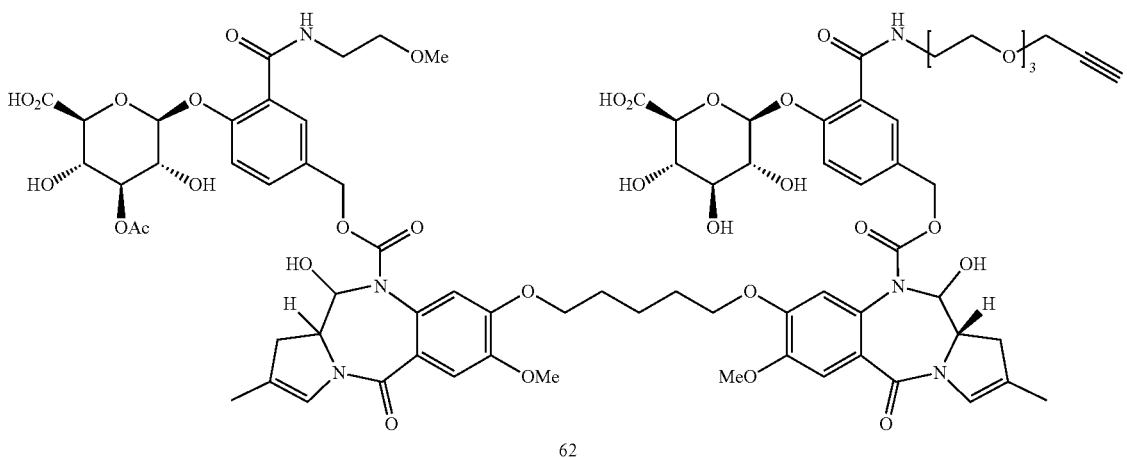
Compound 62 was prepared from Compound 53 and Compound 57 by a method similar to that for the synthesis of Compound 61.
EI-MS m/z: [M+H]$^+$ 1588.7, ½[M+H]$^+$ 795.3.
<Example 22> Preparation of Compound 63
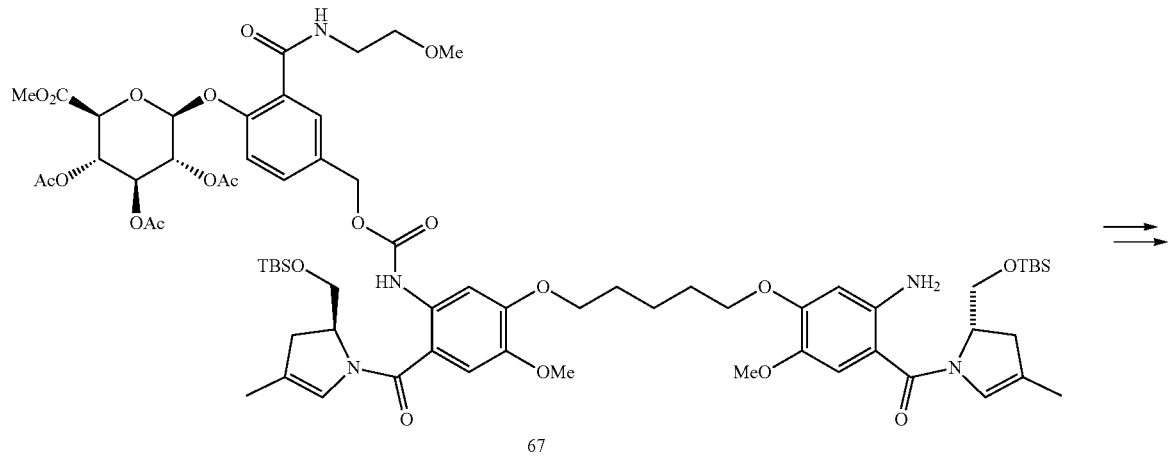

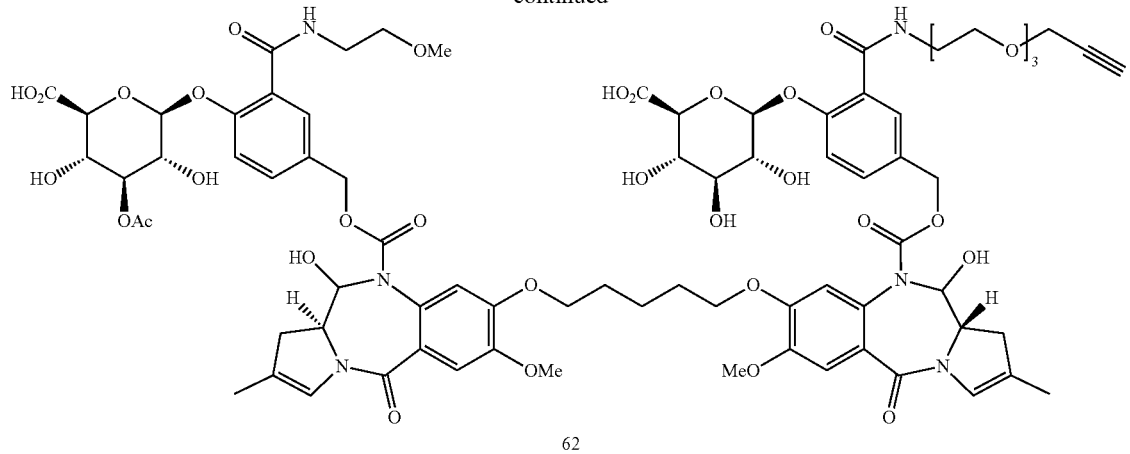

62

Compound 63 was prepared from Compound 55 and Compound 57 by a method similar to that for the synthesis of Compound 61.

EI-MS m/z: [M+H]+ 1575.8, ½[M+H]+ 788.7.

<Example 23> Preparation of Compound 65

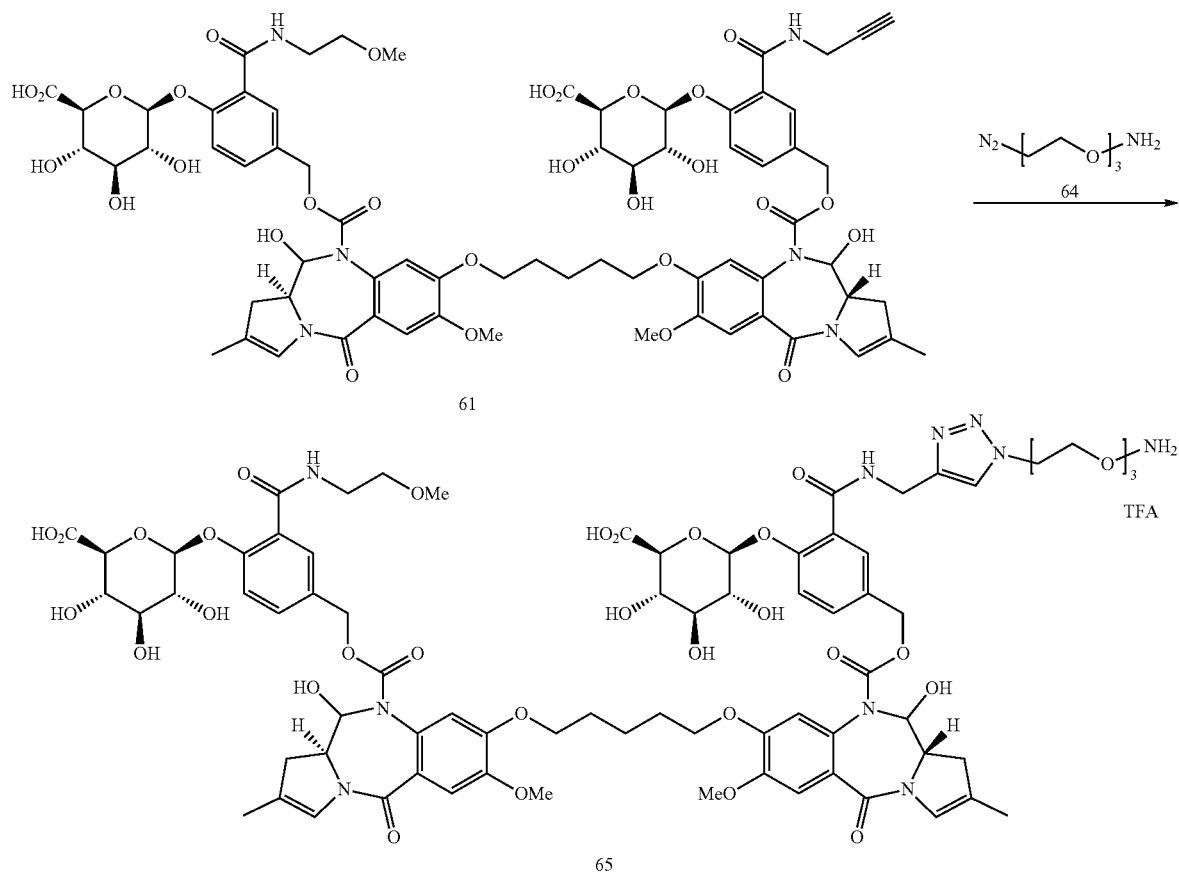

Preparation of Compound 65

Compound 61 (100 mg, 0.068 mmol) was dissolved in dimethylsulfoxide (1.6 mL), then Compound 64 (136 mg, 0.302 mmol, Compound 64 was prepared by the method described in PCT/US2016/063564) was added thereto under a nitrogen atmosphere, and then a solution of a copper(II) sulfate pentahydrate (7.4 mg, 0.03 mmol) and sodium ascorbate (28 mg, 0.15 mmol) in distilled water (0.4 ml) was added to the reaction solution. After being stirred at room temperature for 30 minutes, the reaction solution was concentrated under reduced pressure, then purified by HPLC, and freeze-dried to obtain Compound 65 (15.2 mg, 13%) as a white solid.

EI-MS m/z: [M+H]+ 1645.8, ½[M+H]+ 823.9.

<Example 24> Preparation of Compound 70

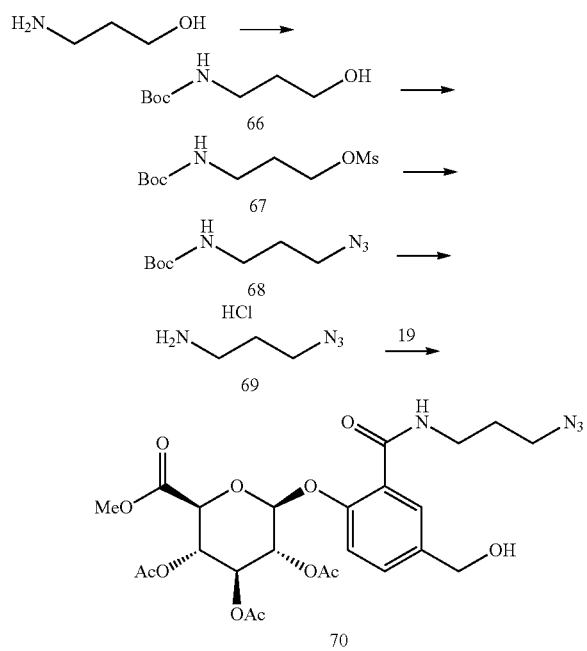

Preparation of Compound 66

In dichloromethane (150 mL), 3-amino-1-propanol (3.0 g, 66.57 mmol) was dissolved, and then di-t-butyl dicarbonate (16 g, 73.2 mmol) was added thereto at 0° C. under a nitrogen atmosphere. After being stirred at room temperature for 12 hours, the reaction solution was concentrated under reduced pressure and purified by column chromatography to obtain Compound 66 (6.4 g, 92%).

$^1$H-NMR (400 MHz, CDCl$_3$) δ 4.78 (s, 1H), 3.65 (m, 2H), 3.30 (m, 2H), 2.90 (s, 1H), 1.68 (m, 2H), 1.48 (s, 9H).

Preparation of Compound 67

Compound 66 (6.04 g, 34.47 mmol) and triethylamine (14.4 mL, 103.4 mmol) were dissolved in tetrahydrofuran (100 mL) and then methanesulfonic anhydride (7.21 g, 41.36 mmol) was gradually added thereto at 0° C. under a nitrogen atmosphere.

The temperature was gradually raised to room temperature, and then the mixture was stirred for 12 hours. The reaction solution was concentrated under reduced pressure and purified by column chromatography to obtain Compound 67 (9.01 g, 98%).

$^1$H-NMR (400 MHz, CDCl$_3$) δ 4.73 (s, 1H), 4.30 (t, J=5.9 Hz, 2H), 3.31-3.24 (m, 2H), 3.04 (s, 3H), 1.94 (t, J=6.1 Hz, 2H), 1.44 (s, 9H).

Preparation of Compound 68

Compound 67 (3.0 g, 11.84 mol) was dissolved in N,N-dimethylformamide (40 mL), then sodium azide (924 mg, 14.21 mmol) was added thereto at room temperature under a nitrogen atmosphere, and the reaction mixture was stirred at 60° C. for 12 hours. Distilled water (50 mL) and a 1 N aqueous hydrochloric acid solution (5 mL) were added to the reaction solution, the mixture was subjected to extraction using ethyl acetate (100 mL), and then the extract was dried over anhydrous sodium sulfate. The resultant was filtered, then concentrated, and purified by column chromatography to obtain Compound 68 (2.3 g, 99%).

$^1$H-NMR (600 MHz, CDCl$_3$) δ 4.63 (s, 1H), 3.36 (t, J=6.6 Hz, 2H), 3.24-3.18 (m, 2H), 1.80-1.75 (m, 2H), 1.45 (s, 9H).

Preparation of Compound 69

Compound 68 (3.8 g, 18.98 mmol) was dissolved in dichloromethane (10 mL), and hydrochloric acid (4 M 1,4-dioxane solution, 10 mL) was gradually added thereto at 0° C. under a nitrogen atmosphere. The reaction mixture was stirred for 12 hours and then concentrated under reduced pressure to obtain Compound 69 (2.5 g, 99%).

$^1$H-NMR (600 MHz, DMSO-d$_6$) δ 8.06 (s, 3H), 3.47 (t, J=6.6 Hz, 2H), 2.82 (t, J=7.2 Hz, 2H), 1.84-1.79 (m, 2H).

Preparation of Compound 70

Compound 19 (4.1 g, 8.46 mmol) and Compound 69 (1.1 g, 11.0 mmol) were dissolved in N,N-dimethylformamide (20 mL), then N,N,N',N'-tetramethyl-O-(1H-benzotriazol-1-yl)uronium hexafluorophosphate (4.39 g, 11.0 mmol) and N,N-diisopropylethylamine (2.96 mL, 16.92 mmol) were added thereto at 0° C. under a nitrogen atmosphere, and then the mixture was stirred at room temperature for 12 hours. A saturated aqueous ammonium chloride solution (100 mL) was added to the reaction solution, and the mixture was subjected to extraction using ethyl acetate (2×100 mL), and then the extract was dried over anhydrous sodium sulfate. The resultant was filtered, then concentrated, and purified by column chromatography to obtain Compound 70 (5.48 g, 88%).

$^1$H-NMR (400 MHz, CDCl$_3$) δ 8.07 (s, 1H), 7.50-7.46 (m, 2H), 7.01 (d, J=8.4 Hz, 1H), 5.45-5.30 (m, 4H), 4.69 (d, J=5.6 Hz, 2H), 4.21 (d, J=9.6 Hz, 1H), 3.74 (s, 3H), 3.67-3.60 (m, 1H), 3.47-3.41 (m, 3H), 2.80 (s, 2H), 2.07-2.05 (m, 9H), 1.98-1.91 (m, 2H), 1.80-1.77 (m, 1H).

<Example 25> Preparation of Compound 72

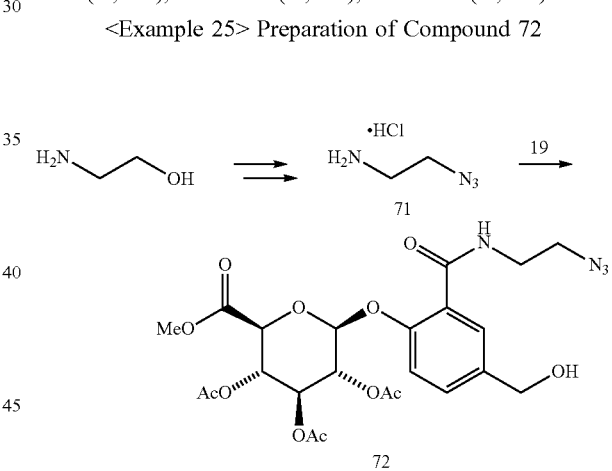

Preparation of Compound 72

Compound 19 (3.6 g, 7.42 mmol) and Compound 71 (1.0 g, 8.16 mmol, Compound 71 was prepared by a method similar to that for the synthesis of Compound 69) were dissolved in N,N-dimethylformamide (15 mL) and then N,N,N',N'-tetramethyl-O-(1H-benzotriazol-1-yl)uronium hexafluorophosphate (4.2 g, 11.2 mmol) and N,N-diisopropylethylamine (3.2 mL, 18.6 mmol) were added thereto at 0° C. under a nitrogen atmosphere. The reaction solution was stirred at room temperature for 14 hours, then a saturated aqueous ammonium chloride solution (50 mL) was added to the reaction solution, and the mixture was subjected to extraction using ethyl acetate (2×50 mL). The combined organic layers were washed with brine (50 mL) and then dried over anhydrous sodium sulfate. The resultant was filtered, then concentrated under reduced pressure, and purified by column chromatography to obtain Compound 72 (3.9 g, 95%).

EI-MS m/z: [M+H]$^+$ 553.3, [M+Na]$^+$ 575.4.

<Example 26> Preparation of Compound 73
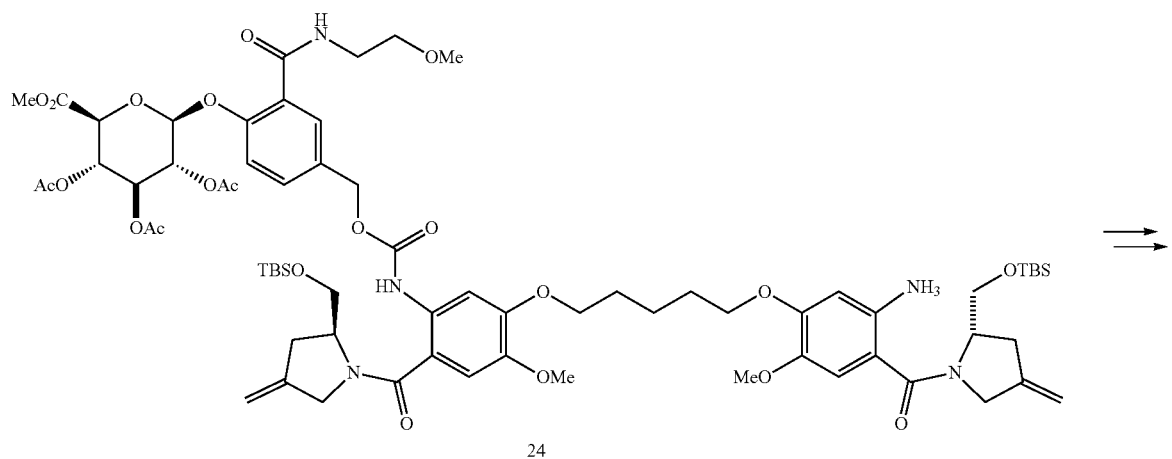
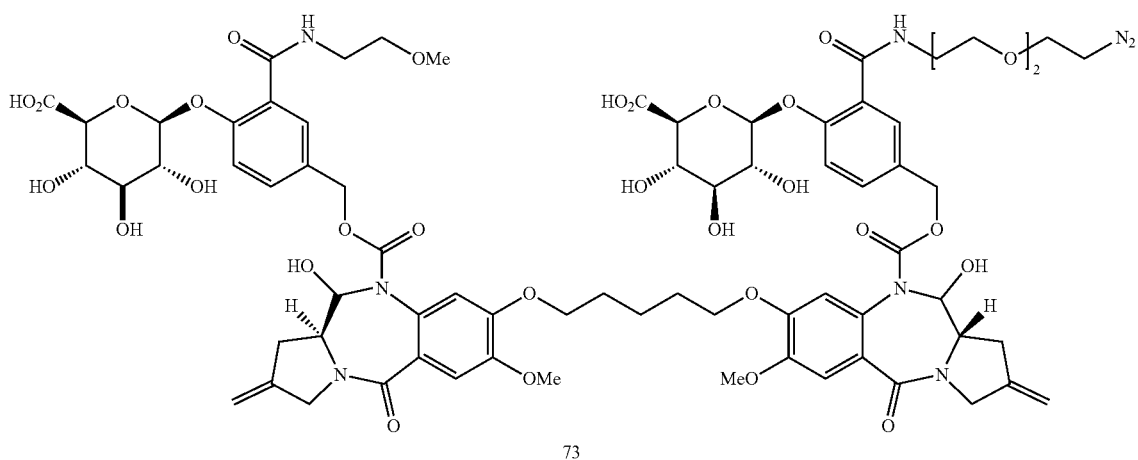
Compound 73 was prepared from Compound 24 and Compound 55 by a method similar to that for the synthesis of Compound 63.
EI-MS m/z: [M+H]$^+$ 1575.7, ½[M+H]$^+$ 788.8.
<Example 27> Preparation of Compound 74
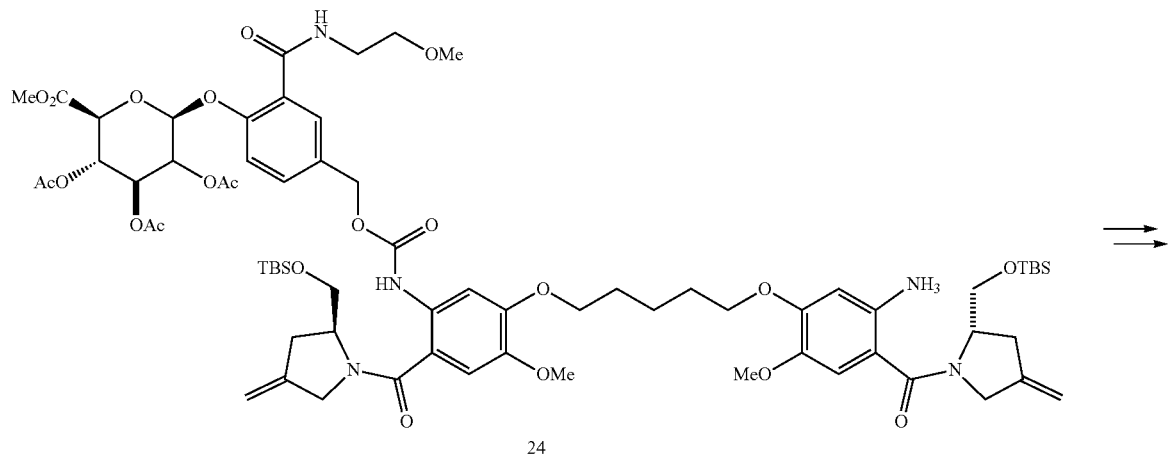

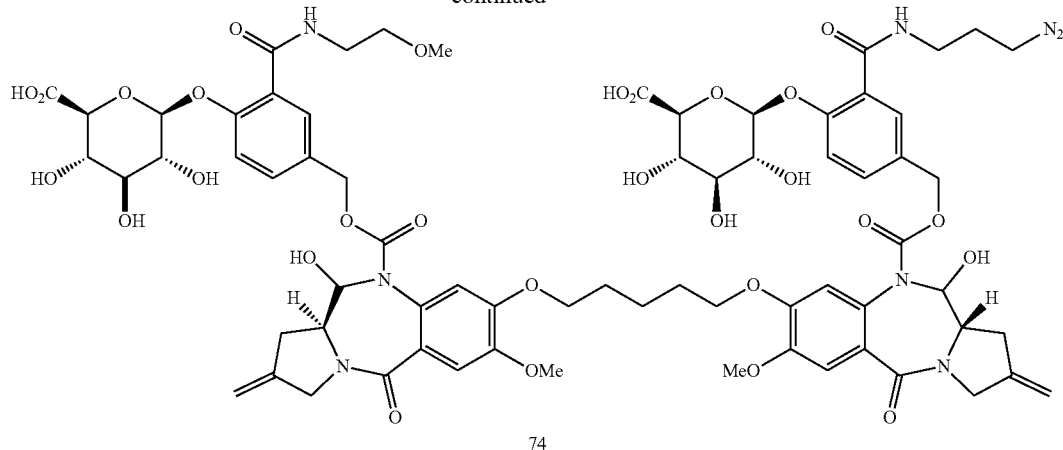
74
Compound 74 was prepared from Compound 24 and Compound 70 by a method similar to that for the synthesis of Compound 63.
EI-MS m/z: [M+H]$^+$ 1500.9, ½[M+H]$^+$ 751.2.
<Example 28> Preparation of Compound 75
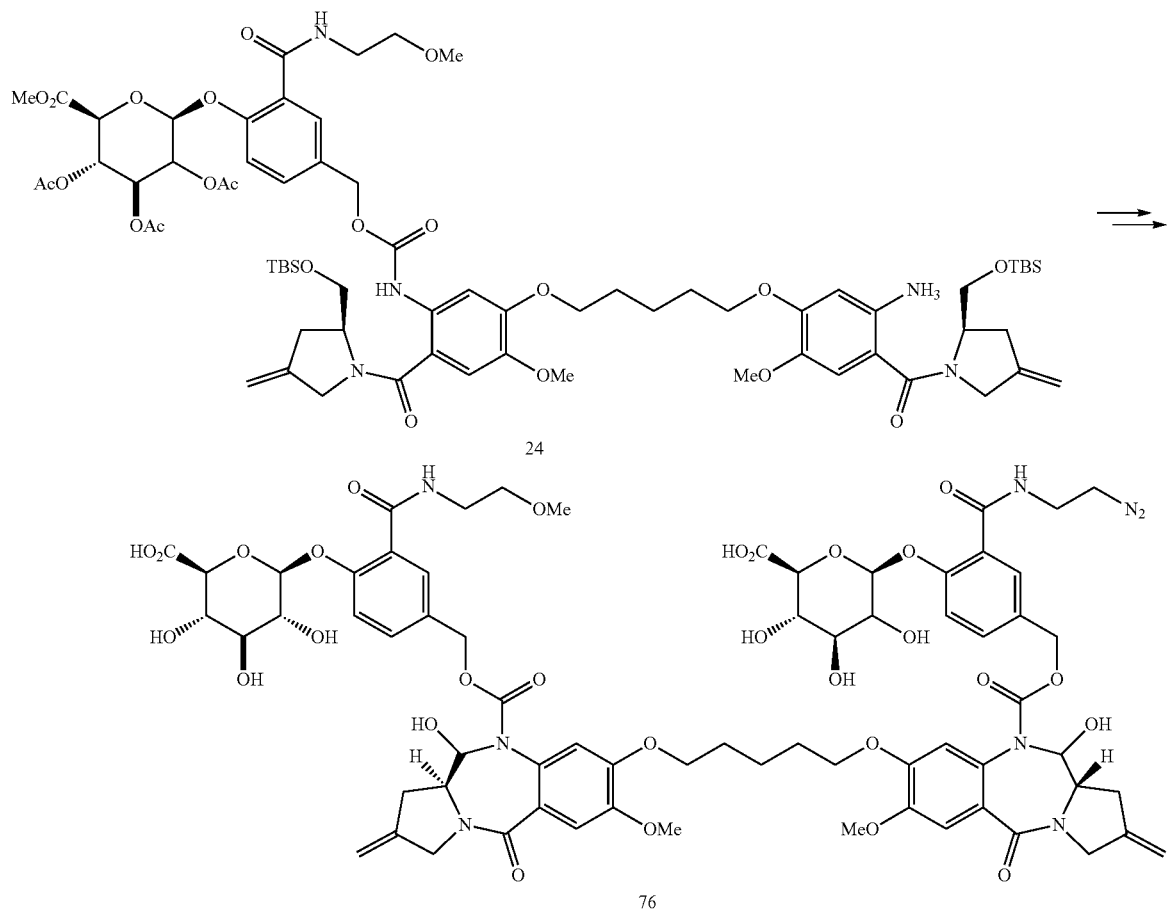
Compound 75 was prepared from Compound 24 and Compound 72 by a method similar to that for the synthesis of Compound 63.
EI-MS m/z: [M+H]$^+$ 1486.42, [M+Na]$^+$ 1509.31.

<Example 29> Preparation of Compound 80

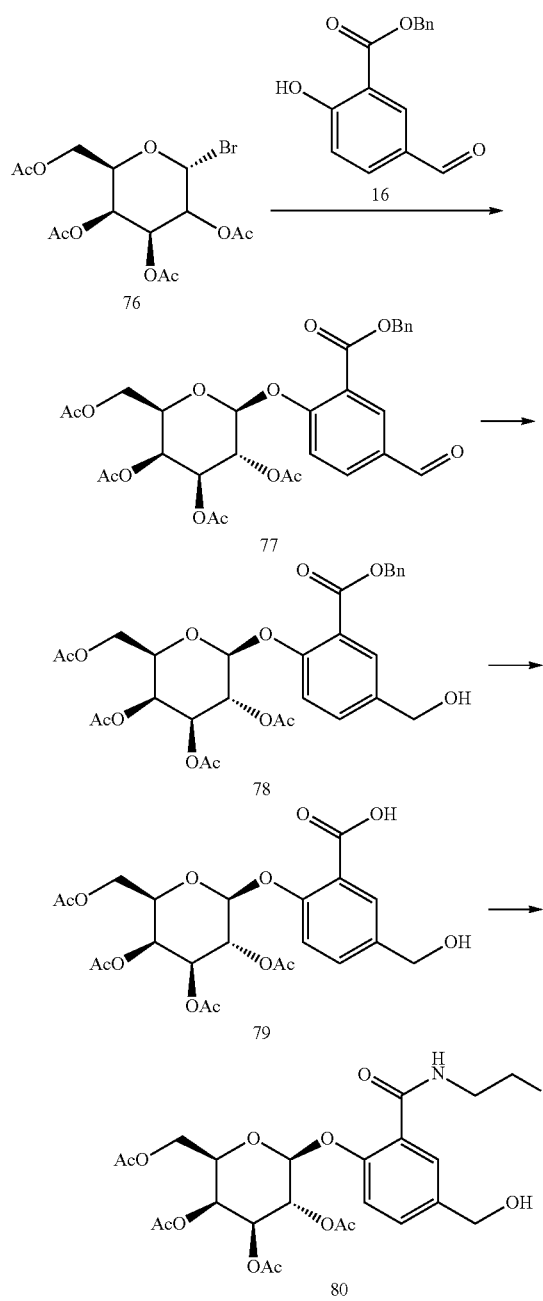

Preparation of Compound 77

Compound 76 (7.30 g, 28.5 mmol, Compound 76 was prepared by the method described in Angew. Chem. Int. Ed., 2016, 55, 12338-12342) and Compound 16 (14.0 g, 29.4 mmol) were dissolved in acetonitrile (145 mL), then 4 Å molecular sieves (14.6 g) and silver(I) oxide (27.0 g, 116.4 mmol) were added thereto, and the mixture was stirred at room temperature for 12 hours under a nitrogen atmosphere. The reaction solution was filtered through Celite, concentrated, and then purified by column chromatography to obtain Compound 77 (15.3 g, 92%).

$^1$H-NMR (400 MHz, CDCl$_3$) δ 9.94 (s, 1H), 8.27 (s, 1H), 7.99 (d, J=8.8 Hz, 1H), 7.46-7.29 (m, 6H), 5.64-5.59 (m, 1H), 5.49-5.48 (m, 1H), 5.36 (s, 2H), 5.18 (d, J=8.0 Hz, 1H), 5.19-5.11 (m, 1H), 4.27-4.10 (m, 3H), 2.19 (s, 3H), 2.08 (s, 3H), 2.04 (s, 3H), 2.03 (s, 3H).

Preparation of Compound 78

Compound 77 (15.30 g, 26.10 mmol) was dissolved in chloroform/isopropanol (200 mL/40 mL), then silica gel (16 g) and sodium borohydride (1.53 g, 40.50 mmol) were added thereto at 0° C. under a nitrogen atmosphere, and the mixture was stirred for 30 minutes. Distilled water (200 mL) was added to the reaction solution, and then the mixture was subjected to extraction using ethyl acetate (400 mL). The organic layer extracted was dried over anhydrous magnesium sulfate, filtered, and concentrated under reduced pressure to obtain Compound 78 (14.0 g, 91%).

$^1$H-NMR (400 MHz, CDCl$_3$) δ 7.73 (s, 1H), 7.47-7.31 (m, 6H), 7.19 (d, J=8.4 Hz, 1H), 5.57 (t, J=9.2 Hz, 1H), 5.46 (d, J=3.2 Hz, 1H), 5.36-5.28 (m, 2H), 5.12-5.04 (m, 2H), 4.66 (d, J=6.0 Hz, 2H), 4.26-4.04 (m, 3H), 2.18 (s, 3H), 2.07 (s, 3H), 2.05 (s, 3H), 2.02 (s, 3H), 1.67 (t, J=5.6 Hz, 1H).

Preparation of Compound 79

Compound 78 (14.0 g, 23.8 mmol) was dissolved in ethanol (550 mL) and then Raney nickel (14.0 g) was added thereto. The reaction solution was stirred at room temperature for 12 hours under a hydrogen atmosphere. The reaction solution was filtered through Celite and concentrated to obtain Compound 79 (11.4 g, 96%).

$^1$H-NMR (400 MHz, CDCl$_3$) δ 8.07 (s, 1H) 7.58 (d, J=8.8 Hz, 1H), 7.17 (d, J=8.8 Hz 1H), 5.57 (t, J=9.2 Hz, 1H), 5.49 (d, J=3.2 Hz, 1H), 5.22 (d, J=8.0 Hz, 1H), 5.17-5.14 (m, 1H), 4.71 (s, 2H), 4.25-4.10 (m, 3H), 2.20 (s, 3H), 2.11 (s, 3H), 2.07 (s, 3H), 2.00 (s, 3H)

Preparation of Compound 80

Compound 79 (3.00 g, 6.00 mmol) and 2-methoxyethylamine (0.57 mL, 6.6 mmol) were dissolved in N,N-dimethylformamide (15 mL), then N,N,N',N'-tetramethyl-O-(1H-benzotriazol-1-yl)uronium hexafluorophosphate (2.86 g, 7.20 mmol) and N,N-diisopropylethylamine (2.10 mL, 12.0 mmol) were added thereto at 0° C. under a nitrogen atmosphere, and then the mixture was stirred at room temperature for 12 hours. A saturated aqueous ammonium chloride solution (100 mL) was added to the reaction solution, and the mixture was subjected to extraction using ethyl acetate (2×100 mL), and then the extract was dried over anhydrous magnesium sulfate. The resultant was filtered, then concentrated, and purified by column chromatography to obtain Compound 80 (2.3 g, 68%).

$^1$H-NMR (400 MHz, CDCl$_3$) δ 8.07 (s, 1H), 7.48-7.44 (m, 2H), 7.06 (d, J=8.4 Hz, 1H), 5.55 (t, J=9.2 Hz, 1H), 5.49 (d, J=2.8 Hz, 1H), 5.20-5.14 (m, 2H), 4.69 (d, J=5.2 Hz, 2H), 4.25-4.09 (m, 3H), 3.78-3.74 (m, 1H), 3.62-3.51 (m, 3H), 3.40 (s, 3H), 2.21 (s, 3H), 2.07 (m, 6H), 2.02 (s, 3H), 1.71 (t, J=6.0 Hz, 1H).

<Example 30> Preparation of Compound 81

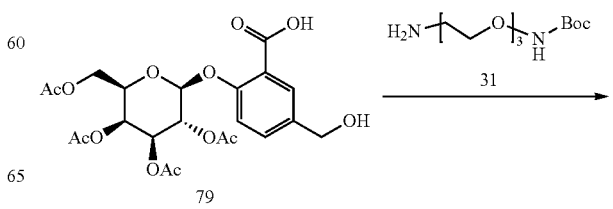

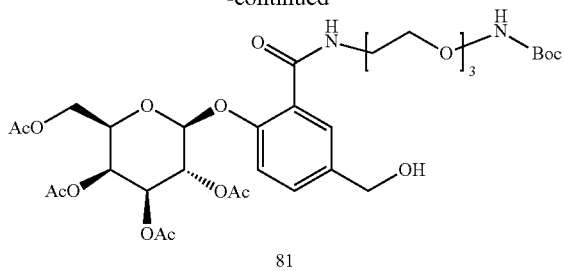

81

Preparation of Compound 81

Compound 79 (2.19 g, 4.38 mmol) and Compound 31 (1.50 g, 5.70 mmol) were dissolved in N,N-dimethylformamide (10 mL), then N,N,N',N'-tetramethyl-O-(1H-benzotriazol-1-yl) uronium hexafluorophosphate (2.26 g, 5.7 mmol) and N,N-diisopropylethylamine (1.53 mL, 8.76 mmol) were added thereto at 0° C. under a nitrogen atmosphere, and then the mixture was stirred at room temperature for 12 hours. A saturated aqueous ammonium chloride solution (100 mL) was added to the reaction solution, the mixture was subjected to extraction using ethyl acetate (2×100 mL), and then the extract was dried over anhydrous magnesium sulfate. The resultant was filtered, then concentrated, and purified by column chromatography to obtain Compound 81 (2.73 g, 84%).

$^1$H-NMR (400 MHz, CDCl$_3$) δ 8.07 (s, 1H), 7.68 (s, 1H), 7.46-7.44 (m, 2H), 7.05 (d, J=8.0 Hz, 1H), 5.56-5.49 (m, 2H), 5.18-5.14 (m, 2H), 4.68 (d, J=4.8 Hz, 2H), 4.27-4.10 (m, 3H), 3.97-3.95 (m, 2H), 3.83-3.78 (m, 1H), 3.71-3.67 (m, 7H), 3.57-3.52 (m, 1H), 2.22 (s, 3H), 2.07 (m, 6H), 2.03 (s, 3H), 1.47 (s, 9H).

<Example 31> Preparation of Compound 82

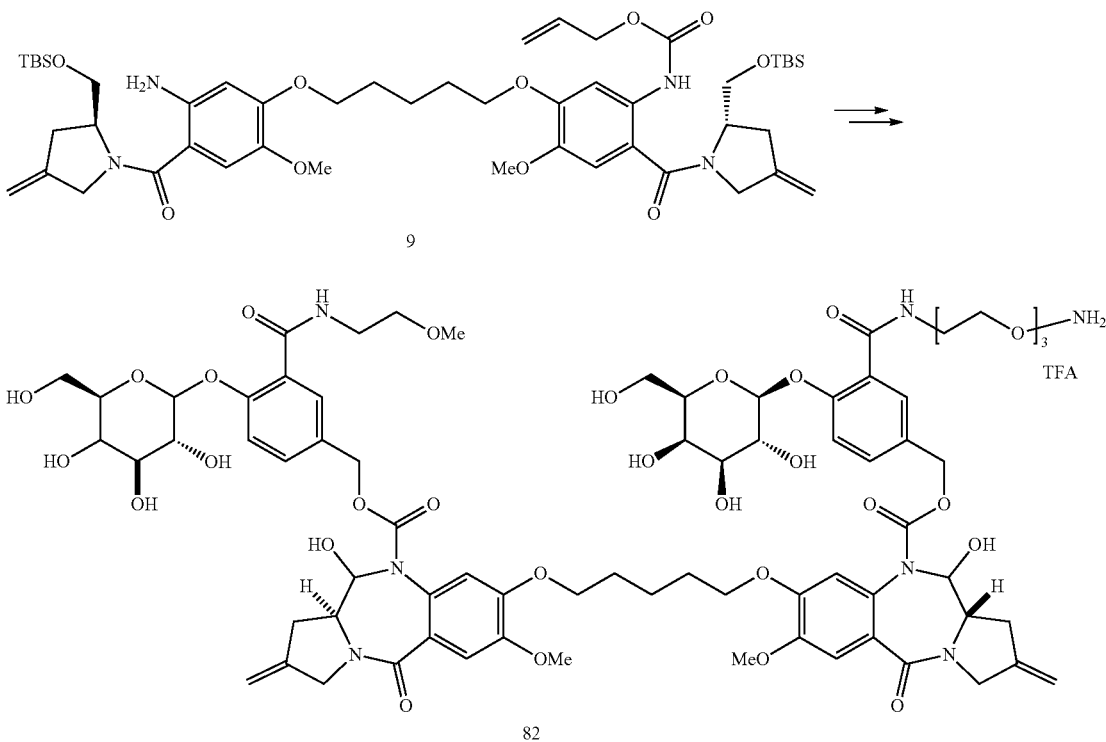

82

Compound 82 was prepared from Compound 9, Compound 80, and Compound 81 by a method similar to that for the synthesis of Compound 28.

EI-MS m/z: [M+H]$^+$ 1537.7, ½[M+H]$^+$ 769.7.

<Example 32> Preparation of Compound 83

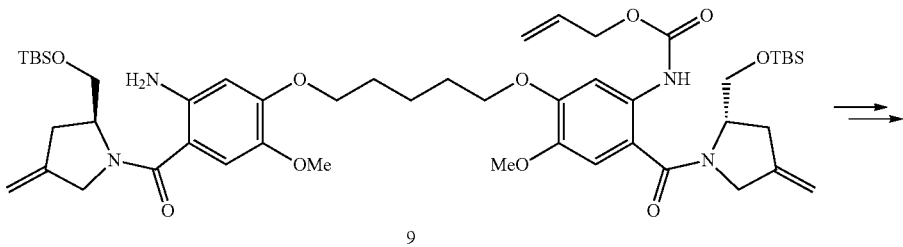

9

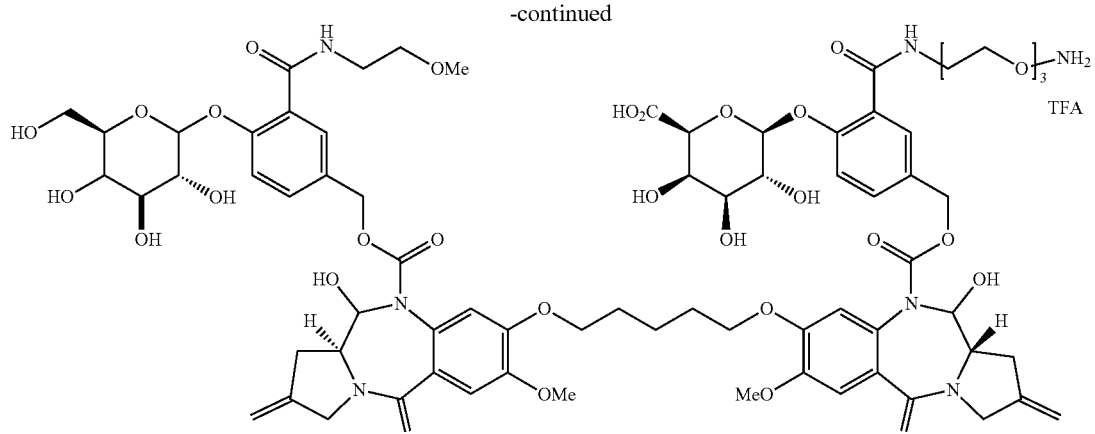
83
Compound 83 was prepared from Compound 9, Compound 80, and Compound 32 by a method similar to that for the synthesis of Compound 28.
EI-MS m/z: $[M+H]^+$ 1551.6, $\frac{1}{2}[M+H]^+$ 776.7.
<Example 33> Preparation of Compound 85
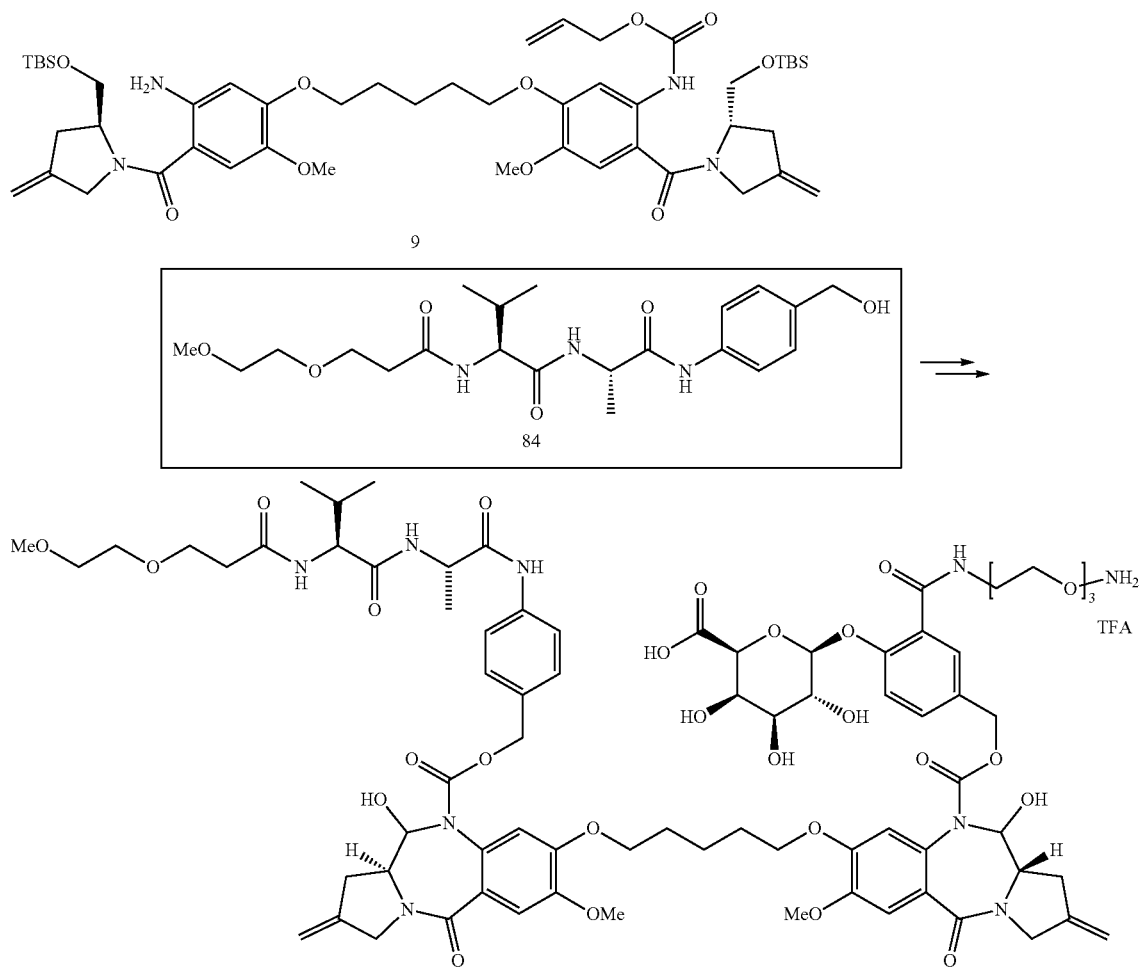

Compound 85 was prepared from Compound 9, Compound 84 (Compound 84 was prepared by the method described in WO2011/130598 A1), and Compound 32 by a method similar to that for the synthesis of Compound 28.
EI-MS m/z: [M+H]$^+$ 1587.8, ½[M+H]$^+$ 794.7.
<Comparative Example 1> Preparation of Compound 86, Compound 87, and Compound 88
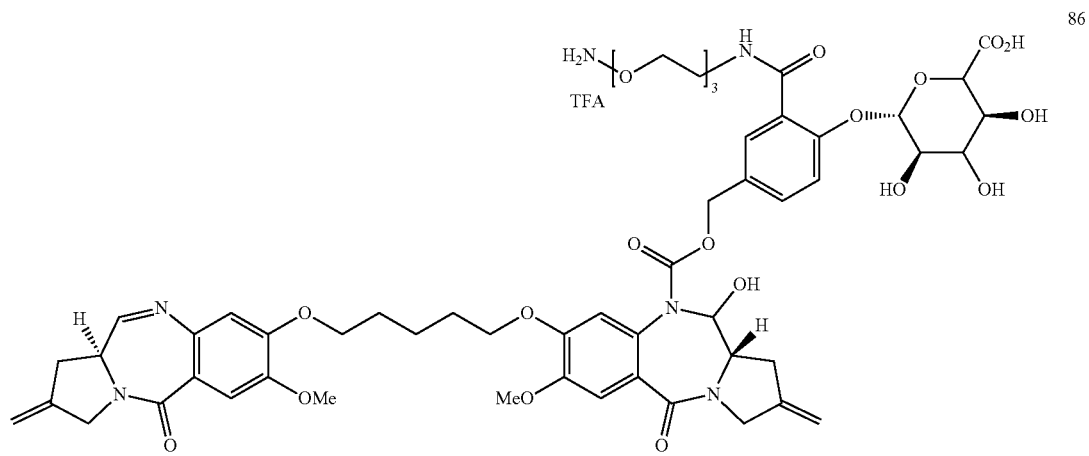
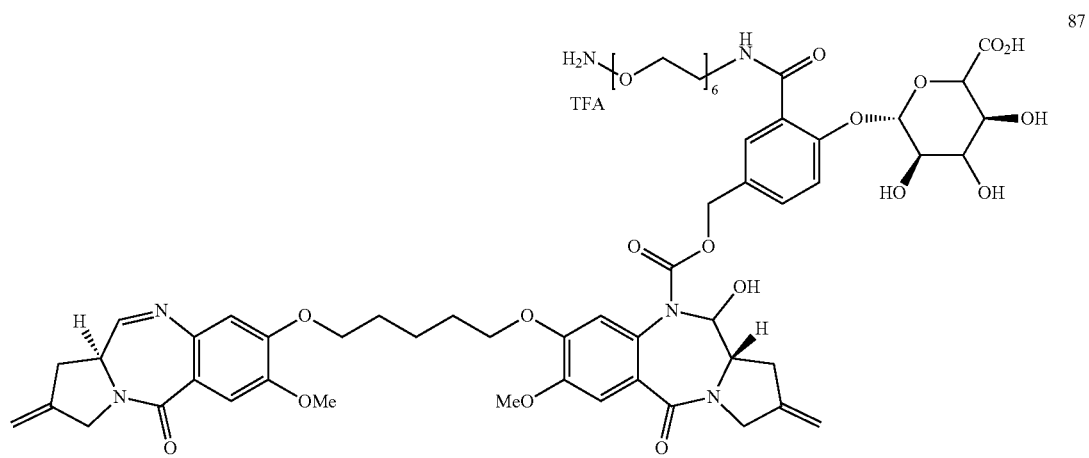
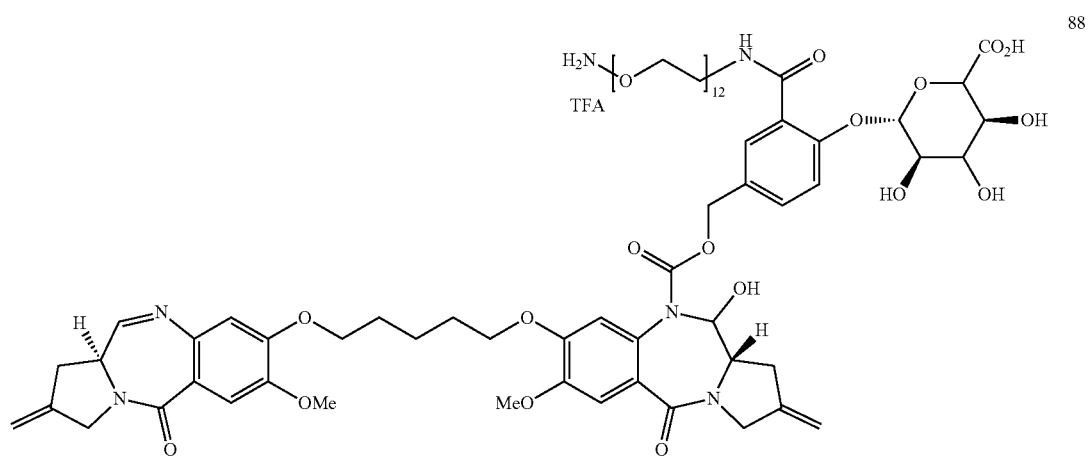

Compound 86, Compound 87, and Compound 88 were prepared by the methods described in PCT/US2016/063564.

<Example 34> Preparation of Compound 94

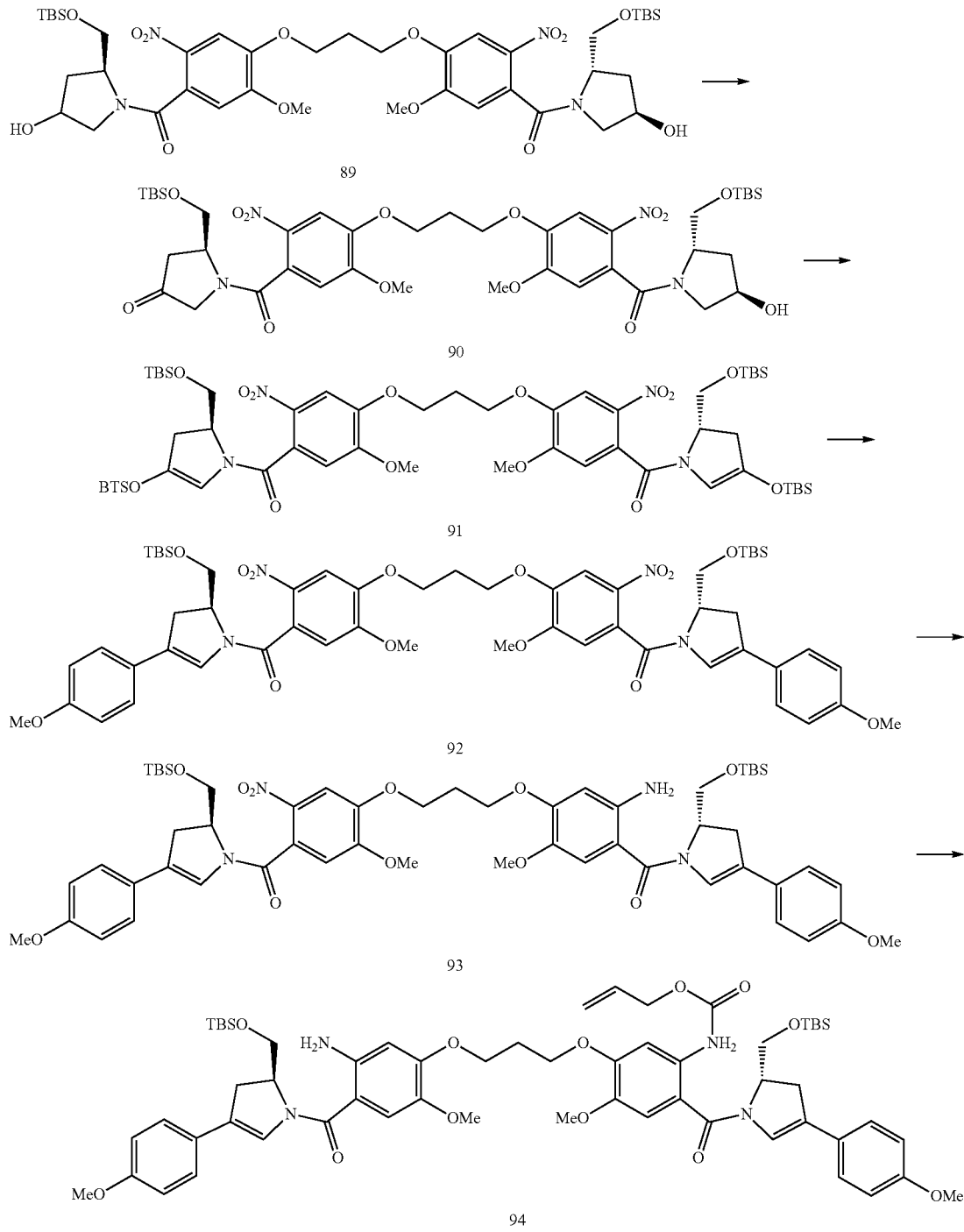

Preparation of Compound 90

Compound 89 (4.5 g, 4.88 mmol, Compound 89 was prepared by the method described in J. Med. Chem., 2004, 47, 1161-1174) was dissolved in dichloromethane (100 mL), and then 2,2,6,6-tetramethyl-1-piperidinyloxy (153 mg, 0.98 mmol) and (diacetoxyiodo)benzene (7.0 g, 21.7 mmol) were added thereto at room temperature under a nitrogen atmosphere. The reaction solution was stirred for 24 hours, then distilled water (200 mL) was added to the reaction solution, and the mixture was subjected to extraction using dichloromethane (2×200 mL). The combined organic layers were dried over anhydrous sodium sulfate, filtered, then concentrated under reduced pressure, and then purified by column chromatography to obtain Compound 90 (4.25 g, 95%).

$^1$H-NMR (400 MHz, CDCl$_3$) δ 7.74 (s, 2H), 6.73 (s, 2H), 4.97 (d, J=8.8 Hz, 1H), 4.39-4.27 (m, 8H), 3.96 (s, 6H), 3.80-3.70 (m, 2H), 3.58-3.52 (m, 2H), 3.42-2.79 (m, 2H), 2.74-2.56 (m, 2H), 2.52-2.44 (m, 2H), 2.08 (s, 2H), 0.85 (s, 18H), 0.97 (s, 12H).

Preparation of Compound 91

Compound 90 (10.0 g, 10.9 mmol) was dissolved in dichloromethane (450 mL) and then 2,6-lutidine (10.0 mL, 87.2 mmol) and triflic anhydride (11.0 mL, 65.4 mmol) were added thereto at −40° C. under a nitrogen atmosphere. The reaction solution was stirred for 2 hours, then a saturated aqueous sodium hydrogencarbonate solution (500 mL) was added to the reaction solution, and the mixture was subjected to extraction using dichloromethane (2×500 mL). The combined organic layers were dried over anhydrous sodium sulfate, filtered, then concentrated under reduced pressure, and then purified by column chromatography to obtain Compound 91 (10.6 g, 47%).

Preparation of Compound 92

Compound 91 (1.7 g, 1.44 mmol) was dissolved in ethanol/toluene/distilled water (12 mL/24 mL/12 mL) and then 4-methylphenylboronic acid (568 mg, 3.74 mmol), sodium carbonate (793 mg, 7.48 mmol), and tetrakis(triphenylphosphine)palladium(0) (133 mg, 0.115 mmol) were added thereto at room temperature under a nitrogen atmosphere. The reaction solution was stirred for 2 hours and then diluted with ethyl acetate (100 mL), and the organic layer was washed with brine (100 mL) and distilled water (100 mL). The combined organic layers were dried over anhydrous sodium sulfate, filtered, then concentrated under reduced pressure, and then purified by column chromatography to obtain Compound 92 (1.25 g, 79%).

$^1$H-NMR (400 MHz, CDCl$_3$) δ 7.80 (s, 2H), 7.13 (d, J=8.8 Hz, 4H), 6.90 (s, 2H), 6.79 (d, J=8.0 Hz, 4H), 6.14 (s, 2H), 4.80-4.50 (m, 2H), 4.39-4.36 (m, 4H), 3.98 (s, 6H), 3.79 (s, 6H), 3.17 (bs, 2H), 3.02-2.98 (m, 2H), 2.50-2.47 (m, 2H), 0.88 (s, 18H), 0.11 (s, 12H). EI-MS m/z: [M+H]$^+$ 1069.8, ½[M+H]$^+$ 535.6.

Preparation of Compound 93

Compound 92 (8.0 g, 7.48 mmol) was dissolved in ethanol (300 mL) and then zinc dust (29 g, 28.1 mmol) and formic acid (5% in EtOH, 320 mL) were added thereto. The reaction solution was stirred at room temperature for 20 minutes and then filtered through Celite, and ethyl acetate (1 L) was added thereto. The organic layer was washed with distilled water (500 mL), a saturated aqueous sodium hydrogencarbonate solution (500 mL), and brine (500 mL) in this order and then dried over anhydrous sodium sulfate. The resultant was filtered, then concentrated, and purified by column chromatography to obtain Compound 93 (4.85 g, 64%).

$^1$H-NMR (400 MHz, CDCl$_3$) δ 7.16 (d, J=8.4 Hz, 4H), 6.78 (d, J=6.4 Hz, 8H), 6.30 (s, 2H), 4.71-4.41 (m, 2H), 4.25 (br s, 4H), 4.19-4.17 (m, 4H), 4.10-4.05 (m, 2H), 3.95-3.81 (m, 2H), 3.73 (s, 6H), 3.72 (s, 6H), 3.64-3.10 (m, 2H), 3.03-2.93 (m, 2H), 2.36-2.34 (m, 2H), 0.81 (s, 18H), 0.11 (s, 12H). EI-MS m/z: [M+H]$^+$ 1010.4, ½[M+H]$^+$ 505.7.

Preparation of Compound 94

Compound 93 (4.6 g, 4.56 mmol) was dissolved in dichloromethane (300 mL) and then pyridine (0.74 mL, 9.11 mmol) and allyl chloroformate (0.48 mL, 4.56 mmol) were added thereto at −78° C. under a nitrogen atmosphere. The reaction solution was stirred for 1 hour, then the reaction temperature was raised to room temperature, and the reaction solution was concentrated and then purified by column chromatography to obtain Compound 94 (1.46 g, 29%).

EI-MS m/z: [M+H]$^+$ 1093.6.

<Example 35> Preparation of Compound 97

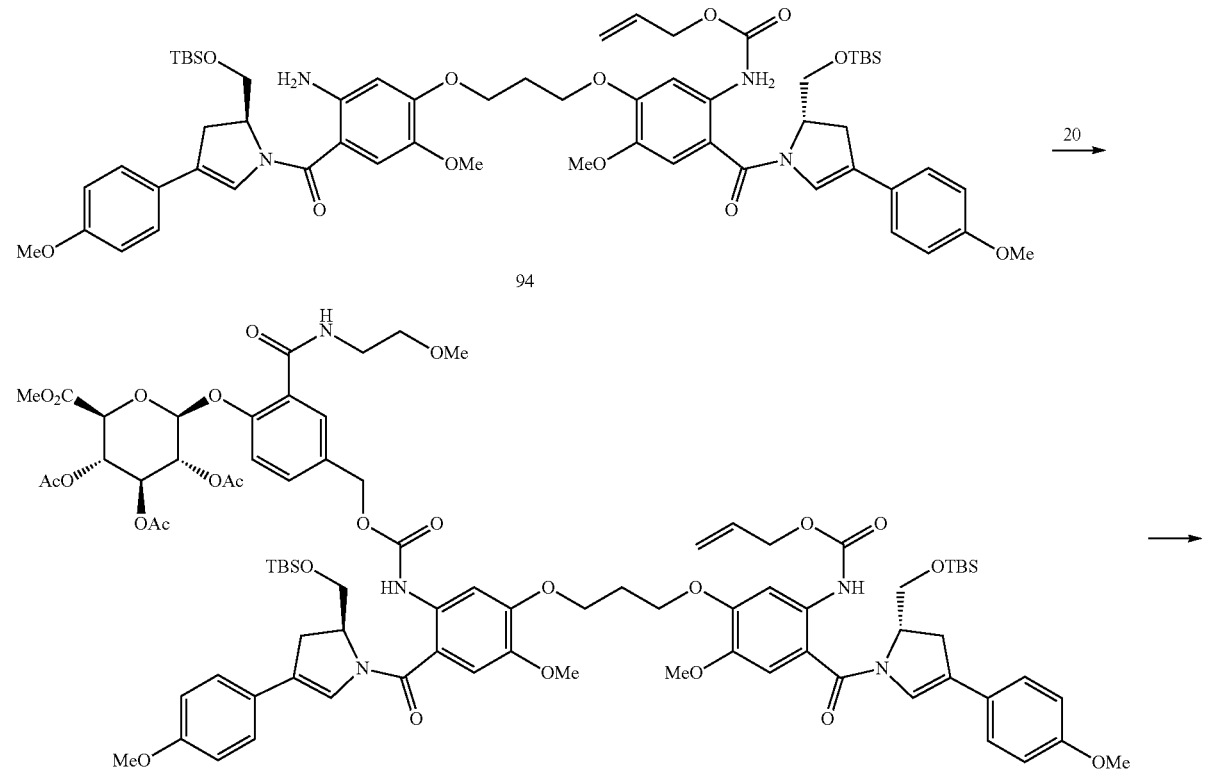

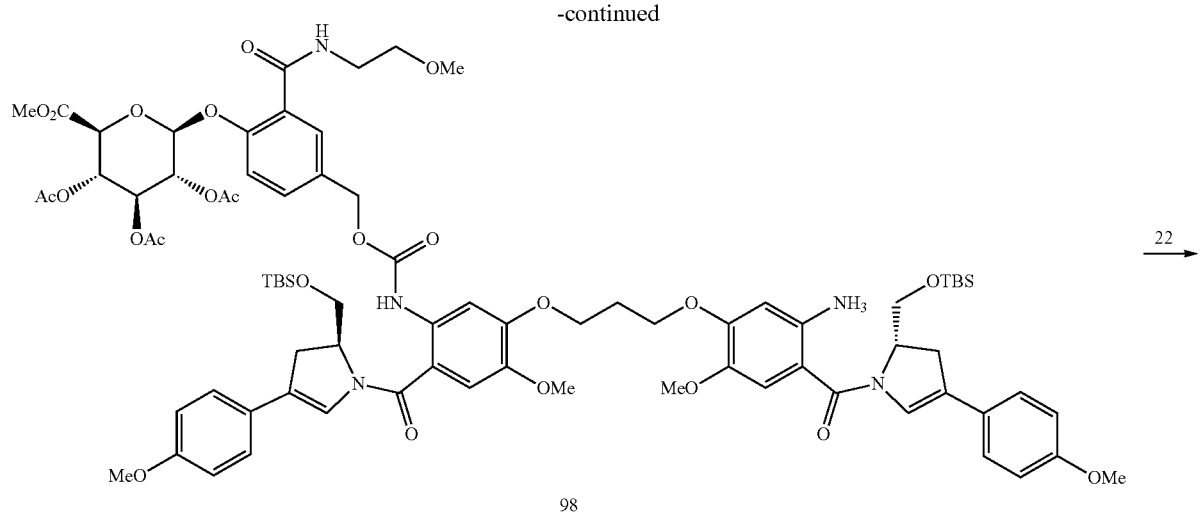

98

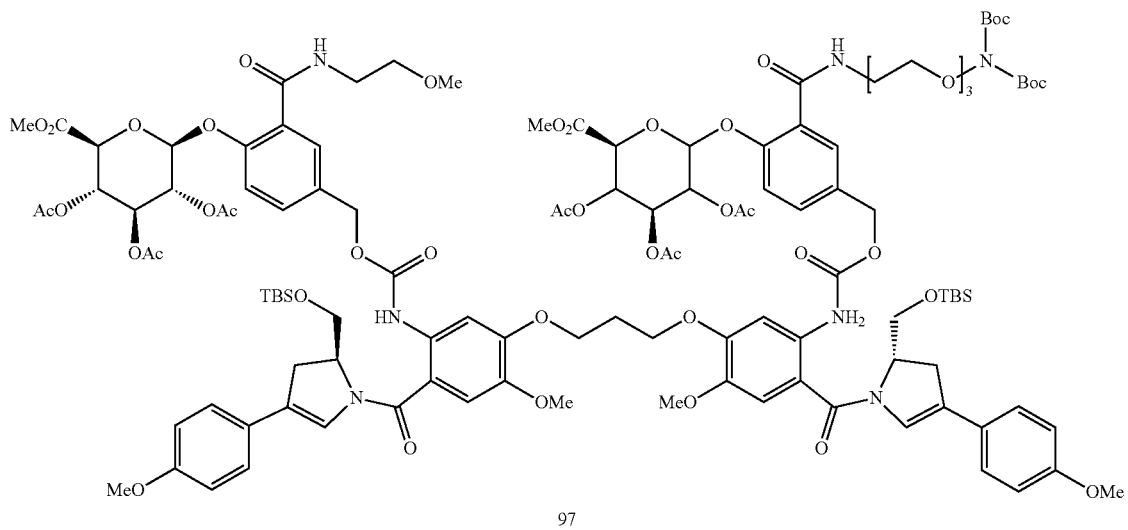

97

Preparation of Compound 95

Compound 94 (200 mg, 0.18 mmol) was dissolved in toluene (7.5 mL), then triphosgene (19 mg, 0.067 mmol) and triethylamine (0.035 mL, 0.25 mmol) were added thereto at −10° C., and the mixture was stirred for 1 hour under a nitrogen atmosphere. Compound 20 was dissolved in dry tetrahydrofuran (7.5 mL), triethylamine (0.035 mL, 0.25 mmol) was added thereto, and then this solution was gradually added to the reaction solution. After 30 minutes, the reaction solution was heated under reflux and stirred for 4 hours. The reaction solution was concentrated, diluted with dichloromethane (30 mL), then washed with brine (20 mL), and dried over anhydrous sodium sulfate. The resultant was filtered, concentrated under reduced pressure, and then purified by column chromatography to obtain Compound 95 (130 mg, 43%).

EI-MS m/z: [M+H]$^+$ 1661.6, ½[M+H]$^+$ 831.4.

Preparation of Compound 96

Compound 95 (380 mg, 0.23 mmol) was dissolved in dichloromethane (10 mL), then pyrrolidine (0.023 mL, 0.27 mmol), tetrakis(triphenylphosphine)palladium(0) (13 mg, 0.011 mmol), and triphenylphosphine (15 mg, 0.057 mmol) were added thereto in this order, and the mixture was stirred at room temperature for 6 hours under a nitrogen atmosphere. The reaction solution was concentrated under reduced pressure and then purified by column chromatography to obtain Compound 96 (260 mg, 72%).

EI-MS m/z: [M+H]$^+$ 1577.6, ½[M+H]$^+$ 789.4.

Preparation of Compound 97

Compound 96 (260 mg, 0.16 mmol) was dissolved in toluene (5 mL), then triphosgene (17.6 mg, 0.06 mmol) and diisopropylethylamine (0.053 mL, 0.30 mmol) were added thereto at −10° C., and the mixture was stirred for 1 hour under a nitrogen atmosphere. Compound 22 was dissolved in dry tetrahydrofuran (5 mL), pyridine (0.066 mL, 0.80 mmol) was added thereto, and then this solution was gradually added to the reaction solution. After 30 minutes, the reaction solution was heated under reflux and stirred for 4 hours. The reaction solution was concentrated, diluted with dichloromethane (50 mL), then washed with brine (30 mL), and dried over anhydrous sodium sulfate. The resultant was filtered, concentrated under reduced pressure, and then purified by column chromatography to obtain Compound 97 (168 mg, 41%).

EI-MS m/z: [M+H]$^+$ 2567.1, ½[M+H]$^+$ 1283.8.

101 102
<Example 36> Preparation of Compound 100
97 ⟶
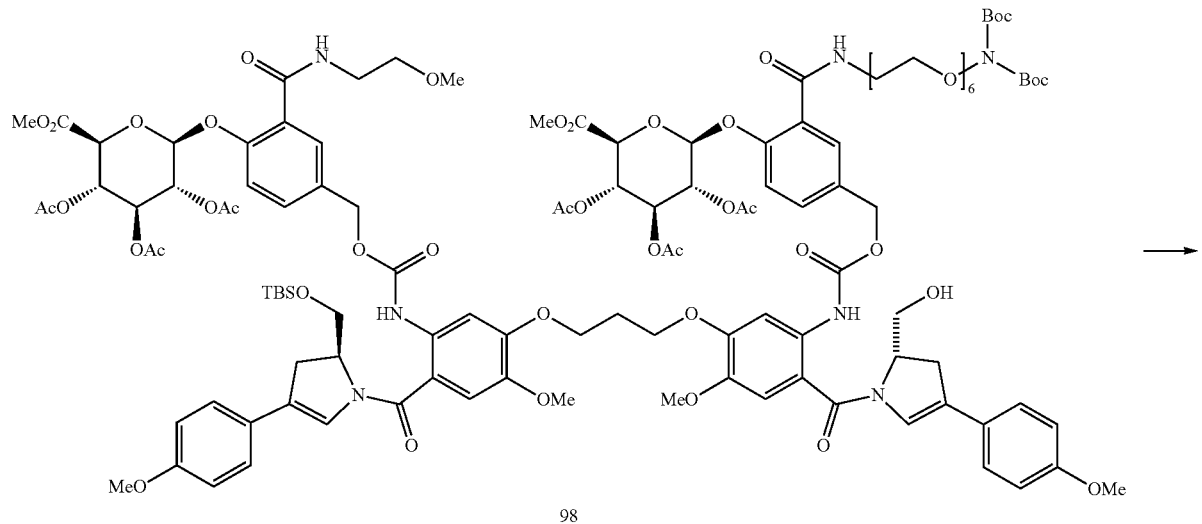
98
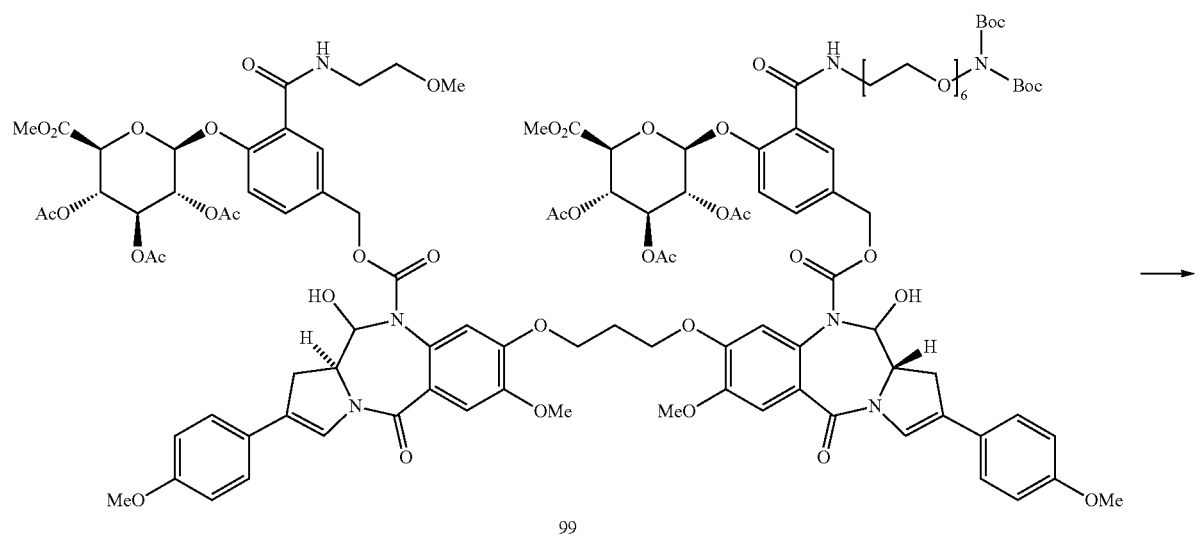
99

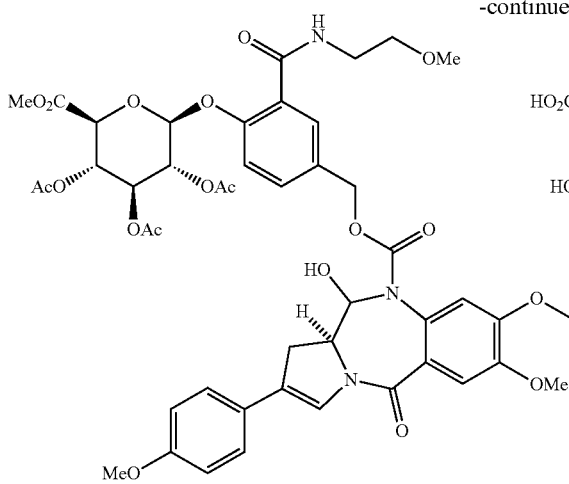
103

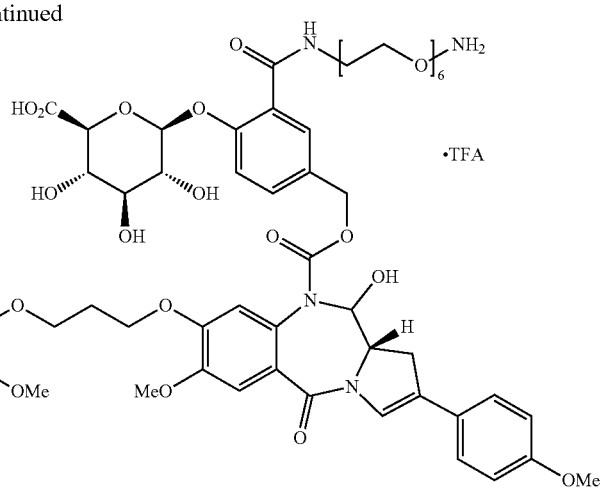
104

-continued

100

Preparation of Compound 98

Compound 97 (168 mg, 0.065 mmol) was dissolved in tetrahydrofuran/distilled water (1 mL/1 mL), acetic acid (2 mL) was added thereto, and then the mixture was stirred at room temperature for 16 hours under a nitrogen atmosphere. The reaction solution was concentrated under reduced pressure and then purified by column chromatography to obtain Compound 98 (130 mg, 85%).

EI-MS m/z: [M+H]$^+$ 2337.8, ½[M+H]$^+$ 1169.5.

Preparation of Compound 99

Compound 98 (130 mg, 0.055 mmol) was dissolved in dichloromethane (5 mL), then Dess-Martin periodinane (57 mg, 0.13 mmol) was added thereto, and the mixture was stirred at room temperature for 3.5 hours under a nitrogen atmosphere. The reaction solution was concentrated under reduced pressure and then purified by column chromatography to obtain Compound 99 (96 mg, 82%).

EI-MS m/z: [M+H]$^+$ 2333.7, ½[M+H]$^+$ 1167.5.

Preparation of Compound 100

Compound 99 (96 mg, 0.041 mmol) was dissolved in methanol/tetrahydrofuran (1 mL/1 mL) and then a solution of lithium hydroxide (16 mg, 0.41 mmol) in distilled water (1 mL) was gradually added thereto at −40° C. The mixture was stirred for 2 hours while gradually raising the reaction temperature to 0° C. The reaction solution was neutralized with acetic acid, then concentrated under reduced pressure, and vacuum dried. The solid obtained was diluted with dichloromethane (2 mL), then trifluoroacetic acid (0.5 mL) was added thereto at 0° C., and the mixture was stirred for 2 hours. The reaction solution was concentrated under reduced pressure, then purified by HPLC, and freeze-dried to obtain Compound 100 (2.4 mg) as a pale yellow solid.

EI-MS m/z: [M+H]$^+$ 1853.8, ½[M+H]$^+$ 927.4.

<Example 37> Preparation of Compound 102

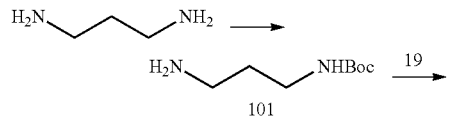
101

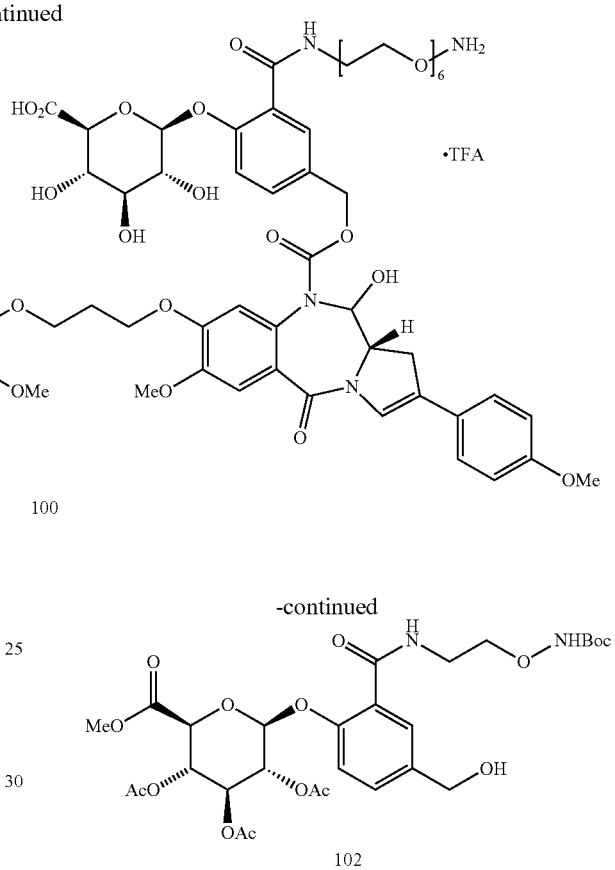
102

Preparation of Compound 101

In dichloromethane (30 mL), 1,3-diaminopropane (0.93 mL, 11.1 mmol) was dissolved, and di-t-butyl dicarbonate (0.84 mL, 3.7 mmol) was added thereto at 0° C. under a nitrogen atmosphere. After the reaction solution was stirred at room temperature for 3 hours, brine (50 mL) was added to the reaction solution, the mixture was subjected to extraction using ethyl acetate (2×100 mL), and then the extract was dried over anhydrous sodium sulfate. After filtration, the reaction solution was filtered, then concentrated under reduced pressure, and purified by column chromatography to obtain Compound 101 (658 mg, 100% based on Boc$_2$O).

$^1$H-NMR (400 MHz, CDCl$_3$) δ 4.88 (br s, 1H), 3.26-3.14 (m, 2H), 2.77 (t, J=6.8 Hz, 2H), 1.66-1.57 (m, 2H), 1.44 (s, 9H), 1.32 (br, 2H).

Preparation of Compound 102

Compound 19 (1.50 g, 3.10 mmol) and Compound 101 (0.65 g, 3.73 mmol) were dissolved in N,N-dimethylformamide (10 mL), then N,N,N',N'-tetramethyl-O-(1H-benzotriazol-1-yl)uronium hexafluorophosphate (1.60 g, 4.03 mmol) and N,N-diisopropylethylamine (1.08 mL, 6.20 mmol) were added thereto at 0° C. under a nitrogen atmosphere, and then the mixture was stirred at room temperature for 12 hours. A saturated aqueous ammonium chloride solution (100 mL) was added to the reaction solution, the mixture was subjected to extraction using ethyl acetate (2×100 mL), and then the extract was dried over anhydrous magnesium sulfate. The resultant was filtered, then concentrated, and purified by column chromatography to obtain Compound 102 (1.67 g, 84%).

$^1$H-NMR (400 MHz, CDCl$_3$) δ 8.05 (s, 1H), 7.49-7.47 (m, 2H), 7.02 (d, J=8.4 Hz, 1H), 5.42-5.30 (m, 4H), 4.69 (d,

J=6.0 Hz, 2H), 4.21 (d, J=9.2 Hz, 1H), 3.74 (s, 3H), 3.63-3.58 (m, 1H), 3.44-3.39 (m, 1H), 322-3.13 (m, 2H), 2.06-2.05 (m, 9H), 1.79-1.74 (m, 2H), 1.45 (s, 9H).
<Example 38> Preparation of Compound 103
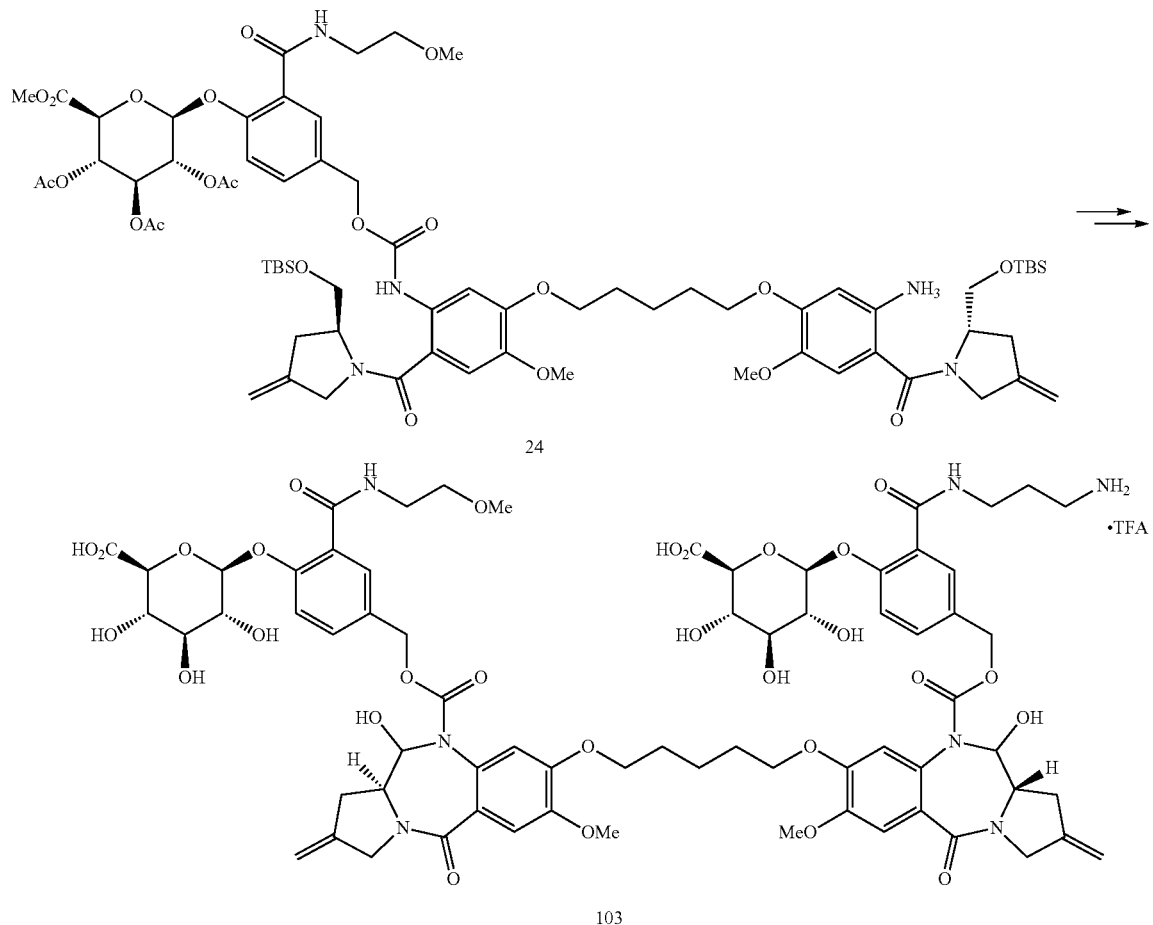
Compound 103 was prepared from Compound 24 and Compound 102 by a method similar to that for the synthesis of Compound 28.
EI-MS m/z: [M+H]⁺ 1475.8, ½[M+H]⁺ 738.3.
<Example 39> Preparation of Compound 104
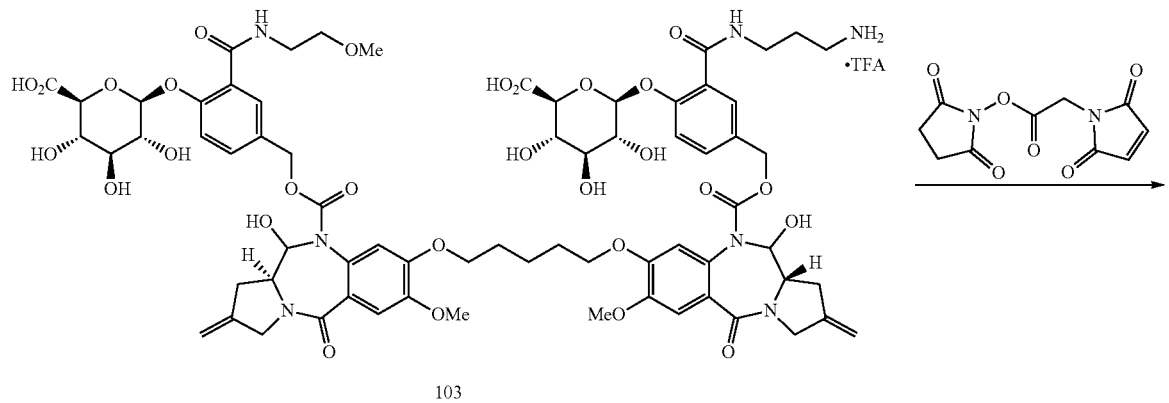

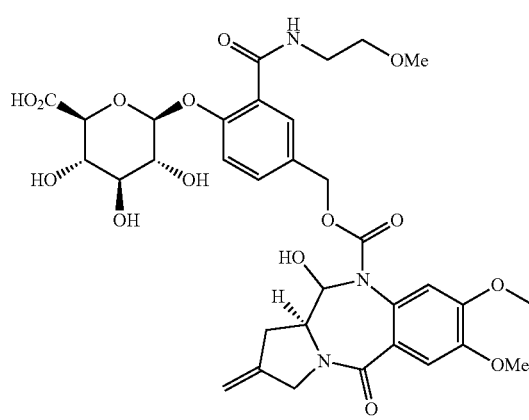
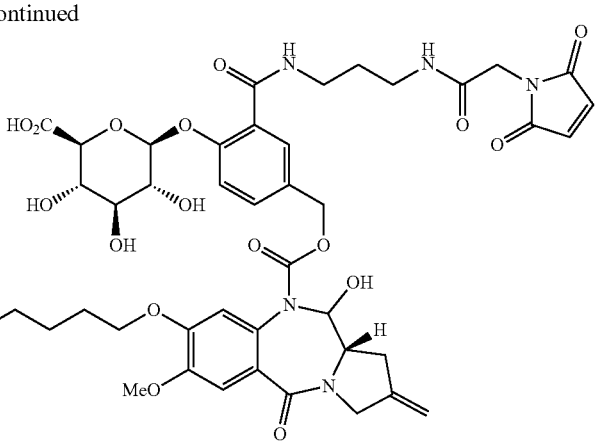

104

Compound 103 (35 mg, 0.024 mmol) and maleimidoacetic acid N-hydroxysuccinimide ester (9 mg, 0.035 mmol) were dissolved in N,N-dimethylformamide (1.5 mL), and then N,N-diisopropylethylamine (0.021 mL, 0.23 mmol) was added thereto at 0° C. under a nitrogen atmosphere. The reaction temperature was gradually raised to room temperature and then the mixture was stirred for 3 hours. The reaction solution was concentrated under reduced pressure, then purified by HPLC, and freeze-dried to obtain Compound 104 (15.1 mg, 37%) as a white solid.

EI-MS m/z: [M+H]$^+$ 1612.6, ½[M+H]$^+$ 807.2.

<Example 40> Preparation of Compound 110

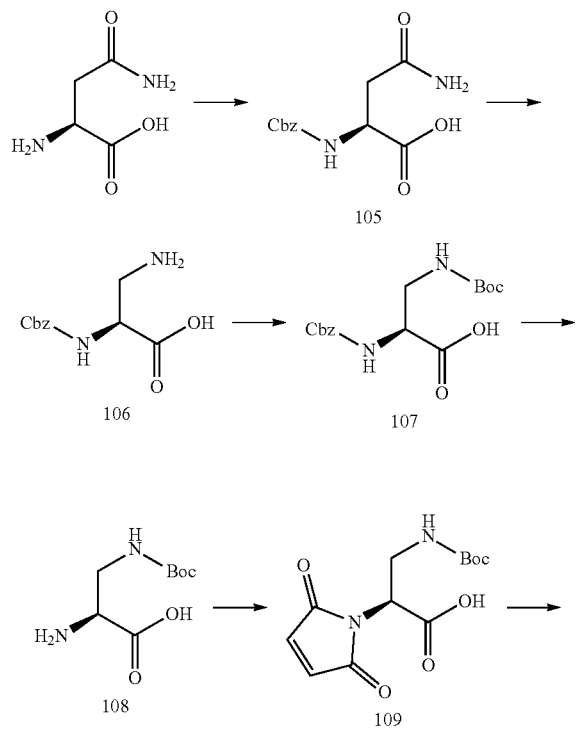

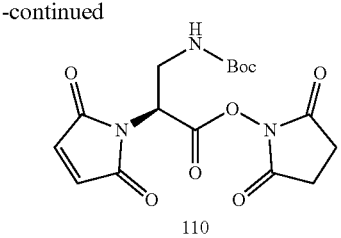

110

Preparation of Compound 105

L-asparagine (3.0 g, 22.7 mmol) was dissolved in 1 N aqueous sodium carbonate solution (30 mL), then benzyl chloroformate (6.3 mL, 45.4 mmol) was added thereto at 0° C., and the mixture was stirred for 12 hours under a nitrogen atmosphere. Distilled water (50 ml) was added to the reaction solution, and then the reaction solution was acidified (pH 2) with a 1 N aqueous hydrochloric acid solution. This mixture was subjected to extraction using ethyl acetate (3×50 mL), and the combined organic layers were dried over anhydrous sodium sulfate. The resultant was filtered, and then concentrated under reduced pressure to obtain Compound 105 (3.5 g, 58%).

$^1$H-NMR (400 MHz, DMSO-d$_6$) δ 7.51-7.40 (d, J=8.0 Hz, 1H), 7.35 (s, 6H), 6.92 (s, 1H), 5.02 (s, 2H), 2.61-2.35 (m, 2H).

Preparation of Compound 106

Compound 105 (3.5 g, 13.1 mmol) was dissolved in ethyl acetate/acetonitrile/distilled water (30 mL/30 mL/15 mL), then (diacetoxyiodo)benzene (5.1 g, 15.7 mmol) was added thereto, and the mixture was stirred for 10 hours under a nitrogen atmosphere. The solid formed was filtered and concentrated under reduced pressure to obtain Compound 106 (2.8 g, 89%).

$^1$H-NMR (400 MHz, DMSO-d$_6$) δ 9.94 (s, 1H), 7.96 (s, 2H), 7.72 (d, J=8.8 Hz, 1H), 7.37 (s, 5H), 5.07 (s, 2H), 4.29 (s, 1H), 3.23 (br, 1H), 3.02 (br, 1H).

Preparation of Compound 107

Compound 106 (2.8 g, 11.7 mmol) was dissolved in 1,4-dioxane/distilled water (25 mL 46 mL), then sodium hydroxide (0.5 g, 11.7 mmol) and di-t-butyl dicarbonate (3.0 mL, 12.9 mmol) were added thereto, and the mixture was stirred at room temperature for 8 hours under a nitrogen atmosphere. Distilled water (50 ml) was added to the reaction solution, and then the mixture was washed with ethyl acetate (2×50 ml). The aqueous layer was acidified by addition of citric acid and subjected to extraction using ethyl acetate (3×50 mL), and then the extract was dried over anhydrous sodium sulfate. The resultant was filtered and concentrated under reduced pressure to obtain Compound 107 (2.7 g, 68%).

$^1$H-NMR (400 MHz, CDCl$_3$) δ 7.31 (s, 5H), 5.15-5.01 (m, 2H), 4.82-4.02 (m, 1H), 3.68-3.43 (m, 2H), 1.39 (s, 9H).

Preparation of Compound 108

Compound 107 (2.7 g, 7.9 mmol) was dissolved in methanol (40 mL) and then palladium/charcoal (10%) (Pd/C, 0.5 g) was added thereto. The reaction solution was stirred at room temperature for 4 hours under a hydrogen atmosphere. The reaction solution was filtered through Celite and concentrated to obtain Compound 108 (1.2 g, 75%).

$^1$H-NMR (400 MHz, D$_2$O) δ 3.70-3.65 (m, 1H), 3.55-3.25 (m, 2H), 1.28 (s, 9H).

Preparation of Compound 109

Compound 108 (0.40 g, 1.96 mmol) and maleic anhydride (192 mg, 1.96 mmol) were dissolved in acetic acid (1.6 mL) and then the solution was stirred at room temperature for 3 hours. The reaction solution was concentrated under reduced pressure, and dichloromethane (10 mL) was added thereto, and the solid produced was filtered and then vacuum dried. This solid dried was diluted with toluene (15 mL), then triethylamine (1.2 mL, 8.6 mmol) and N,N-dimethylacetamide (0.75 mL) were added thereto, and the mixture was heated under reflux. After 16 hours of the reaction, the reaction solution was concentrated under reduced pressure, purified by HPLC, and then freeze-dried to obtain Compound 109 (287 mg, 52%).

$^1$H-NMR (400 MHz, CDCl$_3$) δ 6.66 (s, 2H), 5.17 (br, 1H), 4.61 (br, 1H), 3.68 (br, 1H), 1.35 (s, 9H).

Preparation of Compound 110

Compound 109 (0.15 g, 0.52 mmol) was dissolved in N,N-diisopropylethylamine (3 mL) and then N-(3-dimethylaminopropyl)-N'-ethylcarbodiimide hydrochloride (0.15 g, 0.79 mmol) and N-hydroxysuccinimide (0.09 g, 0.79 mmol) were added thereto. The reaction solution was stirred at room temperature for 12 hours. Distilled water (30 mL) was added to the reaction solution, and then the mixture was subjected to extraction using ethyl acetate (30 mL). The organic layer extracted was dried over anhydrous sodium sulfate, filtered, concentrated under reduced pressure, and then purified by column chromatography to obtain Compound 110 (0.08 g, 40%).

EI-MS m/z: [M+Na]$^+$ 404.3.

<Example 41> Preparation of Compound 112

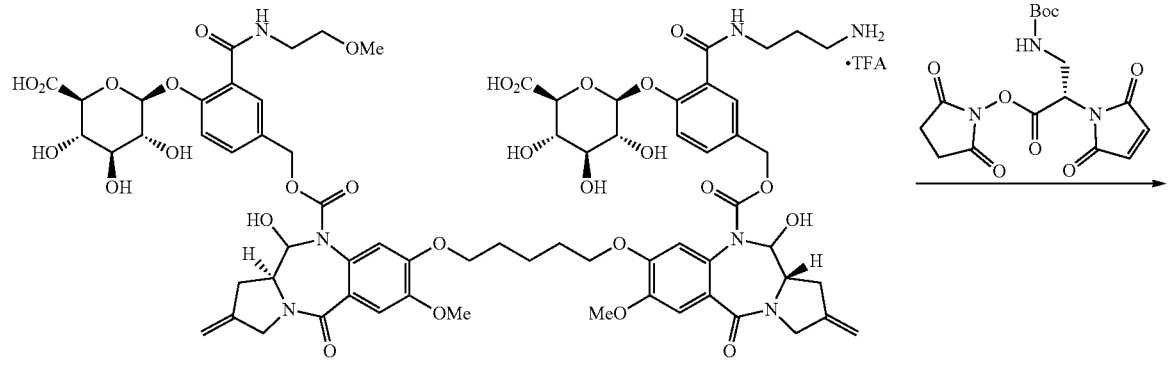

103

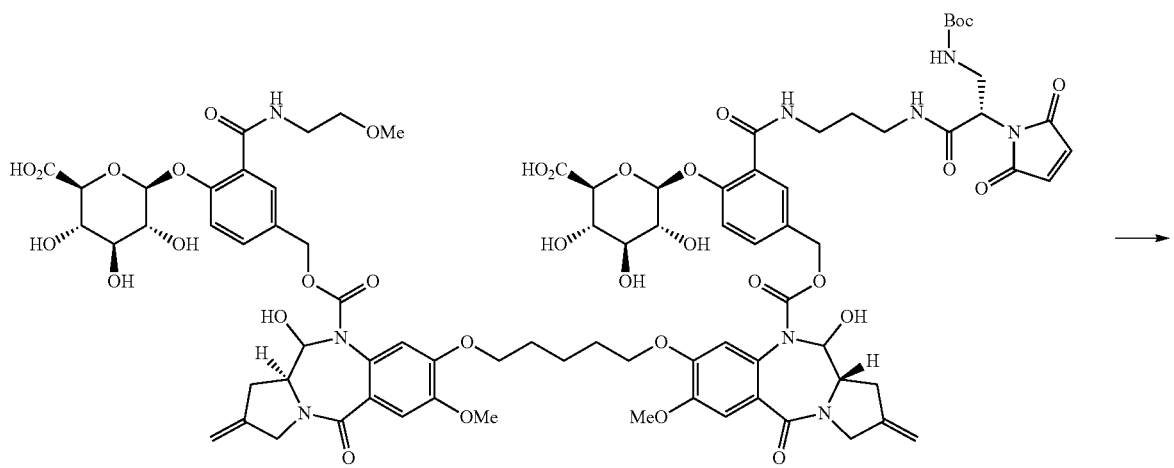

111

111

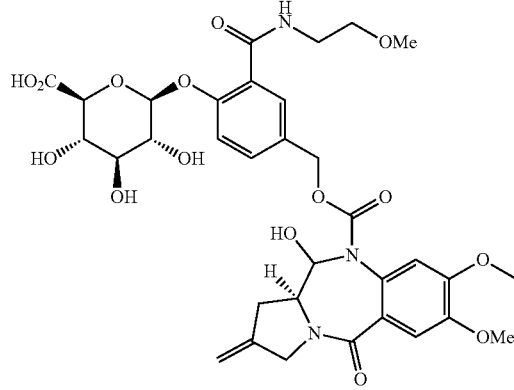

112

-continued

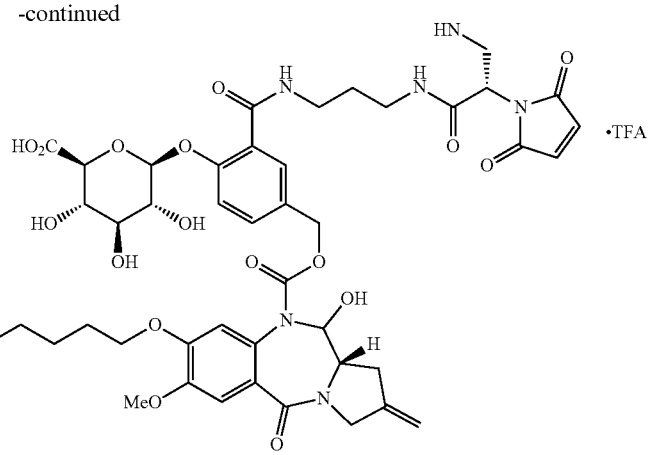

112

Preparation of Compound 111

Compound 103 (57 mg, 0.04 mmol) and Compound 110 (0.016 g, 0.04 mmol) were dissolved in N,N-dimethylformamide (3 mL), then N,N-diisopropylethylamine (0.02 mL, 0.12 mmol) was added thereto, and the mixture was stirred at room temperature for 6 hours under a nitrogen atmosphere. The reaction solution was concentrated under reduced pressure, then purified by HPLC, and freeze-dried to obtain Compound 111 (37 mg, 58%).

EI-MS m/z: [M+H]$^+$ 1741.7, ½[M+H]$^+$ 871.7.

Preparation of Compound 112

Compound 111 (0.035 g, 0.02 mmol) was diluted with dichloromethane (3 mL), then trifluoroacetic acid (0.3 mL) was added thereto at 0° C., and the mixture was stirred for 3 hours. The reaction solution was concentrated under reduced pressure, then purified by HPLC, and freeze-dried to obtain Compound 112 (6.5 mg, 20%) as a white solid.

EI-MS m/z: [M+H]$^+$ 1641.9, ½[M+H]$^+$ 821.8.

<Example 42> Preparation of Compound 115

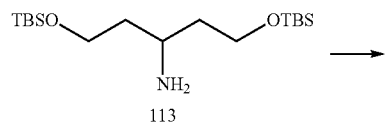

113

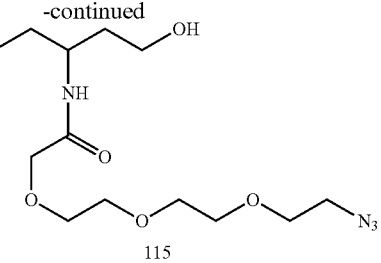

114

-continued

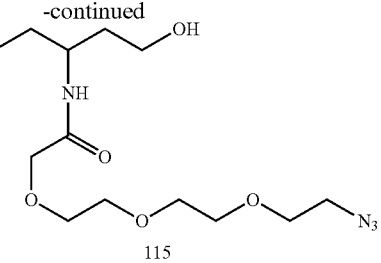

115

Preparation of Compound 114

In dichloromethane (10 mL), 2-[2-[2-(2-azidoethoxy)ethoxy]ethoxy]acetic acid (1.1 g, 4.71 mmol) was dissolved, then 1-hydroxybenzotriazole (0.75 g, 5.60 mmol) and 1-(3-dimethylaminopropyl)-3-ethylcarbodiimide hydrochloride (1.15 g, 6.03 mmol) were added thereto in this order at 0° C. under a nitrogen atmosphere, and the mixture was stirred for 30 minutes. A solution of Compound 113 (1.5 g, 4.31 mmol, Compound 113 was prepared by the method described in WO2017/160569 A1) and triethylamine (1.08 mL, 7.76 mmol) in dichloromethane (10 mL) was added to the mixture under a nitrogen atmosphere. The reaction temperature was raised to room temperature, and this mixture was stirred for 12 hours, then diluted with dichloromethane (100 mL), washed with a saturated aqueous sodium hydrogencarbonate solution (100 mL), and then dried over anhydrous sodium sulfate. The resultant was filtered, then concentrated, and purified by column chromatography to obtain Compound 114 (2.1 g, 87%).

$^1$H-NMR (400 MHz, CDCl$_3$) δ 6.83 (d, 1H), 4.15-4.11 (m, 1H), 3.96 (s, 2H), 3.72-3.62 (m, 14H), 3.39-3.37 (m, 2H) 1.81-1.60 (m, 4H), 0.88 (s, 18H) 0.42 (s, 12H).

Preparation of Compound 115

Compound 114 (2.1 g, 3.73 mmol) was dissolved in methanol (30 mL), then concentrated hydrochloric acid (0.5 mL) was added thereto at 0° C. under a nitrogen atmosphere, and then the mixture was stirred at room temperature for 2 hours. The reaction solution was neutralized with triethylamine, then concentrated, and purified by column chromatography to obtain Compound 115 (1.2 mg, 98%).

$^1$H-NMR (400 MHz, CDCl$_3$) δ7.54 (br s, 1H), 4.31-4.28 (m, 1H), 4.02 (s, 2H), 3.68-3.65 (m, 14H), 3.43-3.40 (m, 2H), 3.21 (br s, 2H), 1.93-1.85 (m, 2H), 1.64-1.57 (m, 2H).

<Example 43> Preparation of Compound 118

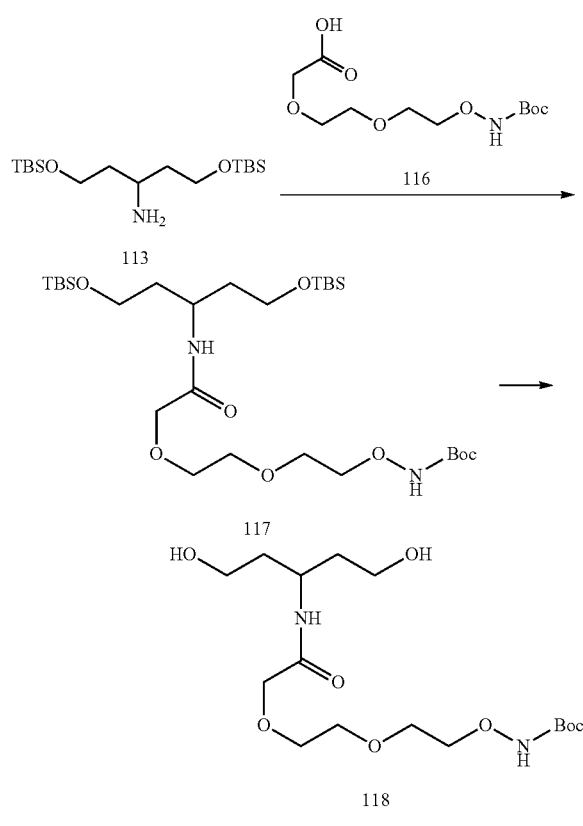

Preparation of Compound 117

Compound 116 (1.32 g, 4.73 mmol, Compound 116 was prepared by the method described in PCT/US2016/063564) was dissolved in dichloromethane (20 mL), and then 1-hydroxybenzotriazole (0.86 g, 5.59 mmol) and 1-(3-dimethylaminopropyl)-3-ethylcarbodiimide hydrochloride were added thereto at 0° C. under a nitrogen atmosphere. A solution of Compound 113 (1.5 g, 4.31 mmol) and triethylamine (1.08 mL, 7.74 mmol) in dichloromethane (5 mL) was added to the mixture at 0° C. under a nitrogen atmosphere. The reaction temperature was raised to room temperature, and this mixture was stirred for 12 hours, then diluted with dichloromethane (100 mL), washed with a saturated aqueous sodium hydrogencarbonate solution (100 mL), and then dried over anhydrous sodium sulfate. The resultant was filtered, then concentrated, and purified by column chromatography to obtain Compound 117 (2.05 g, 79%).

$^1$H-NMR (400 MHz, CDCl$_3$) δ 7.60 (s, 1H), 6.92 (d, J=9.2 Hz, 1H), 4.15-4.10 (m, 1H), 4.05-4.03 (m, 2H), 3.97 (s, 1H), 3.73-3.66 (m, 10H), 1.84-1.72 (m, 4H), 1.48 (s, 9H), 0.89 (m, 18H), 0.05 (s, 12H).

Preparation of Compound 118

Compound 117 (2.05 g, 3.37 mmol) was dissolved in methanol (10 mL), then camphorsulfonic acid (158 mg, 0.68 mmol) was added thereto at 0° C. under a nitrogen atmosphere, and then the mixture was stirred at 0° C. for 4 hours. The reaction solution was neutralized with triethylamine (1 mL), then concentrated, and purified by column chromatography to obtain Compound 118 (1.28 g, 99%).

$^1$H-NMR (400 MHz, CDCl$_3$) δ 7.76 (d, J=7.2 Hz, 1H), 7.64 (s, 1H), 4.32-4.29 (m, 1H), 4.05-4.03 (m, 4H), 3.75-3.69 (m, 10H), 3.48 (br s, 2H), 1.94-1.85 (m, 2H), 1.68-1.61 (m, 4H), 1.48 (s, 9H).

<Example 44> Preparation of Compound 124

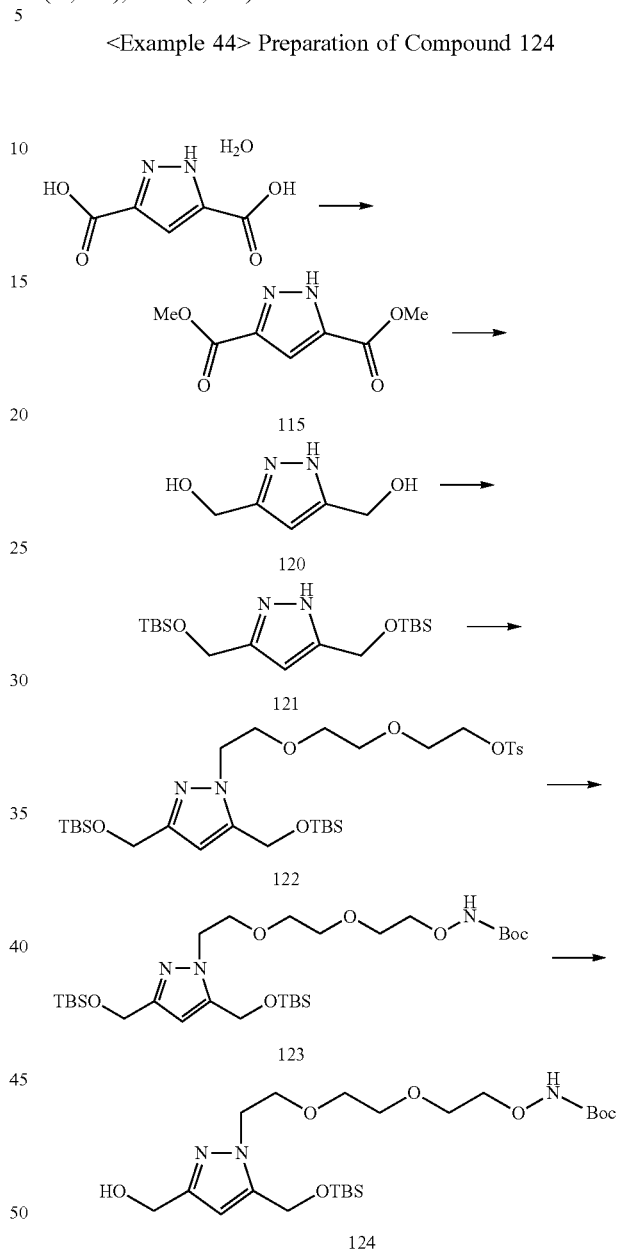

Preparation of Compound 119

In methanol (50 mL), 3,5-pyrazoldicarboxylic acid hydrate (5 g, 28.71 mmol) was dissolved, then thionyl chloride (6.28 mL, 86.15 mmol) was added thereto at 0° C. under a nitrogen atmosphere, and then the mixture was heated to 80° C. The reaction solution was stirred for 4 hours and then concentrated to obtain Compound 119 (7.1 g, 99%).

$^1$H-NMR (400 MHz, CDCl$_3$) δ 7.34 (s, 1H), 3.96 (s, 6H)

Preparation of Compound 120

Compound 119 (3.8 g, 20.63 mmol) was dissolved in tetrahydrofuran (200 mL), then lithium aluminum hydride (1 M tetrahydrofuran solution, 41.2 mL, 41.26 mmol) was added thereto at 0° C. under a nitrogen atmosphere, and then the mixture was heated under reflux and stirred for 12 hours. The reaction mixture was cooled to 0° C., distilled water (50 mL) was gradually added thereto, and then the mixture was concentrated, diluted with methanol (200 mL), and then heated to 80° C. again. The hot reaction product was filtered, and the filtrate was concentrated. The filtrate was diluted with ethanol (10 mL), then hydrochloric acid (4 N 1,4-dioxane solution, 82.6 mL, 22.7 mmol) was added thereto, and the mixture was stirred for 20 minutes. Diethyl ether (200 mL) was added to the reaction solution, and the solid produced was filtered and dried to obtain Compound 120 (2.6 g, 78%).

$^1$H-NMR (400 MHz, DMSO-$d_6$) δ 6.32 (s, 1H), 4.52 (s, 4H).

Preparation of Compound 121

Compound 120 (2.59 g, 15.73 mmol) was dissolved in N,N-dimethylformamide (75 mL), then imidazole (5.35 g, 78.68 mmol) and t-butyldimethylsilyl chloride (5.69 g, 37.8 mmol) were added thereto at 0° C. under a nitrogen atmosphere. The reaction solution was stirred for 4 hours, then diluted with ethyl acetate (100 mL), washed with a saturated aqueous ammonium chloride solution (100 mL) and brine (100 mL) in this order, and dried over anhydrous sodium sulfate. The resultant was filtered, then concentrated, and purified by column chromatography to obtain Compound 121 (4.56 g, 81%).

$^1$H-NMR (400 MHz, CDCl$_3$) δ 6.09 (s, 1H), 4.74 (s, 4H), 0.88 (s, 18H), 0.09 (s, 12H).

Preparation of Compound 122

Compound 121 (1.6 g, 4.48 mmol) was dissolved in N,N-dimethylformamide (25 mL), then cesium carbonate (3.2 g, 9.8 mmol) and triethylene glycol ditosylate (4.05 g, 8.97 mmol) were added thereto at 0° C. under a nitrogen atmosphere, and then the mixture was heated to 50° C. The reaction solution was stirred for 4 hours, then diluted with ethyl acetate (100 mL), then washed with brine (100 mL), and dried over anhydrous sodium sulfate. The resultant was filtered, then concentrated, and purified by column chromatography to obtain Compound 122 (1.69 g, 60%).

$^1$H-NMR (400 MHz, CDCl$_3$) δ 7.78 (d, J=8 Hz, 2H), 7.33 (d, J=8 Hz, 2H), 6.10 (s, 1H), 4.67 (d, J=5.2 Hz, 4H), 4.25-4.22 (m, 2H), 4.13-4.11 (m, 2H), 3.79-3.76 (m, 2H), 3.62-3.60 (m, 2H), 3.49-3.48 (m, 2H), 3.46-3.45 (m, 2H), 0.89 (d, J=18 Hz, 18H), 0.06 (d, J=5.6 Hz, 12H).

Preparation of Compound 123

Compound 122 (1.69 g, 2.62 mmol) was dissolved in acetonitrile (25 mL), then t-butyl N-hydroxycarbamate (1.35 g, 5.51 mmol) and 1,8-diazabicyclo[5.4.0]-7-undecene (0.8 mL, 5.38 mmol) were added thereto at 0° C. under a nitrogen atmosphere, and then the mixture was heated to 50° C. The reaction solution was stirred for 12 hours, then diluted with ethyl acetate (100 mL), then washed with brine (100 mL), and dried over anhydrous sodium sulfate. The resultant was filtered, then concentrated, and purified by column chromatography to obtain Compound 123 (1.5 g, 60%).

$^1$H-NMR (400 MHz, CDCl$_3$) δ 6.14 (s, 1H), 4.70 (d, J=8 Hz, 4H), 4.29-4.26 (m, 2H), 3.83-3.74 (m, 4H), 3.63-3.62 (m, 2H), 3.55-3.53 (m, 2H), 1.49 (s, 9H), 0.92 (d, J=18 Hz, 18H), 0.09 (d, J=0.8 Hz, 12H).

Preparation of Compound 124

Compound 123 (1.5 g, 2.13 mmol) was dissolved in tetrahydrofuran (20 mL), and then tetrabutylammonium fluoride (1 M tetrahydrofuran solution, 8.18 mL, 8.18 mmol) was added thereto at 0° C. under a nitrogen atmosphere. The reaction solution was stirred for 12 hours, then diluted with ethyl acetate (50 mL), washed with a saturated aqueous ammonium chloride solution (50 mL), and then dried over anhydrous sodium sulfate. The resultant was filtered, then concentrated, and purified by column chromatography to obtain Compound 124 (660 mg, 66%).

$^1$H-NMR (400 MHz, CDCl$_3$) δ 6.22 (s, 1H), 4.65 (d, J=4.8 Hz, 2H), 4.57 (d, J=6 Hz, 2H), 4.34-4.31 (m, 2H), 3.38-3.38 (m, 2H), 3.66-3.54 (m, 8H), 1.52 (s, 9H).

<Example 45> Preparation of Compound 131

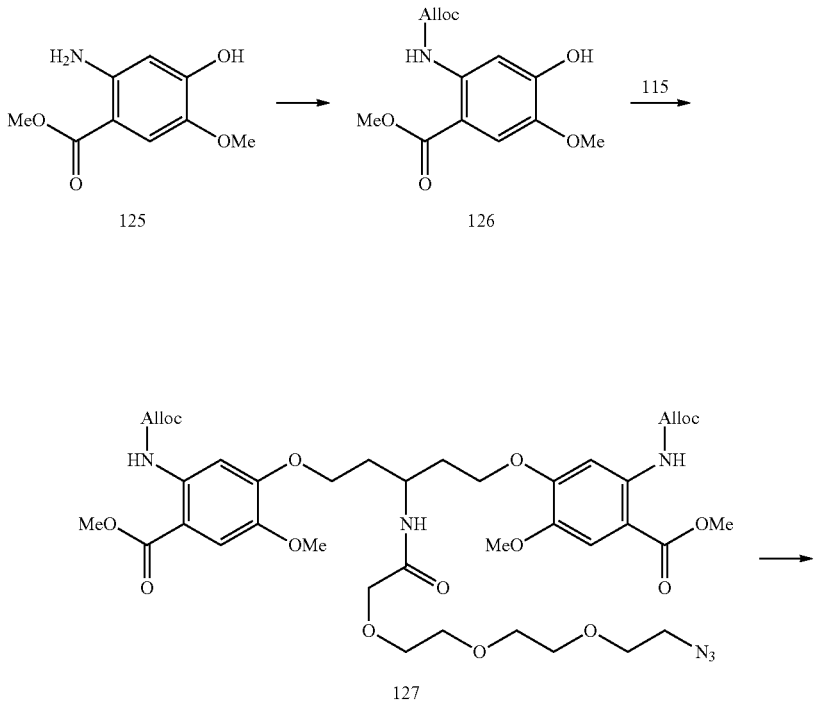

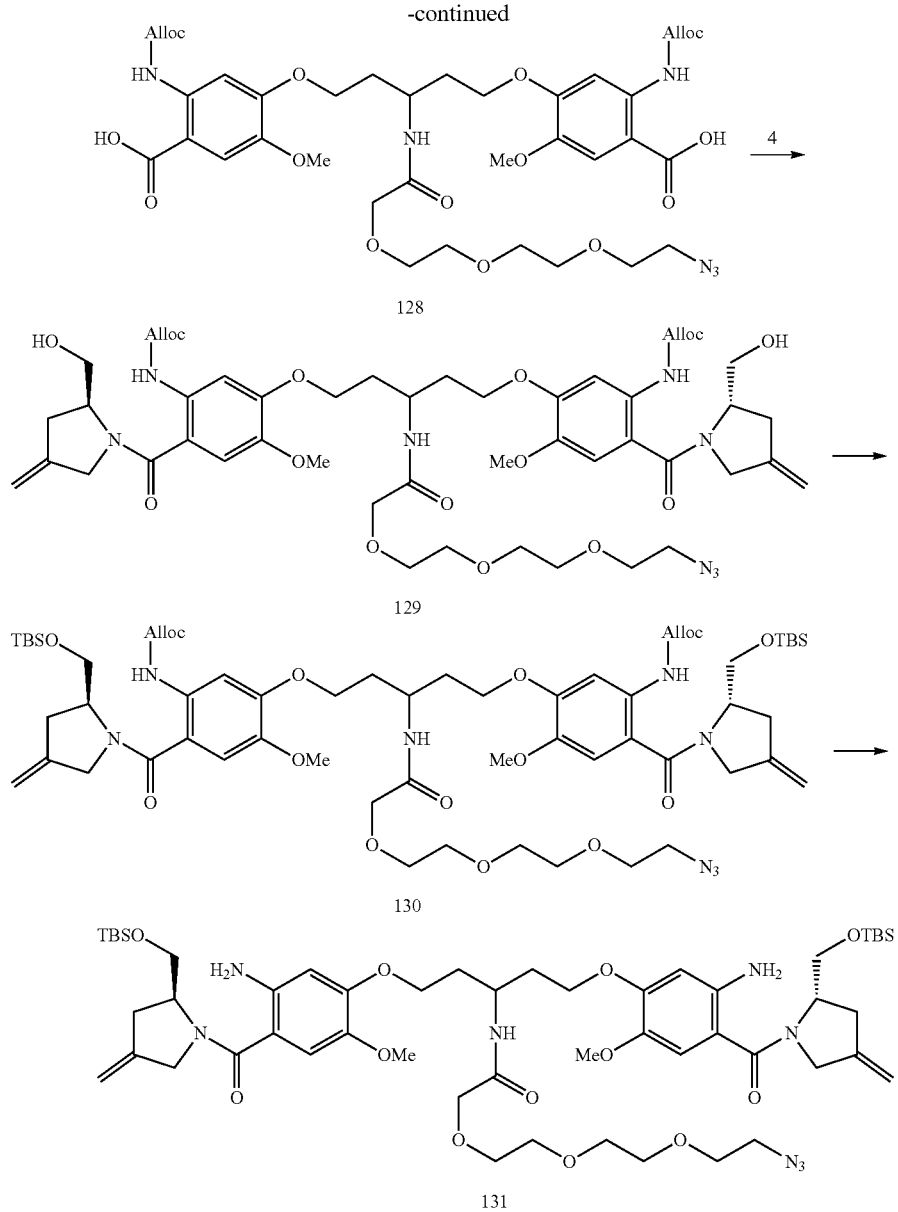

128

129

130

131

Preparation of Compound 126

Compound 125 (1.12 g, 5.67 mmol, Compound 125 was prepared by the method described in WO2016/148674 A1) was dissolved in dichloromethane (30 mL), then pyridine (0.67 mL, 8.51 mmol) and allyl chloroformate (0.66 mL, 6.24 mmol) were added thereto at 0° C. under a nitrogen atmosphere, and then the mixture was stirred for 1 hour. The reaction solution was concentrated and then purified by column chromatography to obtain Compound 126 (1.17 g, 73%).

$^1$H-NMR (400 MHz, CDCl$_3$) δ 10.52 (s, 1H), 8.06 (s, 1H), 7.44 (s, 1H), 6.07 (s, 1H), 6.02-5.92 (m, 1H), 5.36 (d, J=17.2 Hz, 1H), 5.24 (d, J=10.4 Hz, 1H), 4.66 (d, J=5.2, 2H), 3.89 (s, 6H).

Preparation of Compound 127

Compound 115 (920 mg, 2.75 mmol), Compound 126 (1.7 g 6.05 mmol), and triphenylphosphine (2.52 g, 9.35 mmol) were dissolved in dry tetrahydrofuran, then diisopropyl azodicarboxylate (1.66 mL, 8.52 mmol) was added thereto at 0° C. under a nitrogen atmosphere, and then the mixture was stirred at room temperature for 2 hours. The resultant was concentrated and purified by column chromatography to obtain Compound 127 (1.54 g, 65%).

$^1$H-NMR (400 MHz, CDCl$_3$) δ 10.54 (s, 2H), 8.07 (s, 2H), 7.41 (s, 2H), 6.00-5.93 (m, 2H), 5.36 (d, J=17.2 Hz, 2H), 5.25 (d, J=10.0 Hz, 2H), 4.64-4.63 (m, 4H), 4.44 (bs, 1H), 4.23-4.20 (m, 4H), 3.99 (s, 2H), 3.89 (s, 3H), 3.83 (s, 3H), 3.66-3.60 (m, 11H), 3.35-3.34 (m, 2H), 2.25-2.13 (m, 4H).

Preparation of Compound 128

Compound 127 (1.54 g, 1.78 mmol) was dissolved in methanol/tetrahydrofuran/distilled water (15 mL/15 mL/15 mL), then sodium hydroxide (0.28 g, 7.15 mmol) was added thereto, and then the mixture was stirred at 40° C. for 5 hours. The reaction solution was diluted with ethyl acetate (100 mL) and subjected to extraction using distilled water (100 mL). The combined aqueous layers were acidified with 1 N aqueous hydrochloric acid solution and then subjected to extraction using ethyl acetate (100 mL), and the extract was dried over anhydrous sodium sulfate. The resultant was filtered and then concentrated to obtain Compound 128 (1.48 g).

¹H-NMR (400 MHz, DMSO-d₆) δ 10.84 (s, 2H), 7.94 (s, 2H), 7.40 (s, 2H), 6.00-5.95 (m, 2H), 5.34 (d, J=17.2 Hz, 2H), 5.24 (d, J=10.0 Hz, 2H), 4.64-4.63 (m, 4H), 4.18 (br s, 1H), 4.04-4.01 (m, 4H), 3.88 (s, 2H), 3.74 (s, 6H), 3.55-3.51 (m, 12H), 2.05-1.98 (m, 4H).

Preparation of Compound 129

Compound 128 (1.63 g, 1.95 mmol) was dissolved in N,N-dimethylformamide (5 mL), then N,N,N',N'-tetramethyl-O-(1H-benzotriazol-1-yl)uronium hexafluorophosphate (2.22 g, 5.87 mmol) was added thereto at 0° C. under a nitrogen atmosphere, and the mixture was stirred for 30 minutes. A solution of Compound 4 (0.64 g, 4.3 mmol) and N,N-diisopropylethylamine (1.7 mL, 9.78 mmol) in N,N-dimethylformamide (5 mL) was added to the mixture under a nitrogen atmosphere. The reaction temperature was raised to room temperature, and this mixture was stirred for 12 hours, then diluted with ethyl acetate (100 mL), washed with a saturated aqueous sodium hydrogencarbonate solution (200 mL), and then dried over anhydrous sodium sulfate. The resultant was filtered, then concentrated, and purified by column chromatography to obtain Compound 129 (1.2 g).

¹H-NMR (400 MHz, CDCl₃) δ 8.65 (br s, 2H), 7.34 (br s, 2H), 7.21 (d, J=8.8 Hz, 1H), 6.75 (s, 2H), 6.00-5.90 (m, 2H), 5.35 (d, J=16.8 Hz, 2H), 5.23 (d, J=10.4 Hz, 2H), 5.00-4.92 (m, 4H), 4.68-4.57 (m, 6H), 4.48-4.40 (m, 1H), 4.20-4.08 (m, 8H), 3.97 (s, 2H), 3.79 (s, 6H), 3.67-3.63 (m, 14H), 3.39-3.37 (m, 2H), 2.80-2.72 (m, 2H), 2.48-2.44 (m, 2H), 2.22-2.17 (m, 2H), 2.10-2.04 (m, 2H).

Preparation of Compound 130

Compound 129 (1.2 g, 1.17 mmol) was dissolved in dichloromethane (10 mL), and then imidazole (0.4 g, 5.86 mmol) and t-butyldimethylsilyl chloride (0.53 g, 3.5 mmol) were added thereto at 0° C. under a nitrogen atmosphere. The reaction solution was stirred for 12 hours, then brine (50 mL) was added to the reaction solution, and the mixture was subjected to extraction using dichloromethane (2×100 mL), and then the extract was dried over anhydrous sodium sulfate. The resultant was filtered, then concentrated, and purified by column chromatography to obtain Compound 130 (0.98 g, 3 steps 40%).

¹H-NMR (400 MHz, CDCl₃) δ 8.81 (br s, 2H), 7.77 (s, 2H), 7.12 (d, J=8 Hz, 1H), 6.80 (s, 2H), 5.99-5.89 (m, 2H), 5.34 (d, J=17.2 Hz, 2H), 5.23 (d, J=10.4 Hz, 2H), 4.98-4.91 (m, 4H), 4.65-4.56 (m, 6H), 4.54-4.44 (m, 1H), 4.19-4.14 (m, 8H) 4.01 (s, 2H), 3.80 (s, 6H), 3.66-3.61 (m, 14H), 3.39-3.36 (m, 2H), 2.69 (s, 4H), 2.28-2.19 (m, 2H), 2.15-2.05 (m, 2H), 0.87 (s, 18H), 0.03 (s, 12H).

Preparation of Compound 131

Compound 130 (0.98 g, 0.78 mmol) was dissolved in dichloromethane (5 mL), then pyrrolidine (0.16 mL, 1.95 mmol) and tetrakis(triphenylphosphine)palladium(0) (18 mg, 0.015 mmol) were added thereto, and the mixture was stirred at room temperature for 6 hours under a nitrogen atmosphere. Distilled water (50 mL) was added to the reaction solution, the mixture was subjected to extraction using dichloromethane (50 mL), and then the extract was dried over anhydrous sodium sulfate. The resultant was filtered, then concentrated, and purified by column chromatography to obtain Compound 131 (0.59 g, 70%).

¹H-NMR (400 MHz, CDCl₃) δ 7.12. (d, J=9.2 Hz, 1H), 6.73 (s, 2H), 6.26 (s, 2H), 4.96-4.90 (m, 4H), 4.52 (bs, 1H), 4.38-4.35 (m, 4H), 4.21-4.17 (m, 2H), 4.11-4.03 (m, 6H), 4.00 (s, 2H), 3.75 (s, 6H), 3.66-3.61 m, 12H), 3.37-3.34 (m, 2H), 2.7-2.68 (m, 4H) 2.21-2.18 (m, 2H), 2.12-2.05 (m, 2H), 0.87 (s, 18H), 0.02 (s, 12H).

<Example 46> Preparation of Compound 135

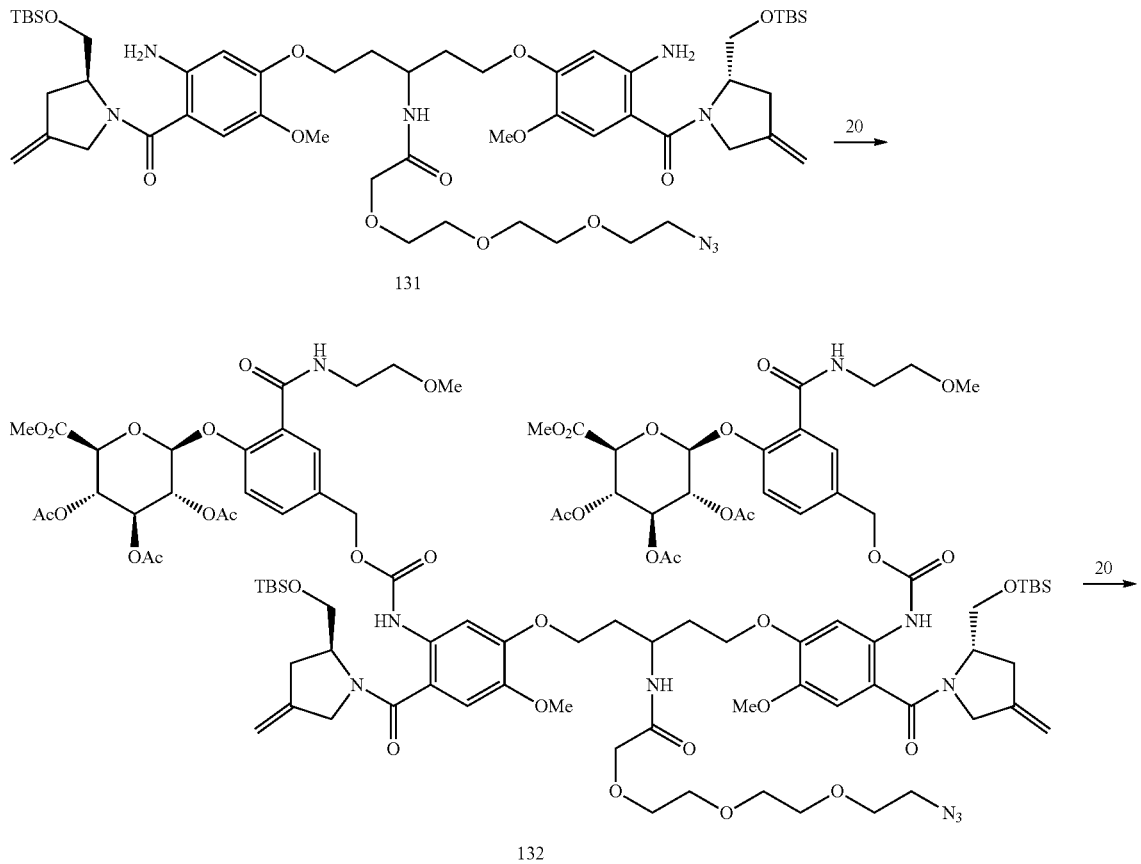

-continued
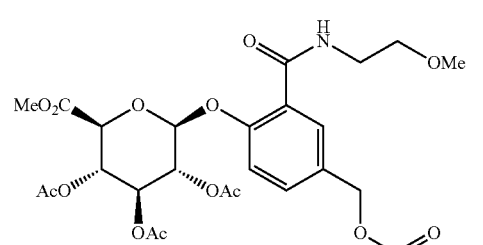
133
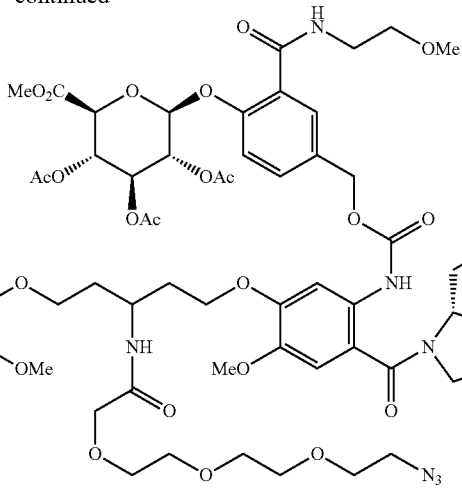
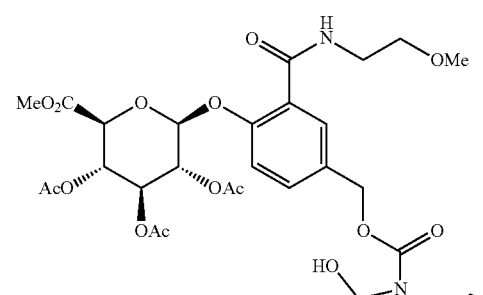
134
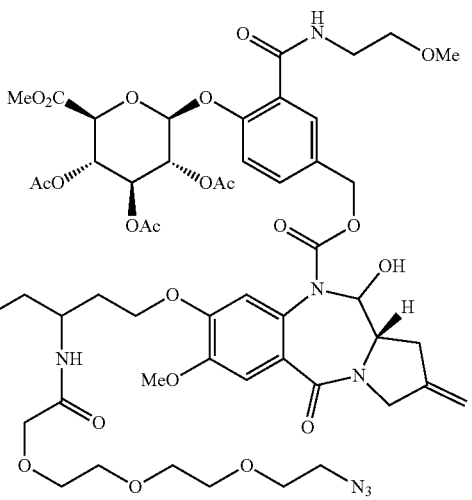
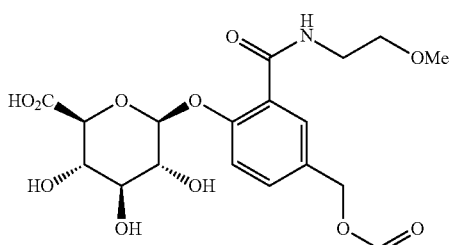
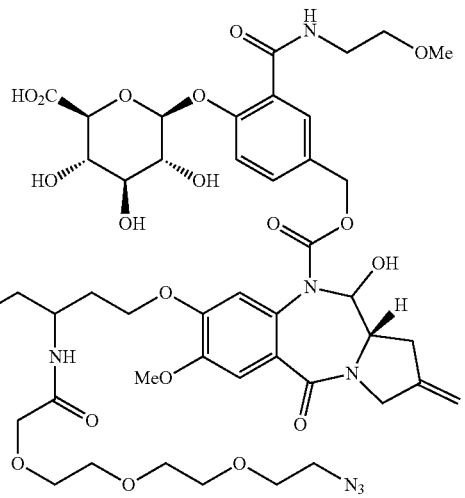
135
Preparation of Compound 132
Compound 131 (590 mg, 0.54 mmol) was dissolved in dry tetrahydrofuran (5 mL), then triphosgene (116 mg, 0.39 mmol) and triethylamine (0.2 mL, 1.47 mmol) were added thereto at −10° C., and the mixture was stirred under a nitrogen atmosphere for 1 hour. Compound 20 (707 mg, 1.30 mmol) was dissolved in dry tetrahydrofuran (5 mL), triethylamine (0.2 mL, 01.47 mmol) was added thereto, and this solution was gradually added to the reaction solution. After 1 hour, the reaction solution was heated under reflux and stirred for 12 hours. The reaction solution was diluted with ethyl acetate (30 mL), then washed with brine (20 mL), and dried over anhydrous sodium sulfate. The resultant was filtered, concentrated under reduced pressure, and then purified by column chromatography to obtain Compound 132 (1.0 g, 83%).

EI-MS m/z: [M+H]$^+$ 2219.10, ½[M+H]$^+$ 1110.30

Preparation of Compound 133

Compound 132 (1 g, 0.45 mmol) was dissolved in tetrahydrofuran/distilled water (5 mL/5 mL), acetic acid (15 mL) was added thereto, and then the mixture was stirred at room temperature for 16 hours under a nitrogen atmosphere. The reaction solution was diluted with ethyl acetate (50 mL), then washed with distilled water (50 mL), and then dried over anhydrous sodium sulfate. The resultant was filtered, then concentrated, and purified by column chromatography to obtain Compound 133 (720 mg, 80%).

EI-MS m/z: [M+H]$^+$ 1990.95, ½[M+H]$^+$ 996.06.

Preparation of Compound 134

Compound 133 (370 mg, 0.18 mmol) was dissolved in dichloromethane (10 mL), then Dess-Martin periodinane (181 mg, 0.42 mmol) was added thereto, and the mixture was stirred at room temperature for 16 hours under a nitrogen atmosphere. The reaction solution was diluted with dichloromethane (20 mL), then washed with a saturated aqueous sodium hydrogencarbonate solution (20 mL), and dried over anhydrous sodium sulfate. The resultant was filtered, concentrated under reduced pressure, and then purified by column chromatography to obtain Compound 134 (350 mg, 90%).

EI-MS m/z: [M+H]$^+$ 1986.61, ½[M+H]$^+$ 994.11.

Preparation of Compound 135

Compound 134 (350 mg, 0.17 mmol) was dissolved in methanol/tetrahydrofuran (7.5 mL/7.5 mL), and then lithium hydroxide (66 mg, 1.58 mmol) dissolved in distilled water (7.5 mL) was gradually added thereto at −40° C. The reaction temperature was gradually raised to 0° C., and the mixture was stirred for 2 hours. The reaction solution was neutralized with acetic acid, then concentrated under reduced pressure, then purified by HPLC, and freeze-dried to obtain Compound 135 (150 mg, 50%) as a white solid.

EI-MS m/z: [M+H]$^+$ 1706.20, ½[M+H]$^+$ 854.00.

<Example 47> Preparation of Compound 137

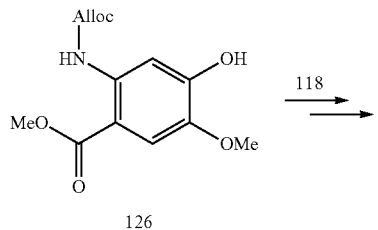

126

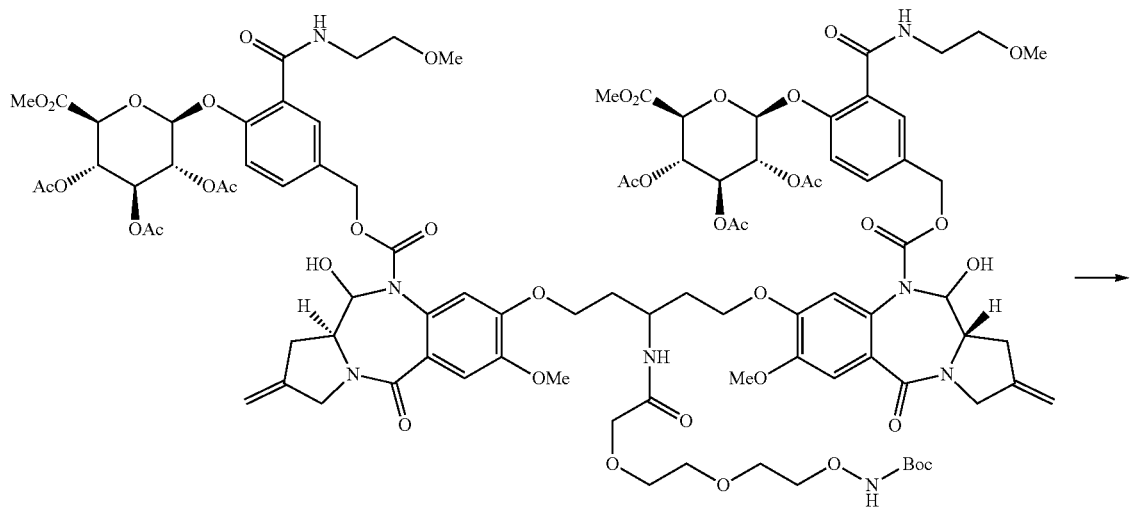

136

125 126

-continued

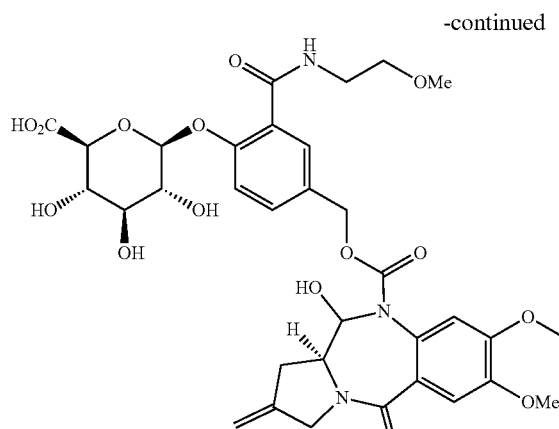
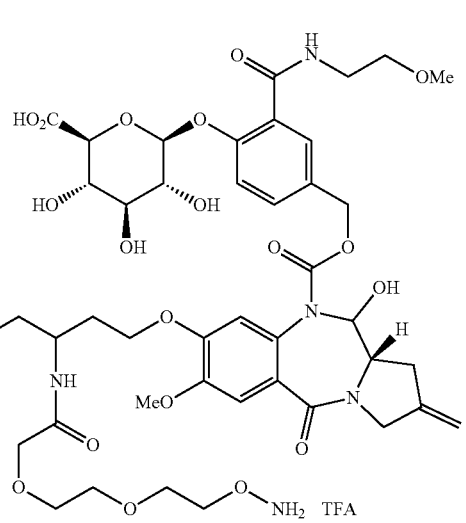

137

Preparation of Compound 136

Compound 136 was prepared from Compound 126 and Compound 118 by a method similar to that for the synthesis of Compound 134.

EI-MS m/z: [M+H]$^+$ 2032.98, ½[M+H]$^+$ 1017.03.

Preparation of Compound 137

Compound 136 (205 mg, 0.10 mmol) was dissolved in methanol/tetrahydrofuran (4 mL/6 mL) and then a solution of lithium hydroxide (38 mg, 0.91 mmol) in distilled water (4 mL) was gradually added thereto at −40° C. The mixture was stirred for 4 hours while gradually raising the reaction temperature to 0° C. The reaction solution was neutralized with acetic acid, then concentrated under reduced pressure, and freeze-dried. The solid obtained was diluted with dichloromethane (5 mL), then trifluoroacetic acid (1.5 mL) was added thereto at 0° C., and the mixture was stirred for 4 hours. The reaction solution was concentrated under reduced pressure, then purified by HPLC, and freeze-dried to obtain Compound 137 (29 mg, 17%) as a white solid.

EI-MS m/z: [M+H]$^+$ 1653.01, ½[M+H]$^+$ 826.89.

<Example 48> Preparation of Compound 138

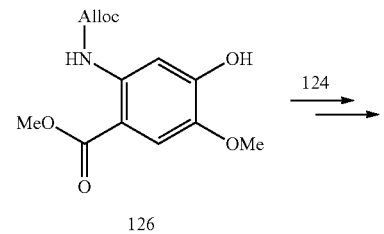

126

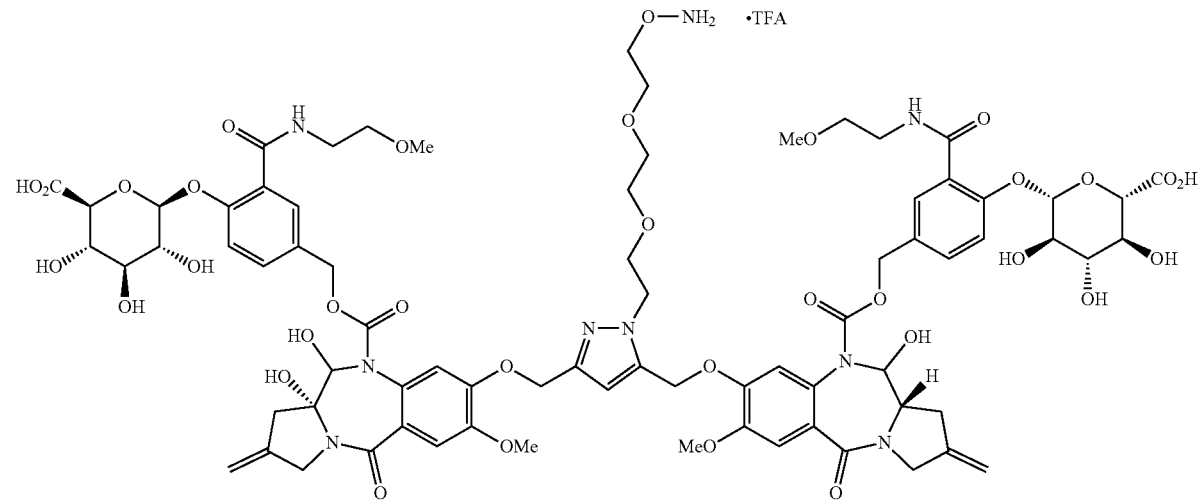

138

Compound 138 was prepared from Compound 126 and Compound 124 by a method similar to that for the synthesis of Compound 137.

EI-MS m/z: [M+H]$^+$ 1647.60, ½[M+H]$^+$ 824.31.

<Example 49> Preparation of Compound 142 was gradually added thereto, and then the mixture was stirred at room temperature for 2 hours. A saturated aqueous ammonium chloride solution (200 mL) was added to the reaction solution, and the mixture was subjected to extraction using dichloromethane (3×100 mL). The combined organic layers were washed with brine (2×100 mL) and then

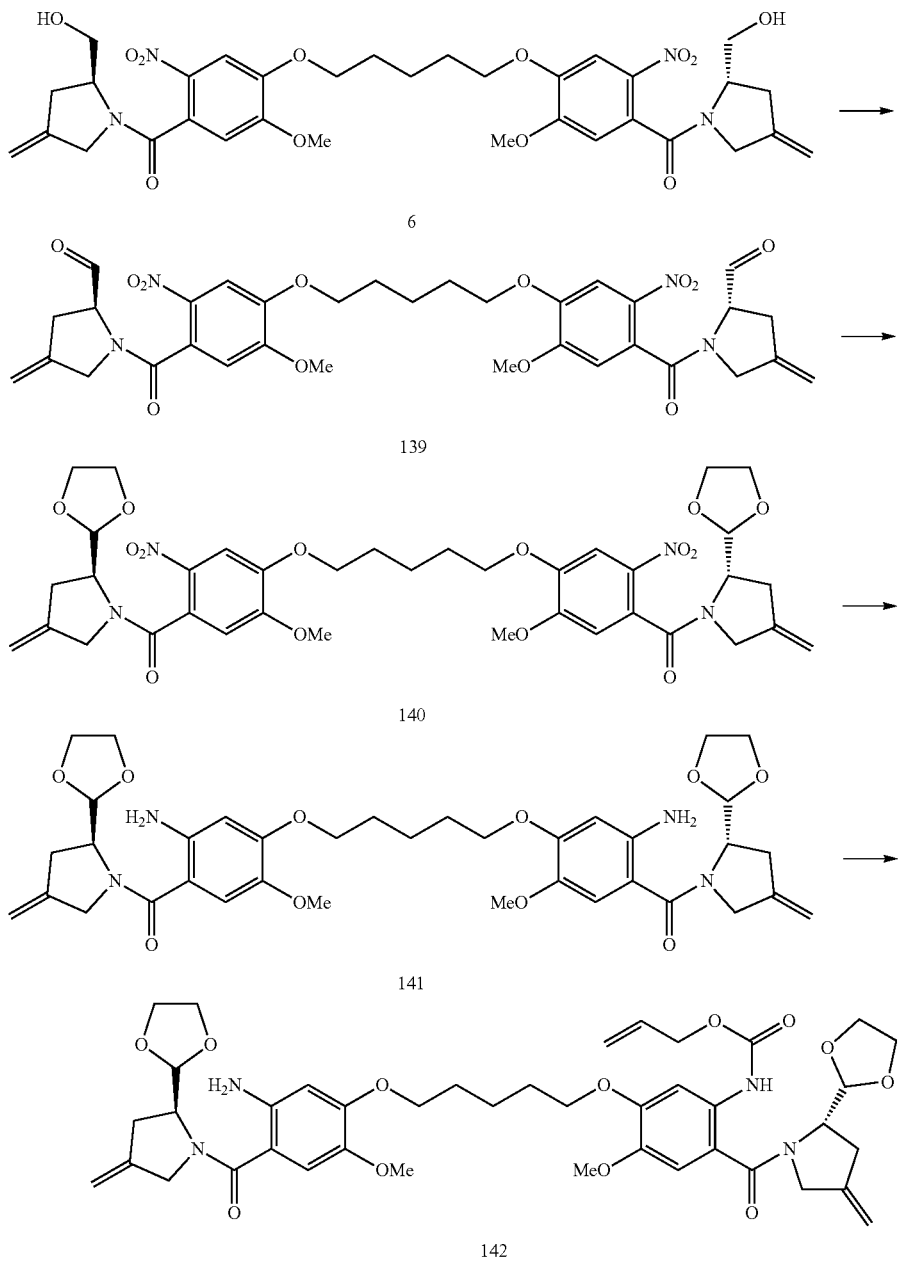

Preparation of Compound 139

Dimethyl sulfoxide (3.53 mL, 3.88 mmol) was dissolved in dichloromethane (30 mL), and then oxalyl chloride (2.0 M dichloromethane solution, 13 mL, 23.9 mmol) was added thereto at −78° C. under a nitrogen atmosphere. Compound 6 (6.8 g, 9.94 mmol) was dissolved in dichloromethane (20 mL) and then this solution was gradually added to the mixture at −78° C. under a nitrogen atmosphere. The reaction solution was stirred for 10 minutes, then the temperature was raised to 0° C., triethylamine (13.85 mL, 4.41 mmol)

dried over anhydrous sodium sulfate. The resultant was filtered, then concentrated, and purified by column chromatography to obtain Compound 139 (5.76 g, 85%).

$^1$H-NMR (400 MHz, CDCl$_3$) δ 9.80 (s, 2H), 7.72 (s, 2H), 6.85 (s, 2H), 5.07 (s, 2H), 4.93 (s, 2H), 4.22-4.10 (m, 6H), 4.00 (s, 6H), 3.94-3.80 (m, 4H), 3.15-2.70 (m, 4H), 2.30-2.10 (m, 2H), 2.12-1.90 (m, 4H), 1.75-1.68 (m, 6H). EI-MS m/z: [M+H]$^+$ 681.6.

Preparation of Compound 140

Compound 139 (1.84 g, 2.71 mmol) was dissolved in benzene and N,N-dimethylformamide (v/v=10:1, 30 mL), and then ethylene glycol (1.5 mL, 27.11 mmol) and camphorsulfonic acid (251 mg, 0.81 mmol) were sequentially added thereto at room temperature under a nitrogen atmosphere. The reaction solution was stirred for 5 minutes, then heated under reflux using a Dean-Stark apparatus, and stirred for 2 hours. The reaction solution was concentrated, diluted with ethyl acetate (100 mL), then a saturated aqueous sodium hydrogencarbonate solution (100 mL) was added to the reaction solution, and the mixture was subjected to extraction using ethyl acetate (3×100 mL). The combined organic layers were washed with brine (2×100 mL) and then dried over anhydrous sodium sulfate. The resultant was filtered, then concentrated, and purified by column chromatography to obtain Compound 140 (1.53 g, 72%).

$^1$H-NMR (400 MHz, CDCl$_3$) δ 7.70 (s, 2H), 6.78 (s, 2H), 5.07 (s, 2H), 4.81 (s, 2H), 4.69 (s, 2H), 4.20-4.02 (m, 6H), 4.00-3.90 (m, 8H), 3.87-3.80 (m, 2H), 3.78-3.70 (m, 4H), 3.60-3.68 (m, 4H), 2.72-2.60 (m, 4H), 2.12-1.92 (m, 4H), 1.65-1.60 (m, 2H). EI-MS m/z: [M+H]$^+$ 769.8.

Preparation of Compound 141

Compound 140 (1.11 g, 1.45 mmol) was dissolved in ethanol (22 mL), and then zinc dust (2.84 g, 43.39 mmol) and formic acid (5% ethanol solution, 1.96 mL) were added thereto. The reaction solution was stirred at room temperature for 3 hours and then filtered through Celite, and ethyl acetate (300 mL) was added thereto. The organic layer was washed with distilled water (2×100 mL), a saturated aqueous sodium hydrogencarbonate solution (2×200 mL), and brine (200 mL) in this order and then dried over anhydrous sodium sulfate. The resultant was filtered, then concentrated, and purified by column chromatography to obtain Compound 141 (800 mg, 78%).

$^1$H-NMR (400 MHz, CDCl$_3$) δ 6.78 (s, 2H), 6.23 (s, 2H), 5.12 (s, 2H), 4.97 (s, 2H), 4.91 (s, 2H), 4.78 (br s, 2H), 4.54 (br s, 2H), 4.33-4.21 (m, 2H), 4.10-3.91 (m, 12H), 3.90-3.82 (m, 4H), 3.78 (s, 6H), 2.72-2.58 (m, 4H), 1.98-1.84 (m, 4H), 1.74-1.58 (m, 2H), 0.87 (s, 18H), 0.02 (s, 12H). EI-MS m/z: [M+H]$^+$ 709.8.

Preparation of Compound 142

Compound 141 (640 mg, 0.90 mmol) was dissolved in dichloromethane (45 mL), and then pyridine (0.15 mL, 1.80 mmol) and allyl chloroformate (86 μL, 0.81 mmol) were added thereto at −78° C. under a nitrogen atmosphere. After the reaction solution was stirred for 1 hour, the reaction temperature was raised to room temperature, and the reaction solution was concentrated and then purified by column chromatography to obtain Compound 142 (320 mg, 43%).

$^1$H-NMR (400 MHz, CDCl$_3$) δ 8.75 (br, 1H), 7.83 (s, 1H), 6.83 (s, 1H), 6.77 (s, 1H), 6.23 (s, 1H), 5.97-5.91 (m, 1H), 5.34, (d, J=17.2 Hz, 1H), 5.23 (d, J=10.0 Hz, 1H), 5.08 (br s, 1H), 5.02-4.88 (m, 6H), 4.80 (br s, 1H), 4.68-4.56 (m, 2H), 4.44 (br s, 2H), 4.30-4.18 (m, 2H), 4.16-4.06 (m, 3H), 3.92-3.84 (m, 3H), 3.83 (s, 3H), 3.78 (s, 3H), 2.74-2.56 (m, 4H), 1.99-1.86 (m, 4H), 1.72-1.60 (m, 2H).

<Example 50> Preparation of Compound 146

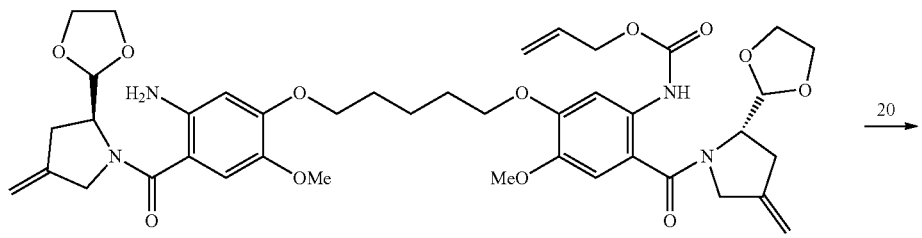

142

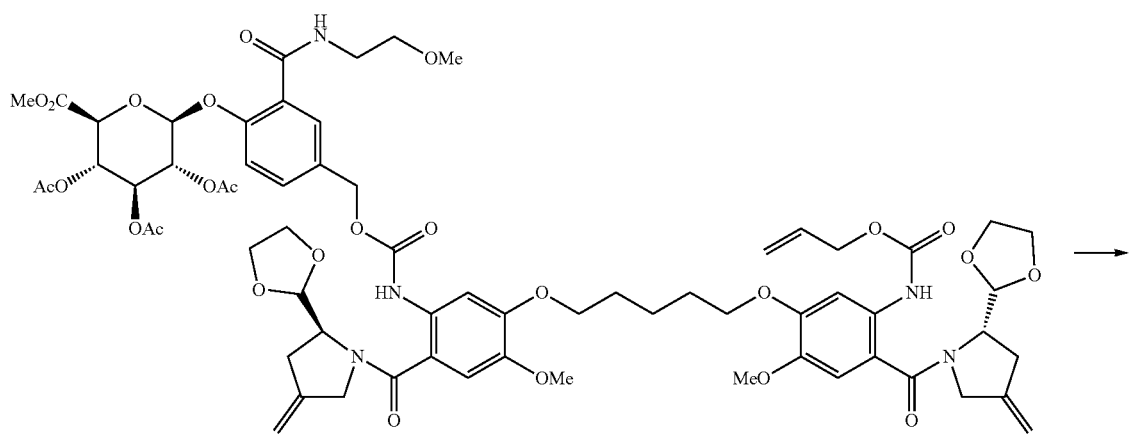

143

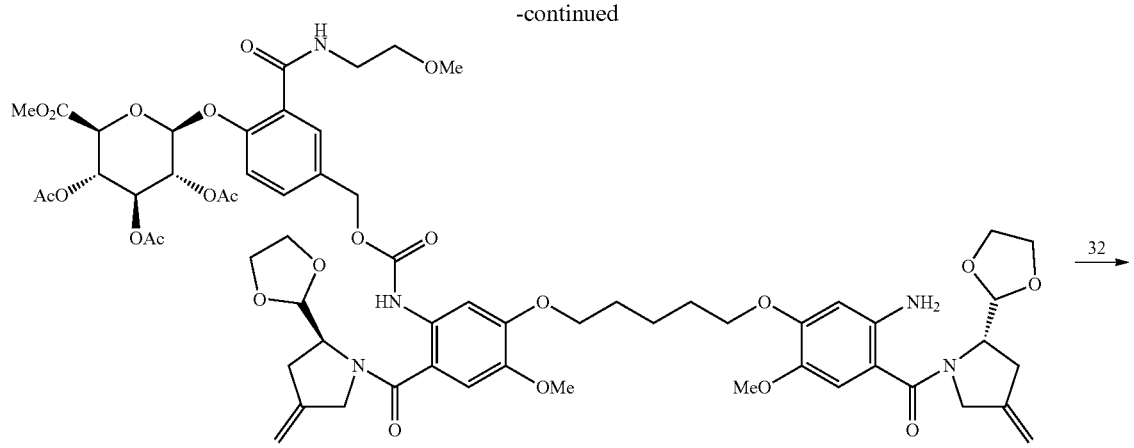

144

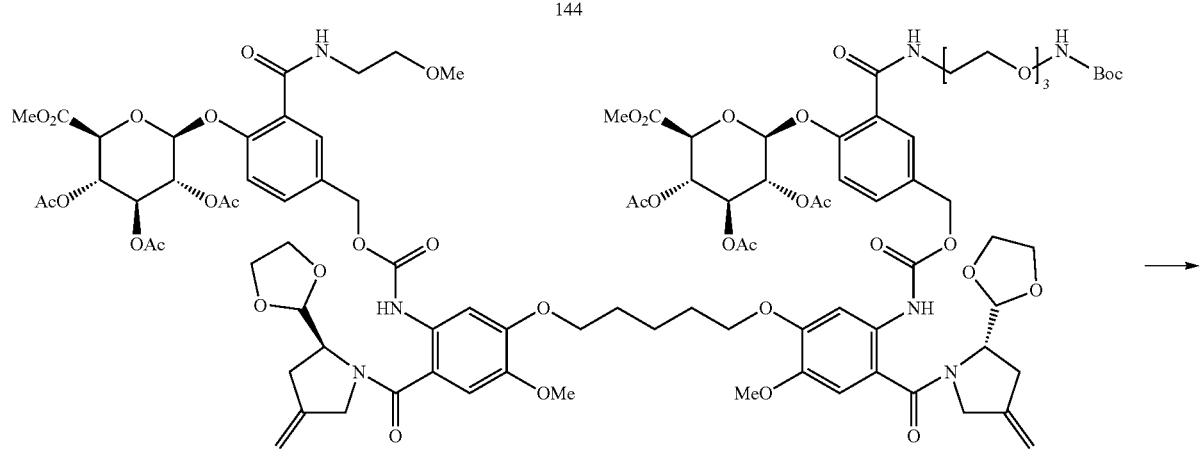

145

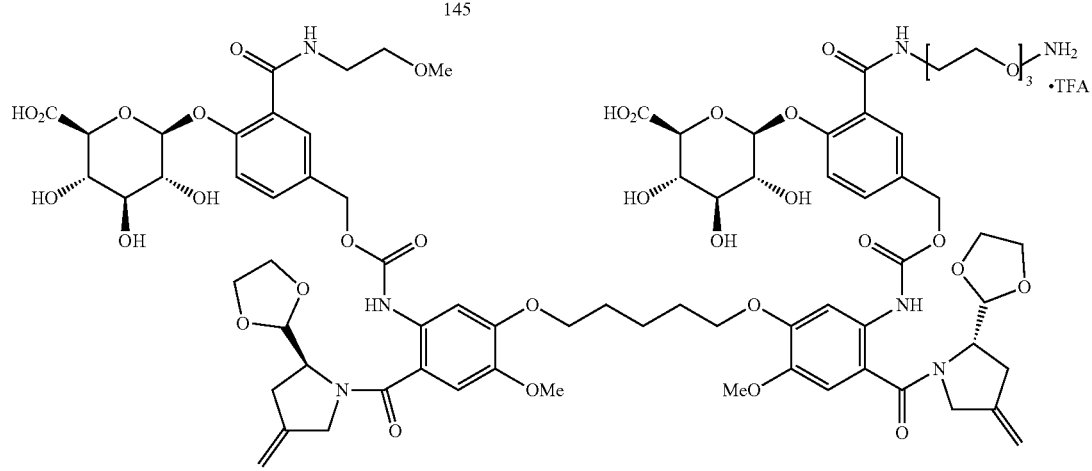

146

Preparation of Compound 143

Compound 142 (260 mg, 0.35 mmol) was dissolved in tetrahydrofuran (4 mL), then triphosgene (40 mg, 0.13 mmol) and triethylamine (0.078 mL, 0.56 mmol) were added thereto at −10° C., and the mixture was stirred for 1 hour under a nitrogen atmosphere. Compound 20 (208 mg, 0.39 mmol) and triethylamine (0.087 mL, 0.62 mmol) were dissolved in dry tetrahydrofuran (3 mL), and this solution was gradually added to the reaction solution. After 30 minutes, the reaction solution was heated under reflux and stirred for 3 hours. The reaction solution was concentrated, diluted with dichloromethane (50 mL), then washed with brine (2×20 mL), and dried over anhydrous sodium sulfate. The resultant was filtered, concentrated under reduced pressure, and then purified by column chromatography to obtain Compound 143 (340 mg, 71%).

$^1$H-NMR (400 MHz, CDCl$_3$) δ 8.78 (br s, 1H), 7.95 (d, J=12.2 Hz, 1H), 7.83 (br s, 1H), 7.52-7.41 (m, 2H), 7.27 (s, 1H), 7.04 (d, J=8.4 Hz, 1H), 6.83 (s, 1H), 6.00-5.88 (m, 1H), 5.42-5.23, (m, 10H), 5.20-5.08 (m, 4H), 5.06-4.82 (m, 8H), 4.67 (s, 1H), 4.28-4.18 (m, 6H), 4.16-4.06 (m, 8H), 4.05-3.86 (m, 6H), 3.86 (s, 3H), 3.76 (s, 3H), 3.52-3.62 (m, 3H), 3.41 (s, 3H), 2.78-2.58 (m, 2H), 2.12-2.06 (m, 2H), 2.05 (s, 9H), 1.86-2.01 (m, 4H), 1.72-1.60 (m, 2H), 1.27 (t, J=7.2 Hz, 2H). EI-MS m/z: [M+H]$^+$ 1361.5, ½[M+H]$^+$ 681.6.

Preparation of Compound 144

Compound 143 (330 mg, 0.24 mmol) was dissolved in dichloromethane (5 mL), then pyrrolidine (0.026 mL, 0.365 mmol) and tetrakis(triphenylphosphine)palladium(0) (14 mg, 0.012 mmol) were added thereto, and the mixture was stirred at room temperature for 5 hours under a nitrogen atmosphere. The reaction solution was concentrated under reduced pressure and then purified by column chromatography to obtain Compound 144 (290 mg, 90%).

$^1$H-NMR (400 MHz, CDCl$_3$) δ 8.82 (br s, 1H), 8.05 (s, 1H), 7.52-7.42 (m, 2H), 7.04 (d, J=8.2 Hz, 1H), 6.82 (s, 1H), 6.78 (s, 1H), 6.24 (s, 1H), 5.44-5.26, (m, 4H), 5.16-5.04 (m, 4H), 5.02-4.86 (m, 5H), 4.52-4.38 (m, 2H), 4.30-4.10 (m, 6H), 4.16-4.07 (m, 5H), 4.04-3.92 (m, 6H), 3.91-3.84 (m, 6H), 3.83 (s, 3H), 3.78 (s, 3H), 3.72 (s, 3H), 3.60-3.52 (m, 3H), 3.41 (s, 3H), 2.71-2.58 (m, 4H), 2.05 (s, 9H), 1.97-1.85 (m, 4H), 1.72-1.58 (m, 4H), 1.25 (t, J=7.2 Hz, 2H). EI-MS m/z: [M+H]$^+$ 1277.2, ½[M+H]$^+$ 639.4.

Preparation of Compound 145

Compound 144 (340 mg, 0.29 mmol) was dissolved in dry tetrahydrofuran (3 mL), then triphosgene (25 mg, 0.09 mmol) and triethylamine (0.060 mL, 0.43 mmol) were added thereto at −10° C., and the mixture was stirred for 1 hour under a nitrogen atmosphere. Compound 32 (229 mg, 0.31 mmol) was dissolved in dry tetrahydrofuran (3 mL), triethylamine (0.060 mL, 0.43 mmol) was added thereto, and then this solution was gradually added to the reaction solution. After 30 minutes, the reaction solution was heated under reflux and stirred for 4 hours. The reaction solution was concentrated, diluted with dichloromethane (100 mL), then washed with brine (2×50 mL), and dried over anhydrous sodium sulfate. The resultant was filtered, concentrated under reduced pressure, and then purified by column chromatography to obtain Compound 145 (250 mg, 43%).

EI-MS m/z: [M+Na]$^+$ 2056.4, ½[M+H]$^+$ 967.7.

Preparation of Compound 146

Compound 145 (230 mg, 0.113 mmol) was dissolved in methanol/tetrahydrofuran (3 mL/3 mL), and then a solution of lithium hydroxide (48 mg, 1.13 mmol) in distilled water (6 mL) was gradually added thereto at −40° C. The mixture was stirred for 2 hours while gradually raising the reaction temperature to 0° C. The reaction solution was neutralized with acetic acid, then concentrated under reduced pressure, and vacuum dried. The solid obtained was diluted with dichloromethane (10 mL), then trifluoroacetic acid (2 mL) was added thereto at 0° C., and the mixture was stirred for 2 hours. The reaction solution was concentrated under reduced pressure, then purified by HPLC, and freeze-dried to obtain Compound 146 (15.6 mg) as a white solid.

EI-MS m/z: [M+H]$^+$ 1653.7, ½[M+H]$^+$ 827.6.

<Example 51> Preparation of Compound 148

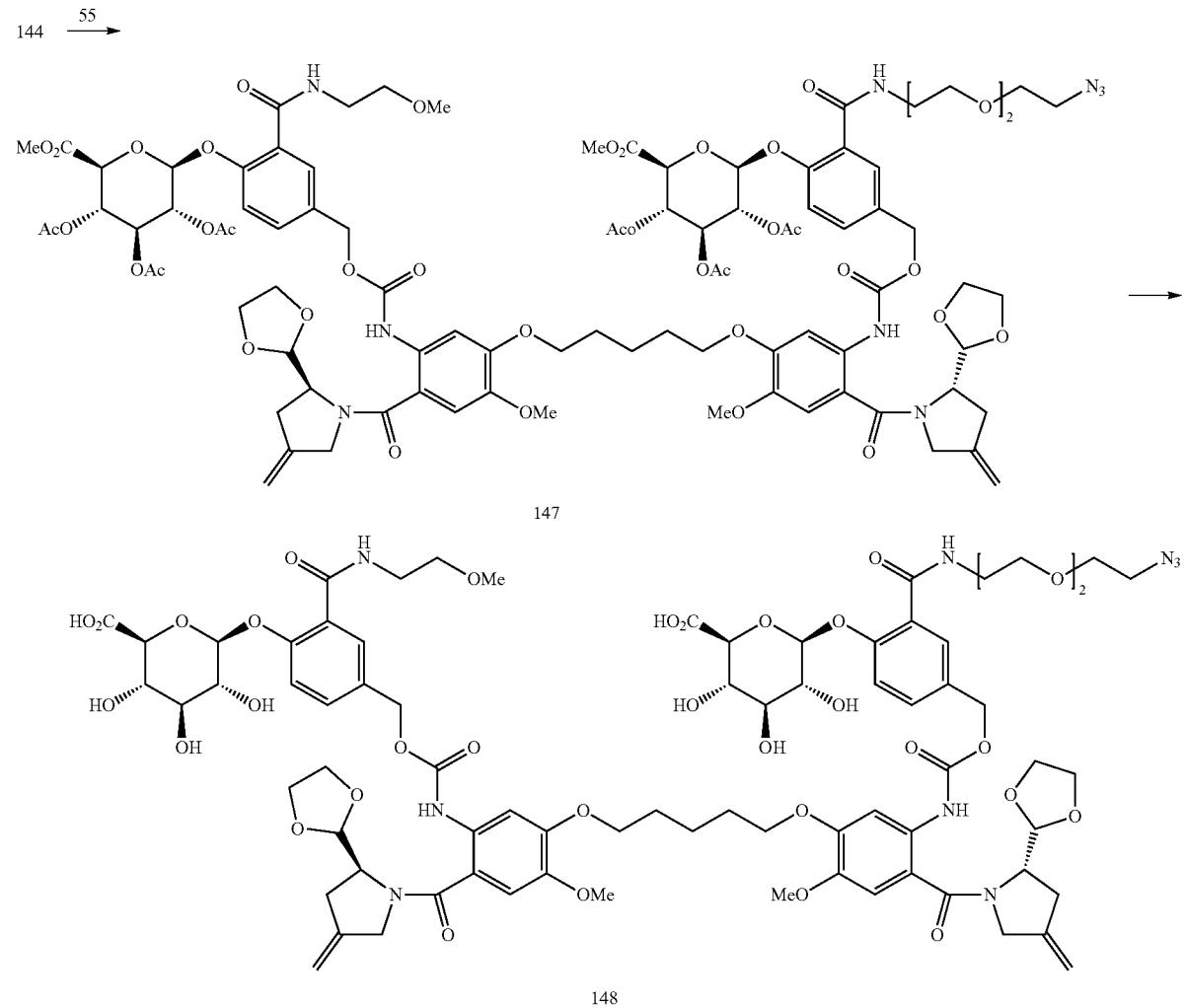

Preparation of Compound 147

Compound 144 (266 mg, 0.21 mmol) was dissolved in dry tetrahydrofuran (3 mL), then triphosgene (16 mg, 0.06 mmol) and triethylamine (0.044 mL, 0.31 mmol) were added thereto at −10° C., and the mixture was stirred for 1 hour under a nitrogen atmosphere. Compound 55 (147 mg, 0.23 mmol) was dissolved in dry tetrahydrofuran (3 mL), triethylamine (0.044 mL, 0.31 mmol) was added thereto, and then this solution was gradually added to the reaction solution. After 30 minutes, the reaction solution was heated under reflux and stirred for 4 hours. The reaction solution was concentrated, diluted with dichloromethane (100 mL), then washed with brine (2×50 mL), and dried over anhydrous sodium sulfate. The resultant was filtered, concentrated under reduced pressure, and then purified by column chromatography to obtain Compound 147 (170 mg, 42%).

EI-MS m/z: $[M+Na]^+$ 1944.6, $\frac{1}{2}[M+H]^+$ 972.8.

Preparation of Compound 148

Compound 147 (120 mg, 0.087 mmol) was dissolved in methanol/tetrahydrofuran (3 mL/3 mL), and then a solution of lithium hydroxide (37 mg, 0.87 mmol) in distilled water (6 mL) was gradually added thereto at −40° C. The mixture was stirred for 2 hours while gradually raising the reaction temperature to 0° C. The reaction solution was neutralized with acetic acid, then concentrated under reduced pressure, and vacuum dried. The solid obtained was diluted with dichloromethane (8 mL), then trifluoroacetic acid (2 mL) was added thereto at 0° C., and the mixture was stirred for 2 hours. The reaction solution was concentrated under reduced pressure, then purified by HPLC, and freeze-dried to obtain Compound 148 (31 mg) as a white solid.

EI-MS m/z: $[M+H]^+$ 1663.4, $\frac{1}{2}[M+H]^+$ 832.7.

<Example 52> Preparation of Compound 155

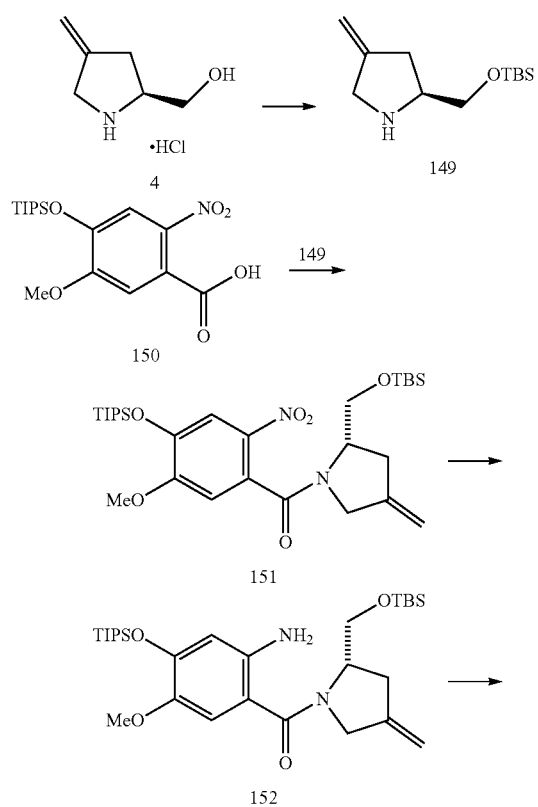

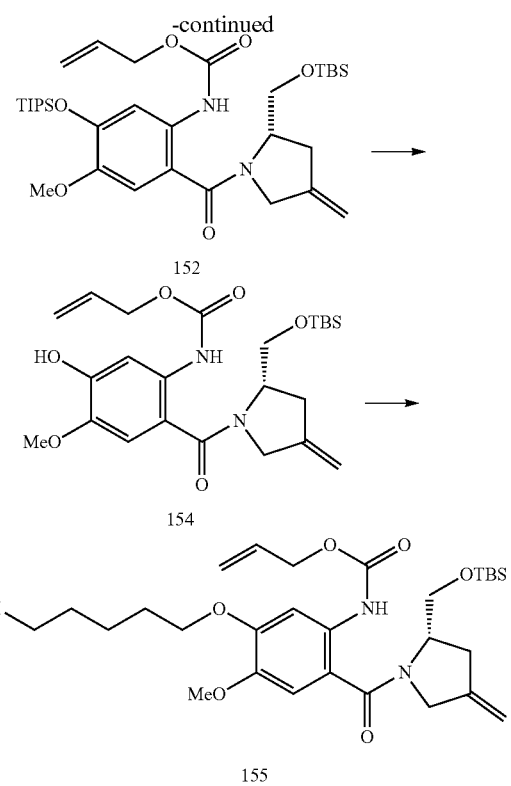

Preparation of Compound 149

Compound 4 (13.8 g, 92.5 mmol) was dissolved in dichloromethane (400 mL), and then imidazole (18.8 g, 277.5 mmol) and t-butyldimethylsilyl chloride (15.3 g, 101.7 mmol) dissolved in dichloromethane (100 mL) were added thereto at 0° C. under a nitrogen atmosphere. The reaction solution was stirred at room temperature for 2 hours, then brine (30 mL) was added to the reaction solution, the mixture was subjected to extraction using dichloromethane (2×300 mL), and the extract was dried over anhydrous sodium sulfate. The resultant was filtered, then concentrated, and purified by column chromatography to obtain Compound 149 (17 g, 80%).

$^1$H-NMR (400 MHz, CDCl$_3$) (rotamers) δ 4.91, (d, J=14.4 Hz, 2H), 3.66-3.47 (m, 4H), 3.27-3.24 (m, 1H), 2.47-2.42 (m, 1H), 2.24-2.18 (m, 1H), 0.91 (s, 9H), 0.05 (s, 6H).

Preparation of Compound 151

Compound 150 (17.3 g, 46.8 mmol, Compound 150 was prepared by the method described in ACS Med. Chem. Lett. 2016, 7, 983) was dissolved in N,N-dimethylformamide (100 mL), then 1-hydroxybenzotriazole (6.8 g, 50.7 mmol) and 1-(3-dimethylaminopropyl)-3-ethylcarbodiimide hydrochloride (10.4 g, 54.6 mmol) were added thereto in this order at 0° C. under a nitrogen atmosphere, and then the mixture was stirred for 30 minutes. A solution of Compound 149 (8.8 g, 39.0 mmol) and triethylamine (9.78 mL, 70.2 mmol) in dichloromethane (50 mL) was added to the mixture under a nitrogen atmosphere. The reaction temperature was raised to room temperature, and this mixture was stirred for 12 hours, then diluted with dichloromethane (100 mL), washed with a saturated aqueous sodium hydrogencarbonate solution (100 mL), and then dried over anhydrous sodium sulfate. The resultant was filtered, then concentrated, and purified by column chromatography to obtain Compound 151 (19.9 g, 89%).

¹H-NMR (400 MHz, CDCl₃) (rotamers) δ 7.69 (s, 1H), 6.72 (s, 1H), 4.97 (s, 1H), 4.82 (s, 1H), 4.57-4.54 (m, 1H) 3.89 (s, 4H), 3.74-3.71 (m, 2H) 3.30-3.27 (m, 1H), 2.76-2.52 (m, 2H), 1.31-1.23 (m, 3H), 1.08 (s, 18H), 0.89 (s, 9H), 0.08 (s, 3H).

Preparation of Compound 152

Compound 151 (29.5 g, 50.9 mmol) was dissolved in ethanol (720 mL), and then zinc dust (66.6 g, 1019.1 mmol) and formic acid (38 mL, 1019.1 mmol) were added thereto. The reaction solution was stirred at room temperature for 40 minutes and then filtered through Celite, and ethyl acetate (500 mL) was added thereto. The organic layer was washed with distilled water (500 mL), a saturated aqueous sodium hydrogencarbonate solution (500 mL), and brine (500 mL) in this order and then dried over anhydrous sodium sulfate. The resultant was filtered, then concentrated, and purified by column chromatography to obtain Compound 152 (27.9 g, 99%).

¹H-NMR (400 MHz, CDCl₃) (rotamers) δ 6.71 (s, 1H), 6.25 (s, 1H), 4.96-4.89 (m, 2H), 4.53 (br s, 1H), 4.21-4.09 (m, 4H), 3.74 (br s, 1H), 3.71 (s, 3H), 3.62 (br s, 1H), 2.73-2.63 (m, 2H), 1.29-1.21 (m, 3H), 1.05 (s, 18H), 0.87 (s, 9H), 0.02 (s, 6H).

Preparation of Compound 153

Compound 152 (27.9 g, 50.8 mmol) was dissolved in dichloromethane (300 mL), and then pyridine (9 mL, 111.8 mmol) and allyl chloroformate (5.9 mL, 55.9 mmol) were added thereto at −78° C. under a nitrogen atmosphere. After the reaction solution was stirred for 1 hour, the reaction temperature was raised to room temperature, and the reaction solution was concentrated and then purified by column chromatography to obtain Compound 153 (31.8 g, 99%).

¹H-NMR (400 MHz, CDCl₃) (rotamers) δ 8.67 (br s, 1H), 7.75 (s, 1H), 6.78 (s, 1H), 5.99-5.89 (m, 1H), 5.33, (d, J=17.2 Hz, 1H), 5.21 (d, J=10.4 Hz, 1H), 4.98-4.90 (m, 2H), 4.66-4.57 (m, 3H), 4.19-4.11 (m, 1H), 4.01 (br s, 1H), 3.86 (br s, 1H), 3.76 (s, 3H), 3.65 (br s, 1H), 2.68 (s, 2H), 1.33-1.24 (m, 3H), 1.05 (s, 18), 0.87 (s, 9H), 0.03 (s, 6H).

Preparation of Compound 154

Compound 153 (31.8 g, 50.2 mmol) was dissolved in N,N-dimethylformamide (300 mL) and distilled water (6 mL), then sodium acetic acid (5 g, 60.2 mmol) was added thereto at 0° C. under a nitrogen atmosphere, and the mixture was stirred at room temperature for 2 hours. The reaction solution was diluted with ethyl acetate (300 mL), then washed with distilled water (300 mL), and dried over anhydrous sodium sulfate. The resultant was filtered, then concentrated, and purified by column chromatography to obtain Compound 154 (17.7 g, 74%).

¹H-NMR (400 MHz, CDCl₃) (rotamers) δ 8.75 (br s, 1H), 7.75 (s, 1H), 6.78 (s, 1H), 6.14 (s, 1H), 5.94-5.90 (m, 1H), 5.32, (d, J=17.2 Hz, 1H), 5.21 (d, J=10.4 Hz, 1H), 4.97-4.90 (m, 2H), 4.65-4.56 (m, 3H), 4.18-4.15 (m, 1H), 4.01 (br s, 1H), 3.85 (s, 4H), 3.65 (br s, 1H), 2.68 (s, 2H), 0.87 (s, 9H), 0.02 (s, 6H).

Preparation of Compound 155

Compound 154 (18.6 g, 39.0 mmol) was dissolved in acetone (200 mL), then 1,5-diiodopentane (11.6 mL, 156 mmol) and potassium carbonate (5.9 g, 42.9 mmol) were added thereto in this order under a nitrogen atmosphere, and then the mixture was stirred at 60° C. for 12 hours. The reaction solution was concentrated and purified by column chromatography to obtain Compound 155 (23 g, 87%).

¹H-NMR (400 MHz, CDCl₃) (rotamers) δ 8.88 (br s, 1H), 7.83 (s, 1H), 6.81 (s, 1H), 5.98-5.90 (m, 1H), 5.34, (d, J=17.2 Hz, 1H), 5.24 (d, J=10.4 Hz, 1H), 4.98-4.90 (m, 2H), 4.67-4.58 (m, 3H), 4.21-4.12 (m, 1H), 4.10-4.06 (m, 3H) 3.82 (s, 4H), 3.64 (br s, 1H), 3.23-3.19 (m, 2H), 2.69 (s, 2H), 1.94-1.84 (m, 4H), 1.62-1.55 (m, 2H), 0.87 (s, 9H), 0.03 (s, 6H).

<Example 53> Preparation of Compound 162

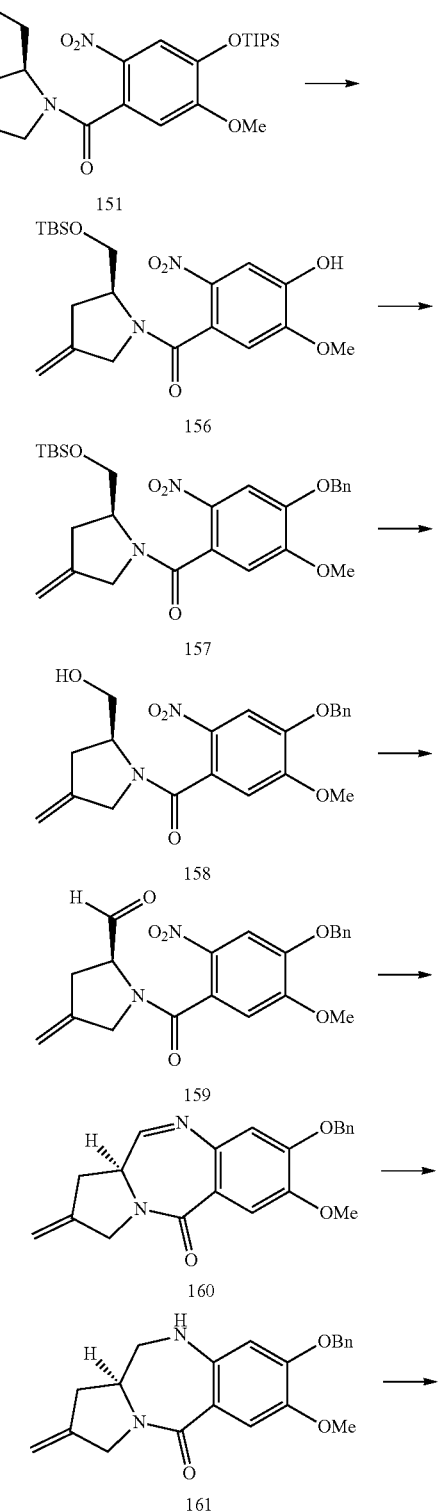

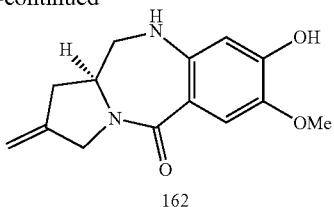

162

Preparation of Compound 156

Compound 151 (9.3 g, 16.0 mmol) was dissolved in N,N-dimethylformamide (100 mL) and distilled water (2 mL), then sodium acetate (1.6 g, 19.2 mmol) was added thereto at 0° C. under a nitrogen atmosphere, and the mixture was stirred at room temperature for 30 minutes. The reaction solution was diluted with ethyl acetate (100 mL), then washed with distilled water (100 mL), and dried over anhydrous sodium sulfate. The resultant was filtered, then concentrated, and purified by column chromatography to obtain Compound 156 (5.4 g, 80%).

$^1$H-NMR (400 MHz, CDCl$_3$) (rotamers) δ 7.75 (s, 1H), 6.76 (s, 1H), 6.07 (s, 1H), 4.98 (s, 1H), 4.83 (s, 1H), 4.58-4.54 (m, 1H), 3.99 (s, 3H), 3.89-3.87 (m, 1H), 3.77-3.70 (m, 2H), 3.33-3.29 (m, 1H), 2.81-2.53 (m, 2H), 0.89 (s, 9H), 0.09 (s, 6H).

Preparation of Compound 157

Compound 156 (3.0 g, 7.1 mmol) was dissolved in N,N-dimethylformamide (30 mL), and then potassium carbonate (1.1 g, 7.8 mmol) and benzyl bromide (0.9 ml, 7.8 mmol) were added thereto at 0° C. under a nitrogen atmosphere. The reaction solution was stirred for 3 hours, then a saturated aqueous ammonium chloride solution (50 mL) was added to the reaction solution, and the mixture was subjected to extraction using ethyl acetate (2×50 mL). The combined organic layers were washed with distilled water (2×100 mL) and brine (100 mL) and then dried over anhydrous sodium sulfate. The resultant was filtered, then concentrated, and purified by column chromatography to obtain Compound 157 (3.6 g, 97%).

$^1$H-NMR (400 MHz, CDCl$_3$) (rotamers) δ 7.77 (d, J=4.8 Hz, 1H), 7.46-7.33 (m, 5H), 6.79 (d, J=18.8 Hz, 1H), 5.22 (d, J=5.2 Hz, 2H), 5.09 (d, J=7.6 Hz, 1H), 4.98 (s, 1H), 4.83 (s, 1H), 4.58 (br s, 1H), 3.96 (s, 3H), 3.87 (br s, 1H), 3.77-3.69 (m, 2H), 3.30-3.28 (m, 1H), 2.81-2.53 (m, 2H), 0.89 (s, 9H), 0.09 (s, 6H).

Preparation of Compound 158

Compound 157 (3.6 mg, 6.9 mmol) was dissolved in tetrahydrofuran/distilled water (15 mL/15 mL), acetic acid (30 mL) was added thereto, and then the mixture was stirred at room temperature for 16 hours under a nitrogen atmosphere. The reaction solution was concentrated under reduced pressure and then purified by column chromatography to obtain Compound 158 (2.8 g, 99%).

$^1$H-NMR (400 MHz, CDCl$_3$) (rotamers) δ7.77 (s, 1H), 7.47-7.35 (m, 5H), 6.81 (s, H), 5.22 (s, 2H), 5.02 (s, 1H), 4.87 (s, 1H), 4.60 (br s, 1H), 3.99 (s, 3H), 3.88 (br s, 1H), 3.83-3.72 (m, 3H), 3.54 (br s, 1H), 2.88-2.82 (m, 1H), 2.52-2.48 (m, 1H).

Preparation of Compound 159

Oxalyl chloride (2.1 mL, 14.1 mmol) was dissolved in dichloromethane (20 mL), and then dimethyl sulfoxide (1.5 mL, 21.1 mmol) was added thereto at −78° C. under a nitrogen atmosphere. After 1 hour, a solution of Compound 158 (2.7 g, 6.9 mmol) in dichloromethane (50 mL) was gradually added to the mixture. The reaction solution was stirred for 2 hours, and then triethylamine (3.4 mL, 42.3 mmol) was diluted with dichloromethane (30 mL) and gradually added thereto. The reaction temperature was gradually raised to 0° C. over 2 hours. The reaction solution was diluted with dichloromethane (100 mL), and the organic layer was washed with a saturated aqueous ammonium chloride solution (200 mL) and brine (200 mL) and then dried over anhydrous sodium sulfate. The resultant was filtered, then concentrated, and purified by column chromatography to obtain Compound 159 (2.7 g, 96%).

$^1$H-NMR (400 MHz, CDCl$_3$) (rotamers) δ 9.79 (s, 1H), 7.79 (s, 1H), 7.46-7.26 (m, 5H), 6.87 (s, 1H), 5.22 (s, 2H), 5.06-4.96 (m, 1H), 4.93-4.90 (m, 1H), 4.78 (br s, 1H), 4.62-4.56 (m, 1H), 3.99 (s, 3H), 3.93 (s, 1H), 3.85 (s, 1H), 2.91-2.62 (m, 2H).

Preparation of Compound 160

Compound 159 (2.7 g, 6.8 mmol) was dissolved in tetrahydrofuran/distilled water (60 mL/40 mL) and then sodium dithionite (Na$_2$S$_2$O$_4$, 11.2 g, 64.4 mmol) was added thereto. The mixture was stirred for 20 hours under a nitrogen atmosphere. The reaction solution was diluted by addition of methanol (60 ml), acidified (pH 2) by addition of a 6 N aqueous hydrochloric acid solution, and stirred for 1 hour. The reaction solution was concentrated under reduced pressure to remove methanol. The reaction solution was acidified (pH 2) by addition of a 6 N aqueous hydrochloric acid solution and subjected to extraction using ethyl acetate (5×100 mL). The combined organic layers were dried over anhydrous sodium sulfate. The resultant was filtered, then concentrated under reduced pressure, and purified by column chromatography to obtain Compound 160 (1.8 g, 77%).

EI-MS m/z: [M+H]$^+$ 349.3, [M+H$_2$O]$^+$ 367.3.

Preparation of Compound 161

Compound 160 (1.8 g, 5.3 mmol) was dissolved in dichloromethane/N,N-dimethylformamide (20 mL/8 mL), then sodium triacetoxyborohydride (1.2 g, 5.8 mmol) was added thereto at 0° C. under a nitrogen atmosphere, and then the mixture was stirred for 2 hours. Distilled water (40 mL) was added to the reaction solution, and then the mixture was subjected to extraction using dichloromethane (2×50 mL). The organic layer extracted was dried over anhydrous sodium sulfate, filtered, concentrated under reduced pressure, and then purified by column chromatography to obtain Compound 161 (1.2 g, 64%).

$^1$H-NMR (400 MHz, CDCl$_3$) δ 7.61 (s, 1H), 7.41-7.30 (m, 5H), 6.05 (s, 1H), 5.12 (s, 2H), 5.06 (s, 1H), 5.02 (s, 1H), 4.38 (d, J=18 Hz, 1H), 4.27 (d, J=16.4 Hz, 1H), 4.04-3.96 (m, 1H), 3.86 (s, 3H), 3.49 (d, J=11 Hz, 1H), 3.29 (dd, J=9.2 Hz, 1H), 2.91-2.85 (m, 1H), 2.40 (dd, J=10 Hz, 1H).

Preparation of Compound 162

Compound 161 (1.3 g, 3.7 mmol) was dissolved in dichloromethane (70 mL), then methanesulfonic acid (25 mL) was added thereto, and the mixture was stirred for 2 hours under a nitrogen atmosphere. Distilled water (20 mL) was added to the reaction solution, and then the reaction solution was neutralized by addition of sodium carbonate. The reaction solution was diluted by addition of water (200 mL) and subjected to extraction using dichloromethane (3×50 mL). The organic layer extracted was dried over anhydrous sodium sulfate, filtered, concentrated under reduced pressure, and then purified by column chromatography to obtain Compound 162 (620 mg, 64%).

$^1$H-NMR (400 MHz, CDCl$_3$) δ 7.60 (s, 1H), 6.17 (s, 1H), 5.88 (br s, 1H), 5.09 (s, 1H), 5.06 (s, 1H), 4.41 (d, J=16.4 Hz, 1H), 4.31 (d, J=16.4 Hz, 1H), 4.08-3.99 (m, 1H), 3.88 (s,

3H), 3.54 (d, J=12.4 Hz, 1H), 3.49 (d, J=11 Hz, 1H), 3.34 (dd, J=9.2 Hz, 1H), 2.95-2.89 (m, 1H), 2.43 (dd, J=6.4 Hz, 1H).

<Example 54> Preparation of Compound 164

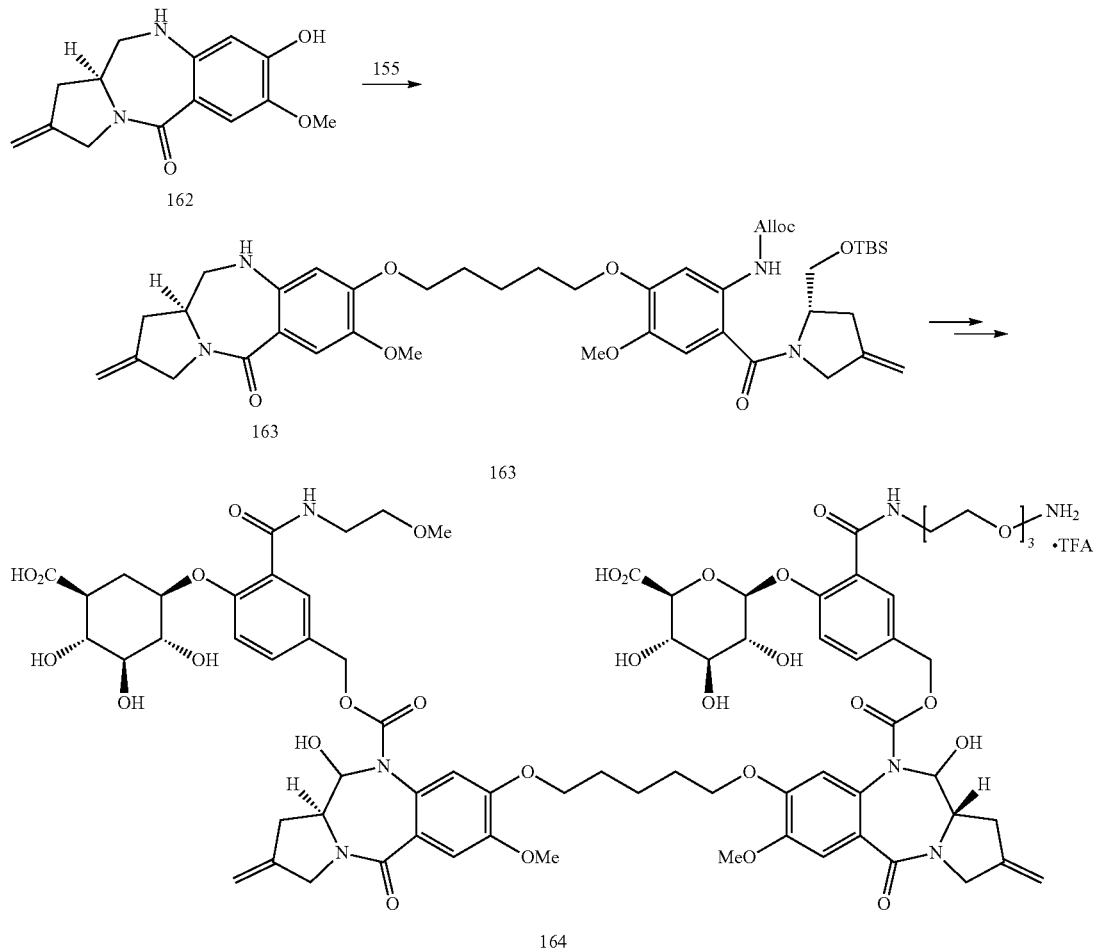

Preparation of Compound 163

Compound 162 (374 mg, 1.4 mmol) and Compound 155 (1.0 g, 1.5 mmol) were dissolved in acetone/N,N-dimethylformamide (20 mL/20 mL), then potassium carbonate (258 mg, 1.8 mmol) was added thereto under a nitrogen atmosphere, and the mixture was heated and stirred at 80° C. for 12 hours. The reaction solution was filtered and then concentrated under reduced pressure, and distilled water (20 mL) was added to the reaction solution, and then the mixture was subjected to extraction using ethyl acetate (3×30 mL). The organic layer extracted was dried over anhydrous sodium sulfate, filtered, concentrated under reduced pressure, and then purified by column chromatography to obtain Compound 163 (620 mg, 53%).

$^1$H-NMR (400 MHz, CDCl$_3$) (rotamers) δ 8.86 (br s, 1H), 7.85 (s, 1H), 7.60 (s, 1H), 6.82 (s, 1H), 6.06 (s, 1H), 6.01-5.91 (m, 1H), 5.36 (d, J=17.2 Hz, 1H), 5.25 (d, J=10.4 Hz, 1H), 5.08 (s, 1H), 5.05 (s, 1H), 5.00 (s, 1H), 4.92 (br s, 1H), 4.63 (d, J=4.8 Hz, 2H), 4.41 (d, J=16.4 Hz, 1H), 4.30 (d, J=16.4 Hz, 1H), 4.20 (d J=14 Hz, 1H), 4.13-4.10 (m, 3H), 4.05-3.98 (m, 3H), 3.85 (s, 3H), 3.82 (s, 3H), 3.66 (bs, 1H), 3.55 (d, J=12.8 Hz, 1H), 3.32 (dd, J=9.2 Hz, 1H), 2.91 (dd, J=8.8 Hz, 1H), 2.70 (br s, 2H), 2.43 (dd, J=7.2 Hz, 1H), 1.97-1.91 (m, 4H), 1.69-1.64 (m, 2H), 0.89 (s, 9H), 0.04 (br s, 6H).

Preparation of Compound 164

Compound 164 was prepared from Compound 163 by a method similar to that for the synthesis of Compound 28.

EI-MS m/z: [M+H]$^+$ 1548, ½[M+H]$^+$ 775.

<Example 55> Preparation of Compound 167

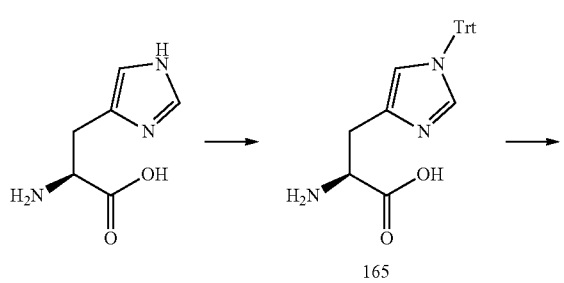

-continued

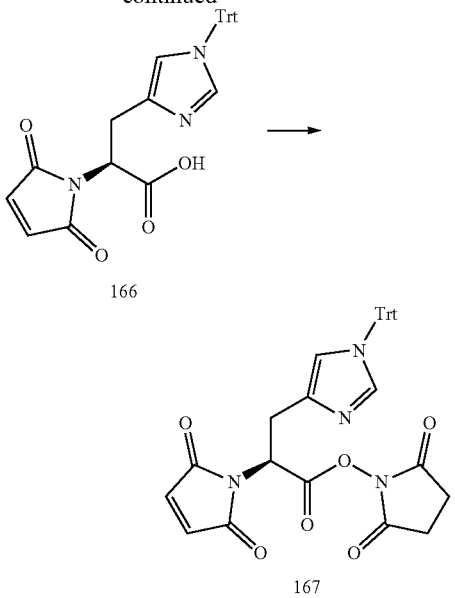

Preparation of Compound 165

L-Histidine (5.0 g, 32.22 mmol) was dissolved in dichloromethane (45 mL), then dichlorodimethylsilane (3.9 mL, 32.22 mmol) and triethylamine (9.0 mL, 64.44 mmol) were added thereto at room temperature, and the reaction solution was heated under reflux for 4 hours under a nitrogen atmosphere. Trityl chloride (8.9 g, 32.22 mmol) and triethylamine (4.5 mL, 32.22 mmol) were added thereto, and the mixture was stirred for 2 hours under a nitrogen atmosphere. Methanol (50 mL) was added to the reaction solution, then the mixture was concentrated under reduced pressure, distilled water (50 mL) and triethylamine were added thereto to adjust the pH to about from 8 to 8.5, the insoluble slurry was filtered off therefrom, and the filtered product was washed with chloroform (50 mL), diethyl ether (50 mL), and distilled water (50 mL) in this order. The white solid compound formed was dried to obtain Compound 165 (triethylamine salt, 12.4 g, 95%).

$^1$H-NMR (400 MHz, CD$_3$OD) δ 7.45-7.32 (m, 10H), 7.21-7.15 (m, 5H), 3.75-3.77 (m, 1H), 3.20 (q, 2H), 3.00-2.97 (m, 1H), 1.32 (t, 3H).

Preparation of Compound 166

Compound 165 (1.0 g, 2.52 mmol) and N-methoxycarbonylmaleimide (429 mg, 2.77 mmol) were dissolved in 1,4-dioxane/distilled water (5 mL/2.5 mL), then sodium carbonate (267 mg, 2.52 mmol) was added thereto, and the mixture was heated under reflux for 12 hours under a nitrogen atmosphere. The reaction solution was concentrated under reduced pressure and dissolved in N,N-dimethylformamide (3 mL), then triethylamine (0.16 mL, 1.12 mmol) was added to the reaction solution, and the mixture was stirred for 10 hours under a nitrogen atmosphere. Distilled water (5 ml) was added to the reaction solution, then the reaction solution was acidified (pH 4) by addition of a 0.5 N aqueous hydrochloric acid solution and subjected to extraction using dichloromethane (3×10 mL), and then the extract was dried over anhydrous sodium sulfate. The resultant was filtered and concentrated under reduced pressure to obtain Compound 166 (504 mg, 32%).

EI-MS m/z: [M+H]$^+$ 478.4, [M+Na]$^+$ 500.4.

Preparation of Compound 167

Compound 166 (252 mg, 0.53 mmol) was dissolved in N,N-diisopropylethylamine (4 mL), and then N-(3-dimethylaminopropyl)-N'-ethylcarbodiimide hydrochloride (132 mg, 0.69 mmol) and N-hydroxysuccinimide (85 mg, 0.74 mmol) were added thereto. The reaction solution was stirred at room temperature for 12 hours. Distilled water (30 mL) was added to the reaction solution, and then the mixture was subjected to extraction using ethyl acetate (2×30 mL). The organic layer extracted was dried over anhydrous sodium sulfate, filtered, concentrated under reduced pressure, and then purified by column chromatography to obtain Compound 167 (274 mg, 90%).

EI-MS m/z: [M+H]$^+$ 575.3.

<Example 56> Preparation of Compound 169

103 ⟶

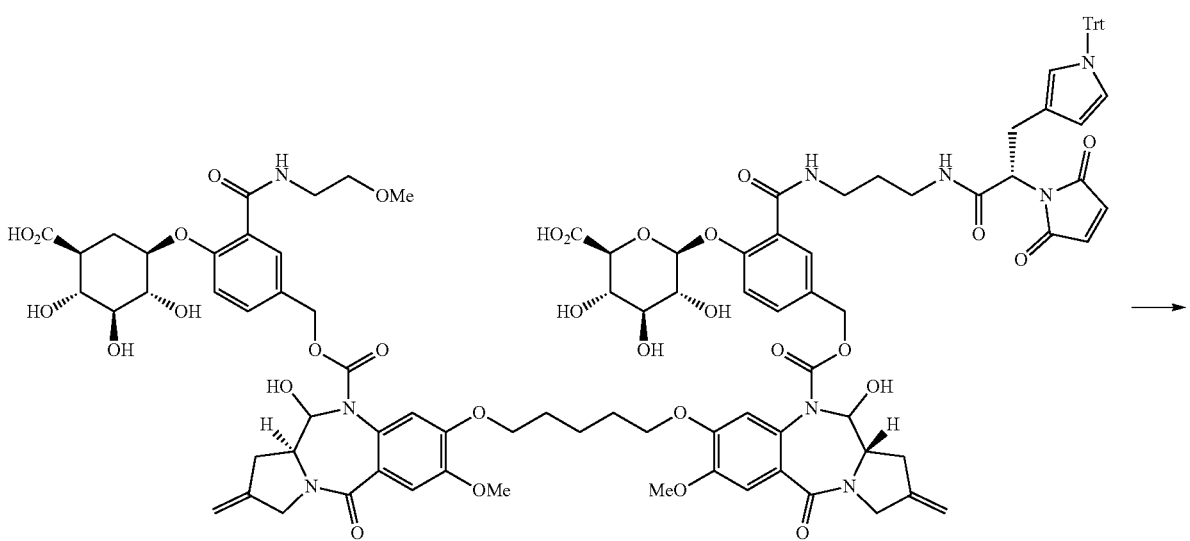

168

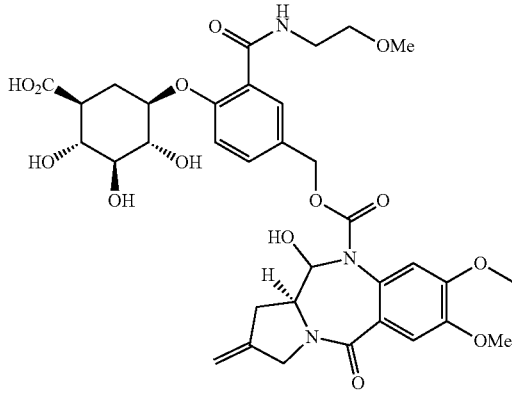
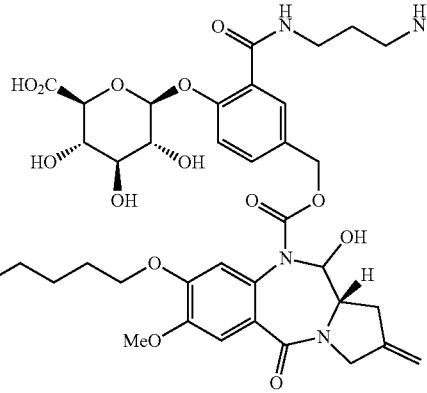

169

Preparation of Compound 168

Compound 103 (50 mg, 0.03 mmol) and Compound 167 (27.4 mg, 0.05 mmol) were dissolved in N,N-dimethylformamide (1 mL), then N,N-diisopropylethylamine (0.01 mL, 0.05 mmol) was added thereto, and the mixture was stirred at room temperature for 12 hours under a nitrogen atmosphere. The reaction solution was concentrated under reduced pressure, then purified by HPLC, and freeze-dried to obtain Compound 168 (11 mg, 18%).

EI-MS m/z: [M+H]$^+$ 1934.8, ½[M+H]$^+$ 968.0.

Preparation of Compound 169

Compound 168 (11 mg, 6 μmol) and anisole (6 μL, 60 μmol) were diluted with dichloromethane (0.75 mL), then trifluoroacetic acid (0.25 mL) was added thereto at 0° C., and the mixture was stirred for 3 hours. The reaction solution was concentrated under reduced pressure, then purified by HPLC, and freeze-dried to obtain Compound 169 (2 mg, 21%) as a white solid.

EI-MS m/z: [M+H]$^+$ 1692.7, ½[M+H]$^+$ 846.9.

<Example 57> Preparation of Compound 171

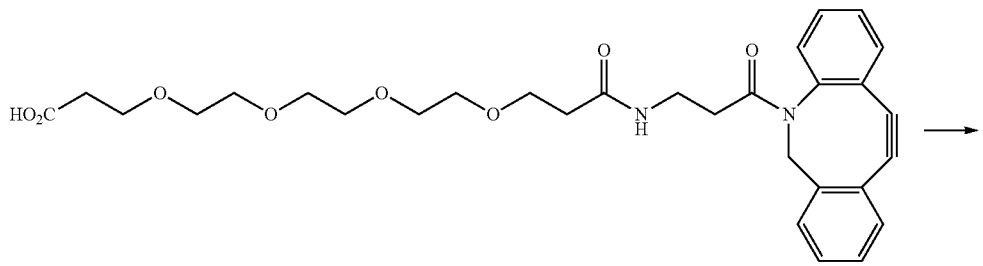

DBCO-PRG4-acid

103 ⟶

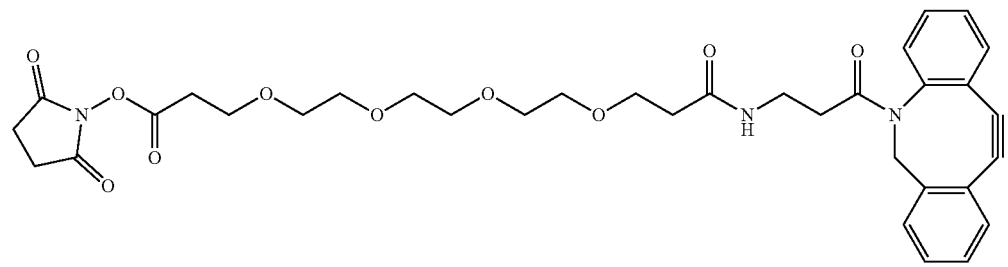

170

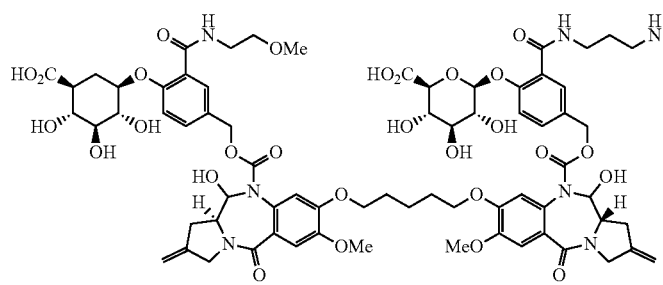
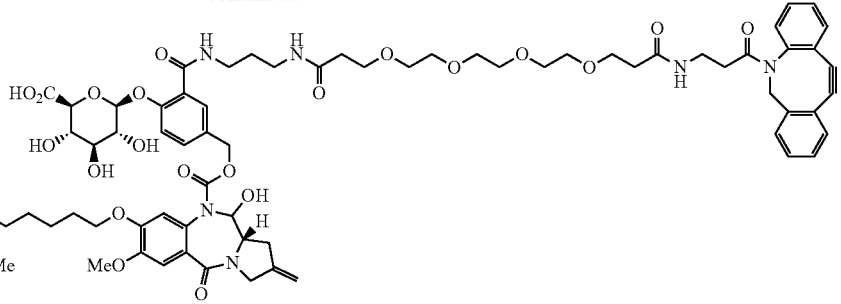

171

Preparation of Compound 170

DBCO-PEG4-acid (50 mg, 91 μmol) was dissolved in dichloromethane (1 mL), then N-(3-dimethylaminopropyl)-N'-ethylcarbodiimide hydrochloride (19 mg, 99 mol) and N-hydroxysuccinimide (11 mg, 99 gmol) were added thereto, and the mixture was stirred at room temperature for 3 hours under a nitrogen atmosphere. The reaction solution was concentrated under reduced pressure to obtain Compound 170 (59 mg).

EI-MS m/z: $[M+H]^+$ 650.7.

Preparation of Compound 171

Compound 103 (47 mg, 32 gmol) and Compound 170 (24 mg, 38 μmol) were dissolved in N,N-dimethylformamide/dichloromethane (1 mL/0.25 mL), then N,N-diisopropylethylamine (51 μL, 38 gmol) was added thereto, and the mixture was stirred at room temperature for 3 hours under a nitrogen atmosphere. The reaction solution was concentrated under reduced pressure, then purified by HPLC, and freeze-dried to obtain Compound 171 (8.1 mg, 14%).

EI-MS m/z: $[M+H]^+$ 2010.1, $½[M+H]^+$ 1005.6.

Preparation of Compounds 172 to 178

Pyrrolobenzodiazepine dimer Compounds 172 to 178 having the structures presented in the following Table 1 were prepared referring to the references.

TABLE 1

| No. | Structure of pyrrolobenzodiazepine dimer compound | Reference |
|---|---|---|
| 172 | | U.S. Pat. No. 8,697,688 |
| 173 | | U.S. Pat. No. 9,713,647 |
| 174 | | U.S. patent application Laid-Open No. 2015-0283258 |
| 175 | | U.S. patent application Laid-Open No. 2015-0283258 |
| 176 | | U.S. patent application Laid-Open No. 2015-0283258 |

TABLE 1-continued

| No. | Structure of pyrrolobenzodiazepine dimer compound | Reference |
|---|---|---|
| 177 | | U.S. patent application Laid-Open No. 2015-0283258 |
| 178 | (structure shown) | U.S. patent application Laid-Open No. 2015-0283258 |

Example 58

Preparation of ADC

ADCs were prepared through two steps, and LCB14-0511, LCB14-0512, and LCB14-0606 which were commonly used were prepared by the method described in Korean Patent Application Laid-Open No. 10-2014-0035393. The structural formulas of LCB14-0606, LCB14-0511, and LCB14-0512 are as follows:

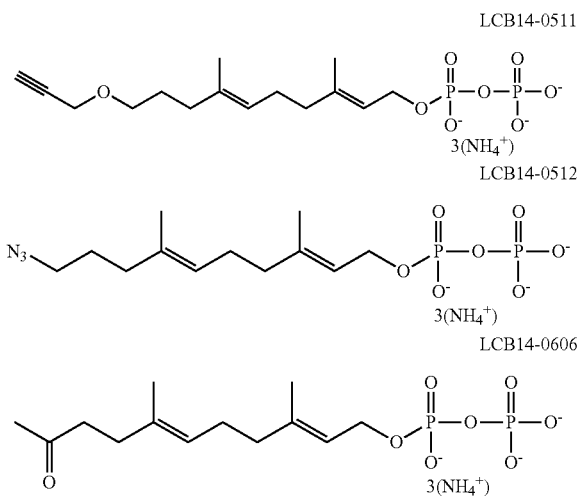

Step 1: Preparation of Prenylated Antibody

The prenylation reaction mixture of antibody was prepared and reacted at 30° C. for 16 hours. The reaction mixture was composed of 24 μM antibody, 200 nM FTase (Calbiochem #344145), and a buffer solution (50 mM Tris-HCl (pH 7.4), 5 mM $MgCl_2$, 10 μM $ZnCl_2$, 0.5 mM DTT) containing 0.144 mM LCB14-0511 or LCB14-0512 or LCB14-0606. After completion of the reaction, the prenylated antibody was desalted with a G25 Sepharose column (AKTA purifier, GE healthcare) equilibrated with PBS buffer solution.

Step 2: Drug-Conjugation Method

<Conjugation by Oxime Bond Formation>

The oxime bond-forming reaction mixture between the prenylated antibody and the linker-drug was prepared by mixing 100 mM Na-acetate buffer solution pH 4.5, 10% DMSO, 24 μM antibody, and 240 μM linker-drug (in house, compound in Table 1 as final product of Example 8 to 10 and Comparative Example 1) together and mildly stirred at 30° C. After 24 hours of reaction, the excess amount of low-molecular compounds used was removed through FPLC (AKTA purifier, GE healthcare), and the protein fractions were collected and concentrated.

<Conjugation by Click Reaction>

The click reaction mixture between the prenylated antibody and the linker-drug was prepared by mixing 10% DMSO, 24 μM antibody, 240 μM linker-drug (in house, compound in Table 1 as final product of Examples 20, 21, 22, 26, 27, 28, and 46), 1 mM copper(II) sulfate pentahydrate, 2 mM $(BimC_4A)_3$ (Sigma-Aldrich 696854), 10 mM sodium ascorbate, and 10 mM aminoguanidine hydrochloride, reacted at 25° C. for 3 hours, then treated with 2.0 mM EDTA, and reacted for 30 minutes. After completion of the reaction, the excess amount of the low-molecular compounds used was removed through FPLC (AKTA purifier, GE healthcare), and the protein fractions were collected and concentrated.

TABLE 2

List of ADC prepared

| # | Compound | ADC# |
|---|---|---|
| Example 8 | 28 | ADC1 |
| Example 9 | 29 | ADC2 |
| Example 10 | 30 | ADC3 |
| Example 12 | 34 | ADC4 |
| Example 14 | 42 | ADC5 |
| Example 20 | 61 | ADC6 |
| Example 21 | 62 | ADC7 |
| Example 22 | 63 | ADC8 |
| Example 23 | 65 | ADC9 |
| Example 26 | 73 | ADC10 |
| Example 27 | 74 | ADC11 |
| Example 28 | 75 | ADC12 |
| Example 31 | 82 | ADC13 |
| Example 32 | 83 | ADC14 |
| Example 33 | 85 | ADC15 |
| Example 36 | 100 | ADC16 |
| Example 39 | 104 | ADC17 |
| Example 41 | 112 | ADC18 |
| Example 46 | 135 | ADC19 |
| Example 47 | 137 | ADC20 |
| Example 57 | 171 | ADC21 |
| Comparative | 86 | ADC22 |
| Example 1 | 87 | ADC23 |
|  | 88 | ADC24 |

<Experimental Example 1> Evaluation on Cytotoxicity In Vitro

The cell proliferation inhibitory activity of the drug and ADCs presented in the following Table 2 on cancer cell lines was measured. As the cancer cell lines, commercially available human breast cancer cell lines MCF-7 (HER2 negative to normal), SK-BR3 (HER2 positive), and JIMT-1 (HER2 positive) were used. MMAF-OMe was used as the drug and the ADCs in Table 1 were used as the ADC. Each of the cancer cell lines was seeded in a 96-well plate by from 5,000 to 13,000 per well for the 72 hour treatment group and from 1,500 to 3,000 per well for the 168 hour treatment group, incubated for 24 hours, and then treated with antibodies and ADCs at a concentration of from 0.0051 to 33.33 nM or from 0.0015 to 10.0 nM (three times serial dilutions) and drugs at a concentration of from 0.023 to 50 nM (three times serial dilutions). After 72/168 hours, the number of living cells was quantified using SRB (Sulforhodamine B) dye.

TABLE 3

Comparison of cytotoxicity of ADC samples

| Test samples | CC50 (nM) | | | | | |
| --- | --- | --- | --- | --- | --- | --- |
| | SK-BR3 | | JIMT-1 | | MCF7 | |
| | 72 hr[a] | 168 hr | 72 hr | 168 hr | 72 hr | 168 hr |
| MMAF-OMe | 0.14 | 0.06 | 0.14 | 0.06 | 0.84 | 0.19 |
| ADC1 | 0.05 | 0.004 | >10 | 0.11 | >10 | >10 |
| ADC2 | 0.06 | 0.01 | >10 | 0.09 | >10 | >10 |
| ADC3 | 0.11 | 0.01 | >10 | 0.19 | >10 | >10 |
| ADC4 | NT[b] | 0.003 | NT | 0.10 | NT | >1 |
| ADC5 | NT | 0.005 | NT | 0.10 | NT | >1 |
| ADC8 | NT | 0.01 | NT | 0.19 | NT | >1 |
| ADC9 | NT | 0.007 | NT | 0.70 | NT | >10 |
| ADC10 | 0.04 | 0.004 | >100 | 0.09 | >100 | 0.82 |
| ADC12 | NT | 0.004 | NT | 0.15 | NT | >10 |
| ADC13 | NT | 0.023 | NT | 0.12 | NT | 0.76 |
| ADC14 | NT | 0.007 | NT | 0.11 | NT | >1 |
| ADC15 | NT | 0.02 | NT | 2.39 | NT | >10 |
| ADC16 | 0.06 | 0.01 | >10 | 0.33 | >10 | 0.48 |
| ADC20 | NT | 18.5[c] | NT | >100[c] | NT | >100[c] |
| ADC21 | NT | 0.006[c] | NT | 0.16[c] | NT | 27.1[c] |
| ADC22 | 15.3 | NT | >33.3 | NT | >33.3 | NT |
| ADC23 | 0.40 | 0.09 | >33.3 | >10 | >33.3 | >10 |
| ADC24 | 1.08 | NT | >33.3 | NT | >33.3 | NT |

It has been found that ADC1, 2, and 3 samples into which prodrug linker-drugs 28, 29, and 30 having a carbamate structure at both N10 positions of pyrrolobenzodiazepine are introduced among antibody-drug conjugates are superior to ADC22, 23, and 24 samples in cytotoxicity in the SK-BR3 and JIMT-1 breast cancer cell lines.

Since the compound is required to be converted into an effective drug by an additional reaction at the time of exposure to blood in the case of being administered in a form of the prodrug according to the present invention, and it is thus advantageous as compared to conventional PBD drugs in that the occurrence of side effects which may occur at the time of unexpected decomposition of linker can be prevented in advance, toxicity to normal cells diminishes, and the drug is more stable.

In addition, in the preparation of antibody-drug conjugate, the content of impurities is high and there is a possibility that the exposed imine group is attacked by nucleophiles and a drug having an unwanted structure is thus formed in the case of an antibody-drug conjugate prepared by the conventional method. However, the antibody-drug conjugate prepared by the method according to the present invention has an advantage of being protected from the attack by nucleophiles since the imine group of PBD dimer is in a form of the prodrug and easily separated since the purity thereof is high and exhibits improved physical properties as compared to the conventional PBD or PBD dimer.

INDUSTRIAL APPLICABILITY

The pyrrolobenzodiazepine dimer prodrug, pyrrolobenzodiazepine dimer prodrug-linker, or pyrrolobenzodiazepine dimer prodrug-linker-ligand conjugate according to the present invention can be used in the targeting and specific treatment of proliferative diseases such as cancer.

[Abstract]
The present disclosure relates to pyrrolobenzodiazepine dimer prodrugs and ligand-linker conjugates thereof. The present disclosure also relates to compositions and uses of said prodrugs and conjugates.

[Abstract]
The present invention relates to a pyrrolobenzodiazepine dimer prodrug and a ligand-linker conjugate compound thereof, a composition containing these, and therapeutic use thereof particularly as an anticancer drug. The stability of the compounds themselves and the stability thereof in plasma are excellent and the compounds are advantageous in terms of manifestation of toxicity, and thus the compounds are industrially useful in that it is possible to target proliferative diseases such as cancer, to perform a specific treatment, to maximize the drug efficacy, and to minimize the occurrence of side effects.

The invention claimed is:

1. A compound having a structure represented by Formula I or a pharmaceutically acceptable salt thereof:

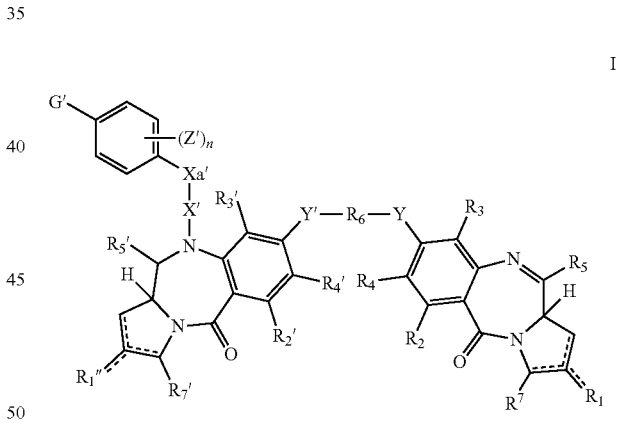

wherein
- $R_1$ and $R_1'$ are each independently selected from H, OH, =O, =CH$_2$, CN, $R^m$, $OR^m$, =CH—$R^{m'}$=C($R^{m'}$)$_2$, O—SO$_2$—$R^m$, CO$_2R^m$, COR$^m$, halo, and dihalo;
- $R^{m'}$ is selected from $R^m$, CO$_2R^m$, COR$^m$, CHO, CO$_2$H, and halo;
- $R^m$ is selected from substituted or unsubstituted $C_{1-12}$ alkyl, substituted or unsubstituted $C_{2-12}$ alkenyl, substituted or unsubstituted $C_{2-12}$ alkynyl, substituted or unsubstituted $C_{5-20}$ aryl, substituted or unsubstituted $C_{3-6}$ heteroaryl, substituted or unsubstituted $C_{3-6}$ cycloalkyl, substituted or unsubstituted 3- to 7-membered heterocyclyl, substituted or unsubstituted 3- to 7-membered heterocycloalkyl, and substituted or unsubstituted 5- to 7-membered heteroaryl, wherein when the $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3- to 7-membered heterocyclyl, 3- to 7-membered heterocycloalkyl, or 5- to 7-membered heteroaryl is substituted, wherein the respective hydrogen atoms in the $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3- to 7-membered heterocyclyl, 3- to 7-membered heterocycloalkyl, or 5- to 7-membered heteroaryl are each independently substituted with any one or more selected from methoxy, $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3- to 7-membered heterocyclyl, 3- to 7-membered heterocycloalkyl, and 5- to 7-membered heteroaryl;

$R_2$, $R_3$, $R_5$, $R_2'$, $R_3'$, and $R_5'$ are each independently selected from H, R′″, OH, OR′″, SH, SR′″, NH$_2$, NHR′″, NR′″R′″′, NO$_2$, Me$_3$Sn, and halo;

$R_4$ and $R_4'$ are each independently selected from H, R′″, OH, OR′″, SH, SR′″, NH$_2$, NHR′″, NR′″R′″′, NO$_2$, Me$_3$Sn, halo, substituted or unsubstituted $C_{1-6}$ alkyl, substituted or unsubstituted $C_{1-6}$ alkoxy, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted 3- to 7-membered heterocycloalkyl, substituted or unsubstituted $C_{5-12}$ aryl, substituted or unsubstituted 5- to 7-membered heteroaryl, —CN, —NCO, —OR″, —OC(O)R″, —OC(O)NR″R″′, —OS(O)R″, —OS(O)$_2$R″, —SR″, —S(O)R″, —S(O)$_2$R″, —S(O)NR″R″′, —S(O)$_2$NR″R″′, —OS(O)NR″R″′, —OS(O)$_2$NR″R″′, —NR″R″′, —NR″C(O)R°, —NR″C(O)OR°, —NR″C(O)NR°R°′, —NR″S(O)R°, —NR″S(O)$_2$R°, —NR″S(O)NR°R°′, —NR″S(O)$_2$NR°R°′, —C(O)R″, —C(O)OR″, and —C(O)NR″R″′, wherein the hydrogen atoms in the $C_{1-6}$ alkyl, $C_{1-6}$ alkoxy, $C_{2-6}$ alkenyl, $C_{2-6}$ alkynyl, $C_{3-6}$ cycloalkyl, 3- to 7-membered heterocycloalkyl, $C_{5-12}$ aryl, and 5- to 7-membered heteroaryl may be each independently substituted with the $C_{1-6}$ alkyl, $C_{1-6}$ alkoxy, $C_{2-6}$ alkenyl, $C_{2-6}$ alkynyl, $C_{3-6}$ cycloalkyl, 3- to 7-membered heterocycloalkyl, $C_{5-12}$ aryl, 5- to 7-membered heteroaryl, —OR$^p$, —OC(O)R$^p$, —OC(O)NR$^p$R$^{p'}$, —OS(O)R$^p$, —OS(O)$_2$R$^p$, —SR$^p$, —S(O)R$^p$, —S(O)$_2$R$^p$, —S(O)NR$^p$R$^{p'}$, —S(O)$_2$NR$^p$R$^{p'}$, —OS(O)NR$^p$R$^{p'}$, —OS(O)$_2$NR$^p$R$^{p'}$, —NR$^p$R$^{p'}$, —NR$^p$C(O)R$^q$, —NR$^p$C(O)OR$^q$, —NR$^p$C(O)NR$^q$H, —NR$^p$S(O)R$^q$, —NR$^p$S(O)$_2$R$^q$, —NR$^p$S(O)NR$^q$H, —NR$^p$S(O)$_2$NR$^q$H, —C(O)R$^p$, —C(O)OR$^p$, or —C(O)NR$^p$R$^p$ when the $C_{1-6}$ alkyl, $C_{1-6}$ alkoxy, $C_{2-6}$ alkenyl, $C_{2-6}$ alkynyl, $C_{3-6}$ cycloalkyl, 3- to 7-membered heterocycloalkyl, $C_{5-12}$ aryl, and 5- to 7-membered heteroaryl are substituted;

R′″, R′″′, R°, R°′ R$^p$, R$^{p'}$, and R$^q$ are each independently selected from H, $C_{1-7}$ alkyl, $C_{2-7}$ alkenyl, $C_{2-7}$ alkynyl, $C_{3-13}$ cycloalkyl, 3- to 7-membered heterocycloalkyl, $C_{6-10}$ aryl, and 5- to 7-membered heteroaryl;

X′ is selected from —C(O)O—, —S(O)O—, —C(O)—, —C(O)NR—, —S(O)$_2$NR—, —P(O)R′NR—, —S(O)NR—, and —PO$_2$NR—;

Xa′ is a bond or substituted or unsubstituted $C_{1-6}$ alkylene, wherein $C_{1-6}$ alkylene is substituted with $C_{1-8}$ alkyl, or $C_{3-8}$ cycloalkyl when being substituted;

R and R′ each independently denote H, OH, N$_3$, CN, NO$_2$, SH, NH$_2$, ONH$_2$, NHNH$_2$, halo, substituted or unsubstituted $C_{1-8}$ alkyl, substituted or unsubstituted $C_{3-8}$ cycloalkyl, substituted or unsubstituted $C_{1-8}$ alkoxy, substituted or unsubstituted $C_{1-8}$ alkylthio, substituted or unsubstituted $C_{3-20}$ heteroaryl, substituted or unsubstituted $C_{5-20}$ aryl, or mono- or di-$C_{1-8}$ alkylamino, wherein the $C_{1-8}$ alkyl, $C_{3-8}$ cycloalkyl, $C_{1-8}$ alkoxy, $C_{1-8}$ alkylthio, $C_{3-20}$ heteroaryl, and $C_{5-20}$ aryl are substituted with a substituent selected from OH, N$_3$, CN, NO$_2$, SH, NH$_2$, ONH$_2$, NHNH$_2$, halo, $C_{1-6}$ alkyl, $C_{1-6}$ alkoxy, and $C_{6-12}$ aryl when being substituted;

Y and Y′ are each independently selected from O, S, and N(H);

$R_6$ is a substituted or unsubstituted saturated or unsaturated $C_{3-12}$ hydrocarbon chain, wherein the chain may be interrupted by one or more heteroatoms, NMe, or a substituted or unsubstituted aromatic ring, the chain or aromatic ring may be substituted with —NH, —NR′″, —NHC(O)R′″, —NHC(O)CH$_2$—[OCH$_2$CH$_2$]$_n$—R, or —[CH$_2$CH$_2$O]$_n$—R at any one or more positions of hydrogen atoms on the chain or aromatic ring or unsubstituted, wherein R′″ and R are each as defined for R′″ and R above, and n is an integer from 1 to 12;

$R_7$ and $R_7'$ are each independently H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted 3- to 7-membered heterocycloalkyl, substituted or unsubstituted $C_{6-10}$ aryl, substituted or unsubstituted 5- to 7-membered heteroaryl, —OR$^r$, —OC(O)R$^r$, —OC(O)NR′R″′, —OS(O)R$^r$, —OS(O)$_2$R$^r$, —SR$^r$, —S(O)R$^r$, —S(O)$_2$R$^r$, —S(O)NR′R″′, —S(O)$_2$NR′R″′, —OS(O)NR′R″′, —OS(O)$_2$NR′R″′, —NR′R″′, —NR′C(O)R$^s$, —NRC(O)OR$^s$, —NRC(O)NR$^s$R$^s$, —NR$^s$(O)R$^s$, —NR′S(O)$_2$R$^s$, —NR$^s$(O)NR$^s$R$^{s'}$, —NR′S(O)$_2$NR$^s$R$^s$, —C(O)R$^r$, —C(O)OR$^s$, or —C(O)NR′R″′, wherein the hydrogen atoms in the $C_{1-6}$ alkyl, $C_{2-6}$ alkenyl, $C_{2-6}$ alkynyl, $C_{3-6}$ cycloalkyl, 3- to 7-membered heterocycloalkyl, $C_{6-10}$ aryl, and 5- to 7-membered heteroaryl are each independently substituted with $C_{1-6}$ alkyl, $C_{2-6}$ alkenyl, $C_{2-6}$ alkynyl, $C_{3-6}$ cycloalkyl, 3- to 7-membered heterocycloalkyl, $C_{6-10}$ aryl, 5- to 7-membered heteroaryl, —OR$^t$, —OC(O)R$^t$, —OC(O)NR′R″′, —OS(O)R$^t$, —OS(O)$_2$R$^t$, —SR$^t$, —S(O)R$^t$, —S(O)$_2$R$^t$, —S(O)NR′R″′, —S(O)$_2$NR′R″′, —OS(O)NR′R″′, —OS(O)$_2$NR′R″′, —NR′R″′, —NR′C(O)R$^u$, —NR′C(O)OR$^u$, —NR′C(O)NR″R″′, —NR′S(O)R$^u$, —NR′S(O)$_2$R$^u$, —NR′S(O)NR″R″′, —NR′S(O)$_2$NR″R″′, —C(O)R$^t$, —C(O)OR$^t$, or —C(O)NR′R″′ when the $C_{1-6}$ alkyl, $C_{2-6}$ alkenyl, $C_{2-6}$ alkynyl, $C_{3-6}$ cycloalkyl, 3- to 7-membered heterocycloalkyl, $C_{6-10}$ aryl, and 5- to 7-membered heteroaryl are substituted;

R$^r$, R$^{r'}$, R$^s$, R$^{s'}$, R$^t$, R$^{t'}$, R$^u$, and R$^{u'}$ are each independently selected from H, $C_{1-7}$ alkyl, $C_{2-7}$ alkenyl, $C_{2-7}$ alkynyl, $C_{3-13}$ cycloalkyl, 3- to 7-membered heterocycloalkyl, $C_{5-10}$ aryl, and 5- to 7-membered heteroaryl;

G′ denotes a glucuronide group or a galactoside group;

each Z′ is independently selected from H, $C_{1-8}$ alkyl, halo, NO$_2$, CN,

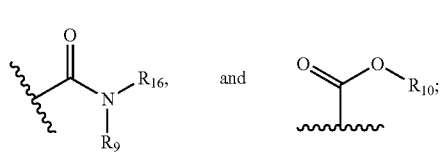

$R_9$, $R_{10}$, and $R_{16}$ are each independently selected from H, $C_{1-8}$ alkyl, $C_{2-6}$ alkenyl, $C_{1-6}$ alkoxy, and methyloxyethyl;

n is an integer from 1 to 3;

W denotes —C(O)—, —C(O)NR''—, —C(O)O—, —S(O)₂NR''—, —P(O)R'''NR''—, —S(O)NR''—, or —PO₂NR''; and R'' and R''' each independently denote H, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl, or $C_{6-20}$ aryl.

2. The compound of claim 1, wherein the compound has a structure represented by Formula Ia, Ib, or a pharmaceutically acceptable salt thereof:

Ia

Ib

3. The compound of claim 2, wherein $R_1'$ is $C_{3-6}$ cycloalkyl.

4. The compound of claim 2, wherein $R_1'$ is substituted or unsubstituted phenyl.

5. The compound of claim 2, wherein $R_1'$ is 5- to 7-membered heteroaryl.

6. The compound of claim 2, wherein $R_1'$ is $C_{1-12}$ alkyl.

7. The compound of claim 2, wherein $R_1'$ is $C_{1-12}$ alkenyl.

8. The compound of claim 2, wherein $R_1$ is substituted or unsubstituted phenyl.

9. The compound of claim 2, wherein $R_1$ is OH.

10. The compound of claim 2, wherein $R_1$ is $C_{1-12}$ alkenyl.

11. The compound of claim 2, wherein $R_1$ is $C_{1-12}$ alkyl.

12. The compound of claim 2, wherein $R_2$ and $R_2'$ are each H.

13. The compound of claim 2, wherein $R_3$ and $R_3'$ are each H.

14. The compound of claim 2, wherein $R_4$ and $R_4'$ are each H.

15. The compound of claim 2, wherein $R_5$ and $R_5'$ are each H.

16. The compound of claim 2, wherein $R_6$ is an unsubstituted saturated $C_{3-12}$ hydrocarbon chain.

17. The compound of claim 2, wherein $R_7$ and $R_7'$ are each H.

18. The compound of claim 2, wherein X' is —C(O)O—.

19. The compound of claim 2, wherein Xa' is unsubstituted $C_{1-6}$ alkylene.

20. The compound of claim 2, wherein G' is a glucuronide group.

21. The compound of claim 2, wherein G' is a galactoside group.

22. The compound of claim 2, wherein Z' is

23. The compound of claim 22, wherein $R_9$ is H.

24. The compound of claim 22, wherein $R_{16}$ is methyloxyethyl.

25. The compound of claim 22, wherein n is 1.

26. The compound of claim 2, wherein:

$R_1'$ is $C_{3-6}$ cycloalkyl, substituted or unsubstituted phenyl, 5- to 7-membered heteroaryl, $C_{1-12}$ alkyl, or $C_{1-12}$ alkenyl;

$R_1$ is substituted or unsubstituted phenyl, OH, $C_{1-12}$ alkenyl, or $C_{1-12}$ alkyl;

$R_2$, $R_2'$, $R_3$, $R_3'$, $R_4$, $R_4'$, $R_5$, $R_5'$, $R_7$, $R_7'$, and $R_9$ are each H;

$R_6$ is an unsubstituted saturated $C_{3-12}$ hydrocarbon chain;

X' is —C(O)O—;

Xa' is unsubstituted $C_{1-6}$ alkylene;

Z' is $R_{16}$ is methyloxyethyl; and n is 1.

27. The compound of claim 1, wherein the compound is:
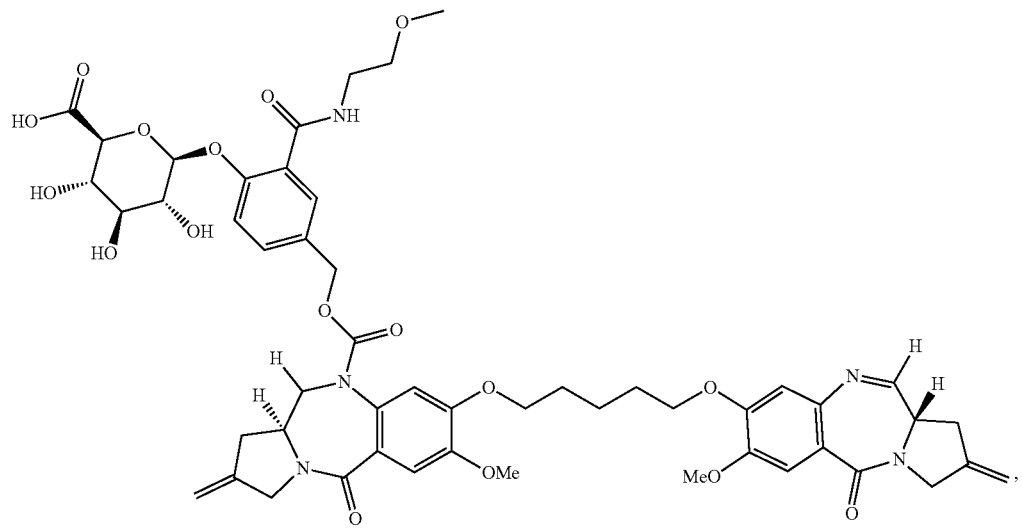
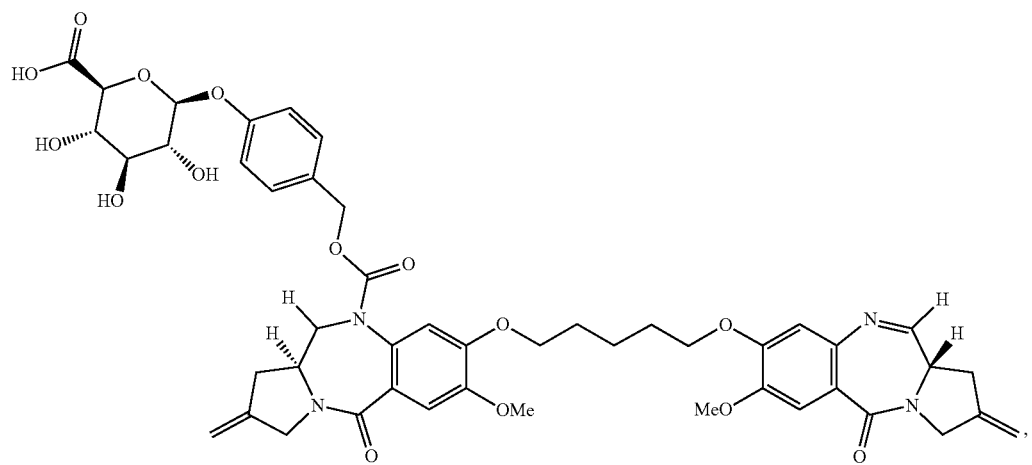
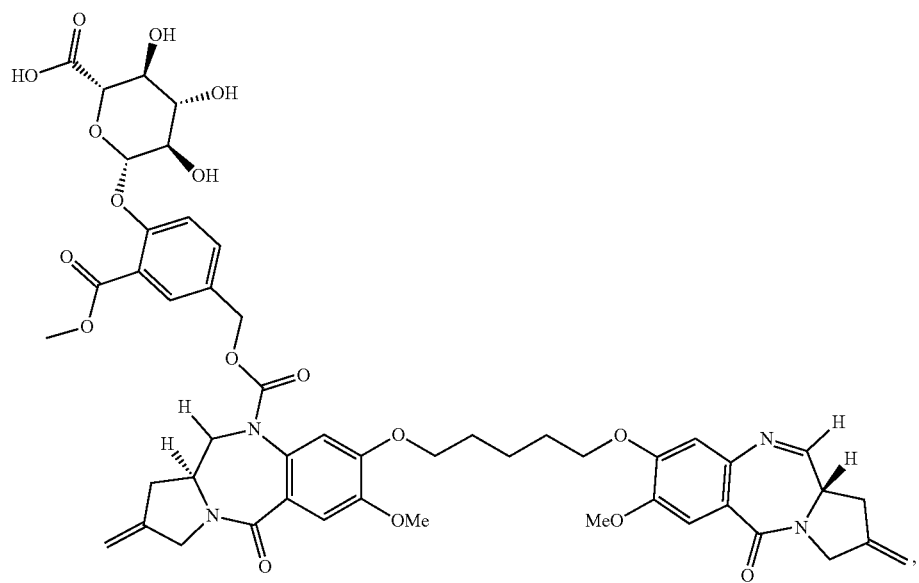

-continued
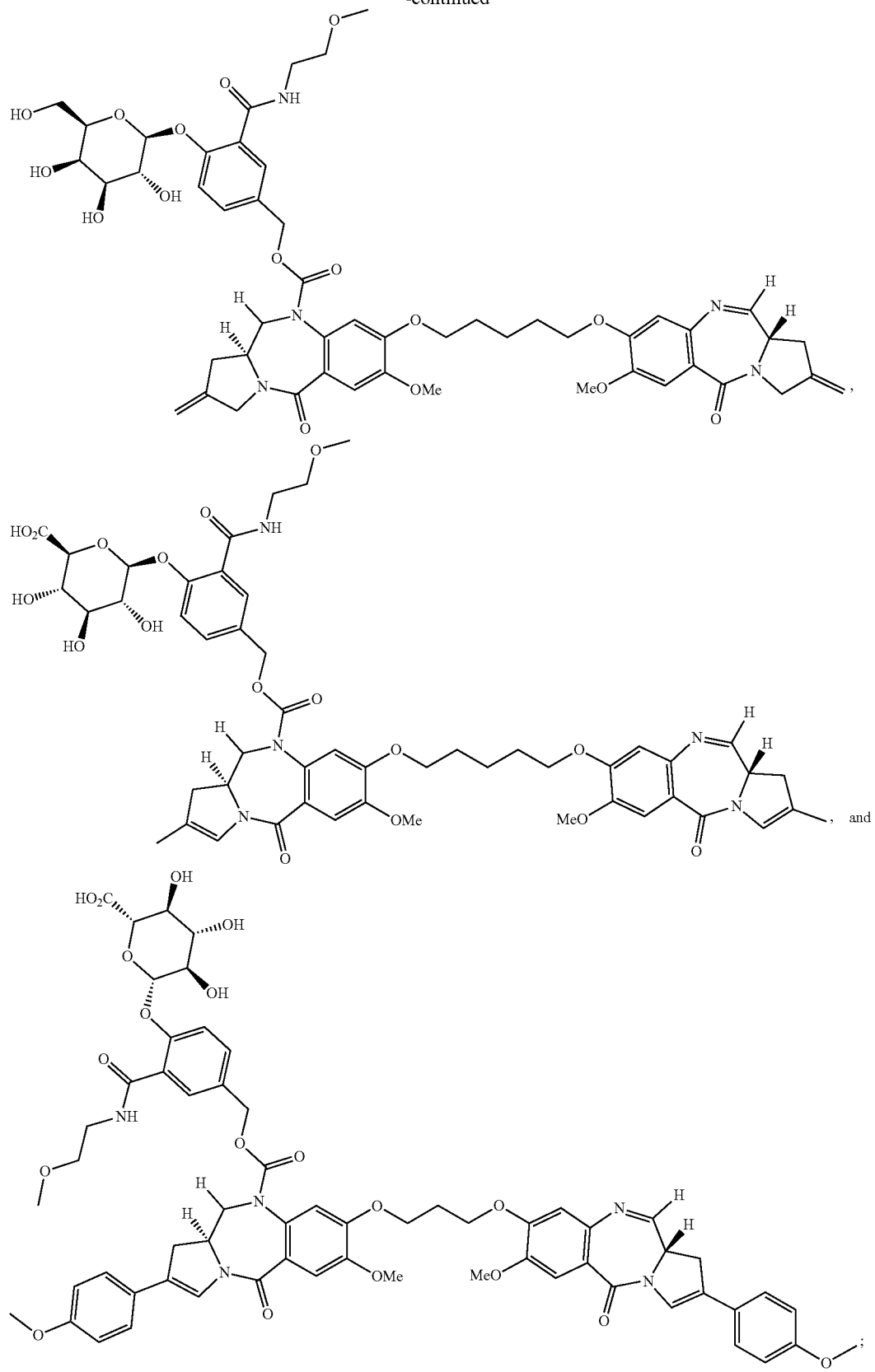
or
a pharmaceutically acceptable salt thereof.

28. A pharmaceutical composition comprising the compound of claim 1 and a pharmaceutically acceptable excipient.

29. A method of treating cancer in a subject in need thereof comprising administering a compound of claim 1 or a pharmaceutically acceptable salt thereof to the subject.

\* \* \* \* \*